(12) United States Patent
Sennhenn et al.

(10) Patent No.: US 12,172,993 B2
(45) Date of Patent: Dec. 24, 2024

(54) HETEROCYCLIC KINASE INHIBITORS AND USES THEREOF

(71) Applicant: iOmx Therapeutics AG, Martinsried (DE)

(72) Inventors: Peter Sennhenn, Martinsried (DE); Sebastian Meier-Ewert, Martinsried (DE); Nisit Khandelwal, Martinsried (DE); David Bancroft, Martinsried (DE)

(73) Assignee: IOMX THERAPEUTICS AG, Planegg/Martinsried (DE)

( * ) Notice: Subject to any disclaimer, the term of this patent is extended or adjusted under 35 U.S.C. 154(b) by 784 days.

(21) Appl. No.: 17/286,178

(22) PCT Filed: Oct. 22, 2019

(86) PCT No.: PCT/EP2019/078751
§ 371 (c)(1),
(2) Date: Apr. 16, 2021

(87) PCT Pub. No.: WO2020/083926
PCT Pub. Date: Apr. 30, 2020

(65) Prior Publication Data
US 2021/0387982 A1    Dec. 16, 2021

(30) Foreign Application Priority Data
Oct. 23, 2018  (EP) .................................. 18202164

(51) Int. Cl.
C07D 417/14    (2006.01)
A61P 35/00     (2006.01)

(52) U.S. Cl.
CPC ............ *C07D 417/14* (2013.01); *A61P 35/00* (2018.01)

(58) Field of Classification Search
CPC ............................... C07D 417/14; A61P 35/00
See application file for complete search history.

(56) References Cited

U.S. PATENT DOCUMENTS

| | | | |
|---|---|---|---|
| 2012/0225880 A1 | 9/2012 | Jiaang et al. | |
| 2023/0212163 A1 | 7/2023 | Fischer | |

FOREIGN PATENT DOCUMENTS

| | | |
|---|---|---|
| CL | 2022002901 A1 | 4/2023 |
| CN | 101534831 A | 9/2016 |
| CN | 106699744 A | 5/2017 |
| EP | 3643703 A1 | 4/2020 |
| EP | 3643713 A1 | 4/2020 |
| RU | 2382039 C2 | 2/2010 |
| RU | 2260592 C9 | 4/2017 |
| WO | 2004041164 A2 | 5/2004 |
| WO | 2006/081172 A2 | 8/2006 |
| WO | WO-2008033746 A2 * | 3/2008 ........... A61K 31/506 |
| WO | 2018193084 A1 | 10/2018 |
| WO | 2023067021 A1 | 4/2023 |

OTHER PUBLICATIONS

International Search Report and Written Opinion dated Jan. 31, 2020 for International Application No. PCT/EP2019/078751, 14 pages.
Beyss-Kahana, Ellen, International Search Report and Written Opinion for corresponding International Application No. PCT/EP2019/078751 dated Jan. 31, 2020, 14 pages.
Alekseyev, "Optical Isomerism and Drugs Pharmacological Activity Of Drugs", Soros' Educational Journal, 1998, pp. 49-55 (See English translation of Office Action issued Russian Application No. 2021114358/04(030505) dated Mar. 31, 2023 for concise explanation of relevance).
Bastin et al., "Salt Selection and Optimisation Procedures for Pharmaceutical New Chemical Entities", Organic Process Research & Development, 2000, vol. 4, p. 427-435.
Belikov, Belikov V.G., "Relationship between the chemical structure, properties of substances, and their effects on the organism", Pharmaceutical Chemistry, Chapter 2.6,—M.: MEDpress-inform, 2007, pp. 27-29 (See English translation of Office Action issued Russian Application No. 2021114358/04(030505) dated Mar. 31, 2023 for concise explanation of relevance).
Bol'shaya, Great Medical Encyclopedia, vol. 25, third edition, Moscow, Sovetskaya Entsiklopediya Publishing House, 1985, p. 11 (See English translation of Office Action issued Russian Application No. 2021114358/04(030505) dated Mar. 31, 2023 for concise explanation of relevance).
Gusev N.B., "Protein Kinases: Structure, Classification, Properties, and Biological Role", Soros' Educational Journal, vol. 6, 12, 2000, pp. 1-12 (See English translation of Office Action issued Russian Application No. 2021114358/04(030505) dated Mar. 31, 2023 for concise explanation of relevance).
Kummerer, "Pharmaceuticals In the Environment", Annual Review Of Environment and Resources, 2010, V. 35, p. 57-75.
Kharkevich, "Pharmacology Textbook", 10th edition, p. 72 (See English translation of Office Action issued Russian Application No. 2021114358/04(030505) dated Mar. 31, 2023 for concise explanation of relevance).

(Continued)

*Primary Examiner* — Matthew P Coughlin
*Assistant Examiner* — Quincy McKoy
(74) *Attorney, Agent, or Firm* — MH2 Technology Law Group, LLP

(57) ABSTRACT

The invention relates to kinase inhibitors, in particular inhibitors of protein kinases including the protein-tyrosine kinases LCK, ABL, SRC, KIT, SIK-family and/or their mutants. Although structurally similar to dasatinib, the kinase inhibitors of the invention can display one or more certain properties distinct to dasatinib. Also, the invention relates to pharmaceutical compositions that comprise one or more of the kinase inhibitors. The kinase inhibitors or pharmaceutical compositions of the invention may be used in the treatment of a disorder or condition, such as a proliferative disorder, for example, a leukaemia or solid tumour. The kinase inhibitors or pharmaceutical compositions may be used in a treatment regimen that corresponds to, is similar to or is distinct from that used with dasatinib for a corresponding disorder, and in particular may be used in a combination treatment regimen together with one or more additional therapeutic agents, such as immune-checkpoint inhibitors.

53 Claims, 24 Drawing Sheets

(56) References Cited

OTHER PUBLICATIONS

Khimicheskiy, Chemical Encyclopedic Dictionary, Moscow, 1983, pp. 130-131 (See English translation of Office Action issued Russian Application No. 2021114358/04(030505) dated Mar. 31, 2023 for concise explanation of relevance).

Kubasov, "Chemical Kinetics and Catalysis. Part 1", Moscow, Publishing House of Moscow University, 2004, pp. 2-3 (See English translation of Office Action issued Russian Application No. 2021114358/04(030505) dated Mar. 31, 2023 for concise explanation of relevance).

"Meditsina", Small Medical Encyclopedia, vol. 5, Moscow, 1996, pp. 90-96 (See English translation of Office Action issued Russian Application No. 2021114358/04(030505) dated Mar. 31, 2023 for concise explanation of relevance).

Mashkovskiy M.D., "Medicaments. A Manual for Doctors", Moscow, Meditsina, 1993, part 1, p. 8 (See English translation of Office Action issued Russian Application No. 2021114358/04(030505) dated Mar. 31, 2023 for concise explanation of relevance).

Smith et al., "Organic Synthesis: The Science Behind the Art" translation from English.—M.: Mir, 2001—573 p., ill., p. 64 (See English translation of Office Action issued Russian Application No. 2021114358/04(030505) dated Mar. 31, 2023 for concise explanation of relevance).

Syroeshkin, et al., "The Influence of Deuterium on the Properties of Pharmaceutical Substances (Review)", Drug Development & Registration, 2020; 9(2): 24-32 (See English translation of Office Action issued Russian Application No. 2021114358/04(030505) dated Mar. 31, 2023 for concise explanation of relevance).

Ayupova et al., "Package of Medicaments: a Textbook in Pharmaceutical Technology", Publishing House of Bashkir State Medical University, 2011.—91 p., see p. 11 (See English translation of Office Action issued Russian Application No. 2021114358/04(030505) dated Mar. 31, 2023 for concise explanation of relevance).

Zakharova N.M., "The Physiological Significance Of Proliferative and Alternative Processes", Progress In Physiological Science, 2013, vol. 44, 3, pp. 33-53 (See English translation of Office Action issued Russian Application No. 2021114358/04(030505) dated Mar. 31, 2023 for concise explanation of relevance).

Office Action for corresponding Russian Application No. 2021114358/04(030505) dated Mar. 31, 2023, 21 pages (English translation).

Database Registry, 2012, RN 1359547-85-5; N-(2,3-Dihydro-1,4-benzodioxin-6-yl)-2-[ (5-fluoro-2-pyridinyl) amino]-4-methyl-5-thiazolecarboxamide; retrieved from STN international [online] on Mar. 2, 2012.

Database Registry, 2012, RN 1358498-08-4; 2-[(5-Fluoro-2-pyridinyl)amino]-4-methyl-N-(3-pyridinylmethyl)-5-thiazolecarboxamide; retrieved from STN international [online] on Feb. 29, 2012.

Database Registry, 2012, RN 1358360-60-7; 2-[(5-Fluoro-2-pyridinyl)amino]-4-methyl-N-(2-pyridinylrnethyl)-5-thiazolecarboxamide; retrieved from STN international [online] on Feb. 29, 2012.

Database Registry, 2012, RN 1358292-34-8; 2-[(5-Fluoro-2-pyridinyl)amino]-4-methyl-N-[2-(2-thienyl)ethyl]-5-thiazolecarboxamide; retrieved from STN international [online] on Feb. 29, 2012.

Database Registry, 2011, RN 1351821-70-9; 2-[(5-Chloro-2-pyridinyl)arnino]-N-[2-(4-ethyl-1-piperazinyl)ethyl]-4-rnethyl-5-thiazolecarboxamide; retrieved from STN international [online] on Dec. 23, 2011.

Database Registry, 2011, RN 1351790-75-4; 2-[(5-Chloro-2-pyridinyl)amino]-N-(2-furanylmethyl)-4-methyl-5-thiazolecarboxamide; retrieved from STN international [online] on Dec. 23, 2011.

Database Registry, 2011, RN 1340965-51-6; 4-Methyl-2-[(6-methyl-2-pyridinyl)amino]-N-[(tetrahydro-2-furanyl) methyl]-5-thiazolecarboxamide; retrieved from STN international [online] on Nov. 4, 2011.

Database Registry, 2011, RN 1340965-30-1; 2-[(5-Chloro-2-pyridinyl)amino]-4-methyl-N-[2-(4-morpholinyl)ethyl]-5-thiazolecarboxamide; retrieved from STN international [online] on Nov. 4, 2011.

Rufet, Jacques (Authorized Officer), International Search Report and Written Opinion, dated Jun. 16, 2021 for International Application No. PCT/EP2021/060338, 13 pages.

Co-pending U.S. Appl. No. 17/996,514, entitled Halogenated-Heteroaryl and Other Heterocyclic Kinase Inhibitors, and Uses Thereof, filed Oct. 19, 2022.

* cited by examiner

FIGURE 3

| Kinase Name | Kinase Family | B3 (1μM) | A8 (1μM) | C7 (1μM) |
|---|---|---|---|---|
| ABL1 | TK | **** | **** | **** |
| ABL2 | TK | **** | **** | **** |
| ACK1 | TK | **** | **** | **** |
| ACV-R1 | TKL | *** | **** | **** |
| ACV-R1B | TKL | *** | **** | **** |
| ACV-R2A | TKL | *** | **** | **** |
| ACV-R2B | TKL | ** | **** | **** |
| ACV-RL1 | TKL | *** | **** | **** |
| AKT1 aa106-480 | AGC | * | * | * |
| AKT2 aa107-481 | AGC | * | * | * |
| AKT3 aa106-479 | AGC | * | * | * |
| ALK (GST-HIS-tag) | TK | * | * | * |
| AMPK-alpha1 aa1-550 | CAMK | * | * | * |
| ARK5 | CAMK | * | * | * |
| ASK1 | STE | * | * | * |
| Aurora-A | OTHER | * | ** | *** |
| Aurora-B | OTHER | * | * | *** |
| Aurora-C | OTHER | * | * | * |
| AXL | TK | ** | * | * |
| BLK | TK | **** | **** | **** |
| BMPR1A | TKL | * | *** | *** |
| BMX | TK | **** | **** | **** |
| B-RAF | TKL | *** | **** | **** |
| BRK | TK | **** | **** | **** |
| BRSK1 | CAMK | * | * | * |
| BRSK2 | CAMK | * | * | * |
| BTK | TK | **** | **** | **** |
| BUB1B | OTHER | * | * | * |
| CAMK1D | CAMK | * | * | * |
| CAMK2A | CAMK | * | * | * |
| CAMK2B | CAMK | * | * | * |
| CAMK2D | CAMK | * | * | * |
| CAMK2G | CAMK | * | * | * |
| CAMK4 | CAMK | * | * | * |
| CAMKK1 | OTHER | * | * | * |
| CAMKK2 | OTHER | * | * | * |
| CDC42BPA | AGC | * | * | ** |
| CDC42BPB | AGC | * | * | * |
| CDC7/DBF4 | OTHER | * | * | * |
| CDK1/CycA2 | CMGC | * | * | * |
| CDK1/CycB1 | CMGC | * | * | * |
| CDK1/CycE1 | CMGC | * | * | * |

FIGURE 3 (cont)

| Kinase Name | Kinase Family | B3 (1µM) | A8 (1µM) | C7 (1µM) |
|---|---|---|---|---|
| CDK16/CycY | CMGC | * | * | * |
| CDK19/CycC | CMGC | * | * | * |
| CDK2/CycA2 | CMGC | * | * | * |
| CDK2/CycE1 | CMGC | * | * | * |
| CDK3/CycC | CMGC | * | * | * |
| CDK3/CycE1 | CMGC | * | * | * |
| CDK4/CycD1 | CMGC | * | * | * |
| CDK4/CycD3 | CMGC | * | * | * |
| CDK5/p25NCK | CMGC | * | * | * |
| CDK5/p35NCK | CMGC | * | * | * |
| CDK6/CycD1 | CMGC | * | * | * |
| CDK6/CycD3 | CMGC | * | * | * |
| CDK7/CycH/MAT1 | CMGC | * | * | * |
| CDK8/CycC | CMGC | * | * | * |
| CDK9/CycK | CMGC | * | * | * |
| CDK9/CycT1 | CMGC | * | * | * |
| CHK1 | CAMK | * | * | * |
| CHK2 | CAMK | * | * | * |
| CK1-alpha1 | CK1 | * | * | * |
| CK1-delta | CK1 | * | * | * |
| CK1-epsilon | CK1 | * | * | * |
| CK1-gamma1 | CK1 | * | * | * |
| CK1-gamma2 | CK1 | * | * | * |
| CK1-gamma3 | CK1 | * | * | * |
| CK2-alpha1 | OTHER | * | * | * |
| CK2-alpha2 | OTHER | * | * | * |
| CLK1 | CMGC | * | * | * |
| CLK2 | CMGC | * | * | * |
| CLK3 | CMGC | * | * | * |
| CLK4 | CMGC | * | * | * |
| COT | STE | * | * | * |
| CSF1-R | TK | **** | **** | **** |
| CSK | TK | **** | **** | **** |
| DAPK1 | CAMK | * | * | * |
| DAPK2 | CAMK | * | * | * |
| DAPK3 | CAMK | * | * | * |
| DCAMKL2 | CAMK | * | * | * |
| DDR2 | TK | **** | **** | **** |
| DMPK | AGC | * | * | ** |
| DNA-PK | ATYPICAL | * | * | * |
| DYRK1A | CMGC | * | * | * |
| DYRK1B | CMGC | * | * | * |

FIGURE 3 (cont)

| Kinase Name | Kinase Family | B3 (1μM) | A8 (1μM) | C7 (1μM) |
|---|---|---|---|---|
| DYRK2 | CMGC | * | * | * |
| DYRK3 | CMGC | * | * | * |
| DYRK4 | CMGC | * | * | * |
| EEF2K | ATYPICAL | * | * | * |
| EGF-R | TK | *** | **** | **** |
| EIF2AK2 | OTHER | * | * | * |
| EIF2AK3 | OTHER | * | * | * |
| EPHA1 | TK | **** | **** | **** |
| EPHA2 | TK | **** | **** | **** |
| EPHA3 | TK | **** | **** | **** |
| EPHA4 | TK | **** | **** | **** |
| EPHA5 | TK | **** | **** | **** |
| EPHA6 | TK | * | *** | *** |
| EPHA7 | TK | * | * | * |
| EPHA8 | TK | **** | **** | **** |
| EPHB1 | TK | **** | **** | **** |
| EPHB2 | TK | **** | **** | **** |
| EPHB3 | TK | **** | **** | **** |
| EPHB4 | TK | **** | **** | **** |
| ERBB2 | TK | * | *** | *** |
| ERBB4 | TK | **** | **** | **** |
| ERK1 | CMGC | * | * | * |
| ERK2 | CMGC | * | * | * |
| ERK5 | CMGC | * | * | * |
| ERK7 | CMGC | * | * | * |
| FAK aa2-1052 | TK | * | * | * |
| FER | TK | * | * | * |
| FES | TK | * | * | * |
| FGF-R1 | TK | * | ** | ** |
| FGF-R2 | TK | ** | *** | **** |
| FGF-R3 | TK | * | * | ** |
| FGF-R4 | TK | * | * | * |
| FGR | TK | **** | **** | **** |
| FLT3 | TK | *** | * | ** |
| FRK | TK | **** | **** | **** |
| FYN | TK | **** | **** | **** |
| GRK2 | AGC | * | * | * |
| GRK3 | AGC | * | * | * |
| GRK4 | AGC | * | * | * |
| GRK5 | AGC | * | * | * |
| GRK6 | AGC | * | * | * |
| GRK7 | AGC | * | * | * |

FIGURE 3 (cont)

| Kinase Name | Kinase Family | B3 (1μM) | A8 (1μM) | C7 (1μM) |
|---|---|---|---|---|
| GSG2 | OTHER | * | * | * |
| GSK3-alpha | CMGC | * | * | * |
| GSK3-beta | CMGC | * | * | * |
| HCK | TK | **** | **** | **** |
| HIPK1 | CMGC | * | * | * |
| HIPK2 | CMGC | * | * | * |
| HIPK3 | CMGC | * | * | * |
| HIPK4 | CMGC | * | * | * |
| HRI | OTHER | * | * | * |
| IGF1-R | TK | * | * | * |
| IKK-alpha | OTHER | * | * | * |
| IKK-beta | OTHER | * | * | * |
| IKK-epsilon | OTHER | * | * | ** |
| INS-R | TK | * | * | * |
| INSR-R | TK | * | * | * |
| IRAK1 | TKL | * | * | * |
| IRAK4 (untagged) | TKL | * | * | ** |
| ITK | TK | * | * | * |
| JAK1 aa583-1154 wt | TK | * | *** | *** |
| JAK2 | TK | ** | ** | ** |
| JAK3 | TK | * | * | ** |
| JNK1 | CMGC | * | * | * |
| JNK2 | CMGC | * | * | * |
| JNK3 | CMGC | * | * | * |
| KIT | TK | **** | **** | **** |
| LCK | TK | **** | **** | **** |
| LIMK1 | TKL | * | * | * |
| LIMK2 | TKL | * | * | * |
| LRRK2 | TKL | * | * | ** |
| LTK | TK | * | * | * |
| LYN | TK | **** | **** | **** |
| MAP3K1 | STE | * | * | * |
| MAP3K10 | STE | * | ** | *** |
| MAP3K11 | STE | ** | *** | **** |
| MAP3K7/MAP3K7IP1 | STE | * | * | * |
| MAP3K9 | STE | * | ** | *** |
| MAP4K2 | STE | * | * | * |
| MAP4K4 | STE | * | * | * |
| MAP4K5 | STE | *** | **** | **** |
| MAPKAPK2 | CAMK | * | * | * |
| MAPKAPK3 | CAMK | * | * | * |
| MAPKAPK5 | CAMK | * | * | * |

FIGURE 3 (cont)

| Kinase Name | Kinase Family | B3 (1μM) | A8 (1μM) | C7 (1μM) |
|---|---|---|---|---|
| MARK1 | CAMK | * | * | * |
| MARK2 | CAMK | * | * | * |
| MARK3 | CAMK | * | * | * |
| MARK4 | CAMK | * | * | * |
| MATK | TK | * | * | * |
| MEK1 | STE | * | * | * |
| MEK2 | STE | * | * | * |
| MEK5 | STE | * | * | * |
| MEKK2 | STE | * | ** | *** |
| MEKK3 | STE | * | ** | *** |
| MELK | CAMK | * | * | * |
| MERTK | TK | * | * | * |
| MET | TK | * | * | * |
| MINK1 | STE | * | ** | ** |
| MKK4 | STE | * | * | * |
| MKK6 S207D/T211D## | STE | * | * | * |
| MKK7 | STE | * | * | * |
| MKNK1 | CAMK | ** | * | * |
| MKNK2 | CAMK | * | * | * |
| MLK4 | TKL | * | * | * |
| MST1 | STE | * | * | * |
| MST2 | STE | * | * | * |
| MST3 | STE | * | * | * |
| MST4 | STE | * | * | *** |
| mTOR | ATYPICAL | * | * | * |
| MUSK | TK | * | * | * |
| MYLK | CAMK | * | * | * |
| MYLK2 | CAMK | * | * | ** |
| MYLK3 | CAMK | * | * | * |
| NEK1 | OTHER | * | * | * |
| NEK11 | OTHER | * | ** | **** |
| NEK2 | OTHER | * | * | * |
| NEK3 | OTHER | * | * | * |
| NEK4 | OTHER | * | * | * |
| NEK6 | OTHER | * | * | * |
| NEK7 | OTHER | * | * | * |
| NEK9 | OTHER | * | * | * |
| NIK | STE | * | * | * |
| NLK | CMGC | *** | **** | **** |
| p38-alpha | CMGC | *** | **** | **** |
| p38-beta | CMGC | ** | **** | **** |
| p38-delta | CMGC | * | * | * |

FIGURE 3 (cont)

| Kinase Name | Kinase Family | B3 (1µM) | A8 (1µM) | C7 (1µM) |
|---|---|---|---|---|
| p38-gamma | CMGC | * | * | * |
| PAK1 | STE | * | * | * |
| PAK2 | STE | * | * | * |
| PAK3 | STE | * | * | * |
| PAK4 | STE | * | * | * |
| PAK6 | STE | * | * | * |
| PAK7 | STE | * | * | * |
| PASK | CAMK | * | * | * |
| PBK | OTHER | * | * | * |
| PDGFR-alpha | TK | **** | **** | **** |
| PDGFR-beta | TK | **** | **** | **** |
| PDK1 | AGC | * | * | * |
| PHKG1 | CAMK | * | * | * |
| PHKG2 | CAMK | * | * | * |
| PIM1 | CAMK | * | * | * |
| PIM2 | CAMK | * | * | * |
| PIM3 | CAMK | * | * | * |
| PKA | AGC | * | ** | * |
| PKC-alpha | AGC | * | * | * |
| PKC-beta1 | AGC | * | * | * |
| PKC-beta2 | AGC | * | * | * |
| PKC-delta | AGC | * | * | * |
| PKC-epsilon | AGC | * | * | * |
| PKC-eta | AGC | * | * | * |
| PKC-gamma | AGC | * | * | * |
| PKC-iota | AGC | * | * | * |
| PKC-mu | AGC | * | * | * |
| PKC-nu | AGC | * | * | * |
| PKC-theta | AGC | * | * | ** |
| PKC-zeta | AGC | * | * | * |
| PKMYT1 | OTHER | * | * | * |
| PLK1 | OTHER | * | * | * |
| PLK3 | OTHER | * | * | * |
| PRK1 | AGC | * | * | * |
| PRK2 | AGC | * | * | * |
| PRKD2 | CAMK | * | * | * |
| PRKG1 | AGC | * | * | * |
| PRKG2 | AGC | * | * | * |
| PRKX | AGC | * | * | ** |
| PYK2 | TK | * | * | * |
| RAF1 Y340D/Y341D (untagged)## | TKL | *** | **** | **** |
| RET | TK | * | *** | **** |

FIGURE 3 (cont)

| Kinase Name | Kinase Family | B3 (1µM) | A8 (1µM) | C7 (1µM) |
|---|---|---|---|---|
| RIPK2 | TKL | **** | **** | **** |
| RIPK5 | TKL | * | * | * |
| ROCK1 | AGC | * | * | * |
| ROCK2 | AGC | * | * | * |
| RON | TK | * | * | * |
| ROS | TK | * | * | * |
| RPS6KA1 | AGC | * | * | * |
| RPS6KA2 | AGC | * | * | ** |
| RPS6KA3 | AGC | * | * | * |
| RPS6KA4 | AGC | * | * | * |
| RPS6KA5 | AGC | * | * | * |
| RPS6KA6 | AGC | * | * | *** |
| S6K | AGC | * | * | * |
| S6K-beta | AGC | * | * | * |
| SAK | OTHER | * | * | * |
| SGK1 | AGC | * | * | * |
| SGK2 | AGC | * | * | * |
| SGK3 | AGC | * | * | * |
| SIK1 | CAMK | **** | **** | **** |
| SIK2 | CAMK | **** | **** | **** |
| SIK3 | CAMK | **** | **** | **** |
| SLK | STE | * | ** | ** |
| SNARK | CAMK | * | * | * |
| SNK | OTHER | * | * | * |
| SRC (GST-HIS-tag) | TK | **** | **** | **** |
| SRMS | TK | *** | **** | **** |
| SRPK1 | CMGC | * | * | * |
| SRPK2 | CMGC | * | * | * |
| STK17A | CAMK | * | * | * |
| STK23 | CAMK | * | * | * |
| STK25 | STE | * | * | ** |
| STK33 | CAMK | * | * | * |
| STK39 | STE | * | * | * |
| SYK aa1-635 | TK | * | ** | ** |
| TAOK2 | STE | * | * | * |
| TAOK3 | STE | * | * | * |
| TBK1 | OTHER | * | * | *** |
| TEC | TK | **** | **** | **** |
| TGFB-R1 | TKL | *** | **** | **** |
| TGFB-R2 | TKL | * | ** | *** |
| TIE2 | TK | * | * | ** |
| TLK1 | AGC | * | * | * |

FIGURE 3 (cont)

| Kinase Name | Kinase Family | B3 (1µM) | A8 (1µM) | C7 (1µM) |
|---|---|---|---|---|
| TLK2 | AGC | * | * | * |
| TNK1 | TK | * | * | ** |
| TRK-A | TK | ** | ** | *** |
| TRK-B | TK | * | * | ** |
| TRK-C | TK | ** | ** | *** |
| TSF1 | OTHER | * | * | * |
| TSK2 | CAMK | * | * | * |
| TSSK1 | CAMK | * | * | * |
| TTBK1 | CK1 | * | * | * |
| TTBK2 | CK1 | * | * | * |
| TTK | OTHER | * | * | * |
| TXK | TK | **** | **** | **** |
| TYK2 | TK | * | * | * |
| TYRO3 | TK | * | * | * |
| VEGF-R1 | TK | * | * | ** |
| VEGF-R2 | TK | * | ** | ** |
| VEGF-R3 | TK | * | * | ** |
| VRK1 | CK1 | * | * | * |
| VRK2 | CK1 | * | * | ** |
| WEE1 | OTHER | * | ** | *** |
| WNK1 | OTHER | * | * | * |
| WNK2 | OTHER | * | ** | *** |
| WNK3 | OTHER | * | * | ** |
| YES | TK | **** | **** | **** |
| ZAK | TKL | **** | **** | **** |
| ZAP70 | TK | * | * | * |
| Selectivity Score | < 50 % residual activity | 0.163 | 0.188 | 0.234 |

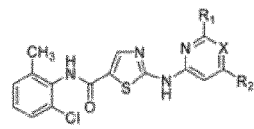

| cmpd | X | R₁ | R₂ | K562 | PC3 | MDA-MB-231 | WiDr |
|---|---|---|---|---|---|---|---|
| 1 | N | CH₃ | CH₃ | 1.6, 2.1 | 67 | | |
| 2 | CH | (imidazole-propyl) | H | <3.0 | 2.8 | <3.0 | 4.1 |
| 3 | CH | (N-methyl-propylamine) | H | <2.0 | 3.6 (2.1) | 6.2 | 23 |
| 4 | CH | (hydroxyethyl-propylamine) | H | <3.0 | 13 (8) | 3.1, 5.4 | 7.9, 47 |
| 5 | CH | (morpholinopropyl) | H | <2.0 | 10 | 42, 34 | 32, 67 |
| 6 | N | H | (4-methyl-morpholinyl) | <3.0 | 24 (16) | 45 (25) | 270 (170) |
| 7 | N | H | (morpholinoethyl) | <2.0 | 82 | 170 | 270 |
| 8 | N | CH₃ | (morpholinoethyl) | <3.0 | 3.6 (2.3) | 16 | 27 |
| 9 | N | CH₃ | (morpholinoethyl) | <1.0 | 25 | 47 | 180 |
| 10 | N | CH₃ | (morpholinopropyl) | <2.0 | 14 | 23, 28 | 92, 27 |
| 11 | N | CH₃ | (hydroxyethyl) | <4.0 | 27 (25) | 140 | 210 (120) |
| 12 | N | CH₃ | (hydroxymethyl-piperidinyl) | <1.0 | 11 (8) | 9.0 (5.1) | 41 |
| 13 | N | CH₃ | (hydroxyethyl-piperazinyl) | <1.0 | 9.4 (5.6) | 12 (10) | 52 (38) |

B

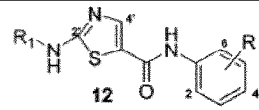

| compd | R | R₁ | hLck IC₅₀[a] (nM) | T-cell IC₅₀[b] (nM) |
|---|---|---|---|---|
| 12a | 2-Cl, 6-Me | 2″-pyridyl | 1.2 | 140 |
| 12b | 2-Cl, 6-Me | 3″-pyridyl | 6.7 | 870 |
| 12c | 2-Cl, 6-Me | 4″-pyridyl | 9.4 | 270 |
| 12d | 2,6-di-Me | 2″-pyridyl | 1.2 | 180 |
| 12e | 2,4,6-tri-Me | 2″-pyridyl | 5 | 510 |
| 12f | 2-Cl, 6-Me | 3″-pyridazinyl | 4 | 350 |
| 12g | 2,6-di-Me | 3″-pyridazinyl | 0.3 | 350 |
| 12h | 2-Cl, 6-Me | 3″,5″-di-Me-2″-pyrazinyl | 6.3 | 570 |
| 12i | 2,4,6-tri-Me | 2″-pyrazinyl | 4.9 | 500 |
| 12j | 2-Cl, 6-Me | 6″-Me-2″-pyridinyl | 0.6 | 110 |
| 12k | 2-Cl, 6-Me | 4″-Me-2″-pyridinyl | 0.5 | 80 |
| 12l | 2-Cl, 6-Me | 4″,6″-di-Me-2″-pyridinyl | 4 | 140 |
| 12m | 2-Cl, 6-Me | 2″,6″-di-Me-4″-pyrimidinyl | 1 | 80 |
| 12n | 2-Cl, 6-Me | 4″,6″-di-Me-2″-pyrimidinyl | 50 | |
| 12o | 2,4,6-tri-Me | 2″,6″-di-Me-4″-pyrimidinyl | 3 | 140 |

[a] n = 3, variation in individual values, <20%. [b] n = 3, variation in individual values, <30%.

HETEROCYCLIC KINASE INHIBITORS AND USES THEREOF

CROSS-REFERENCE TO RELATED APPLICATIONS

This application is a U.S. National Stage application of PCT/EP2019/078751 filed 22 Oct. 2019, which claims priority to European Application No. 18202164.2 filed 23 Oct. 2018, the entire disclosures of which are hereby incorporated by reference in their entireties.

The invention relates to kinase inhibitors, in particular inhibitors of protein kinases including the protein-tyrosine kinases LCK, ABL, SRC, KIT, SIK-family and/or their mutants. Although structurally similar to dasatinib, the kinase inhibitors of the invention can display one or more certain properties distinct to dasatinib. Also, the invention relates to pharmaceutical compositions that comprise one or more of the kinase inhibitors. The kinase inhibitors or pharmaceutical compositions of the invention may be used in the treatment of a disorder or condition, such as a proliferative disorder, for example, a leukaemia or solid tumour. The kinase inhibitors or pharmaceutical compositions may be used in a treatment regimen that corresponds to, is similar to or is distinct from that used with dasatinib for a corresponding disorder, and in particular may be used in a combination treatment regimen together with one or more additional therapeutic agents, such as immune-checkpoint inhibitors.

A kinase inhibitor is an enzyme inhibitor that blocks the action of a kinase. A partial, non-limiting, list of such kinases includes ABL, AKT, BCR-ABL, BLK, BRK, c-KIT, c-MET, CDK1, CDK2, CDK3, CDK4, CDK5, CDK6, CDK7, CDK8, CDK9, CDK10, cRAF1, CSK, EGFR, ERBB2, ERBB3, ERBB4, ERK, PAK, FES, FGFR1, FGFR2, FGFR3, FGFR4, FGFR5, FGR, FIT-1, FPS, FRK, FYN, HCK, IGF-1R, INS-R, JAK, KDR, LCK, LYN, MEK, p38, PDGFR, PIK, PKC, PYK2, ROS, SIK1, SIK2, SIK3, SRC, TIE, TIE2, TRK and ZAP70. Kinases are enzymes that add a phosphate group to a protein or another organic molecule, and have been shown to be key regulators in most cellular functions including cell-signalling, -proliferation, -differentiation, -metabolism, -survival, -apoptosis, -motility, DNA damage repair etc. Phosphorylation, in particular deregulated signalling due to defective control of protein phosphorylation, is implicated in a wide range of diseases; such as diseases associated with aberrant activity (e.g., increased activity) of a kinase. Such diseases include, but are not limited to, proliferative diseases (e.g., cancers, benign neoplasms, pathological angiogenesis, inflammatory diseases, and autoimmune diseases), as wells as allergies and CNS disorders.

Protein-tyrosine kinases (PTKs) are enzymes that, in conjunction with ATP as a substrate, phosphorylate tyrosine residues in peptides and proteins. PTKs comprise, inter alia, receptor protein-tyrosine kinases (RPTKs), including members of the epidermal growth factor kinase family (e.g., HER1 and HER2), platelet derived growth factor (PDGF), and kinases that play a role in angiogenesis (e.g., TIE2 and KDR); and, in addition, non-receptor protein-tyrosine kinases, including members of the SYK, JAK and SRC kinase families (e.g., SRC, FYN, LYN, LCK and BLK kinases). Protein-serine/threonine kinases (STKs) are enzymes that phosphorylate the oxygen atom of a serine or threonine side-chain in in peptides and proteins. STKs comprise, inter alia, AKT1, Aurora kinases, BRAF, MAP kinases, PLK1, SIK1, SIK2 and SIK3.

Inhibiting protein kinases, and therefore the phosphorylation of a substrate peptide or protein, has been shown to be useful in treating many diseases. For example, afatinib, an ERBB inhibitor, is useful in treating non-small cell lung cancer; axitinib, a VEGFR, PDGFR, and c-KIT inhibitor, is useful in treating renal cell carcinoma; bosutinib, an ABL/BCR-ABL inhibitor, is useful in treating chronic myelogenous leukaemia; cabozantinib, a c-MET and VEGFR2 inhibitor, is useful in treating thyroid cancer; crizotinib, an ALK, HGFR, and c-MET inhibitor, is useful in treating non-small cell lung cancer; dasatinib, an ABL/BCR-ABL, SRC, and c-KIT inhibitor, is useful in treating chronic myelogenous leukaemia; erlotinib, an EGFR inhibitor, is useful in treating non-small cell lung cancer and pancreatic cancer; gefitinib, an EGFR inhibitor, is useful in treating non-small cell lung cancer; imatinib, an ABL/BCR-ABL inhibitor, is useful in treating chronic myelogenous leukaemia; lapatinib, a HER2 inhibitor, is useful in treating breast cancer; nilotinib, an ABL/BCR-ABL inhibitor, is useful in treating chronic myelogenous leukaemia; pazopanib, a VEGFR, PDGFR, and c-KIT inhibitor, is useful in treating renal cell carcinoma and soft tissue sarcoma; palbociclib, an inhibitor of CDK4 and CDK6, is useful in treating ER-positive and HER2-negative breast cancer; ponatinib, an ABL/BCR-ABL, BEGFR, PDGFR, FGFR, EPH, SRC, c-KIT, RET, TIE2, and FLT3 inhibitor, is useful in treating chronic myelogenous leukaemia and acute lymphoblastic leukaemia; regorafenib, a RET, VEGFR, and PDGFR inhibitor, is useful in treating colorectal cancer and gastrointestinal stromal tumour; ribociclib, an inhibitor of cyclin D1/CDK4 and CDK6, is useful in treating HR-positive, HER2-negative advanced or metastatic breast cancers; ruxolitinib, a JAK inhibitor, is useful in treating myelofibrosis; sorafenib, a VEGFR, PDGFR, BRAF, and c-KIT inhibitor, is useful in treating renal cell carcinoma and hepatocellular carcinoma; sunitinib, a VEGFR and PDGFR inhibitor, is useful in treating renal cell carcinoma, gastrointestinal stromal tumour, and pancreatic neuroendocrine tumour; tofacitinib, a JAK inhibitor, is useful in treating rheumatoid arthritis; vandetanib, a VEGFR, EGFR, RET and BRK inhibitor, is useful in treating thyroid cancer; and vemurafenib, a BRAF inhibitor, is useful in treating malignant melanoma.

In view of the large number of kinases and associated diseases, there is an ever-existing need for new inhibitors selective for various kinases which might be useful in the treatment of related diseases; in particular there remains a need for new kinase inhibitors, pharmaceutical compositions/formulations and uses thereof for the treatment of diseases associated with aberrant activity of one or more kinases; in particular, there remains a need for new inhibitors that are alternatives to an existing kinase inhibitor, such as dasatinib.

One particular kinase inhibitor is dasatinib (N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate; FIG. 1A), marketed as "SPRYCEL" by Bristol-Myers Squibb, and is indicated for the treatment of adult patients with: (i) newly diagnosed Philadelphia chromosome-positive (Ph+) chronic myelogenous leukaemia (CML) in chronic phase; (ii) chronic, accelerated, or (myeloid or lymphoid) blast phase (Ph+) CML with resistance or intolerance to prior therapy including imatinib; and (iii) Philadelphia chromosome-positive acute lymphoblastic leukaemia (Ph+ ALL) with resistance or intolerance to prior therapy. In the EU, dasatinib is also indicated for the treatment of paediatric patients with newly diagnosed Ph+ CML in chronic phase (Ph+ CML-CP) or Ph+ CML-CP resistant or intolerant to prior therapy including imatinib, and in the US it is indicated for paediatric patients with Ph+ CML in chronic phase.

Notably, despite numerous trials being conducted with dasatinib, it is not indicated in the US or Europe for any cancer other than CML or Ph+ ALL; in particular, as of September 2018, dasatinib is not indicated for any solid tumour. Indeed, numerous clinical trials using dasatinib to investigate its possible use to treat solid tumours were terminated early (for example, due to toxicity issues) or failed to report strong or even encouraging results. For example, according to information on clincialtrials.gov on 9 Sep. 2018, dasatinib has only once reached phase 3 testing for solid tumours: in a single investigation against castrate resistant prostate cancer in combination with docetaxel, the "READY" trial (NCT00744497), but dasatinib failed to improve overall survival over docetaxel alone in such trial (Araujo et al. 2013, Lancet Oncol. 14:13017), despite some suggestion of its activity against chemotherapy-naïve castrate resistant prostate in earlier-stage trials (e.g., Araujo et al. 2012, Cancer 118:63). Despite several trials against other cancers such as breast, skin, pancreatic, brain or lung cancer, dasatinib has not shown satisfactory efficacy or tolerability, and has not been progressed to phase 3 testing against any of these cancers. In particular, more recently dasatinib failed to show increased overall survival in combination with gemcitabine compared to gemcitabine alone in a double-blinded phase 2 trial against locally-advanced unresectable pancreatic patients (Evens et al. 2017, Annal. Onc. 28:354). However, recently, some specialised trails that aim to selected "targeted" therapies to patients having particular cancers (including solid tumours) that express particular drug targets, may potentially test dasatinib depending on the target profile of the patients. For example (i) the "TAPUR" trial ("The Targeted Agent and Profiling Utilization Registry", https://www.tapur.org, NCT02693535) includes dasatinib in one possible treatment arm based on one or more of the following targets: BCR-ABL, SRC, KIT, PDGFRB, EPHA2, FYN, LCK, YES1; and (ii) a Melanoma Institute Australia trial (NCT02645149) involving patients with BRAF and NRAS wild-type unresectable Stage III or Stage IV metastatic melanoma who have progressed on, or are unable to receive standard therapy (in general, immunotherapy), includes dasatinib as one possible therapy depending on KIT mutation(s) being found in the patient's cancer. Dasatinib is also one possible arm of the BMS "FRACTION-Lung" phase 2 trial (NCT02750514) where it may be tested in combination with the immune-oncology drug nivolumab in patients with advanced non-small cell lung cancer. Other arms of this trial use nivolumab in combination with other immune-oncology drugs.

Accordingly, there is a particular need for new kinase inhibitors useful in the treatment of cancers—especially solid tumours—the treatment of which by dasatinib are not indicated, and/or of cancers for which dasatinib has not shown promising results. In particular, there is a need for new kinase inhibitors useful in the treatment of one or more cancers such as breast, lung (e.g., non-small cell), pancreatic or prostate (e.g., castrate or hormone resistant) cancer, as well as melanoma. There also remains the need for new kinase inhibitors useful in the treatment of myeloid or lymphoblastic cancers such as leukaemia, preferably, useful for the treatment of one or more Ph+ leukaemia such as CML and/or ALL.

Dasatinib is described as an inhibitor of the following kinases at nanomolar concentrations: BCR-ABL, SRC family (SRC, LCK, YES, FYN), c-KIT, EPHA2, and PDGFR-beta; where of particular relevance to dasatinib's indication for Ph+ leukaemia, is its inhibition of the hybrid protein kinase BCR-ABL.

The BCL-ABL kinase is directly connected to the presence of a specific genetic abnormality in chromosome 22 of leukaemia cancer cells (particularly CML cells); known as the "Philadelphia chromosome" (or Philadelphia translocation). This reciprocal translocation of genetic material between chromosome 9 and chromosome 22, juxtaposes the ABL1 gene of chromosome 9 onto the BCR gene of chromosome 22, resulting in a coding sequence for a hybrid protein known as "BCR-ABL": a protein-tyrosine kinase that is "always on", causing the cell to divide uncontrollably. The vast majority of CML cases and 20-30% of ALL cases are Ph+. The first selective BRC-ABL inhibitor, imatinib (STI571), marketed as "GLEEVEC/GLIVEC" by Novartis, was considered a breakthrough for the treatment of Ph+ leukaemia. However, despite the increase in overall survival, drug resistance that developed during imatinib treatment led scientists to discover that most of such resistances arise due to the emergence of BCR-ABL mutations, particularly amino acid substitutions within the ABL-derived kinase domain (for review, see Rossari & Orciuolo. 2018, J. Hemat. Oncol. 11:84, incorporated herein in its entirety by reference).

An analysis of BCR-ABL mutation status and the probability of survival for patients treatment with imatinib indicated that mutations within the phosphatase loop (P-loop) of the ABL-position of the BCR-ABL kinase were the most frequent, but that the (rarer) mutations outside of the P-loop (in particularly those within the kinase domain) were associated with a reduction in overall survival of imatinib-treated CML patients (Jabbour et al. 2006, Leukemia 20:1767). A number of emergent BCR-ABL mutations have since been identified and described (see, Table 1 of Manley et al. 2005, Biochem. Biophys. Acta 1754:3; and Table 1 of Rossari & Orciuolo 2018, which also describes mutations of other kinase-targets of dasatinib; both such tables specifically incorporated herein by reference). In particular the following mutations are found in the ATP-binding region of BCR-ABL (with positions indicated for the wild-type ABL protein): V299L, F311L, T315I, T315A, F317L and F317V. Indeed, dasatinib was initially developed as a "second generation" BCR-ABL inhibitor for second-line therapy for CML that had become resistant to imatinib, presumed to arise due to the emergence of one or other of these mutations. Based on modelling studies, dasatinib is predicted to bind to multiple conformations of the ABL kinase, and this is thought to explain why several conformation-altering mutations of ABL are inhibited by dasatinib, but not by imatinib. Indeed, a retrospective analysis comparing mutation development during first-line treatment with dasatinib or with imatinib revealed that fewer different mutation sites emerged with dasatinib treatment (4 different sites) compared with imatinib treatment (12 different sites) (Hughes et al. 2015, Leukemia 29:1832, in particular FIG. 1 thereof). Importantly however: (i) the total proportion of patients developing any type of mutation was approximately the same (17/259 dasatinib patients and 18/260 imatinib patients); (ii) the majority of the mutation sites emerging upon dasatinib treatment were in the ATP-binding region (¾ mutation sites); and (iii) the by far commonest mutation emerging during dasatinib treatment (11/17) was the T315I mutation at the so-called "gate-keeper" residue, which still confers resistance to dasatinib inhibition on the BCR-ABL kinase. A particular set of BCR-ABL mutants that can be tested against kinase inhibitors are provided by the ProQinase ABL1 kinase "Wildtype and Mutant Panel", and includes the ABL1 wild-type protein (amino acids P118-S525) and mutants forms that represent the most prevalent imatinib-resistant mutant forms of BCR-ABL: G250E, Q252H, Y253F, E255K, T315I, F317I, M351T and H396P (www.proqinase.com).

The T315I mutation is one of the most frequently emerging BCR-ABL mutations: arising in 2 to 20% CML cases (Nicolini et al. 2009, Blood 114:5271). That such a mutation is resistant to dasatinib inhibition is one potential draw-back of dasatinib as a kinase inhibitor, which has stimulated the development of the "third generation" BCR-ABL inhibitor known as ponatinib (marketed as ICLUSIG by Incyte & Takeda). However, although ponatinib does indeed strongly inhibit the T315I mutation of the BCR-ABL kinase (in-vitro IC50 of 2.0 nM), it is known to be a more promiscuous kinase inhibitor than dasatinib, and also inhibits a number of other kinases including with in-vitro IC50 concentrations between 0.1 and 20 nM, for at least members of the VEGFR, PDGFR, FGFR, EPH receptors and SRC families of kinases, and KIT, RET, TIE2, and FLT3. Furthermore, US sales of ponatinib were temporarily suspended in October 2013 because of "the risk of life-threatening blood clots and severe narrowing of blood vessels". This suspension was partially lifted in December 2013 with ponatinib being issued revised prescribing information, a new "Black Box Warning" and a "Risk Evaluation and Mitigation Strategy" in place to better evaluate the risks and benefits of using the drug. In addition, the price of ponatinib in the US (it can cost $138,000 a year) has been criticised. Accordingly, substantial drawbacks are shown by ponatinib, such that there still remains a need for new kinase inhibitors, in particular those with the potential to more effectively, safely, easily and/or cheaply treat Ph+ leukaemia (or other cancers); and/or that are more selective to SRC, ABL/BCR-ABL and/or LCK than other kinase inhibitors such as dasatinib or ponatinib.

Compared to imatinib however, dasatinib is not particularly specific to BCR-ABL, and binds to and/or inhibits a significant number of other kinases (see: FIG. 3 of Bantscheff et al. 2007, Nat. Biotech. 25:1035; supplementary FIG. 2 of Anastassiadis et al. 2012, Nat. Biotech. 29:1039). In particular, compared to imatinib, dasatinib is described to more significantly bind to and/or inhibit numerous other kinases, including: BTK, CSK, EPHB2, EPHB4, FYN, GAK, KIT, LYN, QIK, QSK, RIPK2, SRC, TEC, TESK2, YES and ZAK. More specifically, dasatinib is shown to be a significant inhibitor of salt-inducible kinases with IC50 values of <3 nM, <3 nM and 18 nM for the three family members SIK1, SIK2 and SIK3, respectively (Ozanne et al. 2015, Biochem. J. 465:271; also as described in co-pending PCT/EP2018/060172). Indeed, given that dasatinib is a less selective kinase inhibitor, is yet another potential drawback, and this reduced selectively may be causally associated with the not-insignificant toxicity challenges faced when treating patients with dasatinib, in particular with the an increased occurrence of thrombocytopaenia (Wei et al. 2010, J. Hemat. Oncol. 3:47).

As described above, dasatinib is a potent inhibit of KIT, and this receptor tyrosine kinase is becoming an increasingly interesting target for the treatment of certain cancers (Babei et al. 2016, Drug Des. Dev. Thera., 10:2443), not least because mutations in the KIT gene have been detected in cancers such as leukaemia, ovarian cancer and melanoma. It is also known that dasatinib can also inhibit at least the most common KIT mutation in melanoma (Woodman et al. 2009, J. Clin. Onc. 27:9019). However, inhibition of KIT, and in particular the relative activity against FLT3 and KIT of certain tyrosine kinase inhibitors, has been associated with myelosuppression and other side effects such as hair depigmentation (Galanis and Levis 2015: Haematologica 100: e89). Indeed, treatment with dasatinib is associated with severe myelosuppression (see below).

Salt-inducible kinases (SIKs) constitute a serine tyrosine kinase subfamily, belonging to the adenosine monophosphate-activated kinase (AMPK) family. Three members (SIK1, -2, and -3) have been identified so far. Amino acid homology of SIK1 with SIK2 and SIK3 is 78% and 68%, respectively, in the kinase domain. The cloning of SIK1 (also known as SIK and SNF1LK), abundantly expressed in the adrenal glands of high-salt, diet-fed rats, led to subsequent cloning of SIK2 (also known as QIK, KIAA0781 and SNF1LK2), mainly expressed in adipose tissues and the rather ubiquitous SIK3 (also known as QSK, KIAA0999 or L19) (Katoh et al. 2004, Mol. Cell. Endocrinol. 217:109). The three SIKs have a similar structure, with an N-terminal kinase domain (catalytic domain), a middle ubiquitin-associated domain (believed important for phosphorylation by LKB1) and a long C-terminal sequence (believed to be a site for further phosphorylation by PKA). However, there are very diverse roles implicated for the various SIKs. For example, various SIKs have been implicated in biological processes as diverse as osteocyte response to parathyroid hormone (Wein et al. 2016, Nature Commun. 7:13176) to induction of SIK1 by gastrin and inhibition of migration of gastric adenocarcinoma cells (Selvik et al. 2014, PLoS ONE 9:e112485). Other potential roles of salt-inducible kinases (in particular SIK3) are described in co-pending PCT/EP2018/060172 furthermore that SIK3 is a gene involved in tumour cell resistance to cell-mediated immune responses, in particular tumour cell resistance to TNF.

Hence there still remains a need for new kinase inhibitors, in particular those that exhibit a different profile of kinases to the kinases inhibited by dasatinib, in particular. For example, new kinase inhibitors which: (i) are more specific to key disease-related kinases (e.g., ABL/BCR-ABL, SRC, LCK, and/or EPHA2, EPHA4, CSF-R1, HCK, ACK1 and/or KIT), relative to other kinases, than the specificity shown by dasatinib to one or more such other kinases; (ii) inhibit key disease- or side-effect-related kinases in a different profile than dasatinib (e.g. to KIT and/or FLT3); and/or (iii) inhibit one or more mutant of a disease-related kinase, in particular a mutant that is resistant to one or other kinase inhibitor, such as mutants of ABL/BCR-ABL or KIT.

Furthermore, although dasatinib is metabolised in humans primarily by the cytochrome P450 enzyme 3A4 (CYP3A4), it is also a time-dependent inhibitor of CYP3A4. Indeed, the dosage of dasatinib must be significantly reduced (e.g., from 100 mg daily to 20 mg daily) if the patient is concomitantly medicated with a strong CYP3A4 inhibitor (e.g., ketoconazole, itraconazole, clarithromycin, atazanavir, indinavir, nefazodone, nelfinavir, ritonavir, saquinavir, telithromycin, and voriconazole), as these may increase dasatinib plasma concentrations to potentially unsafe levels. Grapefruit juice may also increase plasma concentrations of dasatinib and should also be avoided. Accordingly, there remains a need for new kinase inhibitors that show a pattern of cytochrome P450 inhibition (eg, to CYP3A4) that is different to dasatinib.

Importantly, the dosage and administration of dasatinib should be stopped (or reduced) upon occurrence of myelosuppression. Indeed, myelosuppression is described as just one "Warning and Precaution" in the US Prescribing Information for dasatinib, because treatment with dasatinib is associated with severe (NCI CTC Grade 3 or 4) thrombocytopenia, neutropenia, and anaemia. In addition to causing thrombocytopenia in human subjects, in all clinical studies with dasatinib: (i) severe central nervous system (CNS) haemorrhages (including fatalities) occurred in 1% of patients; (ii) severe gastrointestinal haemorrhage, including fatalities, occurred in 4% of patients and generally required treatment interruptions and transfusions; and (iii) other cases of severe haemorrhage occurred in 2% of patients.

Yet further "Warning and Precautions" of dasatinib include that: (x) it is associated with fluid retention, with severe fluid retention reported in up to 10% of patients in clinical trials; (y) it has the potential to prolong cardiac ventricular repolarization (QT interval), and up to 1% of CML patients in clinical trials experienced a QT prolongation; and (z) cardiac adverse reactions were reported in 5.8% of 258 patients taking dasatinib, including 1.6% of patients with cardiomyopathy, heart failure congestive, diastolic dysfunction, fatal myocardial infarction, and left ventricular dysfunction. Indeed, dasatinib is known to be an inhibitor of hERG (Pharmacological/Toxicity Review and Evaluation of NDA 21-986, page 31). hERG (the human "Ether-h-go-go-Related Gene") is an ion channel that contributes to the electrical activity of the heart and coordinates the heart's beating. When this channel's ability to conduct electrical current across the cell membrane is inhibited or compromised (e.g., by administration of a drug) it can result in "long QT syndrome" which can be potentially fatal. Accordingly, there remains a need for new kinase inhibitors that show inhibition of hERG that is different to dasatinib. For example, it would be advantageous to provide new kinase inhibitors that exhibit an IC50 to hERG that is greater than that of dasatinib.

Compared to other BCR-ABL inhibitors, dasatinib has an extremely short half-life: with an overall mean terminal half-life of only 3-5 hours (section 12.3 "Pharmacokinetics" of the Full Prescribing Information). In stark contrast: the elimination half-life of imatinib is approximately 18 hours; the mean terminal phase elimination half-life of bosutinib is 22.5 hours; the apparent elimination half-life for nilotinib is approximately 17 hours; and the geometric mean terminal elimination half-life of ponatinib is approximately 24 hours. Without being bound by theory, the short half-life of dasatinib—indicated for dosage once daily—may account for limited activity associated with lower in-vivo drug-concentrations later in the day and/or side effects associated with peak/higher in-vivodrug-concentrations soon after dosage. Accordingly, there remains a need for new kinase inhibitors that exhibit properties of longer half-lives (e.g., than those shown by dasatinib). For example, an advantageous kinase inhibitor may be one that is more stable than dasatinib, for example by exhibiting a longer half-life in a plasma and/or liver-microsome stability assay.

Further precautions, adverse events and other prescribing information of dasatinib can be found from the respective Summary of Product Characteristics (SmPC) of Full Prescribing Information as may be found from the respective web site of the EMA and FDA (respectively shown below, accessed 20 Aug. 2018, and the contents of each are incorporated by reference in their entirety herein): (i) http://www.ema.europa.eu/docs/en_GB/document_library/EPAR_-_Product_Information/human/000709/WC500056998.pdf, and (ii) https://www.accessdata.fda.gov/drugsatfda_docs/label/2010/021986s7s81bl.pdf.

Numerous variants of dasatinib have been synthesised and demonstrated to have in-vitro biochemical inhibitory activity against one or more kinase and/or antiproliferative effects on cells. In particular, such variants were synthesised: (i) during the discovery phase of dasatinib to understand and describe its structure-activity relationship (SAR) (Lombardo et al 2004, J Med Chem 47:6658; Das et al 2006, J Med Chem 49:6819); and (ii) to provide alternative kinase inhibitors and/or drug candidates (eg, WO 2006/081172 and WO 2008/033746). The variants of dasatinib described therein carry a phenyl moiety at the carboxamide. These disclosures demonstrate other positions, and the substantial range of substituents that may be substituted thereat, that provide compounds that are kinase inhibitors and/or possess cellular antiproliferative activity (FIG. 8).

WO 2018/193084 (to the present applicant, and published 25 Oct. 2018) discloses a dasatinib variant carrying a pyridinyl moiety. Beutner et al (2018, Org Lett 20:4218) describes a method of forming challenging amide bonds, including those to certain pyridines pyrazines and pyrimidines. Pennington et al (2017, J Med Chem 60:3552) describes that the replacement of a CH group with a N atom in aromatic and heteroaromatic ring systems can have effects on molecular and physiological properties. However, making such a substitution has been empirically shown to result in improved potency statistically no better than mere chance: a matched molecular pair analysis (MMPA) of internal data at Abbott (Hajduk & Sauer 2008, J Med Chem 51:553) found that, as with most substituent replacements, there is an approximate equal probability of increasing or decreasing potency by exchanging CH groups and N atoms. Indeed, this analysis further revealed that the probability for realising a 10-fold increase in potency with such replacements is less than 1 in 10 and that for achieving a 100-fold is less than 1 in 100; similar to the probabilities observed when investigating the effect of such replacements to improve binding affinity (Hu et al 2014, F1000Research 3:36; de la Vega de Leon et al 2014, MedChemComm 5:64).

Accordingly, it is one object of the present invention to provide one or more kinase inhibitor that has one or more properties (such as those shown by in-vitro and/or in-vivo assays) that address one or more of these or other problems. In other objects, the present invention provides an alternative and/or improved kinase inhibitor to dasatinib (or one or other kinase inhibitor, such as those described herein). For example, a kinase inhibitor that can exhibit one or more functional (e.g., kinase selectivity) and/or ADMET properties that are different to, and/or are improved compared to, dasatinib (or one or other kinase inhibitor, such as those described herein), would be particularly advantageous. An object underlying the present invention is solved by the subject matter as disclosed or defined anywhere herein, for example by the subject matter of the attached claims.

SUMMARY OF THE INVENTION

Generally, and by way of brief description, the main aspects of the present invention can be summarised as follows:

In a first aspect, the present invention provides a compound selected from the group consisting of a kinase inhibitor of the formula:

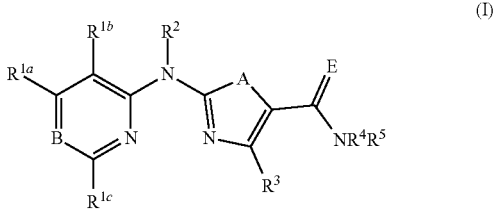

(I)

and solvates, salts, N-oxides, complexes, polymorphs, crystalline forms, racemic mixtures, diastereomers, enantiomers, tautomers, conformers, isotopically labeled forms, prodrugs, and combinations thereof; wherein $R^{1a}$, $R^{1b}$, $R^{1c}$, $R^2$, $R^3$, $R^4$, $R^5$, A, B, and E are as defined herein.

In a second aspect, the present application provides a pharmaceutical composition comprising a compound of the first aspect and, optionally, a pharmaceutically acceptable carrier.

In a third aspect, the present application provides a compound of the first aspect or a pharmaceutical composition of the second aspect for use in therapy.

In a fourth aspect, the present application provides a compound of the first aspect or a pharmaceutical composition of the second aspect for use in a method for the treatment of a disease, disorder or condition in an individual (in particular a human patient), wherein the disease or condition is associated with a kinase.

Further aspects of the invention are disclosed herein.

BRIEF DESCRIPTION OF THE FIGURES

The figures show:

FIG. 3: depicts selectivity of kinase inhibition by % residual activity (at 1 uM compound) of B3 (a kinase inhibitor of formula (I)), dasatinib (A8) and C7 (another kinase inhibitor of formula (I)): **<25% residual activity; *25% to <50% residual activity; **50% to <75% residual activity; *>75% residual activity. Classification of protein kinase families (Manning et al. Science 6 Dec. 2002: Vol. 298 no. 5600 pp. 1912-1934): AGC: containing PKA, PKG and PKC families; CAMK: Calcium/Calmodulin-dependent protein kinases; CK1: Casein kinase-like; CMGC: containing CDK, MAPK, GSK3 and CLK families; TK: Tyrosine Kinase; TKL: Tyrosine Kinase-like; STE: Homologs of Yeast Sterile 7, Sterile 11, Sterile 20 Kinases. ##Constitutively active kinase.

FIG. 8: depicts: (A) the cellular antiproliferative activity of dasatinib variants taken from Table 1 of Lombardo et al 2004 (J Med Chem 47:6658), showing the potency of various derivatives of dasatinib against the indicated cell lines. a Antiproliferative activities were determined based on tetrazolium dye conversion following 72 h compound exposure. IC50 values are reported as the mean of at least three individual determinations or as individual IC50 values in the case of less than three measurements. Variability around the mean value was <50% unless otherwise indicated by an SE value in parentheses; and (B) biochemical and cellular antiproliferative activity of dasatinib variants from Table 4 of Das et al 2006 (J Med Chem 49:6819). a n=3, variation in individual values, <20%. b n=3, individual values, <30%.

DETAILS OF THE PRESENT INVENTION

Figure 1:
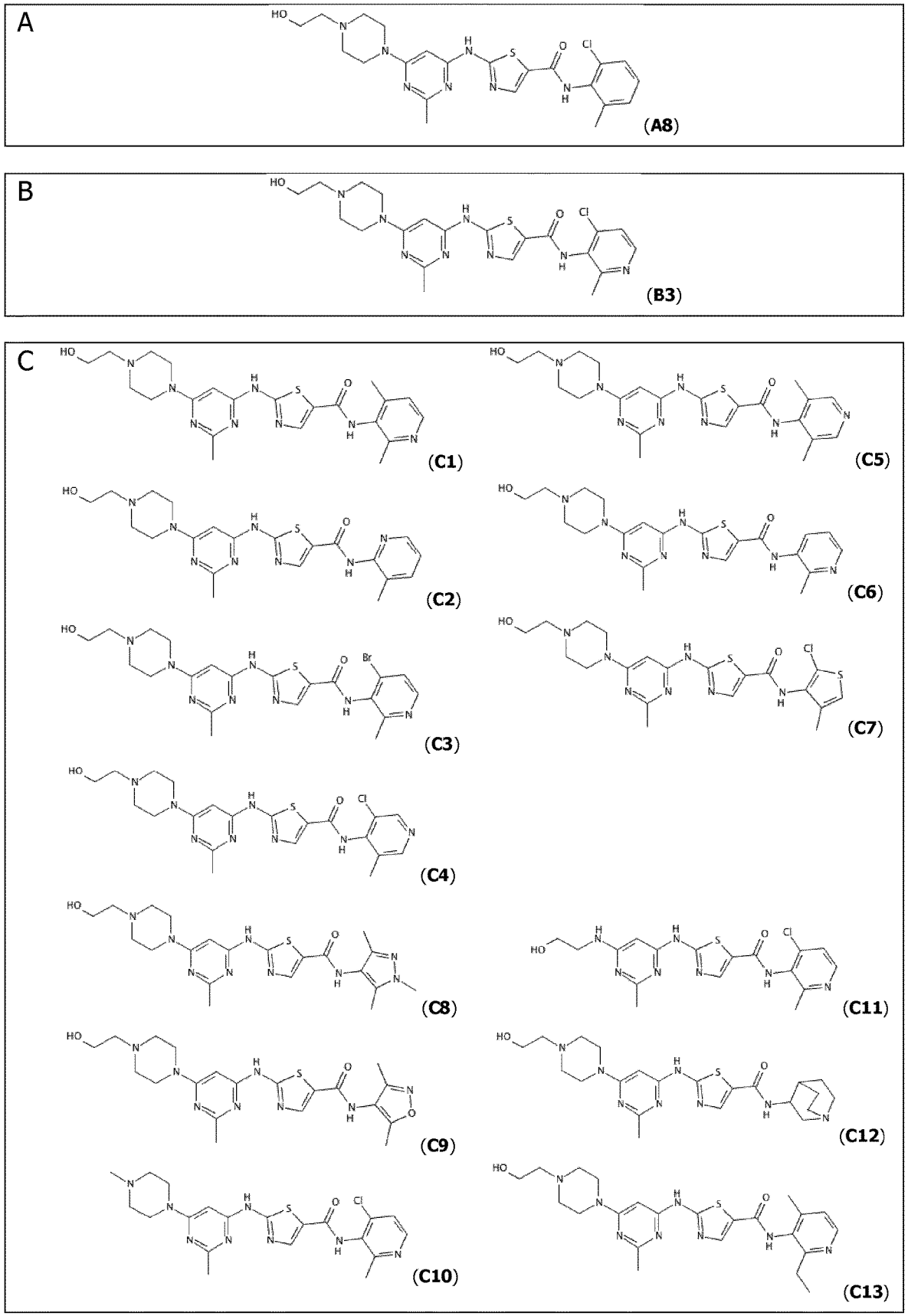
FIG. 1: depicts the chemical structures of: (A) dasatinib (compound A8), N-(2-chloro-6-methylphenyl)-2-((6-(4-(2-hydroxyethyl)piperazin-1-yl)-2-methylpyrimidin-4-yl)amino)thiazole-5-carboxamide; (B) the kinase inhibitor B3, N-(4-chloro-2-methylpyridin-3-yl)-2-((6-(4-(2-hydroxyethyl)piperazin-1-yl)-2-methylpyrimidin-4-yl)amino)thiazole-5-carboxamide; (C) certain other kinase inhibitors of formula (I) C1 to C13; and (D) certain further kinase inhibitors of formula (I) D1 to D10.
Figure 1:
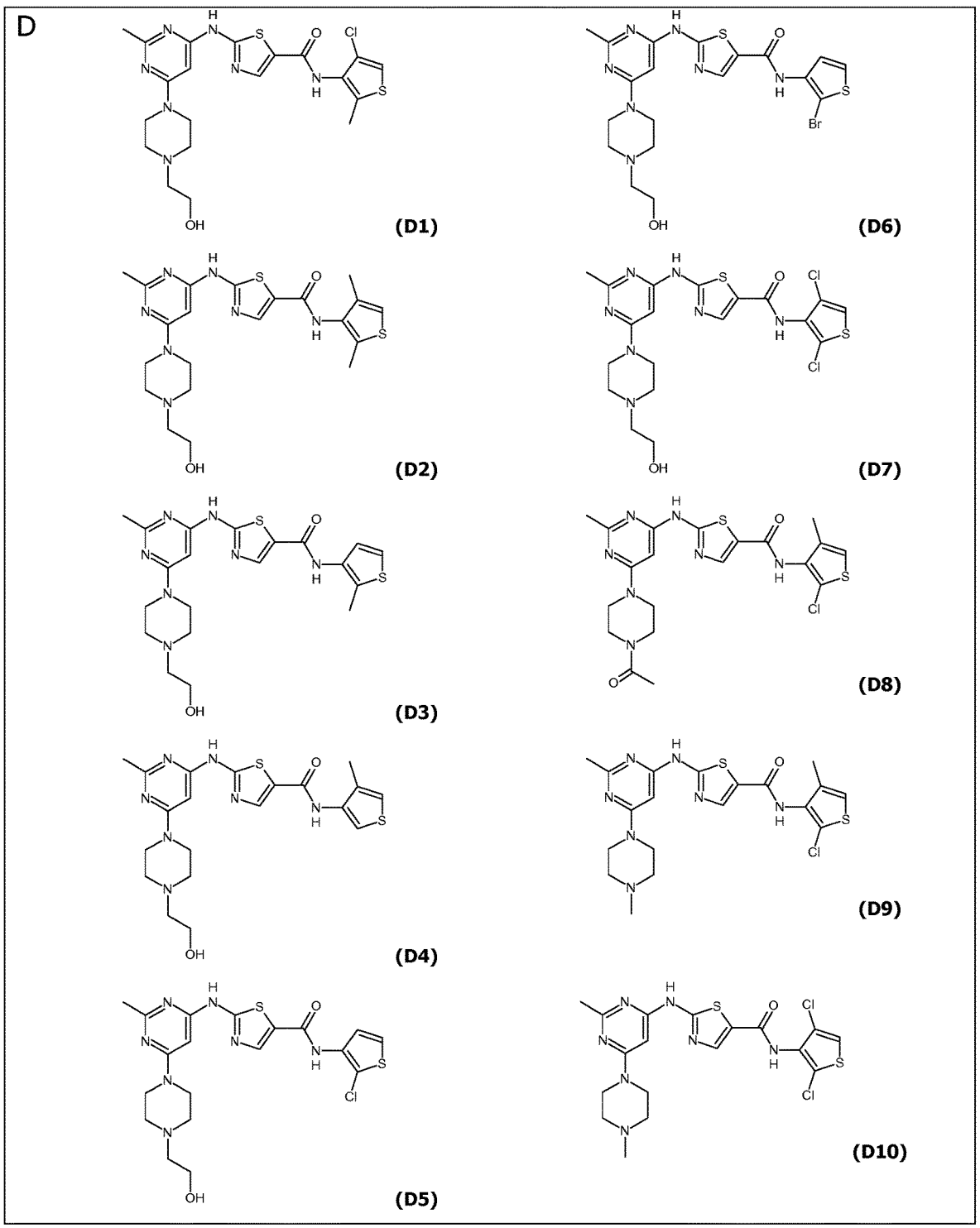

The present invention, and particular non-limiting aspects and/or embodiments thereof, can be described in more detail as follows.

Although the present invention may be further described in more detail, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by what is described, defined or otherwise disclosed herein, in particular in any itemised embodiments or the appended claims.

Herein, certain elements of the present invention are described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description of this application should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in one embodiment of the compound of the invention L is a bond and in another embodiment of the compound of the invention $R^3$ is H, then in a preferred embodiment of the compound of the invention, L is a bond and $R^3$ is H, or if in one embodiment of the use of a compound of the invention the subject is an adult human and in another embodiment of the use of a compound of the invention the proliferative disorder is prostate cancer, then in a preferred embodiment of the use of a compound of the invention, the subject is an adult human and the proliferative disorder is prostate cancer.

General Definitions

Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., Molecular Cloning: A Laboratory Manual, $2^{nd}$ Edition, 1. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance or group of members, integers or steps of any essential significance. For example, a pharmaceutical composition consisting essentially of the members/components as defined herein (such as a compound as defined in any of the aspects of the invention and optionally one additional therapeutic agent) would exclude further therapeutic agents (besides the compound as defined in any of the aspects of the invention and the optional one additional therapeutic agent) but would not exclude contaminants (e.g., those from the isolation and purification method) in trace amounts (e.g., the amount of the contaminant (preferably the amount of all contaminants present in the composition) is less than 5% by weight, such as less than 4% by weight, 3% by weight, 2% by weight, 1% by weight, 0.5% by weight, 0.4% by weight, 0.3% by weight, 0.2% by weight, 0.1% by weight, 0.05% by weight, with respect to the total composition) and/or pharmaceutically acceptable excipients (such as carriers, e.g., phosphate buffered saline, preservatives, and the like). The term "consisting of" means excluding all other members, integers or steps of significance or group of members, integers or steps of significance. For example, a pharmaceutical composition consisting of the members/components as defined herein (such as a compound as defined in any of the aspects of the invention, one excipient, and optionally one additional therapeutic agent) would exclude any other compound (including a second or further excipient) in an amount of more than 2% by weight (such as any other compound in an amount of more 1% by weight, more than 0.5% by weight, more than 0.4% by weight, more than 0.3% by weight, more than 0.2% by weight, more than 0.1% by weight, more than 0.09% by weight, more than 0.08% by weight, more than 0.07% by weight, more than 0.06% by weight, more than 0.05% by weight, more than 0.04% by weight, more than 0.03% by weight, more than 0.02% by weight, more than 0.01% by weight) with respect to the total composition. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

Where used herein, "and/or" is to be taken as specific disclosure of each of the two specified features or components with or without the other. For example, "X and/or Y" is to be taken as specific disclosure of each of (i) X, (ii) Y, and (iii) X and Y, just as if each is set out individually herein.

In the context of the present invention, the terms "about" and "approximately" are used interchangeably and denote an interval of accuracy that the person of ordinary skill will understand to still ensure the technical effect of the feature in question. The term typically indicates deviation from the indicated numerical value by ±5%, ±4%, ±3%, ±2%, ±1%, ±0.9%, ±0.8%, ±0.7%, ±0.6%, ±0.5%, ±0.4%, ±0.3%, ±0.2%, ±0.1%, ±0.05%, and for example±0.01%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect.

The terms "a", "an" and "the" and similar references used in the context of describing the invention (especially in the context of the claims) are to be construed to cover both the singular and the plural, unless otherwise indicated herein or clearly contradicted by the context.

Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by the context.

The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The terms "of the [present] invention", "in accordance with the [present] invention", "according to the [present] invention" and the like, as used herein are intended to refer to all aspects and embodiments of the invention described and/or claimed herein.

It is to be understood that the application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above or below are not limited to any particular aspect or embodiment of the invention and apply equally to all aspects and embodiments that are described.

The term "alkyl" refers to a monoradical of a saturated straight or branched hydrocarbon. Preferably, the alkyl group comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. Exemplary alkyl groups include methyl, ethyl, propyl, iso-propyl (also called 2-propyl or 1-methylethyl), butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethylhexyl, n-nonyl, n-decyl, n-undecyl, n-dodecyl, and the like. A "substituted alkyl" means that one or more (such as 1 to the maximum number of hydrogen atoms bound to an alkyl group, e.g., 1, 2, 3, 4, 5, 6, 7, 8, 9, or up to 10, such as between 1 to 5, 1 to 4, or 1 to 3, or 1 or 2) hydrogen atoms of the alkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —OH, —NH$_2$, —NHCH$_3$, —N(CH$_3$)$_2$, —CN, —OCH$_3$, —OCF$_3$, or optionally substituted aryl. Examples of a substituted alkyl include trifluoromethyl, 2,2,2-trichloroethyl, 2-hydroxyethyl, 2-aminoethyl, 2-(dimethylamino)ethyl, arylalkyl (also called "aralkyl", e.g., benzyl, chloro(phenyl)methyl, 4-methylphenylmethyl, (2,4-dimethylphenyl)methyl, o-fluorophenylmethyl, 2-phenylpropyl, 2-, 3-, or 4-carboxyphenylalkyl), or heteroarylalkyl (also called "heteroaralkyl").

The term "alkylene" refers to a diradical of a saturated straight or branched hydrocarbon. Preferably, the alkylene comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylene isomers (e.g., 1,1-hexylene, 1,2-hexylene, 1,3-hexylene, 1,4-hexylene, 1,5-hexylene, 1,6-hexylene, and 1,1-isohexylene), the heptylene isomers (e.g., 1,1-heptylene, 1,2-heptylene, 1,3-heptylene, 1,4-heptylene, 1,5-heptylene, 1,6-heptylene, 1,7-heptylene, and 1,1-isoheptylene), the octylene isomers (e.g., 1,1-octylene, 1,2-octylene, 1,3-octylene, 1,4-octylene, 1,5-octylene, 1,6-octylene, 1,7-octylene, 1,8-octylene, and 1,1-isooctylene), and the like. The straight alkylene moieties having at least 3 carbon atoms and a free valence at each end can also be designated as a multiple of methylene (e.g., 1,4-butylene can also be called tetramethylene). Generally, instead of using the ending "ylene" for alkylene moieties as specified above, one can also use the ending "diyl" (e.g., 1,2-butylene can also be called butan-1,2-diyl). A "substituted alkylene" means that one or more (such as 1 to the maximum number of hydrogen atoms bound to an alkylene group, e.g., 1, 2, 3, 4, 5, 6, 7, 8, 9, or up to 10, such as between 1 to 5, 1 to 4, or 1 to 3, or 1 or 2) hydrogen atoms of the alkylene group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkylene include chloromethylene, dichloromethylene, fluoromethylene, and difluoromethylene.

The term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 6 (such as 1 to 4), i.e., 1, 2, 3, 4, 5, or 6, carbon-carbon double bonds. Preferably, the alkenyl group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkenyl group comprises from 2 to 12 (e.g., 2 to 10) carbon atoms and 1, 2, 3, 4, 5, or 6 (e.g., 1, 2, 3, 4, or 5) carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, and the like. If an alkenyl group is attached to a nitrogen atom, the double bond cannot be alpha to the nitrogen atom. A "substituted alkenyl" means that one or more (such as 1 to the maximum number of hydrogen atoms bound to an alkenyl group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. An example of a substituted alkenyl is styryl (i.e., 2-phenylvinyl).

The term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 6 (such as 1 to 4), i.e., 1, 2, 3, 4, 5, or 6, carbon-carbon double bonds. Preferably, the alkenylene group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkenylene group comprises from 2 to 12 (such as 2 to 10 carbon) atoms and 1, 2, 3, 4, 5, or 6 (such as 1, 2, 3, 4, or 5) carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenylene groups include ethen-1,2-diyl, vinylidene (also called ethenylidene), 1-propen-1,2-diyl, 1-propen-1,3-diyl, 1-propen-2,3-diyl, allylidene, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like. If an alkenylene group is attached to a nitrogen atom, the double bond cannot be alpha to the nitrogen atom. A "substituted alkenylene" means that one or more (such as 1 to the maximum number of hydrogen atoms bound to an alkenylene group, e.g., 1, 2, 3, 4, 5, 6, 7, 8, 9, or up to 10, such as between 1 to 5, 1 to 4, or 1 to 3, or 1 or 2) hydrogen atoms of the alkenylene group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a 3$^{rd}$ level substituent as specified herein, such as halogen or optionally substituted aryl. Examples of a substituted alkenylene are 1-phenyl-ethen-1,2-diyl and 2-phenyl-ethen-1,2-diyl.

The term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 6 (such as 1 to 4), i.e., 1, 2, 3, 4, 5, or 6, more preferably 1 or 2 carbon-carbon triple bonds. Preferably, the alkynyl group comprises from 2 to 12 (such as 2 to 10) carbon atoms (such as 1, 2, 3, 4, 5, 6, 7, 8, 9, or 10 carbon atoms), i.e., 2, 3, 4, 5, 6, 7, 8, 9, 10, 11, or 12 carbon atoms, more preferably 2 to 8 carbon atoms, such as 2 to 6 carbon atoms or 2 to 4 carbon atoms. Thus, in a preferred embodiment, the alkynyl group comprises from 2 to 12 (such as 2 to 10) carbon atoms and 1, 2, 3, 4, 5, or 6 (such as 1, 2, 3, 4, or 5 (preferably 1, 2, or 3)) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom. A "substituted alkynyl" means that one or more (such as 1 to the maximum number of hydrogen atoms bound to an alkynyl group, e.g., 1, 2, 3, 4, 5, 6, 7, 8, 9, or up to 10, such as between 1 to 5, 1 to 4, or 1 to 3, or 1 or 2) hydrogen atoms of the alkynyl group are replaced with a substituent other than hydrogen (when more than one hydrogen atom is replaced the substituents may be the same or different). Preferably, the substituent other than hydrogen is a 1$^{st}$ level substituent, a 2$^{nd}$ level substituent, or a 3$^{rd}$ level substituent as specified herein, such as halogen or optionally substituted aryl.

The term "alkynylene" refers to a diradical of an unsaturated straight or branched hydrocarbon having at least one carbon-carbon triple bond. Generally, the maximal number of carbon-carbon triple bonds in the alkynylene group can be equal to the integer which is calculated by dividing the number of carbon atoms in the alkynylene group by 2 and, if the number of carbon atoms in the alkynylene group is uneven, rounding the result of the division down to the next integer. For example, for an alkynylene group having 9 carbon atoms, the maximum number of carbon-carbon triple bonds is 4. Preferably, the alkynylene group has 1 to 6 (such as 1 to 4), i.e., 1, 2, 3, 4, 5, or 6 (such as 1, 2, 3, or 4), more preferably 1 or 2 carbon-carbon triple bonds. Preferably, the alkynylene group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkynylene group comprises from 2 to 12 (such as 2 to 10) carbon atoms and 1, 2, 3, 4, 5, or 6 (such as 1, 2, 3, 4, or 5 (preferably 1, 2, or 3)) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynylene groups include ethyn-1,2-diyl, 1-propyn-1,3-diyl, 1-propyn-3,3-diyl, 1-butyn-1,3-diyl, 1-butyn-1,4-diyl, 1-butyn-3,4-diyl, 2-butyn-1,4-diyl and the like. If an alkynylene group is attached to a nitrogen atom, the triple bond cannot be alpha to the nitrogen atom. A "substituted alkynylene" means that one or more (such as 1 to the maximum number of hydrogen atoms bound to an alkynylene group, e.g., 1, 2, 3, 4, 5, 6, 7, 8, 9, or up to 10, such as between 1 to 5, 1 to 4, or 1 to 3, or 1 or 2) hydrogen atoms of the alkynylene group are replaced with a substituent other than hydrogen (when more than one hydrogen atom is replaced the substituents may be the same or different). Preferably, the substituent other than hydrogen is a 1$^{st}$ level substituent, a 2$^{nd}$ level substituent, or a 3$^{rd}$ level substituent as specified herein, such as halogen or optionally substituted aryl.

The term "aryl" or "aromatic ring" refers to a monoradical of an aromatic cyclic hydrocarbon. Preferably, the aryl group contains 3 to 14 (e.g., 5, 6, 7, 8, 9, or 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. Aryl does not encompass fullerenes. A "substituted aryl" means that one or more (such as 1 to the maximum number of hydrogen atoms bound to an aryl group, e.g., 1, 2, 3, 4, 5, 6, 7, 8, 9, or up to 10, such as between 1 to 5, 1 to 4, or 1 to 3, or 1 or 2) hydrogen atoms of the aryl group are replaced with a substituent other than hydrogen (when more than one hydrogen atom is replaced the substituents may be the same or different). Preferably, the substituent other than hydrogen is a 1$^{st}$ level substituent, a 2$^{nd}$ level substituent, or a 3$^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), alkyl (e.g., C$_{1-6}$ alkyl), alkenyl (e.g., C$_{2-6}$ alkenyl), and alkynyl (e.g., C$_{2-6}$ alkynyl). Examples of a substituted aryl include biphenyl, 2-fluorophenyl, 2-chloro-6-methylphenyl, anilinyl, 3-nitrophenyl, 4-hydroxyphenyl, methoxyphenyl (i.e., 2-, 3-, or 4-methoxyphenyl), and 4-ethoxyphenyl.

The term "heteroaryl" or "heteroaromatic ring" means an aryl group as defined above in which one or more carbon atoms in the aryl group are replaced by heteroatoms (such as O, S, or N). Preferably, heteroaryl refers to a five or six-membered aromatic monocyclic ring, wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. For example, 3- to 14-membered heteroaryl encompasses monocyclic heteroaryl (e.g., 5- or 6-membered), bicyclic heteroaryl (e.g., 9- or 10-membered), and tricyclic heteroaryl (e.g., 13- or 14-membered). Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl (also called pyridinyl), pyrimidinyl, pyrazinyl, triazinyl (1,2,3-, 1,2,4-, and 1,3,5-), benzofuranyl (1- and 2), indolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, and pyrrolopyrrolyl. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5), pyridyl, pyrimidinyl, pyrazinyl, triazinyl (1,2,3-, 1,2,4-, and 1,3,5-), and pyridazinyl. A "substituted heteroaryl" means that one or more (such as 1 to the maximum number of hydrogen atoms bound to a heteroaryl group, e.g., 1, 2, 3, 4, 5, 6, 7, 8, 9, or up to 10, such as between 1 to 5, 1 to 4, or 1 to 3, or 1 or 2) hydrogen atoms of the heteroaryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, CN, nitro, —$OR^{11}$ (e.g., —OH), —$SR^{11}$ (e.g., —SH), —$N(R^{12})(R^{13})$ (e.g., —$NH_2$), alkyl (e.g., $C_{1-6}$ alkyl), alkenyl (e.g., $C_{2-6}$ alkenyl), and alkynyl (e.g., $C_{2-6}$ alkynyl). Examples of a substituted heteroaryl include 2,4-dimethylpyridin-3-yl, 2-methyl-4-bromopyridin-3-yl, 3-methyl-2-pyridin-2-yl, 3-chloro-5-methylpyridin-4-yl, 4-chloro-2-methylpyridin-3-yl, 3,5-dimethylpyridin-4-yl, 2-methylpyridin-3-yl, 2-chloro-4-methyl-thien-3-yl, 1,3,5-trimethylpyrazol-4-yl, 3,5-dimethyl-1,2-dioxazol-4-yl, 1,2,4-trimethylpyrrol-3-yl, 3-phenylpyrrolyl, 2,3'-bifuryl, 4-methylpyridyl, 2-, or 3-ethylindolyl.

The term "cycloalkyl" or "cycloaliphatic" represents cyclic non-aromatic versions of "alkyl" and "alkenyl" with preferably 3 to 14 carbon atoms, such as 3 to 12 or 3 to 10 carbon atoms, i.e., 3, 4, 5, 6, 7, 8, 9, 10, 11, 12, 13, or 14 carbon atoms (such as 3, 4, 5, 6, 7, 8, 9, or 10 carbon atoms), more preferably 3 to 7 carbon atoms. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_{3-8}$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0] octyl. Cycloalkyl does not encompass fullerenes. A "substituted cycloalkyl" means that one or more (such as 1 to the maximum number of hydrogen atoms bound to a cycloalkyl group, e.g., 1, 2, 3, 4, 5, 6, 7, 8, 9, or up to 10, such as between 1 to 5, 1 to 4, or 1 to 3, or 1 or 2) hydrogen atoms of the cycloalkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —$OR^{11}$ (e.g., —OH), —$SR^{11}$ (e.g., —SH), —$N(R^{12})(R^{13})$ (e.g., —$NH_2$), =X (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted cycloalkyl include oxocyclohexyl, oxocyclopentyl, fluorocyclohexyl, and oxocyclohexenyl.

The term "heterocyclyl" or "heterocyclic ring" means a cycloalkyl group as defined above in which from 1, 2, 3, or 4 ring carbon atoms in the cycloalkyl group are replaced by heteroatoms (such as those selected from the group consisting of O, S, S(O), S(O)$_2$, N, B, Si, and P, preferably selected from the group consisting of O, S, S(O)$_2$, and N, more preferably selected from the group consisting of O, S, and N). If a ring of the heterocyclyl group only contains one type of heteroatom, the maximum number of said heteroatom in the ring of said heterocyclyl group may be as follows: 20 atoms (preferably 10 atom); 2 S atoms (preferably 1 S atom); 4 N atoms (such as 1, 2, or 3 N atoms); 2 B atoms (preferably 1 B atom); 1 Si atom; and/or 1 P atom. If a ring of the heterocyclyl group contains two or more types of heteroatoms, the maximum number of said heteroatoms in the ring of said heterocyclyl group may be as follows: 10 atom; 1 S atom; 2 N atoms (preferably 1 N atom); 1 B atom; 1 Si atom; and/or 1 P atom, wherein the maximum total number of heteroatoms in the ring of said heterocyclyl group is 4 and the maximum total number of each heteroatom in the ring of said heterocyclyl group is as follows: 10 atom; 1 S atom; 1 or 2 N atoms; 1 B atom (preferably 0 B atom); 1 Si atom (preferably 0 Si atom); and/or 1 P atom (preferably 0 P atom). In one embodiment, the heteroatoms of the heterocyclyl group are selected from the group consisting of O, S, and N. In this embodiment, preferably, in each ring of the heterocyclyl group the maximum number of 0 atoms is 1, the maximum number of S atoms is 1, and the maximum total number of 0 and S atoms is 2. For example, 3- to 14-membered heterocyclyl encompasses monocyclic heterocyclyl (e.g., 3-, 4-, 5-, 6-, or 7-membered, preferably 4- to 7-membered), bicyclic heterocyclyl (e.g., 8-, 9-, or 10-membered), and tricyclic heterocyclyl (e.g., 12-, 13-, or 14-membered). If a heterocyclyl group comprises two or more rings, these rings either are fused (such as in quinolinyl or purinyl), are a spiro moiety, are a bridged structure, are linked via a double bond, or are a combination thereof. In other words, an unsubstituted heterocyclyl group does not encompass two heterocyclyl groups linked via a single bond. The term "heterocyclyl" is also meant to encompass partially or completely hydrogenated forms (such as dihydro, tetrahydro, hexahydro, octahydro, decahydro, dodecahydro, etc., or perhydro forms) of the above-mentioned heteroaryl groups. Exemplary heterocyclyl groups include azetidinyl, morpholino, isochromanyl, chromanyl, pyrrolidinyl, imidazolidinyl, pyrazolidinyl, piperidinyl, piperazinyl, indolinyl, isoindolinyl, triazininanyl (1,2,3-, 1,2,4-, and 1,3,5-), di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiazolyl, di- and tetrahydrothiadiazolyl (1,2,3- and 1,2,5-), di- and tetrahydropyridyl, di-, tetra- and hexahydropyrimidinyl, di- and tetrahydropyrazinyl, di- and tetrahydrotriazinyl (1,2,3-, 1,2,4-, and 1,3,5-), di-, tetra-, hexa- and octahydrobenzofuranyl (1- and 2-), di-, tetra-, hexa- and octahydroindolyl, di-, tetra-, hexa- and octahydroisoindolyl, di-, tetra-, hexa- and octahydrobenzothienyl (1- and 2), di-, tetra-, hexa- and octahydro-1H-indazolyl, di-, tetra-, hexa- and octahydrobenzimidazolyl, di-, tetra-, hexa- and octahydrobenzoxazolyl, di-, tetra-, hexa- and octahydroindoxazinyl, di-, tetra-, hexa- and octahydrobenzisoxazolyl, di-, tetra-, hexa- and octahydrobenzothiazolyl, di-, tetra-, hexa- and octahydrobenzisothiazolyl, di-, tetra-, hexa- and octahydrobenzotriazolyl, di-, tetra-, hexa-, octa- and decahydroquinolinyl, di-, tetra-, hexa-, octa- and decahydroisoquinolinyl, di-, tetra-, hexa-, octa- and decahydrobenzodiazinyl, di-, tetra-, hexa-, octa- and decahydroquinoxalinyl, di-, tetra-, hexa-, octa- and decahydroquinazolinyl, di-, tetra-, hexa-, octa- and decahydrobenzotriazinyl (1,2,3- and 1,2,4-), di-, tetra-, and hexahydropyridazinyl, di-, tetra-, hexa-, octa-, deca- and dodecahydrophenoxazinyl, di-, tetra-, hexa-, and octahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro[1,3]thiazolo[5,4-c]pyridin-2-yl or 4,5,6-7-tetrahydro[1,3]thiazolo[4,5-c]pyridin-2-yl), di-, tetra-, and hexahydropyrrolothiazolyl, di-, tetra-, hexa-, octa- and decahydrophenothiazinyl, di-, tetra-, hexa-, and octahydroisobenzofuranyl, di-, tetra-, hexa-, and octahydrochromenyl, di-, tetra-, hexa-, octa-, deca-, and dodecahydroxanthenyl, di-, tetra-, hexa-, octa-, deca-, and dodecahydrophenoxathiinyl, di-, tetra-, and hexahydropyrrolizinyl, di-, tetra-, hexa-, and octahydroindolizinyl, di-, tetra-, hexa-, and octahydroindazolyl, di-, tetra-, hexa-, and octahydropurinyl, di-, tetra-, hexa-, and octahydroquinolizinyl, di-, tetra-, hexa-, octa- and decahydrophthalazinyl, di-, tetra-, hexa-, octa- and decahydronaphthyridinyl (1,5-, 1,6-, 1,7-, 1,8-, and 2,6-), di-, tetra-, hexa-, octa- and decahydrocinnolinyl, di-, tetra-, hexa-, octa-, and decahydropteridinyl, di-, tetra-, hexa-, octa-, deca- and dodecahydrocarbazolyl, di-, tetra-, hexa-, octa-, deca-, dodeca-, and tetradecahydrophenanthridinyl, di-, tetra-, hexa-, octa-, deca-, dodeca-, and tetradecahydroacridinyl, di-, tetra-, hexa-, octa-, deca- and dodecahydroperimidinyl, di-, tetra-, hexa-, octa-, deca-, dodeca-, and tetradecahydrophenanthrolinyl (1,7-, 1,8-, 1,10-, 3,8-, and 4,7-), di-, tetra-, hexa-, octa-, deca-, dodeca-, and tetradecahydrophenazinyl, di-, tetra-, hexa- and octahydrooxazolopyridinyl, di-, tetra-, hexa- and octahydroisoxazolopyridinyl, di-, tetra-, hexa- and octahydrocyclopentapyrrolyl, di-, tetra-, hexa- and octahydrocyclopentpyrazolyl, di-, tetra-, hexa- and octahydrocyclopentaimidazolyl, di-, tetra-, hexa- and octahydro-cyclopentathiazolyl, di-, tetra-, hexa- and octahydrocyclopentaoxazolyl, di-, tetra-, hexa- and octahydropyrrolopyrrolyl, di-, tetra-, hexa- and octahydropyrrolopyrazolyl, di-, tetra-, hexa- and octahydropyrroloimidazolyl, di-, tetra-, hexa- and octahydropyrrolothiazolyl (such as 5,6-dihydro-4H-pyrrolo[3,4-d][1,3]thiazolyl), di-, tetra-, hexa- and octahydropyrrolooxazolyl, di-, tetra-, hexa- and octahydropyrazolopyrazolyl, di-, tetra-, hexa- and octahydro-pyrazoloimidazolyl, di-, tetra-, hexa- and octahydropyrazolothiazolyl, di-, tetra-, hexa- and octahydropyrazolooxazolyl, di-, tetra-, hexa- and octahydroimidazoimidazolyl, di-, tetra-, hexa- and octahydroimidazothiazolyl, di-, tetra-, hexa- and octahydroimidazooxazolyl, di-, tetra-, hexa- and octahydrothiazolothiazolyl, di-, tetra-, hexa- and octahydrothiazolooxazolyl, and di-, tetra-, hexa- and octahydrooxazolooxazolyl. Exemplary 5- or 6-membered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di-, tetra-, and hexahydropyrimidinyl, di- and tetrahydropyrazinyl, di- and tetrahydrotriazinyl (1,2,3-, 1,2,4-, and 1,3,5-), and triazinanyl (1,2,3-, 1,2,4-, and 1,3,5-). A "substituted heterocyclyl" means that one or more (such as 1 to the maximum number of hydrogen atoms bound to a heterocyclyl group, e.g., 1, 2, 3, 4, 5, 6, 7, 8, 9, or up to 10, such as between 1 to 5, 1 to 4, or 1 to 3, or 1 or 2) hydrogen atoms of the heterocyclyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl).

The expression "partially hydrogenated form" of an unsaturated compound or group as used herein means that part of the unsaturation has been removed by formally adding hydrogen to the initially unsaturated compound or group without removing all unsaturated moieties. The phrase "completely hydrogenated form" of an unsaturated compound or group is used herein interchangeably with the term "perhydro" and means that all unsaturation has been removed by formally adding hydroagen to the initially unsaturated compound or group. For example, partially hydrogenated forms of a 5-membered heteroaryl group (containing 2 double bonds in the ring, such as furan) include dihydro forms of said 5-membered heteroaryl group (such as 2,3-dihydrofuran or 2,5-dihydrofuran), whereas the tetrahydro form of said 5-membered heteroaryl group (e.g., tetrahydrofuran, i.e., THF) is a completely hydrogenated (or perhydro) form of said 5-membered heteroaryl group. Likewise, for a 6-membered heteroaryl group having 3 double bonds in the ring (such as pyridyl), partially hydrogenated forms include di- and tetrahydro forms (such as di- and tetrahydropyridyl), whereas the hexahydro form (such as piperidinyl in case of the heteroaryl pyridyl) is the completely hydrogenated (or perhydro) derivative of said 6-membered heteroaryl group. Consequently, a hexahydro form of an aryl or heteroaryl can only be considered a partially hydrogenated form according to the present invention if the aryl or heteroaryl contains at least 4 unsaturated moieties consisting of double and triple bonds between ring atoms.

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The term "polycyclic" as used herein means that the structure has two or more (such as 2, 3, 4, 5, 6, 7, 8, 9, or 10), preferably, 2, 3, 4, or 5, more preferably, 2, 3, or 4, rings. Therefore, according to the invention, the term "polycyclic" does not encompass monocyclic structures, wherein the structures only contain one ring. Examples of polycyclic groups are fused structures (such as naphthyl or anthryl), spiro compounds, rings that are linked via single or double bonds (such as biphenyl), and bridged structures (such as bornyl). Exemplary polycyclic structures are those aryl, heteroaryl, cycloalkyl, and heterocyclyl groups specified above which have at least two rings.

The term "halogen" or "halo" means fluoro, chloro, bromo, or iodo.

The term "azido" means —$N_3$.

The term "N-oxide" means an amine oxide or amine-N-oxide which is a chemical compound containing the functional group $(R'')_3N^+$—$O^-$, i.e., an N—O coordinate covalent bond, wherein $R''$ is independently selected from the group consisting of hydrogen, alkyl, alkenyl, alkynyl, aryl, heteroaryl, cycloalkyl, and heterocyclyl, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, the $R^{30}$ preferably being a $1^{st}$ level substituent, a $2^{nd}$ level substituent, or a $3^{rd}$ level substituent as specified herein.

As described elsewhere herein, $R^5$ is -L-$R^6$, and $R^6$ is heteroaryl or heterocyclyl each of which is optionally substituted with one or more independently selected $R^7$. In relation thereto, the expression "any two $R^7$ which are bound to the same atom of $R^6$ may join together to form =O" as used herein means that two monoradicals (i.e., $R^7$) when substituting in total 2 hydrogen atoms bound to only one ring atom of $R^6$ can form the diradical =O. For example, according to the invention, $R^6$ being

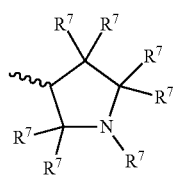

wherein ⌇ represents the bond by which $R^6$ is bound to the remainder of the compound) encompasses not only (1) the possibility that each of the $R^7$ groups is a monoradical independently selected from the particular moieties specified herein (e.g., methyl or $C_1$) but also (2) the possibility that any two $R^7$ groups bound to the same atom of $R^6$ join together to form the diradical =O resulting in a $R^6$ group having the formula

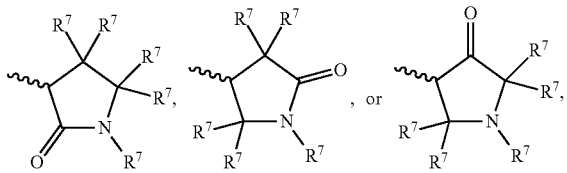

wherein the remaining $R^7$ groups are monoradicals. Likewise, in case $R^6$ is 3-tetrahydrothienyl substituted with four $R^7$, such substituted $R^6$ encompasses the following formulas:

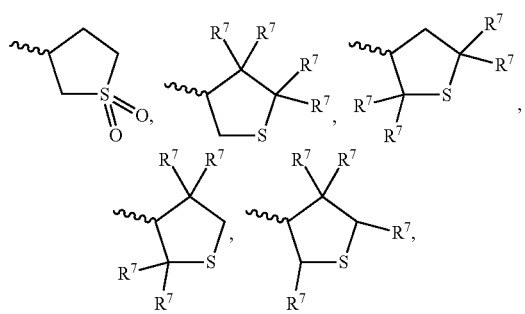

etc. Similar terms such as "any two $R^{30}$ which are bound to the same carbon atom of a cycloalkyl or heterocyclyl group may join together to form =$X^{1}$" as used herein are to be interpreted in an analogous manner. In this respect, it is to be understood that in those embodiments, where any two $R^7$ which are bound to the same atom of $R^6$ may join together to form =O, $R^6$ initially (i.e., without the modification =O) has to be a heterocyclic ring (because in a heteroaromatic ring there is no carbon ring atom having two free valences).

The expression "one $R^7$ group is bound to a ring atom of $R^6$ at position 2 relative to the ring atom by which $R^6$ is bound to the remainder of the compound" as used herein means that at least one of the two ring atoms directly adjacent to the ring atom by which $R^6$ is attached to the remainder of the compound bears one $R^7$ group. In other words, at least one of the ortho positions of $R^6$, relative to the ring atom by which $R^6$ is bound to the remainder of the compound (i.e., "yl position" of $R^6$), bears a $R^7$ group. For example, applying the above expression to the case where $R^6$ is 3-pyridyl (thus, the yl position is the ring carbon at position 3 relative to the ring nitrogen atom) substituted with one $R^7$, it follows that this $R^7$ group is at position 2 or 4 of the 3-pyridyl group, as shown in the following formulas:

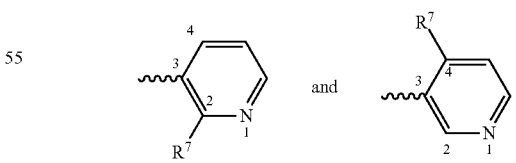

wherein ⌇ represents the bond by which $R^6$ is bound to the remainder of the compound. Furthermore, in case $R^6$ is substituted with more than one (such as two or three) $R^7$ groups, the expression "one $R^7$ group is bound to a ring atom of $R^6$ at position 2 relative to the ring atom by which $R^6$ is bound to the remainder of the compound" encompasses the situation that each of the two ring atoms directly adjacent to the ring atom by which $R^6$ is attached to the remainder of the compound bears one $R^7$ group (i.e., $R^6$ being an k-membered ring bears one $R^7$ group at each of positions 2 and k, relative to the ring atom by which $R^6$ is bound to the remainder of the compound, i.e., $R^6$ is substituted at both of its ortho positions). For example, in case $R^6$ is 3-pyrrolyl (thus, the yl position is the ring carbon at position 3 relative to the ring nitrogen atom) substituted with two $R^7$ groups, the expression "one $R^7$ group is bound to a ring atom of $R^6$ at position 2 relative to the ring atom by which $R^6$ is bound to the remainder of the compound" encompasses the following structures:

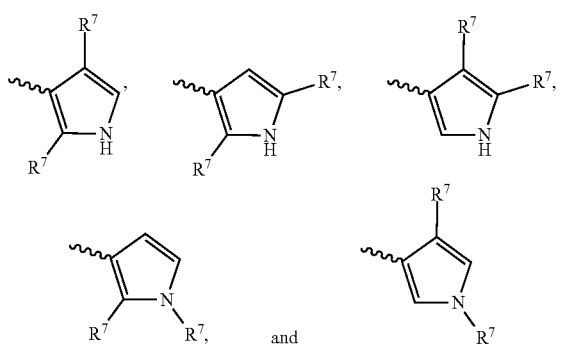

but excludes the following structure:

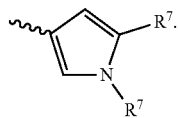

The term "k-membered ring" as used herein means that the ring has k ring atoms. E.g., for pyrazolyl k is 5; thus, relative to the ring atom (yl position) by which the pyrazolyl group is bound to the remainder of the compound, the ortho positions are positions 2 and 5 and position k–1 is position 4. Furthermore, for pyridinyl being a 6-membered heteroaryl, the ortho positions are positions 2 and 6 and position k–1 is position 5, relative to the ring atom (yl position) by which the pyridinyl group is bound to the remainder of the compound.

The expression "⁀⁀⁀ represents the bond by which $R^6$ is bound to the remainder of the compound" as used herein refers to the bond through which $R^6$ is attached to the remainder of the compound (i.e., attached to either (i) L in case L is not a bond or (ii) the nitrogen atom of the carbox(thio)amide group $—C(E)N(R^4)(R^5)$ of formula (I) in case L is a bond). For example, in case $R^6$ is

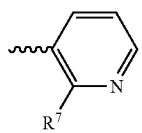

and L is (i) methylene or (ii) a bond, the compound of formula (I) has the following structure (A1) and (A2), respectively:

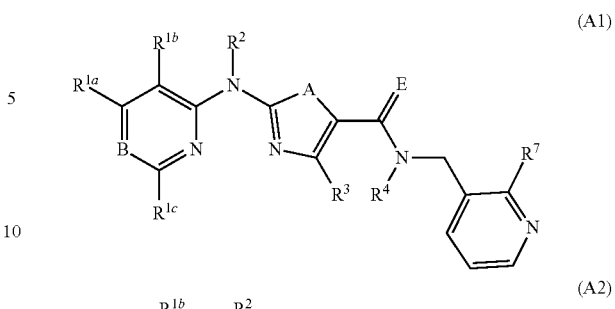

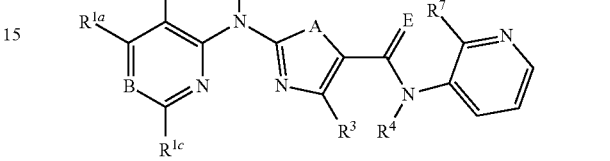

The term "optionally substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group (i.e., a $1^{st}$ level substituent) different from hydrogen such as alkyl (preferably, $C_{1-6}$ alkyl), alkenyl (preferably, $C_{2-6}$ alkenyl), alkynyl (preferably, $C_{2-6}$ alkynyl), aryl (preferably, 6- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, azido, —NO$_2$, —OR$^{71}$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$R$^{71}$, —NR$^{71}$S(O)$_{1-2}$OR$^{71}$, —NR$^{71}$S(O)$_{1-2}$N(R$^{72}$)(R$^{73}$), —OP(O)(OR$^{71}$)$_2$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two $1^{st}$ level substituents which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups of the $1^{st}$ level substituent may themselves be substituted by one or more (e.g., one, two or three) substituents (i.e., a $2^{nd}$ level substituent) selected from the group consisting of $C_{1-6}$ alkyl, $C_{2-6}$ alkenyl, $C_{2-6}$ alkynyl, 6- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —S(O)$_{0-2}$R$^{81}$, —S(O)$_{1-2}$OR$^{81}$, —OS(O)$_{1-2}$R$^{81}$, —OS(O)$_{1-2}$OR$^{81}$, —S(O)$_{1-2}$N(R$^{82}$)(R$^{83}$), —OS(O)$_{1-2}$N(R$^{82}$)(R$^{83}$), —N(R$^{81}$)S(O)$_{1-2}$R$^{81}$, —NR$^{81}$S(O)$_{1-2}$OR$^{81}$, —NR$^{81}$S(O)$_{1-2}$N(R$^{82}$)(R$^{83}$), —OP(O)(OR$^{81}$)$_2$, —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two $2^{nd}$ level substituents which are bound to the same carbon atom of a cycloalkyl or heterocyclyl group being a $1^{st}$ level substituent may join together to form =X$^2$, wherein each of the $C_{1-6}$ alkyl, $C_{2-6}$ alkenyl, $C_{2-6}$ alkynyl, 6- to 14-membered aryl, 3- to 14-membered heteroaryl, 3- to 14-membered cycloalkyl, 3- to 14-membered heterocyclyl groups of the $2^{nd}$ level substituent is optionally substituted with one or more (e.g., one, two or three) substituents (i.e., a $3^{rd}$ level substituent) independently selected from the group consisting of $C_{1-3}$ alkyl, halogen, —CF$_3$, —CN, azido, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$ $(C_{1-3}$ alkyl$)_z$, —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =N($C_{1-3}$ alkyl);
wherein
  each of $R^{71}$, $R^{72}$, and $R^{73}$ is independently selected from the group consisting of H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents independently selected from the group consisting of $C_{1-3}$ alkyl, halogen, —CF$_3$, —CN, azido, —NO$_2$, —OH, —O($C_{1-3}$ alkyl), —OCF$_3$, =O, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl$)_z$, —C(=O)($C_{1-3}$ alkyl), —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl;
  each of $R^{81}$, $R^{82}$, and $R^{83}$ is independently selected from the group consisting of H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents independently selected from the group consisting of $C_{1-3}$ alkyl, halogen, —CF$_3$, —CN, azido, —NO$_2$, —OH, —O($C_{1-3}$ alkyl), —OCF$_3$, =O, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl$)_z$, —C(=O)($C_{1-3}$ alkyl), —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl; and
  each of $X^1$ and $X^2$ is independently selected from O, S, and N($R^{84}$), wherein $R^{84}$ is H or $C_{1-3}$ alkyl.

Typical $1^{st}$ level substituents are preferably selected from the group consisting of $C_{1-6}$ alkyl, $C_{2-6}$ alkenyl, $C_{2-6}$ alkynyl, 6- to 14-membered (such as 6- to 10-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, halogen, —CN, azido, —NO$_2$, —OR$^{71}$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$R$^{71}$, —NR$^{71}$S(O)$_{1-2}$OR$^{71}$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, such as $C_{1-4}$ alkyl, $C_{2-4}$ alkenyl, $C_{2-4}$ alkynyl, 6-membered aryl, 5- or 6-membered heteroaryl, 3- to 7-membered cycloalkyl, 3- to 7-membered (such as 5- or 6-membered) heterocyclyl, halogen, —CF$_3$, —CN, azido, —NO$_2$, —OH, —O($C_{1-3}$ alkyl), —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl$)_z$, —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl; wherein $X^1$ is independently selected from O, S, NH and N(CH$_3$); and each of $R^{71}$, $R^{72}$, and $R^{73}$ is as defined above or, preferably, is independently selected from the group consisting of H, $C_{1-4}$ alkyl, $C_{2-4}$ alkenyl, $C_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents independently selected from the group consisting of $C_{1-3}$ alkyl, halogen, —CF$_3$, —CN, azido, —NO$_2$, —OH, —O($C_{1-3}$ alkyl), —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl$)_z$, —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl. Particular examples of $1^{st}$ level substituents are independently selected from the group consisting of $C_{1-3}$ alkyl, phenyl, imidazolyl, thiazolyl, cyclopentyl, cyclohexyl, dihydrothiazolyl, thiazolidinyl, halogen, —CF$_3$, —CN, —OH, —O($C_{1-3}$ alkyl), —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl. Particularly preferred $1^{st}$ level substituents are independently selected from the group consisting of $C_{1-3}$ alkyl, phenyl, thiazolidinyl, halogen (such as F, Cl, or Br), —NH$_2$, —NHS(O)$_2$($C_{1-3}$ alkyl), —NHC(=O)($C_{1-3}$ alkyl), and —NHC(=NH)NH$_{z-2}$($C_{1-3}$ alkyl$)_z$, wherein z is 0, 1, or 2 and each $C_{1-3}$ alkyl is independently methyl, ethyl, propyl or isopropyl.

Typical $2^{nd}$ level substituents are preferably selected from the group consisting of $C_{1-4}$ alkyl, $C_{2-4}$ alkenyl, $C_{2-4}$ alkynyl, 6- or 10-membered aryl, 5- or 6-membered heteroaryl, 5- or 6-membered cycloalkyl, 5- or 6-membered heterocyclyl, halogen, =O, =S, —CF$_3$, —CN, azido, —NO$_2$, —OH, —O($C_{1-3}$ alkyl), —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl$)_z$, —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)NH$_{2-z}$($C_{1-3}$ alkyl$)_z$, wherein each z is independently 0, 1, or 2 and each $C_{1-3}$ alkyl is independently methyl, ethyl, propyl or isopropyl. Particular examples of $2^{nd}$ level substituents are independently selected from the group consisting of $C_{1-3}$ alkyl, phenyl, 5- or 6-membered heteroaryl, 5- or 6-membered cycloalkyl, 5- or 6-membered heterocyclyl, halogen, =O, =S, —CF$_3$, —CN, —OH, —O($C_{1-3}$ alkyl), —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —C(=O)OH, —C(=O)O($C_{1-3}$ alkyl), —C(=O)NH$_{2-z}$($C_{1-3}$ alkyl$)_z$, —NHC(=O)($C_{1-3}$ alkyl), —NHC(=NH)NH$_{z-2}$($C_{1-3}$ alkyl$)_z$, and —N($C_{1-3}$ alkyl)C(=NH)$NH_{2-z}$($C_{1-3}$ alkyl)$_z$, wherein each z is independently 0, 1, or 2 and each $C_{1-3}$ alkyl is independently methyl, ethyl, propyl or isopropyl. Particularly preferred $2^{nd}$ level substituents are independently selected from the group consisting of methyl, ethyl, propyl, isopropyl, phenyl, =O, and =S.

Typical $3^{rd}$ level substituents are preferably selected from the group consisting of $C_{1-3}$ alkyl, phenyl, halogen, —$CF_3$, —OH, —$OCH_3$, —$SCH_3$, —$NH_{2-z}(CH_3)_z$, —C(=O)OH, and —C(=O)$OCH_3$, wherein z is 0, 1, or 2 and $C_{1-3}$ alkyl is methyl, ethyl, propyl or isopropyl. Particularly preferred $3^{rd}$ level substituents are selected from the group consisting of methyl, ethyl, propyl, isopropyl, halogen (such as F, $C_1$, or Br), and —$CF_3$, such as halogen (e.g., F, $C_1$, or Br), and —$CF_3$.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical (spatial) positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (f). "Diastereomers" are stereoisomers which are non-superimposable and which are not mirror-images of each other. "Tautomers" are structural isomers of the same chemical substance that spontaneously and reversibly interconvert into each other, even when pure, due to the migration of individual atoms or groups of atoms; i.e., the tautomers are in a dynamic chemical equilibrium with each other. An example of tautomers are the isomers of the keto-enol-tautomerism. "Conformers" are stereoisomers that can be interconverted just by rotations about formally single bonds, and include—in particular—those leading to different 3-dimentional forms of (hetero)cyclic rings, such as chair, half-chair, boat, and twist-boat forms of cyclohexane.

In case a structural formula shown in the present application can be interpreted to encompass more than one isomer, said structural formula, unless explicitly stated otherwise, encompasses all possible isomers and, hence, each individual isomer. For example, a compound of formula (I), wherein $R^6$ is 1-azabocyclo[2.2.2]oct-3-yl (optionally substituted with one or more $R^7$ groups) encompasses both isomers, e.g., the isomer having the following formula (B1) and the isomer having the following formula (B2) (wherein n1 is 0, 1, 2, 3, or more):

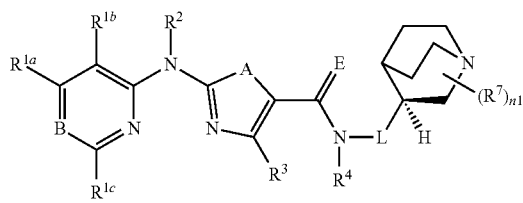

(B1)

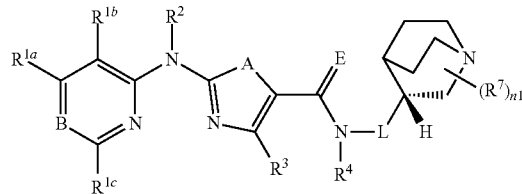

(B2)

"Polymorphism" as referred to herein means that a solid material (such as a compound) is able to exist in more than one form or crystalline structure, i.e., "polymorphic modifications" or "polymorphic forms". The terms "polymorphic modifications", "polymorphic forms", and "polymorphs" are used interchangeable in the present invention. According to the present invention, these "polymorphic modifications" include crystalline forms, amorphous forms, solvates, and hydrates. Mainly, the reason for the existence of different polymorphic forms lies in the use of different conditions during the crystallization process, such as the following:

solvent effects (the packing of crystal may be different in polar and nonpolar solvents);
certain impurities inhibiting growth pattern and favor the growth of a metastable polymorphs;
the level of supersaturation from which material is crystallized (in which generally the higher the concentration above the solubility, the more likelihood of metastable formation);
temperature at which crystallization is carried out;
geometry of covalent bonds (differences leading to conformational polymorphism);
change in stirring conditions.

Polymorphic forms may have different chemical, physical, and/or pharmacological properties, including but not limited to, melting point, X-ray crystal and diffraction pattern, chemical reactivity, solubility, dissolution rate, vapor pressure, density, hygroscopicity, flowability, stability, compactability, and bioavailability. Polymorphic forms may spontaneously convert from a metastable form (unstable form) to the stable form at a particular temperature. According to Ostwald's rule, in general it is not the most stable but the least stable polymorph that crystallizes first. Thus, quality, efficacy, safety, processability and/or manufacture of a chemical compound, such as a compound of the present invention, can be affected by polymorphism. Often, the most stable polymorph of a compound (such as a compound of the present invention) is chosen due to the minimal potential for conversion to another polymorph. However, a polymorphic form which is not the most stable polymorphic form may be chosen due to reasons other than stability, e.g. solubility, dissolution rate, and/or bioavailability.

The term "crystalline form" of a material as used herein means that the smallest components (i.e., atoms, molecule or ions) of said material form crystal structures. A "crystal structure" as referred to herein means a unique three-dimensional arrangement of atoms or molecules in a crystalline liquid or solid and is characterized by a pattern, a set of atoms arranged in a particular manner, and a lattice exhibiting long-range order and symmetry. A lattice is an array of points repeating periodically in three dimensions and patterns are located upon the points of a lattice. The subunit of the lattice is the unit cell. The lattice parameters are the lengths of the edges of a unit cell and the angles between them. The symmetry properties of the crystal are embodied in its space group. In order to describe a crystal structure the following parameters are required: chemical formula, lattice parameters, space group, the coordinates of the atoms and occupation number of the point positions.

The term "amorphous form" of a material as used herein means that the smallest components (i.e., atoms, molecule or ions) of said material are not arranged in a lattice but are arranged randomly. Thus, unlike crystals in which a short-range order (constant distances to the next neighbor atoms) and a long-range order (periodical repetition of a basic lattice) exist, only a short-range order exists in an amorphous form.

The term "complex of a compound" as used herein refers to a compound of higher order which is generated by association of the compound with other one or more other molecules. Exemplary complexes of a compound include, but are not limited to, solvates, clusters, and chelates of said compound.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds of the present invention include deuterium, $^{11}$C, $^{13}$C, $^{14}$C, $^{15}$N, $^{18}$F, $^{32}$P, $^{32}$S, $^{35}$S, $^{36}$Cl, and $^{125}$I.

The term "half-life" relates to the period of time which is needed to eliminate half of the activity, amount, or number of molecules. In the context of the present invention, the half-life of a compound of formula (I) or (Ia) is indicative for the stability of said compound.

The terms "subject", "patient", "individual", or "animal" relate to multicellular animals, such as vertebrates. For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals (in particular vertebrates) of zoos. Mammals in the context of the present invention include, but are not limited to, humans, non-human primates, domesticated mammals, such as dogs, cats, sheep, cattle, goats, pigs, horses etc., laboratory mammals such as mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc.; while particular non-limiting examples of bony or cartilaginous fish include those suitable for cultivation by aquiculture, and include bony fish such as salmon, trout, perch, carp, cat-fish, etc.

The compound dasatinib (herein also referred to as compound A8) has the following structure:

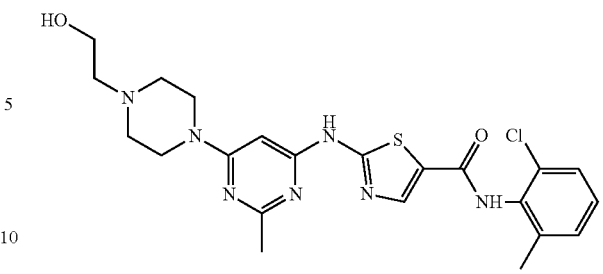

Compounds

In a first aspect, and as may be further described, defined, claimed or otherwise disclosed herein, the present invention provides a compound selected from the group consisting of a kinase inhibitor of the formula:

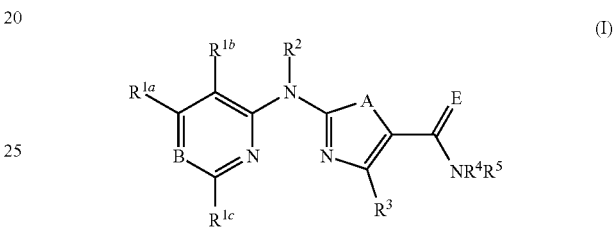

(I)

and solvates, salts, N-oxides, complexes, polymorphs, crystalline forms, racemic mixtures, diastereomers, enantiomers, tautomers, conformers, isotopically labeled forms, prodrugs, and combinations thereof;

wherein:

$R^{1a}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

each of R$^{1b}$ and R$^{1c}$ is independently selected from the group consisting of H, C$_{1-6}$ alkyl, C$_{2-6}$ alkenyl, C$_{2-6}$ alkynyl, C$_{3-7}$ cycloalkyl, C$_{6-10}$ aryl, 3- to 7-membered heteroaryl, 3- to 7-membered heterocyclyl, —O(CH$_2$)$_{0-2}$(C$_{3-7}$ cycloalkyl), —O(CH$_2$)$_{0-2}$(C$_{6-10}$ aryl), —O(CH$_2$)$_{0-2}$(3- to 7-membered heteroaryl), —O(CH$_2$)$_{0-2}$(3- to 7-membered heterocyclyl), —NH(CH$_2$)$_{0-2}$(C$_{3-7}$ cycloalkyl), —NH(CH$_2$)$_{0-2}$(C$_{6-10}$ aryl), —NH(CH$_2$)$_{0-2}$(3- to 7-membered heteroaryl), —NH(CH$_2$)$_{0-2}$(3- to 7-membered heterocyclyl), halogen, —CF$_3$, —CN, azido, —NO$_2$, —OH, —O(C$_{1-6}$ alkyl), —OCF$_3$, —S(C$_{1-6}$ alkyl), —NH$_2$, —NH(C$_{1-6}$ alkyl), —N(C$_{1-6}$ alkyl)$_2$, —NHS(O)$_2$(C$_{1-6}$ alkyl), —S(O)$_2$NH$_{2-z}$(C$_{1-6}$ alkyl)$_z$, —C(=O)(C$_{1-6}$ alkyl), —C(=O)OH, —C(=O)O(C$_{1-6}$ alkyl), —C(=O)NH$_{2-z}$(C$_{1-6}$ alkyl)$_z$, —NHC(=O)(C$_{1-6}$ alkyl), —NHC(=NH)NH$_{z-2}$(C$_{1-6}$ alkyl)$_z$, and —N(C$_{1-6}$ alkyl)C(=NH)NH$_{2-z}$(C$_{1-6}$ alkyl)$_z$, wherein z is 0, 1, or 2 and each of the C$_{1-6}$ alkyl, C$_{2-6}$ alkenyl, C$_{2-6}$ alkynyl, C$_{3-7}$ cycloalkyl, C$_{6-10}$ aryl, 3- to 7-membered heteroaryl, and 3- to 7-membered heterocyclyl groups is optionally substituted with one, two, or three moieties independently selected from the group consisting of —OH, methyl, ethyl, —OCH$_3$, —SCH$_3$, and —NH$_{2-z}$(CH$_3$)$_z$;

$R^2$ is H;

$R^3$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

$R^4$ is H;

$R^5$ is -L-R$^6$;

L is selected from the group consisting of a bond, C$_{1-6}$ alkylene, C$_{2-6}$ alkenylene, C$_{2-6}$ alkynylene, and —(CH$_2$)$_m$—[Y—(CH$_2$)$_n$]$_o$—, wherein m is an integer between 0 and 3, n is an integer between 1 and 6, o is an integer between 1 and 3, wherein if n is 0 then o is 1; Y is independently selected from O, S, and —N(R$^{13}$)—; and each of the C$_{1-6}$ alkylene, C$_{2-6}$ alkenylene, C$_{2-6}$ alkynylene, —(CH$_2$)$_m$—, and —(CH$_2$)$_n$— groups is optionally substituted with one or two independently selected R$^{30}$;

$R^6$ is heteroaryl or heterocyclyl each of which is optionally substituted with one or more independently selected R$^7$;

$R^7$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, and/or any two R$^7$ which are bound to the same atom of R$^6$ being a heterocyclyl group may join together to form =O, wherein each of the alkyl, alkenyl, alkynyl, cycloalkyl, aryl, heterocyclyl, and heteroaryl groups is optionally substituted with one or more independently selected R$^{30}$;

A is selected from the group consisting of S, O, NR$^8$, and C(R$^9$)$_2$;

$R^8$ is selected from the group consisting of H, alkyl, alkenyl, alkynyl, cycloalkyl, aryl, heterocyclyl, and heteroaryl, wherein each of the alkyl, alkenyl, alkynyl, cycloalkyl, aryl, heterocyclyl, and heteroaryl groups is optionally substituted with one or more independently selected R$^{30}$;

$R^9$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

X is independently selected from the group consisting of O, S, and N(R$^{14}$);

E is O or S;

B is N or CR$^{1d}$;

$R^{1d}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

$R^{11}$ is independently selected from the group consisting of H, alkyl, alkenyl, alkynyl, cycloalkyl, aryl, heteroaryl, and heterocyclyl, wherein each of the alkyl, alkynyl, cycloalkyl, aryl, heteroaryl, and heterocyclyl groups is optionally substituted with one or more independently selected R$^{30}$;

each of R$^{12}$ and R$^{13}$ is independently selected from the group consisting of H, alkyl, alkenyl, alkynyl, cycloalkyl, aryl, heteroaryl, and heterocyclyl, or R$^{12}$ and R$^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more independently selected R$^{30}$;

$R^{14}$ is independently selected from the group consisting of H, alkyl, alkenyl, alkynyl, cycloalkyl, aryl, heteroaryl, heterocyclyl, and —OR$^{11}$, wherein each of the alkyl, alkenyl, alkynyl, cycloalkyl, aryl, heteroaryl, and heterocyclyl groups is optionally substituted with one or more independently selected R$^{30}$;

each of R$^{15}$ and R$^{16}$ is independently selected from the group consisting of H, alkyl, alkenyl, alkynyl, cycloalkyl, aryl, heteroaryl, heterocyclyl, and —NH$_y$R$^{20}_{2-y}$, or R$^{15}$ and R$^{16}$ may join together with the atom to which they are attached to form a ring which is optionally substituted with one or more independently selected R$^{30}$, wherein each of the alkyl, alkenyl, alkynyl, cycloalkyl, aryl, heteroaryl, and heterocyclyl groups is optionally substituted with one or more independently selected R$^{30}$;

y is an integer from 0 to 2;

$R^{20}$ is independently selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected R$^{30}$; and $R^{30}$ is a 1$^{st}$ level substituent and is, in each case, independently selected from the group consisting of alkyl, alkenyl, alkynyl, aryl, heteroaryl, cycloalkyl, heterocyclyl, halogen, —CN, azido, —NO$_2$, —OR$^{71}$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$R$^{71}$, —NR$^{71}$S(O)$_{1-2}$OR$^{71}$, —NR$^{71}$S(O)$_{1-2}$N(R$^{72}$)(R$^{73}$), —P(O)(OR$^{71}$)$_2$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two R$^{30}$ which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups being a 1$^{st}$ level substituent is optionally substituted by one or more 2$^{nd}$ level substituents, wherein said 2$^{nd}$ level substituent is, in each case, independently selected from the group consisting of C$_{1-6}$ alkyl, C$_{2-6}$ alkenyl, C$_{2-6}$ alkynyl, 6- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —S(O)$_{0-2}$R$^{81}$, —S(O)$_{1-2}$OR$^{81}$, —OS(O)$_{1-2}$R$^{81}$, —OS(O)$_{1-2}$OR$^{81}$, —S(O)$_{1-2}$N(R$^{82}$)(R$^{83}$), —OS(O)$_{1-2}$N(R$^{82}$)(R$^{83}$), —N(R$^{81}$)S(O)$_{1-2}$R$^{81}$, —NR$^{8'}$S(O)$_{1-2}$OR$^{81}$, —NR$^{81}$S(O)$_{1-2}$N(R$^{82}$)(R$^{83}$), —OP(O)(OR$^{81}$)$_2$, —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two 2$^{nd}$ level substituents which are bound to the same carbon atom of a cycloalkyl or heterocyclyl group being a 1$^{st}$ level substituent may join together to form =X$^2$, wherein each of the C$_{1-6}$ alkyl, C$_{2-6}$ alkenyl, C$_{2-6}$ alkynyl, 6- to 14-membered aryl, 3- to 14-membered heteroaryl, 3- to 14-membered cycloalkyl, 3- to 14-membered heterocyclyl groups being a 2$^{nd}$ level substituent is optionally substituted with one or more 3$^{rd}$ level substituents, wherein said 3$^{rd}$ level substituent is, in each case, independently selected from the group consisting of C$_{1-3}$ alkyl, halogen, —CF$_3$, —CN, azido, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein each z is independently 0, 1, or 2 and each C$_{1-3}$ alkyl is methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N(C$_{1-3}$ alkyl);

wherein
each of R$^{71}$, R$^{72}$, and R$^{73}$ is independently selected from the group consisting of H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents independently selected from the group consisting of C$_{1-3}$ alkyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein each z is independently 0, 1, or 2 and each C$_{1-3}$ alkyl is independently methyl, ethyl, propyl or isopropyl;
each of R$^{81}$, R$^{82}$, and R$^{83}$ is independently selected from the group consisting of H, C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl, wherein each of the C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents independently selected from the group consisting of C$_{1-3}$ alkyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein each z is independently 0, 1, or 2 and each C$_{1-3}$ alkyl is independently methyl, ethyl, propyl or isopropyl; and
each of X$^1$ and X$^2$ is independently selected from O, S, and N(R$^{84}$), wherein R$^{84}$ is H or C$_{1-3}$ alkyl.

In one embodiment, the kinase inhibitor has the formula (II):

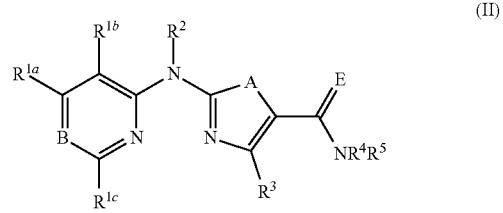

(II)

wherein R$^{1b}$, R$^{1c}$, R$^2$, R$^3$, R$^4$, R$^5$, A, B, and E are as defined above (in particular with respect to formula (I)) or below, and R$^{1a}$ is selected from the group consisting of alkyl, —O(alkyl), —S(alkyl), —NH(alkyl), —N(alkyl)$_2$, and heterocyclyl, wherein each of the alkyl and heterocyclyl groups is optionally substituted with one or more (e.g., one, two, or three) independently selected R$^{30}$. Preferably, each R$^{30}$ is independently a 1$^{st}$ level substituent, a 2$^{nd}$ level substituent, or a 3$^{rd}$ level substituent as specified herein, such as alkyl (e.g., C$_{1-6}$ alkyl), —(CH$_2$)$_{1-3}$OH, alkenyl (e.g., C$_{2-6}$ alkenyl), alkynyl (e.g., C$_{2-6}$ alkynyl), halogen, —CN, nitro, —OR$^{11}$ (e.g., —OH), —SR$^{11}$ (e.g., —SH), —N(R$^{12}$)(R$^{13}$) (e.g., —NH$_2$), and —C(=O)R$^{11}$ (e.g., —C(=O)(C$_{1-3}$ alkyl)).

In one embodiment of the kinase inhibitor of formula (II), R$^{1b}$, R$^{1c}$, R$^2$, R$^3$, R$^4$, R$^1$, A, B, and E are as defined above (in particular with respect to formula (I)) or below, and R$^{1a}$ is selected from the group consisting of C$_{1-3}$ alkyl, —O(C$_{1-3}$ alkyl), —S(C$_{1-3}$ alkyl), —NH(C$_{1-3}$ alkyl), —N(C$_{1-3}$ alkyl)$_2$, and 3- to 7-membered heterocyclyl, wherein the 3- to 7-membered heterocyclyl group is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)(C$_{1-3}$ alkyl), —(CH$_2$)$_{1-3}$COOH, and —NH$_{2-z}$(CH$_3$)$_z$, wherein z is 0, 1, or 2; and each of the C$_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2.

In one embodiment of the kinase inhibitor of formula (II), R$^{1b}$, R$^{1c}$, R$^2$, R$^3$, R$^4$, R$^5$, A, B, and E are as defined above (in particular with respect to formula (I)) or below, and $R^{1a}$ is selected from the group consisting of $C_{1-3}$ alkyl, —O($C_{1-3}$ alkyl), —S($C_{1-3}$ alkyl), —NH($C_{1-3}$ alkyl), piperazinyl, morpholinyl, piperidinyl, and pyrrolidinyl, wherein each of the piperazinyl, morpholinyl, piperidinyl, and pyrrolidinyl groups is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)($C_{1-3}$ alkyl), —(CH$_2$)$_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2.

In one embodiment of the kinase inhibitor of formula (II), $R^{1b}$, $R^{1c}$, $R^2$, $R^3$, $R^4$, $R^5$, A, B, and E are as defined above (in particular with respect to formula (I)) or below, and $R^{1a}$ is selected from the group consisting of —NH($C_{1-3}$ alkyl), piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the $C_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2.

In one embodiment of the kinase inhibitor of formula (II), $R^{1b}$, $R^{1c}$, $R^2$, $R^3$, $R^4$, $R^5$, A, B, and E are as defined above (in particular with respect to formula (I)) or below, and $R^{1a}$ is selected from the group consisting of 4-(2-hydroxyethyl)piperazinyl, 4-methylpiperazinyl, 4-acetylpiperazinyl, (2-hydroxyethyl)amino, 4-aminopiperidinyl, 4-(4-methylpiperazinyl)piperidinyl, (4-carboxymethylpiperazinyl), and 3-hydroxypyrrolidinyl, such as from the group consisting of 4-(2-hydroxyethyl)piperazinyl, 4-methylpiperazinyl, 4-acetylpiperazinyl, and (2-hydroxyethyl)amino.

In an alternative embodiment of the kinase inhibitor of formula (II), $R^{1b}$, $R^{1c}$, $R^2$, $R^3$, $R^4$, $R^5$, A, B, and E are as defined above (in particular with respect to formula (I)) or below, and $R^{1a}$ is a leaving group (e.g., a halogen (such as Cl, Br, or F), nitro, benzotriazol-1-yloxy, $C_1$-$C_{10}$ alkylsulfonate, $C_1$-$C_{10}$ haloalkylsulfonate, nonaflate (CF$_3$CF$_2$CF$_2$CF$_2$SO$_3$—), CF$_3$C(=O)O—, phenylsulfonate (wherein the phenyl is optionally substituted with 1, 2, or 3 groups which are each independently selected from halogen and $C_1$-$C_4$ alkyl), or an ammonium salt of the formula —[N($R^x$)($R^y$)($R^z$)]$^+$[G]$^-$, wherein $R^x$, $R^y$, and $R^z$ are independently hydrogen or alkyl, and G is the conjugate base of a strong acid (e.g., G$^-$ is Cl$^-$)).

In one embodiment, the kinase inhibitor has the general formula (III)

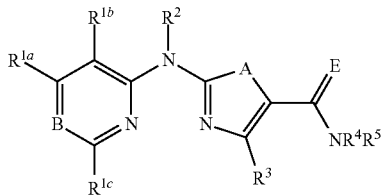

(III)

wherein $R^{1a}$, $R^2$, $R^3$, $R^4$, $R^5$, A, B, and E are as defined above (in particular with respect to formula (I) and/or (II)) or below, and each of $R^{1b}$ and $R^{1c}$ is independently selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, phenyl, pyridinyl, pyrazolyl, phenoxy, pyridinyloxy, imidazolylamino, and tetrahydrofuranylmethoxy, wherein z is 0, 1, or 2; and each of the phenyl, pyridinyl, pyrazolyl, phenoxy, pyridinyloxy, imidazolylamino, and tetrahydrofuranylmethoxy groups is optionally substituted with one, two or three moieties independently selected from methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, and —NH$_{2-z}$(CH$_3$)$_z$, wherein z is 0, 1, or 2.

In one embodiment of the kinase inhibitor of formula (III), $R^{1a}$, $R^2$, $R^3$, $R^4$, $R^5$, A, B, and E are as defined above (in particular with respect to formula (I) and/or (II)) or below, and at least one of $R^{1b}$ and $R^{1c}$ is selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, and phenyl, wherein z is 0, 1, or 2. In this embodiment, the other of $R^{1b}$ and $R^{1c}$ may be as defined above (in particular with respect to formula (I), (II) and/or (III)), e.g., the other of $R^{1b}$ and $R^{1c}$ may be selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, phenyl, pyridinyl, pyrazolyl, phenoxy, pyridinyloxy, imidazolylamino, and tetrahydrofuranylmethoxy, wherein z is 0, 1, or 2; and wherein each of the phenyl, pyridinyl, pyrazolyl, phenoxy, pyridinyloxy, imidazolylamino, and tetrahydrofuranylmethoxy groups is optionally substituted with one, two or three moieties independently selected from methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, and —NH$_{2-z}$(CH$_3$)$_z$, wherein z is 0, 1, or 2. Alternatively, each of $R^{1b}$ and $R^{1c}$ is independently selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, and phenyl, wherein z is 0, 1, or 2.

In one embodiment of the kinase inhibitor of formula (III), $R^{1a}$, $R^2$, $R^3$, $R^4$, $R^5$, A, B, and E are as defined above (in particular with respect to formula (I) and/or (II)) or below, and $R^{1b}$ is methyl, ethyl, propyl, or isopropyl, preferably methyl; and $R^{1c}$ is H. In an alternative embodiment, $R^{1b}$ is H; and $R^{1c}$ is methyl, ethyl, propyl, isopropyl, or phenyl, preferably methyl.

In a related aspect, the present invention provides a compound selected from the group consisting of a kinase inhibitor of the formula (Ia):

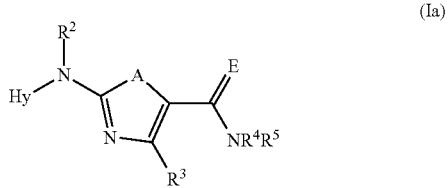

(Ia)

and solvates, salts, N-oxides, complexes, polymorphs, crystalline forms, racemic mixtures, diastereomers, enantiomers, tautomers, conformers, isotopically labeled forms, prodrugs, and combinations thereof; wherein each of $R^2$, $R^3$, $R^4$, A and E are independently as defined above (in particular with respect to formula (I)) or below (in particular with respect to formula (IV), (VI), (VII), and/or (VIII)); $R^5$ is -L-$R^6$, wherein L is a bond, and $R^6$ is a 5- or 6-membered heteroaryl which is optionally substituted with one or more independently selected $R^7$ (in particular, $R^6$ is a 5- or 6-membered heteroaryl optionally substituted with one or more independently selected $R^7$ as defined with respect to formula (V) below); Hy is a heteroaryl or heterocyclyl which is optionally substituted with one or more (such as 1 to the maximum number of hydrogen atoms bound to the heteroaryl or heterocyclyl group, e.g., 1, 2, 3, 4, 5, 6, 7, 8, 9, or up to 10, such as between 1 to 5, 1 to 4, or 1 to 3, or 1 or 2) independently selected $R^{1e}$; each $R^{1e}$ is independently selected from the group consisting of $R^{1a}$, $R^{1b}$, $R^{1c}$ and $R^{1d}$; and each of $R^{1a}$, $R^{1b}$ $R^{1c}$ and $R^{1d}$ is independently as defined above (in particular with respect to formula (I), (II), and/or (III)) or below (in particular with respect to formula (VII) and/or (VIII)).

In one embodiment of the kinase inhibitor of formula (Ia), $R^2$, $R^3$, $R^4$, A and E are independently as defined above (in particular with respect to formula (I)) or below (in particular with respect to formula (IV), (VI), (VII), and/or (VIII)), $R^6$ is a 5- or 6-membered heteroaryl which is optionally substituted with one or more independently selected $R^7$ (in particular, $R^6$ is a 5- or 6-membered heteroaryl optionally substituted with one or more independently selected $R^7$ as defined with respect to formula (V) below); and Hy is a 3- to 10-membered heteroaryl or a 3- to 10-membered heterocyclyl, each of which is optionally substituted with one, two, three, four, five, or six independently selected $R^{1e}$. In one embodiment of the kinase inhibitor of formula (Ia), $R^2$, $R^3$, $R^4$, A and E are independently as defined above (in particular with respect to formula (I)) or below (in particular with respect to formula (IV), (VI), (VII), and/or (VIII)); $R^6$ is a 5- or 6-membered heteroaryl which is optionally substituted with one or more independently selected $R^7$ (in particular, $R^6$ is a 5- or 6-membered heteroaryl optionally substituted with one or more independently selected $R^7$ as defined with respect to formula (V) below); and Hy is a mono- or bicyclic heteroaryl or a mono- or bicyclic heterocyclyl, each of which is optionally substituted with one, two, three, four, five, or six independently selected $R^{1e}$. In one embodiment of the kinase inhibitor of formula (Ia), $R^2$, $R^3$, $R^4$, A and E are independently as defined above (in particular with respect to formula (I)) or below (in particular with respect to formula (IV), (VI), (VII), and/or (VIII)); $R^6$ is a 5- or 6-membered heteroaryl which is optionally substituted with one or more independently selected $R^7$ (in particular, $R^6$ is a 5- or 6-membered heteroaryl optionally substituted with one or more independently selected $R^7$ as defined with respect to formula (V) below); and Hy is selected from the group consisting of a 5- to 6-membered monocyclic heteroaryl, a 5- to 6-membered monocyclic heterocyclyl, a 9- to 10-membered bicyclic heteroaryl, and a 8- to 10-membered bicyclic heterocyclyl, each of which is optionally substituted with one, two, three, four, five, or six independently selected $R^{1e}$. In one embodiment of the kinase inhibitor of formula (Ia), $R^2$, $R^3$, $R^4$, A and E are independently as defined above (in particular with respect to formula (I)) or below (in particular with respect to formula (IV), (VI), (VII), and/or (VIII)); $R^6$ is a 5- or 6-membered heteroaryl which is optionally substituted with one or more independently selected $R^7$ (in particular, $R^6$ is a 5- or 6-membered heteroaryl optionally substituted with one or more independently selected $R^7$ as defined with respect to formula (V) below); and Hy is selected from the group consisting of pyridinyl, pyrimidinyl, pyrazinyl, pyridazinyl, triazinyl (e.g., 1,2,3-triazinyl, 1,2,4-triazinyl, 1,3,5-triazinyl), pyrazolyl, oxadiazolyl, thiazolyl, triazolyl, thiadiazolyl, cyclopentapyrimidinyl, dihydrocyclopentapyrimidinyl, pyrrolopyrimidinyl, indolizinyl, dihydroindolizinyl, teterahydroindolizinyl, quinazolinyl, dihydroquinazolinyl, tetrahydroquinazolinyl, pyridopyrimidinyl, pyranopyrimidinyl, dihydropyranopyrimidinyl, tetrahydropyranopyrimidinyl, piperidinyl, tetrahydropyranyl, and 1,1-dioxidotetrahydrothiopyranyl, each of which is optionally substituted with one, two, three, four, five, or six independently selected $R^{1e}$. In one embodiment of the kinase inhibitor of formula (Ia), $R^2$, $R^3$, $R^4$, A and E are independently as defined above (in particular with respect to formula (I)) or below (in particular with respect to formula (IV), (VI), (VII), and/or (VIII)); $R^6$ is a 5- or 6-membered heteroaryl which is optionally substituted with one or more independently selected $R^7$ (in particular, $R^6$ is a 5- or 6-membered heteroaryl optionally substituted with one or more independently selected $R^7$ as defined with respect to formula (V) below); and Hy is selected from the group consisting of:

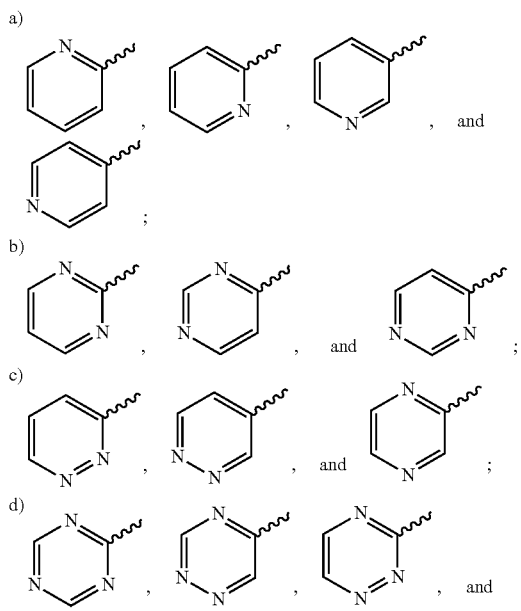

-continued

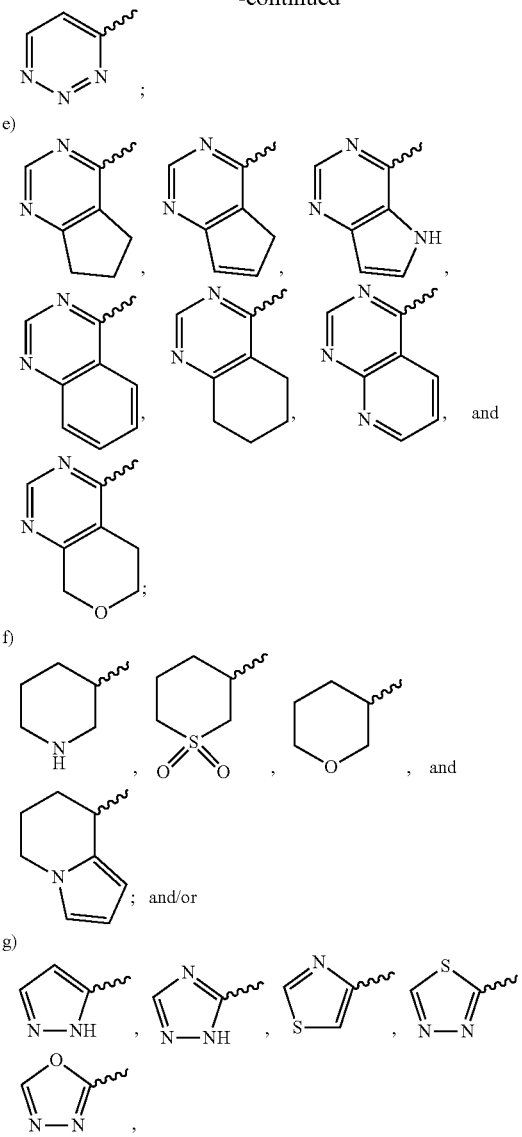

f)

g)

wherein each of the groups specified under a), b), c), d), e), f), and g) above is optionally substituted with one, two, three, four, five, or six independently selected $R^{1e}$, and wherein ⁓⁓⁓ represents the bond by which Hy is attached to the nitrogen atom of the $NR^2$ moiety in formula (Ia). In case Hy contains an NH moiety as ring member, it is preferred that the hydrogen atom is replaced with alkyl, such as $C_{1-6}$ or $C_{1-3}$ alkyl, more preferably methyl (resulting in an alkyl substituted N ring atom), and Hy is optionally further substituted with one, two, three, four, or five independently selected $R^{1e}$. Examples of such N alkyl substituted Hy groups include

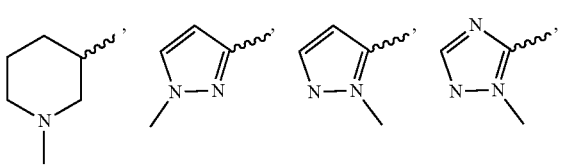

-continued
and

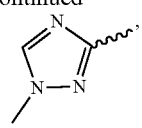

wherein ⁓⁓⁓ represents the bond by which Hy is attached to the nitrogen atom of the $NR^2$ moiety in formula (Ia).

In any of the above embodiments of the kinase inhibitor of formula (Ia), Hy may be substituted with one $R^{1b}$, one $R^{1c}$ and between 1 and 4, such as 1, 2 or 3, $R^{1a}$ or $R^{1d}$; for example, Hy may be substituted with one (or two) $R^{1a}$ and (as defined above, in particular with respect to formula (II), or below), and with one (or two) of $R^{1b}$ or $R^{1c}$ (as defined above, in particular with respect to formula (III), or below), and all other $R^{1e}$ are H.

In any of the above embodiments of the kinase inhibitor of formula (Ia), it is preferred that A is S and/or E is O.

In one embodiment, the kinase inhibitor has the general formula (IV)

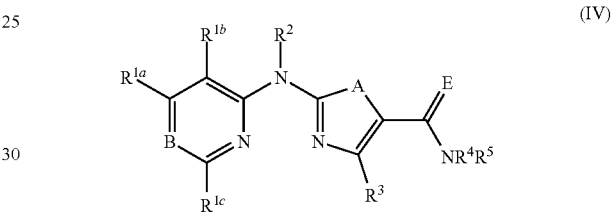

(IV)

wherein $R^{1a}$, $R^{1b}$, $R^{1c}$, $R^2$, $R^4$, $R^5$, A, B, and E are as defined above (in particular with respect to formula (I), (II), and/or (III)) or below, and $R^3$ is selected from the group consisting of H, $C_{1-6}$ alkyl, $C_{2-6}$ alkenyl, $C_{2-6}$ alkynyl, $C_{3-6}$ cycloalkyl, phenyl, halogen, —CN, azido, —NO$_2$, —O($C_{1-6}$ alkyl), —OCF$_3$, —S($C_{1-6}$ alkyl), —NH$_2$, —NH($C_{1-6}$ alkyl), —N($C_{1-6}$ alkyl)$_2$, —NHS(O)$_2$($C_{1-6}$ alkyl), —S(O)$_2$NH$_{2-z}$ ($C_{1-6}$ alkyl)$_z$, —C(=O)($C_{1-6}$ alkyl), —C(=O)OH, —C(=O)O($C_{1-6}$ alkyl), —C(=O)NH$_{2-z}$($C_{1-6}$ alkyl)$_z$, —NHC(=O)($C_{1-6}$ alkyl), —NHC(=NH)NH$_{2-z}$($C_{1-6}$ alkyl)$_z$, and —N($C_{1-6}$ alkyl)C(=NH)NH$_{2-z}$($C_{1-6}$ alkyl)$_z$, wherein z is 0, 1, or 2 and wherein each of the $C_{1-6}$ alkyl, $C_{2-6}$ alkenyl, $C_{2-6}$ alkynyl, $C_{3-6}$ cycloalkyl, and phenyl groups is optionally substituted with one or more independently selected $R^{30}$.

In one embodiment of the kinase inhibitor of formula (IV), $R^{1a}$, $R^{1b}$, $R^{1c}$, $R^2$, $R^4$, $R^5$, A, B, and E are as defined above (in particular with respect to formula (I), (II), and/or (III)) or below, and $R^3$ is selected from the group consisting of H, $C_{1-4}$ alkyl, $C_{3-6}$ cycloalkyl, phenyl, halogen, —CN, —O($C_{1-4}$ alkyl), —OCF$_3$, —S($C_{1-4}$ alkyl), —NH$_2$, —NH ($C_{1-4}$ alkyl), —N($C_{1-4}$ alkyl)$_2$, —C(=O)($C_{1-4}$ alkyl), —C(=O)OH, —C(=O)O($C_{1-4}$ alkyl), —C(=O)NH$_{2-z}$ ($C_{1-4}$ alkyl)$_z$, —NHC(=O)($C_{1-4}$ alkyl), —NHC(=NH) NH$_{2-z}$(Cia alkyl)$_z$, and —N(Cia alkyl)C(=NH)NH$_{2-z}$($C_{1-4}$ alkyl)$_z$, wherein the phenyl group is optionally substituted with one, two or groups independently selected from the group consisting of halogen, methyl, isopropyl, —CN, —CF$_3$, —OCF$_3$, —OH, —NH$_2$, —NH($C_{1-3}$ alkyl), —N($C_{1-3}$ alkyl)$_2$, —NHC(=O)($C_{1-3}$ alkyl), —C(=O) NH$_{2-z}$($C_{1-3}$ alkyl)$_z$, —(CH$_2$)$_{1-3}$NH$_2$, —(CH$_2$)$_{1-3}$NH($C_{1-3}$ alkyl), —(CH$_2$)$_{1-3}$N($C_{1-3}$ alkyl)$_2$, —(CH$_2$)$_{1-3}$OH, and —(CH$_2$)$_{1-3}$O($C_{1-3}$ alkyl); and wherein z is 0, 1, or 2.

In one embodiment of the kinase inhibitor of formula (IV), $R^{1a}$, $R^{1b}$, $R^{1c}$, $R^2$, $R^4$, $R^5$, A, B, and E are as defined above (in particular with respect to formula (I), (II), and/or (III)) or below, and $R^3$ is selected from the group consisting of H, methyl, ethyl, propyl, isopropyl, phenyl, and halogen.

In one embodiment of the kinase inhibitor of formula (IV), $R^{1a}$, $R^{1b}$, $R^{1c}$, $R^2$, $R^4$, $R^5$, A, B, and E are as defined above (in particular with respect to formula (I), (II), and/or (III)) or below, and $R^3$ is H.

In one embodiment, the kinase inhibitor has the general formula (V)

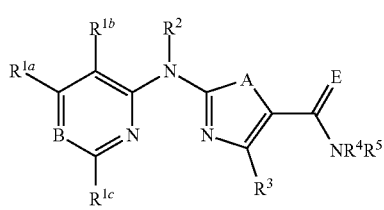

(V)

wherein $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^5$ is -L-$R^6$, wherein $R^6$ is a heteroaryl containing at least one ring heteroatom selected from the group consisting of N, O, and S, or is a heterocyclyl containing at least one ring heteroatom selected from the group consisting of N, O, and S, wherein each of the heteroaryl and heterocyclyl groups is optionally substituted with one, two, or three independently selected $R^7$. For example, $R^6$ may be a heteroaryl containing at least one ring heteroatom selected from the group consisting of N and O (i.e., the heteroaryl does not contain S as ring heteroatom; and in some embodiments does not contain 0 as ring heteroatom, i.e., $R^6$ may by an N-heteroaryl), or is a heterocyclyl containing at least one ring heteroatom selected from the group consisting of N and O (i.e., the heterocyclyl does not contain S as ring heteroatom; and in some embodiments does not contain 0 as ring heteroatom, i.e., $R^6$ may by an N-heterocyclyl), wherein each of the heteroaryl and heterocyclyl groups is optionally substituted with one, two, or three independently selected $R^7$.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected $R^7$.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is a mono- or bicyclic heteroaryl (e.g., containing at least one ring heteroatom selected from the group consisting of N, O, and S, such as from the group consisting of N and O) or a mono- or bicyclic heterocyclyl (e.g., containing at least one ring heteroatom selected from the group consisting of N, O, and S, such as from the group consisting of N and O), each of which is optionally substituted with one, two, or three independently selected $R^7$.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is selected from the group consisting of a 5- to 6-membered monocyclic heteroaryl (e.g., containing at least one ring heteroatom selected from the group consisting of N, O, and S, such as from the group consisting of N and O), a 4- to 6-membered monocyclic heterocyclyl (e.g., containing at least one ring heteroatom selected from the group consisting of N, O, and S, such as from the group consisting of N and O), a 7- to 9-membered bicyclic heteroaryl (e.g., containing at least one ring heteroatom selected from the group consisting of N, O, and S, such as from the group consisting of N and O), and a 7- to 9-membered bicyclic heterocyclyl (e.g., containing at least one ring heteroatom selected from the group consisting of N, O, and S, such as from the group consisting of N and O), each of which is optionally substituted with one, two, or three independently selected $R^7$.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is a 5- to 6-membered monocyclic heteroaryl (e.g., containing at least one ring heteroatom selected from the group consisting of N, O, and S, such as from the group consisting of N and O), which is optionally substituted with one, two, or three independently selected $R^7$.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is a 7- to 9-membered bicyclic heterocyclyl (e.g., containing at least one ring heteroatom selected from the group consisting of N, O, and S, such as from the group consisting of N and O), which is optionally substituted with one, two, or three independently selected $R^7$.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is selected from the group consisting of pyridinyl, thienyl, pyridazinyl, furanyl, pyrrolyl, pyrazolyl, oxazolyl, isoxazolyl, oxadiazolyl, imidazoimidazolyl, indolyl, naphthyridinyl, thienopyridinyl, tetrahydropyranyl, piperidinyl, pyrrolidinyl, azetidinyl, azabicycloheptanyl, azabicyclooctanyl, azapentacyclooctanyl, piperazinyl, morpholinyl, and tetrahydrothiophenyl, each of which is optionally substituted with one, two, or three independently selected $R^7$, preferably $R^6$ is selected from the group consisting of pyridinyl, thienyl, pyrazolyl, isoxazolyl, pyrrolyl, piperidinyl, pyrrolidinyl, azetidinyl, and azabicyclooctanyl, each of which is optionally substituted with one, two, or three independently selected $R^7$.

In any of the above embodiments of the kinase inhibitor of formula (V) (including those of formulas (I), (II), (III), and (IV)), $R^7$ may be independently selected from the group consisting of $C_{1-6}$ alkyl, $C_{2-6}$ alkenyl, $C_{2-6}$ alkynyl, halogen, —CN, —O($C_{1-6}$ alkyl), —NH($C_{1-6}$ alkyl), —N($C_{1-6}$ alkyl)$_2$, —NHS(O)$_{1-2}$($C_{1-6}$ alkyl), —NHS(O)$_{1-20}$($C_{1-6}$ alkyl), —C(=O)($C_{1-6}$ alkyl), and —OC(=O)($C_{1-6}$ alkyl), and/or any two $R^7$ which are bound to the same atom of $R^6$ being a heterocyclyl group may join together to form =O, wherein each of the $C_{1-6}$ alkyl, $C_{2-6}$ alkenyl, and $C_{2-6}$ alkynyl groups is optionally substituted with one or more independently selected $R^{30}$. For example, $R^7$ may be independently selected from the group consisting of $C_{1-3}$ alkyl, halogen, —CN, —O($C_{1-3}$ alkyl), —NH($C_{1-3}$ alkyl), and —N($C_{1-3}$ alkyl)$_2$, and/or any two R$^7$ which are bound to the same atom of R$^6$ being a heterocyclyl group may join together to form =O, wherein each of the C$_{1-3}$ alkyl groups is optionally substituted with one or more independently selected R$^{30}$. In any of the above embodiments of the kinase inhibitor of formula (V) (including those of formulas (I), (II), (III), and (IV)), R$^7$ may be independently selected from the group consisting of Cl, Br, methyl, and ethyl, such as from the group consisting of C$_1$, Br, and methyl.

In any of the above embodiments of the kinase inhibitor of formula (V) (including those of formulas (I), (II), (III), and (IV)), where R$^6$ is substituted, it is preferred that one R$^7$ group is bound to a ring atom of R$^6$ at position 2 relative to the ring atom by which R$^6$ is bound to the remainder of the compound (i.e., it is preferred that R$^6$ bears an ortho R$^7$ group). In any of the above embodiments of the kinase inhibitor of formula (V) (including those of formulas (I), (II), (III), and (IV)), where R$^6$ is substituted with two or more (such as two, three, or four) R$^7$ groups, it is preferred that one of the two or more R$^7$ groups is bound to a ring atom of R$^6$ at position 2 relative to the ring atom by which R$^6$ is bound to the remainder of the compound (i.e., R$^6$ bears an ortho R$^7$ group), and the remaining R$^7$ group(s) is (are) attached to ring atom(s) of R$^6$ at positions other than position 2. E.g., in any of the above embodiments of the kinase inhibitor of formula (V) (including those of formulas (I), (II), (III), and (IV)), where R$^6$ is an k-membered ring substituted with two or more R$^7$ groups, it is preferred that one of the two or more R$^7$ groups is bound to a ring atom of R$^6$ at position 2 relative to the ring atom by which R$^6$ is bound to the remainder of the compound (i.e., relative to the yl position) and that the remaining R$^7$ group(s) is (are) bound to ring atoms of R$^6$ at positions other than position 2, e.g., at position 3, 4, 5, . . . k. For example, in case R$^6$ is a 5-membered ring, it is preferred that one of the two or more R$^7$ groups is bound to a ring atom of R$^6$ at position 2 (relative to the yl position) and that the remaining R$^7$ group(s) is (are) bound to ring atoms of R$^6$ at positions 3, 4, or 5 (relative to the yl position). Moreover, in any of the above embodiments of the kinase inhibitor of formula (V) (including those of formulas (I), (II), (III), and (IV)), where R$^6$ is substituted with two or more (such as two, three, or four) R$^7$ groups, it is preferred that each of the two ring atoms directly adjacent to the ring atom by which R$^6$ is attached to the remainder of the compound bears one R$^7$ group (e.g., R$^6$ being an k-membered ring bears one R$^7$ group at each of positions 2 and k, relative to the ring atom by which R$^6$ is bound to the remainder of the compound, e.g., R$^6$ is substituted at both of its ortho positions). Additionally, in any of the above embodiments of the kinase inhibitor of formula (V) (including those of formulas (I), (II), (III), and (IV)), where R$^6$ is substituted with three or more (such as three or four) R$^7$ groups, it is preferred that each of the two ring atoms directly adjacent to the ring atom by which R$^6$ is attached to the remainder of the compound bears one R$^7$ group (e.g., R$^6$ being an k-membered ring bears one R$^7$ group at each of positions 2 and k, relative to the ring atom by which R$^6$ is bound to the remainder of the compound, e.g., R$^6$ is substituted at both of its ortho positions), and that the third R$^7$ group is bound to a ring atom of R$^6$ which is directly adjacent to one of the ortho ring atoms but which is not the ring atom by which R$^6$ is bound to the remainder of the compound (e.g., R$^6$ being an k-membered ring bears the third R$^7$ group at one of positions 3 and k-1, relative to the ring atom by which R$^6$ is bound to the remainder of the compound).

In one embodiment of the kinase inhibitor of formula (V), R$^{1a}$, R$^{1b}$, R$^{1c}$, R$^2$, R$^3$, R$^4$, A, B, and E are as defined above (in particular with respect to formula (I), (II), (III), and/or (IV)) or below, and R$^6$ is selected from the following formulas:

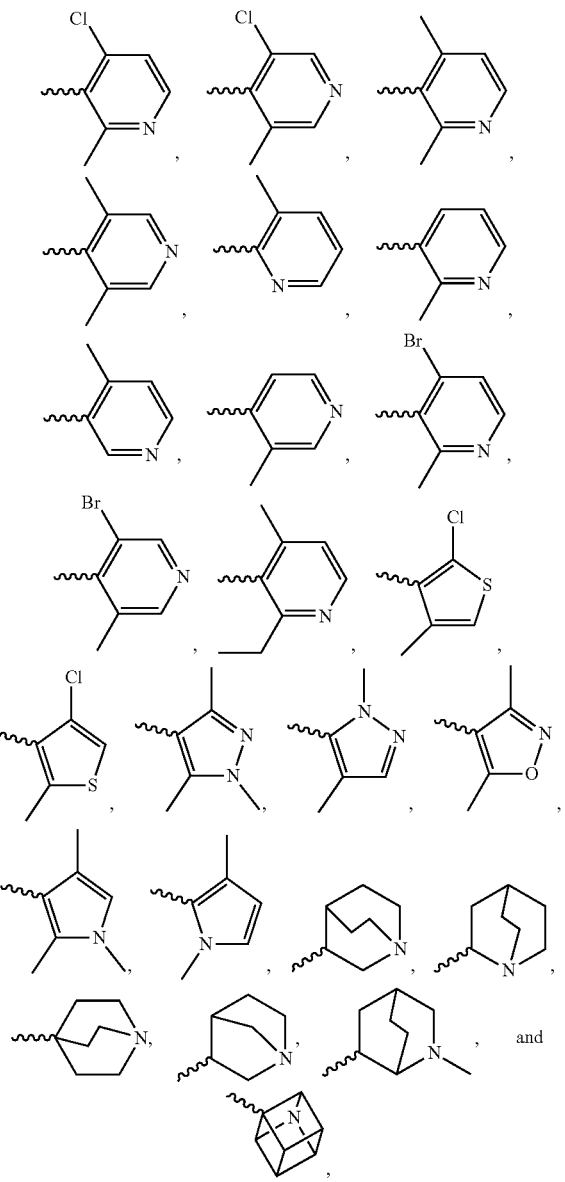

wherein ∿∿∿ represents the bond by which R$^6$ is bound to the remainder of the compound.

In one embodiment of the kinase inhibitor of formula (V), R$^{1a}$, R$^{1b}$, R$^{1c}$, R$^2$, R$^3$, R$^4$, A, B, and E are as defined above (in particular with respect to formula (I), (II), (III), and/or (IV)) or below, and R$^6$ is selected from the following formulas:

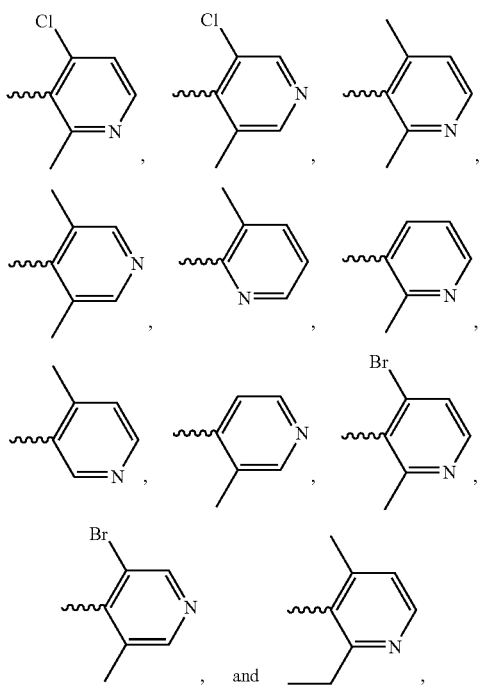

wherein ~~~ represents the bond by which $R^6$ is bound to the remainder of the compound.

In one embodiment of the kinase inhibitor of formula (V), $R^a$, $R^{1b}$, $R^{1c}$, $R^2$, $R^3$, $R^4$, A, B, and E are as defined above (in particular with respect to formula (I), (II), (III), and/or (IV)) or below, and $R^6$ is selected from the following formulas:

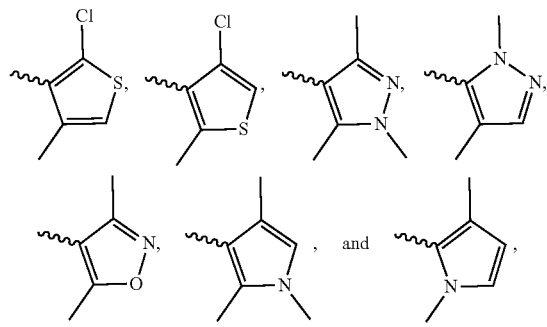

wherein ~~~ represents the bond by which $R^6$ is bound to the remainder of the compound.

In one embodiment of the kinase inhibitor of formula (V), $R^{1a}$, $R^{1b}$, $R^{1c}$, $R^2$, $R^3$, $R^4$, A, B, and E are as defined above (in particular with respect to formula (I), (II), (III), and/or (IV)) or below, and $R^6$ is selected from the following formulas:

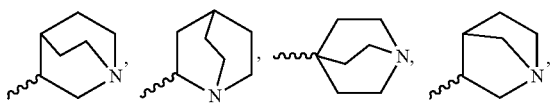

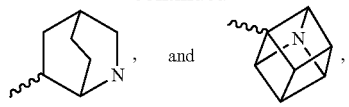

wherein ~~~ represents the bond by which $R^6$ is bound to the remainder of the compound.

In any of the above embodiments of the kinase inhibitor of formula (V) (including those of formulas (I), (II), (III), and (IV)), L may be selected from the group consisting of a bond, $C_{1-6}$ alkylene, $C_{2-6}$ alkenylene, $C_{2-6}$ alkynylene, and $-(CH_2)_m-[Y-(CH_2)_n]_o-$, wherein m is 1, 2, or 3, n is 0, 1, or 2, o is 1, 2, or 3, wherein if n is 0 then o is 1; Y is independently selected from O, S, and NH, wherein each of the $C_{1-6}$ alkylene, $C_{2-6}$ alkenylene, $C_{2-6}$ alkynylene, $-(CH_2)_m-$, and $-(CH_2)_n-$ groups is optionally substituted with one or more independently selected $R^{30}$. For example, in any of the above embodiments of the kinase inhibitor of formula (V) (including those of formulas (I), (II), (III), and (IV)), L may be selected from the group consisting of a bond; $C_1$ alkylene, optionally substituted with one $R^{30}$; $C_2$ alkylene (in particular 1,2-ethylene or 1,1-ethylene), optionally substituted with one $R^{30}$; $C_3$ alkylene (in particular trimethylene), optionally substituted with one $R^{30}$; $C_4$ alkylene (in particular tetramethylene or 2,4-butandiyl), optionally substituted with one $R^{30}$; $-(CH_2)_mO-$; and $-(CH_2)_mNH-$, wherein m is 1, 2, or 3. Particularly, in any of the above embodiments of the kinase inhibitor of formula (V), (including those of formulas (I), (II), (III), and (IV)), L may be a bond.

In any of the above embodiments of the kinase inhibitor of formula (V) (including those of formulas (I), (II), (III), and (IV)), where $R^6$ is a heterocyclyl or heteroaryl (e.g., a 5-membered heteroaryl) containing an N atom as ring heteroatom, L may be attached to $R^6$ via the N ring atom of the heterocyclyl or heteroaryl group.

In one embodiment, the kinase inhibitor has the general formula (VI)

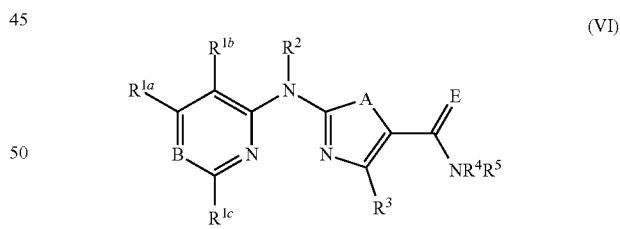

(VI)

wherein $R^{1a}$, $R^{1b}$, $R^{1c}$, $R^2$, $R^3$, $R^4$, $R^5$, B, and E are as defined above (in particular with respect to formula (I), (II), (III), (IV), and/or (V)) or below, and A is selected from the group consisting of S, O, NH, $N(C_{1-6}$ alkyl), and $C(C_{1-6}$ alkyl)$_2$. In any of the above embodiments of the kinase inhibitor of formula (VI), (including those of formulas (I), (II), (III), (IV), and (V)), A may be S, O, or $N(CH_3)_2$. In any of the above embodiments of the kinase inhibitor of formula (VI) (including those of formulas (I), (II), (III), (IV), and (V)), it is preferred that A is S.

In one embodiment, the kinase inhibitor has the general formula (VII)

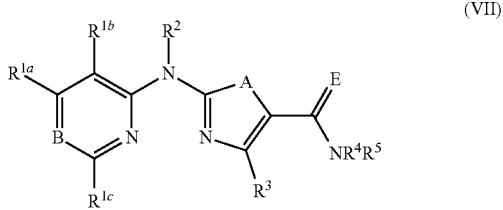

(VII)

wherein $R^{1a}$, $R^{1b}$, $R^{1c}$, $R^2$, $R^3$, $R^4$, $R^5$, and A are as defined above (in particular with respect to formula (I), (II), (III), (IV), (V), and/or (VI)) or below, E is O or S (preferably O), and B is N or $CR^{1d}$, wherein $R^{1d}$ is selected from the group consisting of $C_{1-3}$ alkyl, halogen, —O($C_{1-3}$ alkyl), —S($C_{1-3}$ alkyl), —NH($C_{1-3}$ alkyl), and —N($C_{1-3}$ alkyl)$_2$, wherein each of the $C_{1-3}$ alkyl groups is optionally substituted with one or two moieties independently selected from the group consisting of halogen, —OH, —OCH$_3$, —SCH, and —NH$_{2-z}$(CH$_3$)$_z$, wherein z is 0, 1, or 2. In any of the above embodiments of the kinase inhibitor of formula (VII) (including those of formulas (I), (II), (III), (IV), (V), and (VI)), E is O or S (preferably O), and B is N or $CR^{1d}$, wherein $R^{1d}$ may be selected from the group consisting of $C_{1-3}$ alkyl, halogen, —O($C_{1-3}$ alkyl), —S($C_{1-3}$ alkyl), —NH($C_{1-3}$ alkyl), and —N($C_{1-3}$ alkyl)$_2$. In any of the above embodiments of the kinase inhibitor of formula (VII) (including those of formulas (I), (II), (III), (IV), (V), and (VI)), it is preferred that B is N, and is more preferred that E is O and B is N.

In one embodiment, the kinase inhibitor has the general formula (VIII)

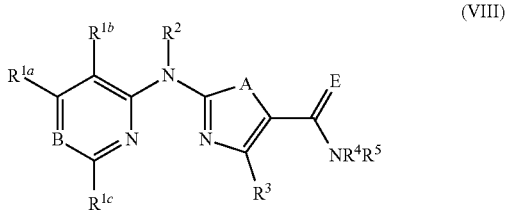

(VIII)

wherein $R^{1a}$, $R^{1b}$, $R^{1c}$, $R^2$, $R^3$, $R^4$, $R^1$, A, B, and E are as defined above (in particular with respect to formula (I), (II), (III), (IV), (V), (VI), and/or (VII)) or below, and is L is a bond. In preferred embodiments of the kinase inhibitor having general formula (VIII):

(A) $R^{1a}$ is selected from the group consisting of alkyl, —O(alkyl), —S(alkyl), —NH(alkyl), —N(alkyl)$_2$, and heterocyclyl, wherein each of the alkyl and heterocyclyl groups is optionally substituted with one or more (e.g., one, two, or three) independently selected $R^{30}$. Preferably, each $R^{30}$ is independently a $1^{st}$ level substituent, a $2^{nd}$ level substituent, or a $3^{rd}$ level substituent as specified herein, such as alkyl (e.g., $C_{1-6}$ alkyl), —(CH$_2$)$_{1-3}$OH, alkenyl (e.g., $C_{2-6}$ alkenyl), alkynyl (e.g., $C_{2-6}$ alkynyl), halogen, —CN, nitro, —OR$^{11}$ (e.g., —OH), —SR$^{11}$ (e.g., —SH), —N(R$^{12}$)(R$^{13}$) (e.g., —NH$_2$), and —C(=O)R$^{11}$ (e.g., —C(=O)(C$_{1-3}$ alkyl));

(B) each of $R^{1b}$ and $R^{1c}$ is independently selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, phenyl, pyridinyl, pyrazolyl, phenoxy, pyridinyloxy, imidazolylamino, and tetrahydrofuranylmethoxy, wherein z is 0, 1, or 2; and each of the phenyl, pyridinyl, pyrazolyl, phenoxy, pyridinyloxy, imidazolylamino, and tetrahydrofuranylmethoxy groups is optionally substituted with one, two or three moieties independently selected from methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, and —NH$_{2-z}$(CH$_3$)$_z$, wherein z is 0, 1, or 2;

(C) $R^3$ is selected from the group consisting of H, $C_{1-6}$ alkyl, $C_{2-6}$ alkenyl, $C_{2-6}$ alkynyl, $C_{3-6}$ cycloalkyl, phenyl, halogen, —CN, azido, —NO$_2$, —O($C_{1-6}$ alkyl), —OCF$_3$, —S($C_{1-6}$ alkyl), —NH$_2$, —NH($C_{1-6}$ alkyl), —N($C_{1-6}$ alkyl)$_2$, —NHS(O)$_2$($C_{1-6}$ alkyl), —S(O)$_2$NH$_{2-z}$($C_{1-6}$ alkyl)$_z$, —C(=O)($C_{1-6}$ alkyl), —C(=O)OH, —C(=O)O($C_{1-6}$ alkyl), —C(=O)NH$_{2-z}$($C_{1-6}$ alkyl)$_z$, —NHC(=O)($C_{1-6}$ alkyl), —NHC(=NH)NH$_{z-2}$ ($C_{1-6}$ alkyl)$_z$, and —N($C_{1-6}$ alkyl)C(=NH)NH$_{2-z}$ ($C_{1-6}$ alkyl)$_z$, wherein z is 0, 1, or 2 and wherein each of the $C_{1-6}$ alkyl, $C_{2-6}$ alkenyl, $C_{2-6}$ alkynyl, $C_{3-6}$ cycloalkyl, and phenyl groups is optionally substituted with one or more independently selected $R^{30}$;

(D) $R^6$ is as defined above (in particular with respect to formula (V)), and is preferably a 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected $R^7$;

(E) A is selected from the group consisting of S, O, NH, N($C_{1-6}$ alkyl), and C($C_{1-6}$ alkyl)$_2$;

(F) B is N or $CR^{1d}$, wherein $R^{1d}$ is selected from the group consisting of $C_{1-3}$ alkyl, halogen, —O($C_{1-3}$ alkyl), —S($C_{1-3}$ alkyl), —NH($C_{1-3}$ alkyl), and —N($C_{1-3}$ alkyl)$_2$, wherein each of the $C_{1-3}$ alkyl groups is optionally substituted with one or two moieties independently selected from the group consisting of halogen, —OH, —OCH$_3$, —SCH, and —NH$_{2-z}$(CH$_3$)$_z$, wherein z is 0, 1, or 2; and/or (G) E is O or S, preferably O.

In a preferred embodiment of the kinase inhibitor having general formula (VIII), $R^{1a}$ is as specified above under (A); $R^{1b}$ and $R^{1c}$ are as defined above under (B); $R^3$ is as specified above under (C); $R^6$ is as defined above (in particular with respect to formula (V)), and is preferably a 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected $R^7$; A is as specified above under (E); B is as specified above under (F); and E is as specified above under (G).

In further preferred embodiments of the kinase inhibitor having general formula (VIII):

(A') $R^{1a}$ is selected from the group consisting of $C_{1-3}$ alkyl, —O($C_{1-3}$ alkyl), —S($C_{1-3}$ alkyl), —NH($C_{1-3}$ alkyl), —N($C_{1-3}$ alkyl)$_2$, and 3- to 7-membered heterocyclyl, wherein the 3- to 7-membered heterocyclyl group is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)(C$_{1-3}$ alkyl), —(CH$_2$)$_{1-3}$COOH, and —NH$_{2-z}$(CH$_3$)$_z$, wherein z is 0, 1, or 2; and each of the C$_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2;

(B') at least one of R$^{1b}$ and R$^{1c}$ is selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, and phenyl, wherein z is 0, 1, or 2, and the other of R$^{1b}$ and R$^{1c}$ is as defined above under (B);

(C') R$^3$ is selected from the group consisting of H, C$_{1-4}$ alkyl, C$_{3-6}$ cycloalkyl, phenyl, halogen, —CN, —O(C$_{1-4}$ alkyl), —OCF$_3$, —S(C$_{1-4}$ alkyl), —NH$_2$, —NH(Cia alkyl), —N(C$_{1-4}$ alkyl)$_2$, —C(=O)(C$_{1-4}$ alkyl), —C(=O)OH, —C(=O)O(C$_{1-4}$ alkyl), —C(=O)NH$_{2-z}$(C$_{1-4}$ alkyl)$_z$, —NHC(=O)(C$_{1-4}$ alkyl), —NHC(=NH)NH$_{z-2}$(C$_{1-4}$ alkyl)$_z$, and —N(C$_{1-4}$ alkyl)C(=NH)NH$_{z-z}$(C$_{1-4}$ alkyl)$_z$, wherein the phenyl group is optionally substituted with one, two or groups independently selected from the group consisting of halogen, methyl, isopropyl, —CN, —CF$_3$, —OCF$_3$, —OH, —NH$_2$, —NH(C$_{1-3}$ alkyl), —N(C$_{1-3}$ alkyl)$_2$, —NHC(=O)(C$_{1-3}$ alkyl), —C(=O)NH$_{2-z}$(C$_{1-3}$ alkyl)$_z$, —(CH$_2$)$_{1-3}$NH$_2$, —(CH$_2$)$_{1-3}$NH(C$_{1-3}$ alkyl), —(CH$_2$)$_{1-3}$N(C$_{1-3}$ alkyl)$_2$, —(CH$_2$)$_{1-3}$OH, and —(CH$_2$)$_{1-3}$O(C$_{1-3}$ alkyl); and wherein z is 0, 1, or 2;

(D') R$^6$ is as defined above (in particular with respect to formula (V)), and is preferably a 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected R$^7$, more preferably R$^6$ is a mono- or bicyclic heteroaryl or a mono- or bicyclic heterocyclyl, each of which is optionally substituted with one, two, or three independently selected R$^7$;

(E') A is S, O, or N(CH$_3$)$_2$; and/or (F') B is N or CR$^{1d}$, wherein R$^{1d}$ is selected from the group consisting of C$_{1-3}$ alkyl, halogen, —O(C$_{1-3}$ alkyl), —S(C$_{1-3}$ alkyl), —NH(C$_{1-3}$ alkyl), and —N(C$_{1-3}$ alkyl)$_2$; and/or (G') E is O or S, preferably O.

In a preferred embodiment of the kinase inhibitor having general formula (VIII), R$^{1a}$ is as specified above under (A'); R$^{1b}$ and R$^{1c}$ are as defined above under (B'); R$^3$ is as specified above under (C'); R$^6$ is as defined above (in particular with respect to formula (V)), and is preferably a 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected R$^7$, more preferably R$^6$ is a mono- or bicyclic heteroaryl (e.g., containing at least one ring heteroatom selected from the group consisting of N, O, and S, such as from the group consisting of N and O) or a mono- or bicyclic heterocyclyl (e.g., containing at least one ring heteroatom selected from the group consisting of N, O, and S, such as from the group consisting of N and O), each of which is optionally substituted with one, two, or three independently selected R$^7$; A is as specified above under (E'); B is as specified above under (F'); and E is as specified above under (G').

In further preferred embodiments of the kinase inhibitor having general formula (VIII):

(A") R$^{1a}$ is selected from the group consisting of —NH(C$_{1-3}$ alkyl), piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the C$_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2;

(B") (a) R$^{1b}$ is methyl, ethyl, propyl, or isopropyl, preferably methyl; and R$^{1c}$ is H; or (b) R$^{1b}$ is H; and R$^{1c}$ is methyl, ethyl, propyl, isopropyl, or phenyl, preferably methyl;

(C") R$^3$ is selected from the group consisting of H, methyl, ethyl, propyl, isopropyl, phenyl, and halogen;

(D") R$^6$ is as defined above (in particular with respect to formula (V)), and is preferably a 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected R$^7$, more preferably R$^6$ is a mono- or bicyclic heteroaryl (e.g., containing at least one ring heteroatom selected from the group consisting of N, O, and S, such as from the group consisting of N and O) or a mono- or bicyclic heterocyclyl (e.g., containing at least one ring heteroatom selected from the group consisting of N, O, and S, such as from the group consisting of N and O), each of which is optionally substituted with one, two, or three independently selected R$^7$, more preferably R$^6$ is selected from the group consisting of a 5- to 6-membered monocyclic heteroaryl (e.g., containing at least one ring heteroatom selected from the group consisting of N, O, and S, such as from the group consisting of N and O), a 4- to 6-membered monocyclic heterocyclyl (e.g., containing at least one ring heteroatom selected from the group consisting of N, O, and S, such as from the group consisting of N and O), a 7- to 9-membered bicyclic heteroaryl (e.g., containing at least one ring heteroatom selected from the group consisting of N, O, and S, such as from the group consisting of N and O), and a 7- to 9-membered bicyclic heterocyclyl (e.g., containing at least one ring heteroatom selected from the group consisting of N, O, and S, such as from the group consisting of N and O), each of which is optionally substituted with one, two, or three independently selected R⁷, more preferably R⁶ is a 5- to 6-membered monocyclic heteroaryl (e.g., containing at least one ring heteroatom selected from the group consisting of N, O, and S, such as from the group consisting of N and O) or a 7- to 9-membered bicyclic heterocyclyl (e.g., containing at least one ring heteroatom selected from the group consisting of N, O, and S, such as from the group consisting of N and O), each of which is optionally substituted with one, two, or three independently selected R⁷;

(E'') A is S;
(F'') B is N; and/or
(G'') E is O.

In a preferred embodiment of the kinase inhibitor having general formula (VIII), $R^{1a}$ is as specified above under (A''); $R^{1b}$ and $R^{1c}$ are as defined above under (B''); $R^3$ is as specified above under (C''); $R^6$ is as defined above (in particular with respect to formula (V)), and is preferably a 3- to 10-membered heteroaryl (e.g., containing at least one ring heteroatom selected from the group consisting of N, O, and S, such as from the group consisting of N and O) or a 3- to 10-membered heterocyclyl (e.g., containing at least one ring heteroatom selected from the group consisting of N, O, and S, such as from the group consisting of N and O), each of which is optionally substituted with one, two, or three independently selected $R^7$, more preferably $R^6$ is a mono- or bicyclic heteroaryl (e.g., containing at least one ring heteroatom selected from the group consisting of N, O, and S, such as from the group consisting of N and O) or a mono- or bicyclic heterocyclyl (e.g., containing at least one ring heteroatom selected from the group consisting of N, O, and S, such as from the group consisting of N and O), each of which is optionally substituted with one, two, or three independently selected $R^7$, more preferably $R^6$ is selected from the group consisting of a 5- to 6-membered monocyclic heteroaryl (e.g., containing at least one ring heteroatom selected from the group consisting of N, O, and S, such as from the group consisting of N and O), a 4- to 6-membered monocyclic heterocyclyl (e.g., containing at least one ring heteroatom selected from the group consisting of N, O, and S, such as from the group consisting of N and O), a 7- to 9-membered bicyclic heteroaryl (e.g., containing at least one ring heteroatom selected from the group consisting of N, O, and S, such as from the group consisting of N and O), and a 7- to 9-membered bicyclic heterocyclyl (e.g., containing at least one ring heteroatom selected from the group consisting of N, O, and S, such as from the group consisting of N and O), each of which is optionally substituted with one, two, or three independently selected $R^7$, more preferably $R^6$ is a 5- to 6-membered monocyclic heteroaryl (e.g., containing at least one ring heteroatom selected from the group consisting of N, O, and S, such as from the group consisting of N and O) or a 7- to 9-membered bicyclic heterocyclyl (e.g., containing at least one ring heteroatom selected from the group consisting of N, O, and S, such as from the group consisting of N and O), each of which is optionally substituted with one, two, or three independently selected $R^7$; A is as specified above under (E''); B is as specified above under (F''); and E is as specified above under (G'').

In one embodiment, the compound of the invention is selected from the compounds shown in Table A and/or Table B.

It is intended that the compounds of the present invention (in particular, the compounds of any one of formulas (I), (Ia), (II), (III), (IV), (V), (VI), (VII) and (VIII) such as those depicted in Table A and/or Table B, below) encompass not only the compounds as depicted but also their solvates (e.g., hydrates), salts (in particular, pharmaceutically acceptable salts), N-oxides (in particular, N-oxides of $R^{1a}$ and/or $R^6$), complexes, polymorphs, crystalline forms, non-crystalline forms, amorphous forms, racemic mixtures, non-racemic mixtures, diastereomers, enantiomers, tautomers, conformers, isotopically labeled forms, prodrugs, and any combinations thereof.

A selection of compounds, including those which have been synthesized and tested, within the scope of, or for use within the methods of, the present invention—and/or that represent examples of various exemplary or preferred $R^{1a}$ substituents, $R^{1b}$ substituents, $R^{1c}$ substituents, $R^2$ substituents, $R^3$ substituents, $R^4$ substituents, $R^5$ moieties, A moieties, and/or B moieties, each individually or in any combination are useful for synthesising further compounds of the invention—is listed in the following Table A and/or Table B.

TABLE A

Kinase inhibitors of formula (I).

| Compound Number | Structure | Name |
|---|---|---|
| C1 | 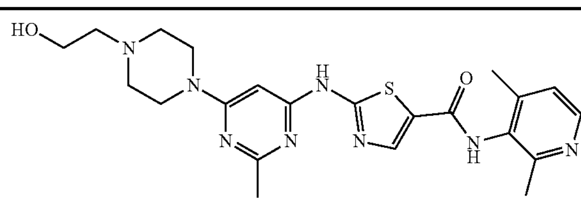 | N-(2,4-dimethylpyridin-3-yl)-2-((6-(4-(2-hydroxyethyl)piperazin-1-yl)-2-methylpyrimidin-4-yl)amino)thiazole-5-carboxamide |
| C2 | 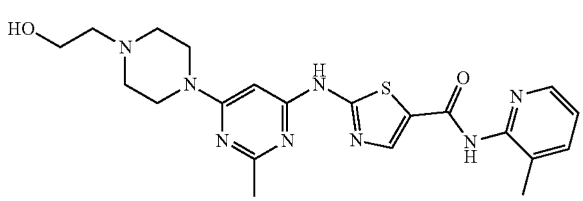 [SMILES: Cc1nc(Nc2ncc(C(=O)Nc3ncccc3C)s2)cc(N2CCN(CCO)CC2)n1] | 2-((6-(4-(2-hydroxyethyl)piperazin-1-yl)-2-methylpyrimidin-4-yl)amino)-N-(3-methylpyridin-2-yl)thiazole-5-carboxamide |

TABLE A-continued

Kinase inhibitors of formula (I).

| Compound Number | Structure | Name |
|---|---|---|
| C3 | 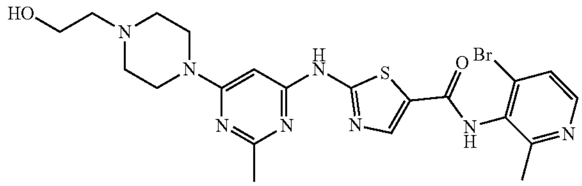 [SMILES: Cc1nc(Nc2ncc(C(=O)Nc3c(Br)ccnc3C)s2)cc(N2CCN(CCO)CC2)n1] | N-(4-bromo-2-methylpyridin-3-yl)-2-((6-(4-(2-hydroxyethyl)piperazin-1-yl)-2-methylpyrimidin-4-yl)amino)thiazole-5-carboxamide |
| C4 | 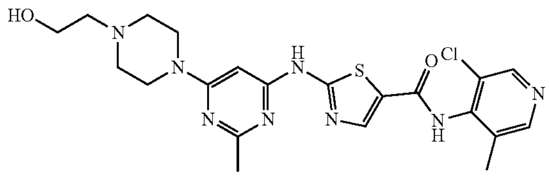 [SMILES: Cc1nc(Nc2ncc(C(=O)Nc3c(C)cncc3Cl)s2)cc(N2CCN(CCO)CC2)n1] | N-(3-chloro-5-methylpyridin-4-yl)-2-((6-(4-(2-hydroxyethyl)piperazin-1-yl)-2-methylpyrimidin-4-yl)amino)thiazole-5-carboxamide |
| C5 | 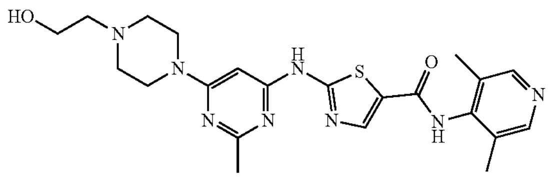 [SMILES: Cc1nc(Nc2ncc(C(=O)Nc3c(C)cncc3C)s2)cc(N2CCN(CCO)CC2)n1] | N-(3,5-dimethylpyridin-4-yl)-2-((6-(4-(2-hydroxyethyl)piperazin-1-yl)-2-methylpyrimidin-4-yl)amino)thiazole-5-carboxamide |
| C6 | 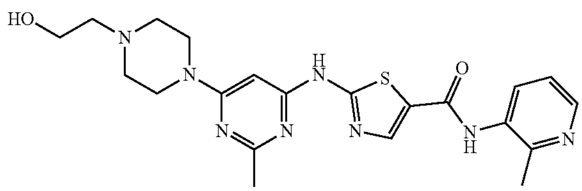 [SMILES: Cc1nc(Nc2ncc(C(=O)Nc3cccnc3C)s2)cc(N2CCN(CCO)CC2)n1] | 2-((6-(4-(2-hydroxyethyl)piperazin-1-yl)-2-methylpyrimidin-4-yl)amino)-N-(2-methylpyridin-3-yl)thiazole-5-carboxamide |
| C7 | 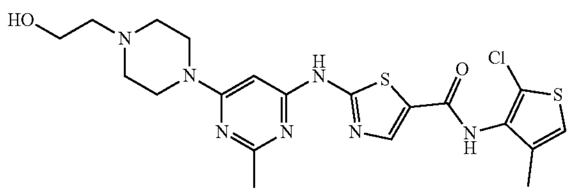 [SMILES: Cc1nc(Nc2ncc(C(=O)Nc3c(C)csc3Cl)s2)cc(N2CCN(CCO)CC2)n1] | N-(2-chloro-4-methylthiophen-3-yl)-2-((6-(4-(2-hydroxyethyl)piperazin-1-yl)-2-methylpyrimidin-4-yl)amino)thiazole-5-carboxamide |
| C8 | 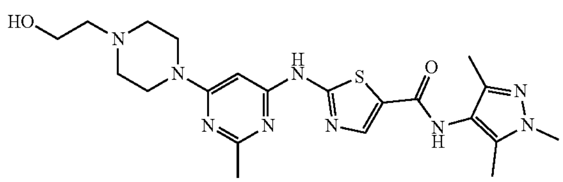 [SMILES: Cc1nc(Nc2ncc(C(=O)Nc3c(C)nn(C)c3C)s2)cc(N2CCN(CCO)CC2)n1] | 2-((6-(4-(2-hydroxyethyl)piperazin-1-yl)-2-methylpyrimidin-4-yl)amino)-N-(1,3,5-trimethyl-1H-pyrazol-4-yl)thiazole-5-carboxamide |
| C9 | 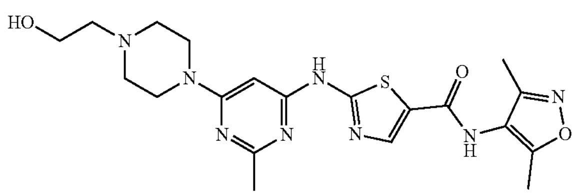 [SMILES: Cc1nc(Nc2ncc(C(=O)Nc3c(C)noc3C)s2)cc(N2CCN(CCO)CC2)n1] | N-(3,5-dimethyl-1,2-isoxazolyl)-3-((6-(4-(2-hydroxyethyl)piperazin-1-yl)-2-methylpyrimidin-4-yl)amino)thiazole-5-carboxamide |
| C10 | 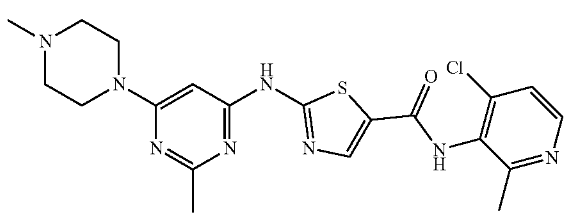 [SMILES: Cc1nc(Nc2ncc(C(=O)Nc3c(Cl)ccnc3C)s2)cc(N2CCN(C)CC2)n1] | N-(4-chloro-2-methylpyridin-3-yl)-2-((2-methyl)-6-(4-methylpiperazin-1-yl)pyrimidin-4-yl)amino)thiazole-5-carboxamide |

TABLE A-continued

Kinase inhibitors of formula (I).

| Compound Number | Structure | Name |
| --- | --- | --- |
| C11 | 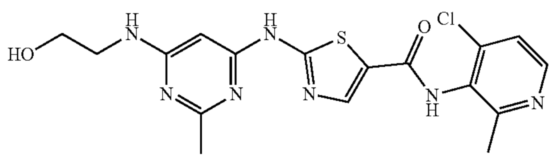 [SMILES: Cc1nc(NCCO)cc(Nc2ncc(C(=O)Nc3c(Cl)ccnc3C)s2)n1] | N-(4-chloro-2-methylpyridin-3-yl)-2-((6-((2-hydroxyethyl)amino)-2-methylpyrimidin-4-yl)amino)thiazole-5-carboxamide |
| C12 | 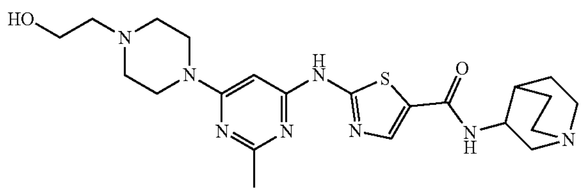 [SMILES: Cc1nc(Nc2ncc(C(=O)NC3CN4CCC3CC4)s2)cc(N2CCN(CCO)CC2)n1] | 2-((6-(4-(2-hydroxyethyl)piperazin-1-yl)-2-methylpyrimidin-4-yl)amino)-N-(quinuclidine-3-yl)thiazole-5-carboxamide |
| C13 | 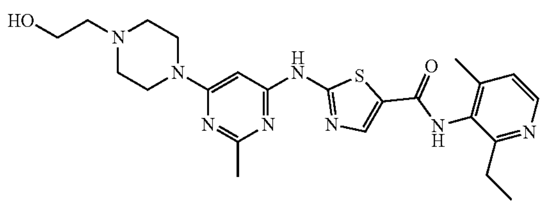 [SMILES: CCc1nccc(C)c1NC(=O)c1cnc(Nc2cc(N3CCN(CCO)CC3)nc(C)n2)s1] | N-(2-ethyl-4-methylpyridin-3-yl)-2-((6-(4-(2-hydroxyethyl)piperazin-1-yl)-2-methylpyrimidin-4-yl)amino)thiazole-5-carboxamide |
| B3* | 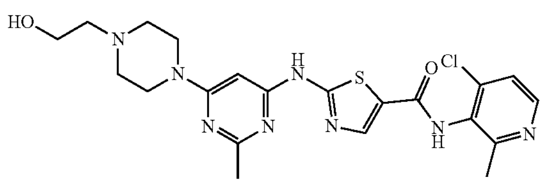 [SMILES: Cc1nc(Nc2ncc(C(=O)Nc3c(Cl)ccnc3C)s2)cc(N2CCN(CCO)CC2)n1] | N-(4-chloro-2-methylpyridin-3-yl)-2-((6-(4-(2-hydroxyethyl)piperazin-1-yl)-2-methylpyrimidin-4-yl)amino)thiazole-5-carboxamide |

*Compound B3 is included in Table 1 of co-pending PCT/EP2018/060172.

TABLE B

Further kinase inhibitors of formula (I)

| Compound Number | Structure | Name |
| --- | --- | --- |
| D1 | 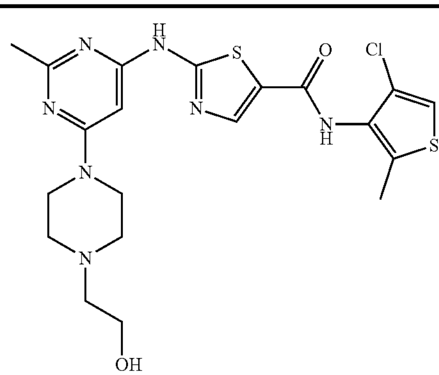 | N-(4-chloro-2-methylthiophen-3-yl)-2-((6-(4-(2-hydroxyethyl)piperazin-1-yl)-2-methylpyrimidin-4-yl)amino)thiazole-5-carboxamidexs |

TABLE B-continued

Further kinase inhibitors of formula (I)

| Compound Number | Structure | Name |
|---|---|---|
| D2 | 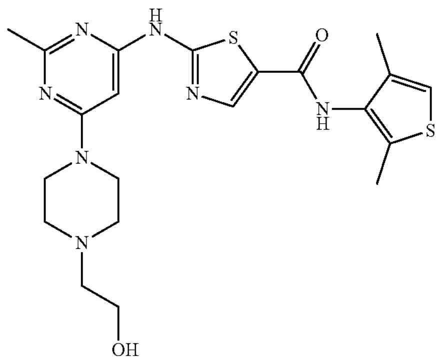 [SMILES: Cc1nc(Nc2ncc(C(=O)Nc3c(C)csc3C)s2)cc(N2CCN(CCO)CC2)n1] | N-(2,4-dimethylthiophen-3-yl)-2-((6-(4-(2-hydroxyethyl)piperazin-1-yl)-2-methylpyrimidin-4-yl)amino)thiazole-5-carboxamide |
| D3 | 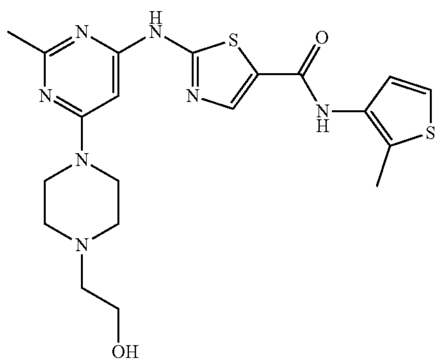 [SMILES: Cc1nc(Nc2ncc(C(=O)Nc3ccsc3C)s2)cc(N2CCN(CCO)CC2)n1] | 2-((6-(4-(2-hydroxyethyl)piperazin-1-yl)-2-methylpyrimidin-4-yl)amino)-N-(2-methylthiophen-3-yt)thiazole-5-carboxamide |
| D4 | 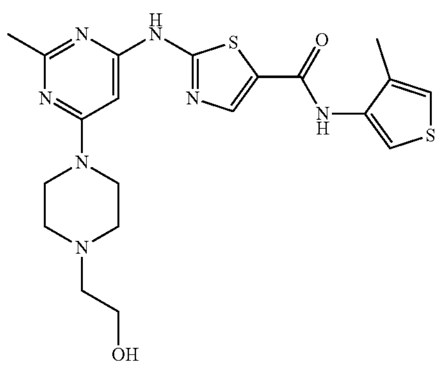 [SMILES: Cc1nc(Nc2ncc(C(=O)Nc3cscc3C)s2)cc(N2CCN(CCO)CC2)n1] | 2-((6-(4-(2-hydroxyethyl)piperazin-1-yl)-2-methylpyrimidin-4-yl)amino)-N-(4-methylthiophen-3-yl)thiazole-5-carboxamide |
| D5 | 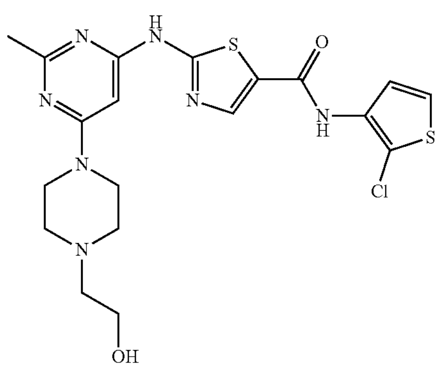 [SMILES: Cc1nc(Nc2ncc(C(=O)Nc3ccsc3Cl)s2)cc(N2CCN(CCO)CC2)n1] | N-(2-chlorothiophen-3-yl)-2-((6-(4-(2-hydroxyethyl)piperazin-1-yl)-2-methylpyrimidin-4-yl)amino)thiazole-5-carboxamide |

TABLE B-continued

Further kinase inhibitors of formula (I)

| Compound Number | Structure | Name |
|---|---|---|
| D6 | 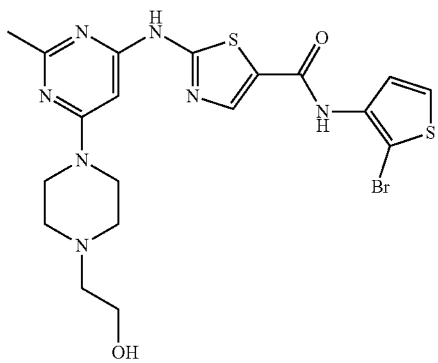 [SMILES: Cc1nc(Nc2ncc(C(=O)Nc3ccsc3Br)s2)cc(N2CCN(CCO)CC2)n1] | N-(2-bromothiophen-3-yl)-2-((6-(4-(2-hydroxyethyl)piperazin-1-yl)-2-methylpyrimidin-4-yl)amino)thiazole-5-carboxamide |
| D7 | 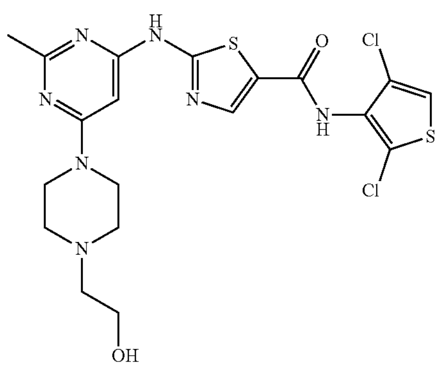 [SMILES: Cc1nc(Nc2ncc(C(=O)Nc3c(Cl)csc3Cl)s2)cc(N2CCN(CCO)CC2)n1] | N-(2,4-dichlorothiophen-3-yl)-2-((6-(4-(2-hydroxyethyl)piperazin-1-yl)-2-methylpyrimidin-4-yl)amino)thiazole-5-carboxamide |
| D8 | 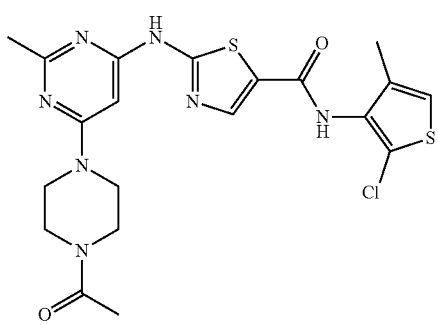 [SMILES: CC(=O)N1CCN(c2cc(Nc3ncc(C(=O)Nc4c(C)csc4Cl)s3)nc(C)n2)CC1] | 2-((6-(4-acetylpiperazin-1-yl)-2-methylpyrimidin-4-yl)amino)-N-(2-chloro-4-methylthiophen-3-yl)thiazole-5-carboxamide |
| D9 | 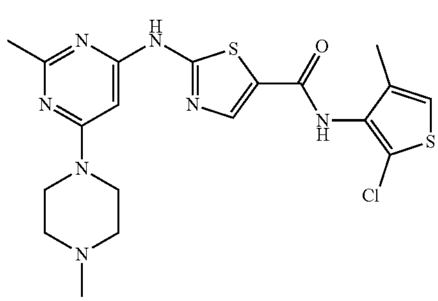 [SMILES: Cc1nc(Nc2ncc(C(=O)Nc3c(C)csc3Cl)s2)cc(N2CCN(C)CC2)n1] | N-(2-chloro-4-methylthiophen-3-yl)-2-((2-methyl-6-(4-methylpiperazin-1-yl)pyrimidin-4-yl)amino)thiazole-5-carboxamide |

TABLE B-continued

Further kinase inhibitors of formula (I)

| Compound Number | Structure | Name |
|---|---|---|
| D10 | 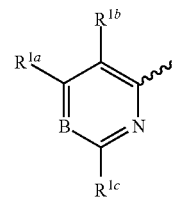 | N-(2,4-dichlorothiophen-3-yl)-2-((2-methyl-6-(4-methylpiperazin-1-yl)pyrimidin-4-yl)amino)thiazole-5-carboxamide |

In particular embodiments, the compound of the invention is selected from the group consisting of C7 and C8 and/or D1 and/or D9, or in certain embodiments the compound of the invention is B3; and also their solvates, salts, N-oxides, complexes, polymorphs, crystalline forms, tautomers, conformers, isotopically labelled forms, prodrugs, and combinations thereof.

In another certain embodiment, the compound of the invention is C12, or a solvate, salt, N-oxide, complex, polymorph, crystalline form, racemic mixture, diastereomer, enantiomer, tautomer, conformer, isotopically labelled form, prodrug, or combination thereof.

In certain embodiments, the invention may relate to a solvate, salt, N-oxide, complex, racemic mixture, diastereomer, enantiomer, tautomer, conformer, isotopically labeled form, prodrug, or combination thereof, of any of the compounds of the invention; such as a solvate, salt, complex, racemic mixture, diastereomer, enantiomer, tautomer, conformer, isotopically labeled form, or combination thereof, of such compound.

In one embodiment, the compounds of the invention do not encompass compounds of one or more of the following groups (1) to (5) of formula (I) (in the groups (1) to (5) a moiety (such as methyl) is unsubstituted unless it is explicitly specified that said moiety is substituted):

(1) when $R^{1a}$ is 4-(2-hydroxyethyl)piperazin-1-yl or Cl; $R^{1b}$ is H; $R^{1c}$ is methyl; B is N; E is O; $R^3$ is H; A is S; and L is a bond; then $R^6$ is not 4-chloro-2-methylpyridin-3-yl;

(2) when $R^{1a}$ is methoxy; $R^{1b}$ is H; $R^{1c}$ is methoxy; B is N; E is O; $R^3$ is H; A is S; and L is a bond; then $R^6$ is not 2,2-difluoro-5H-1,3-dioxolo[4,5-f]benzimidazol-6-yl;

(3) when $R^3$ is H; A is S; L is a bond; $R^6$ is 1-methyl-4-piperidinyl; $R^{1b}$ is H; B is N; E is O; and
  (i) $R^{1a}$ is methyl; then $R^{1c}$ is not N-tert-butoxycarbonylpiperidin-4-yl; or
  (ii) $R^{1c}$ is methyl; then $R^{1a}$ is not N-tert-butoxycarbonylpiperidin-4-yl or N-tert-butoxycarbonylpiperidin-3-yl;

(4) when E is O; B is $CR^{1d}$ and $R^{1d}$ is either H, F, Cl or Br, then $R^{1a}$ is not H; and (5) when $R^{1a}$ is methyl; each of $R^{1b}$ and $R^{1c}$ is H; B is CH; E is O; A is S; and $R^3$ is methyl; then $R^5$ is not 1,3-benzodioxol-5-ylmethyl, 2-furanylmethyl, 1,3-benzodioxol-5-yl, 2-(2-thienyl)ethyl, 2-(4-morpholinyl)ethyl, 2-(2-pyridinyl)ethyl, 2-pyridinylmethyl, or tetrahydro-2-furanylmethyl.

In one embodiment, the compounds of the invention do not encompass compounds of one or more of the following groups (6) to (8) having formula (Ia) (in the groups (6) to (8) a moiety (such as methyl) is unsubstituted unless it is explicitly specified that said moiety is substituted):

(6) when Hy is:

and (i) when $R^{1a}$ is 4-(2-hydroxyethyl)piperazin-1-yl or Cl; $R^{1b}$ is H; $R^{1c}$ is methyl; B is N; E is O; $R^2$ is H; $R^3$ is H; $R^4$ is H; and A is S; then $R^6$ is not 4-chloro-2-methylpyridin-3-yl;

(ii) when $R^{1a}$ is methoxy; $R^{1b}$ is H; $R^{1c}$ is methoxy; B is N; E is O; $R^2$ is H; $R^3$ is H; $R^4$ is H; and A is S; then $R^6$ is not 2,2-difluoro-5H-1,3-dioxolo[4,5-f]benzimidazol-6-yl;

(7) when Hy is 1-{(2E)-4-[(2-methoxyethyl)amino]-1-oxo-2-buten-1-yl}piperidine-4-yl; $R^2$ is H; $R^3$ is H; $R^4$ is H; A is O; E is O; then $R^6$ is not 5-methyl-pyridin-2-yl;

(8) when $R^2$ is H; $R^3$ is trifluoromethyl; $R^4$ is H; A is O; E is O; and
  (i) $R^6$ is 6-{4-[(2-fluorophenyl)carbamoyl]piperazin-1-yl}pyridine-3-yl; then Hy is not 1-(phenylmethyl)-piperidine-4-yl, 1-(phenylmethyl)pyrrolidine-3-yl, or tetrahydro-2H-pyran-4-yl; or
  (ii) Hy is 1-(phenylmethyl)piperidine-4-yl; then $R^6$ is not 6-(3-{[(2-fluorophenyl)carbamoyl]amino}-pyrrolidin-1-yl)pyridine-3-yl or 6-({1-[(2-fluorophenyl)carbamoyl]piperidin-4-yl}amino)pyridine-3-yl; or
  (iii) Hy is 1-(phenylmethyl)pyrrolidine-3-yl; then $R^6$ is not 6-({(3S)-1-[(2-fluorophenyl)carbamoyl]-pyrrolidin-3-yl}amino)pyridine-3-yl or 6-({(3R)-1-[(2-fluorophenyl)carbamoyl]pyrrolidin-3-yl}-amino)pyridine-3-yl.

In certain other embodiments, the compound is not one selected from the group consisting of:

5-Thiazolecarboxamide, 2-[(6-chloro-2-methyl-4-pyrimidinyl)amino]-N-[2-[4-(2-hydroxyethyl)-1-piperazinyl]-6-methylphenyl]—(CAS Registry no: 2048106-50-7), 5-Thiazolecarboxamide, 2-[[7-[4-cyano-3-(trifluoromethyl)phenyl]-5,6,7,8-tetrahydropyrido[3,4-d]pyrimidin-4-yl]amino]-N-[(1R)-1-(1,3,4-oxadiazol-2-yl)ethyl]-4-(trifluoromethyl)—(CAS Registry no: 1831086-00-0), 5-Thiazolecarboxamide, 2-[[6-methoxy-7-[3-(4-morpholinyl)propoxy]-4-quinazolinyl]amino]-N-(2-pyrazinylmethyl)—(CAS Registry no: 385780-87-0), 5-Thiazolecarboxamide, 2-[[6-methoxy-7-[3-(4-morpholinyl)propoxy]-4-quinazolinyl]amino]-N-[2-(3-pyridinyl)ethyl]—(CAS Registry no: 385780-82-5), 5-Thiazolecarboxamide, N-1H-indol-5-yl-2-[[6-methoxy-7-[3-(4-morpholinyl)propoxy]-4-quinazolinyl]amino]—(CAS Registry no: 385780-79-0), 5-Thiazolecarboxamide, 2-[[6-methoxy-7-[3-(4-morpholinyl)propoxy]-4-quinazolinyl]amino]-N-(2-thienylmethyl)—(CAS Registry no: 385780-69-8), 5-Thiazolecarboxamide, N-(2-furanylmethyl)-2-[[6-methoxy-7-[3-(4-morpholinyl)propoxy]-4-quinazolinyl]amino]—(CAS Registry no: 385780-66-5), 5-Thiazolecarboxamide, 2-[[6-methoxy-7-[3-(4-morpholinyl)propoxy]-4-quinazolinyl]amino]-N-2-pyridinyl—(CAS Registry no: 385780-57-4), and 5-Thiazolecarboxamide, 2-[[6-methoxy-7-[3-(4-morpholinyl)propoxy]-4-quinazolinyl]amino]-N-4-pyridinyl—(CAS Registry no: 385779-93-1).

In other certain other embodiments, the compound is not one selected from the group consisting of:

Imidazo[4,5-d]pyrrolo[2,3-b]pyridine-7-carboxamide, N,N-dicyclopropyl-6-ethyl-1,6-dihydro-1-methyl-4-[[4-methyl-5-[[(tetrahydro-2H-pyran-4-yl)amino]carbonyl]-2-thiazolyl]amino]—(CAS Registry no: 1271022-78-6), Imidazo[4,5-d]pyrrolo[2,3-b]pyridine-7-carboxamide, N,N-dicyclopropyl-6-ethyl-1,6-dihydro-1-methyl-4-[[4-methyl-5-[[(tetrahydro-1,1-dioxido-3-thienyl)amino]carbonyl]-2-thiazolyl]amino]—(CAS Registry no: 1271022-57-1), Imidazo[4,5-d]pyrrolo[2,3-b]pyridine-7-carboxamide, N,N-dicyclopropyl-6-ethyl-1,6-dihydro-1-methyl-4-[[4-methyl-5-[[[2-(4-morpholinyl)ethyl]amino]carbonyl]-2-thiazolyl]amino]—(CAS Registry no: 1271022-45-7), and Imidazo[4,5-d]pyrrolo[2,3-b]pyridine-7-carboxamide, N,N-dicyclopropyl-6-ethyl-1,6-dihydro-1-methyl-4-[[5-[[methyl(tetrahydro-1,1-dioxido-3-thienyl)amino]carbonyl]-2-thiazolyl]amino]—(CAS Registry no: 1271021-43-2)

2-[(6-{[3-(1H-imidazol-1-yl)propyl]amino}pyridin-2-yl)amino]-4-methyl-N-[1-(phenylmethyl)-1H-indazol-5-yl]-1,3-thiazole-5-carboxamide (CAS Registry no: 302963-64-0)

2-[(6-{[3-(1H-imidazol-1-yl)propyl]amino}pyridin-2-yl)amino]-N-[1-(phenylmethyl)-1H-indazol-5-yl]-1,3-thiazole-5-carboxamide (CAS Registry no: 302963-55-9)

In certain alternatives of one or more aspects herein, the compound is N-(2-chloro-6-methylphenyl)-2-((6-(4-(2-hydroxyethyl)piperazin-1-yl)-2-methylpyrimidin-4-yl)amino)thiazole-5-carboxamide (dasatinib; A8).

The compounds of the invention which contain a basic functionality may form salts with a variety of inorganic or organic acids. The compounds of the invention which contain an acidic functionality may form salts with a variety of inorganic or organic bases. Exemplary inorganic and organic acids/bases as well as exemplary acid/base addition salts of the compounds of the present invention are given in the definition of "pharmaceutically acceptable salt" in the section "Pharmaceutical composition", below. The compounds of the invention which contain both basic and acidic functionalities may be converted into either base or acid addition salt. The neutral forms of the compounds of the invention may be regenerated by contacting the salt with a base or acid and isolating the parent compound in the conventional manner.

The compounds of the invention may be in the form of an N-oxide, i.e., they can contain the functional group functional group =N+—O— (e.g., $(R'')_3$N+—O—, i.e., an N—O coordinate covalent bond, wherein $R''$ is independently selected from the group consisting of hydrogen, alkyl, alkenyl, alkynyl, aryl, heteroaryl, cycloalkyl, and heterocyclyl, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, the $R^{30}$ preferably being a $1^{st}$ level substituent, a $2^{nd}$ level substituent, or a $3^{rd}$ level substituent as specified herein). Particular examples of N-oxides of compounds of the invention are those, wherein $R^{1a}$ and/or $R^6$ contains the functional group =N+—O—. Non-limiting examples of $R^{1a}$ substituents which can occur as N-oxides include the following:

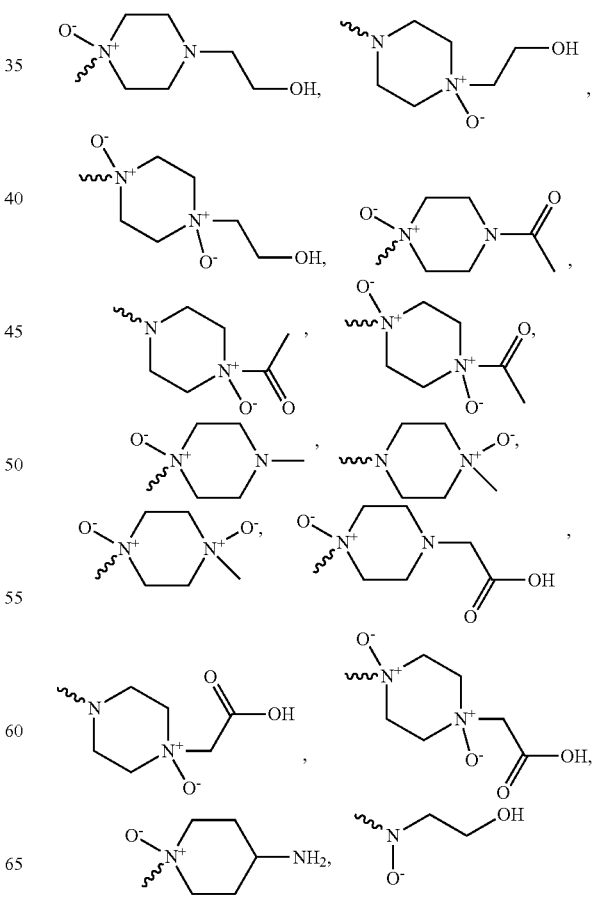

-continued

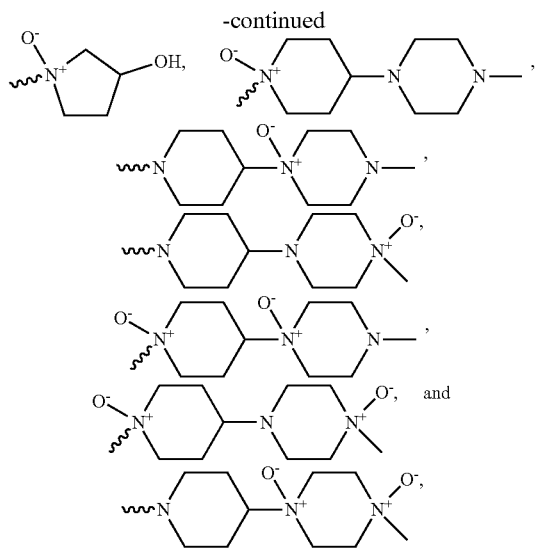

wherein ⁓⁓⁓ represents the bond by which the $R^{1a}$ substituent is bound to the remainder of the compound. Non-limiting examples of $R^6$ substituents which can occur as N-oxides include the following:

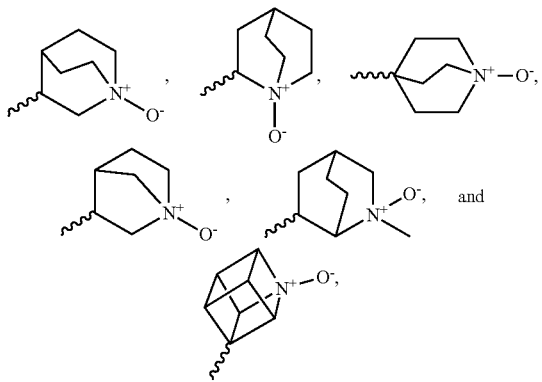

wherein ⁓⁓⁓ represents the bond by which the $R^6$ substituent is bound to the remainder of the compound.

The compounds of the invention may be in a prodrug form. Prodrugs of the compounds of the invention are those compounds that upon administration to an individual undergo chemical conversion under physiological conditions to provide the compounds of the invention. Additionally, prodrugs can be converted to the compounds of the invention by chemical or biochemical methods in an ex vivo environment. For example, prodrugs can be slowly converted to the compounds of the invention when, for example, placed in a transdermal patch reservoir with a suitable enzyme or chemical reagent. Exemplary prodrugs are esters (using an alcohol or a carboxy group contained in the kinase inhibitor of the invention) or amides (using an amino or a carboxy group contained in the kinase inhibitor of the invention) which are hydrolyzable in vivo. Specifically, any amino group which is contained in the kinase inhibitor of the invention and which bears at least one hydrogen atom can be converted into a prodrug form. Typical N-prodrug forms include carbamates (1), Mannich bases (2), enamines (3), and enaminones (4).

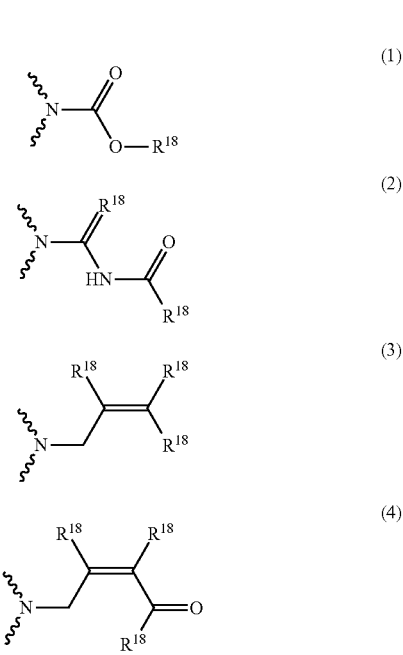

wherein $R^{18}$ is selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is as defined herein (preferably, each $R^{30}$ is independently a $1^{st}$ level substituent, a $2^{nd}$ level substituent, or a $3^{rd}$ level substituent as specified herein). The prodrug properties (such as solubility, permeability, stability, how fast cleaved, where in the body cleaved under what conditions, target specificity, etc.) can be fine-tuned via modification of $R^{18}$.

Particular prodrug forms of the compounds of the invention are those (prodrugs) having the formula (IXa), (IXb), (IXc), or (IXd):

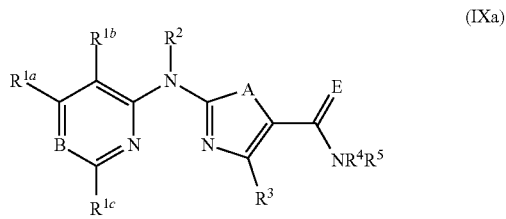

(IXa)

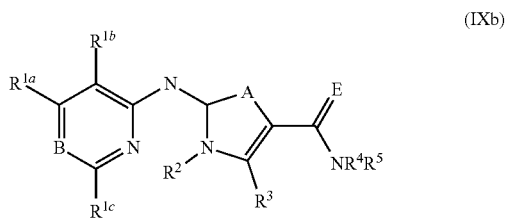

(IXb)

-continued

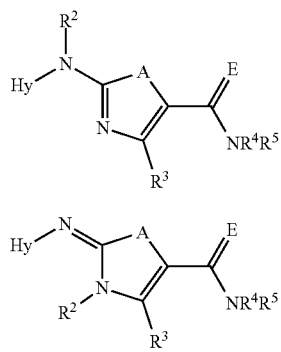
(IXc)

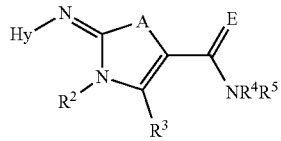
(IXd)

and solvates, salts, N-oxides, complexes, polymorphs, crystalline forms, racemic mixtures, diastereomers, enantiomers, tautomers, conformers, isotopically labeled forms and combinations thereof, wherein $R^{1a}$, $R^{1b}$, $R^{1c}$, $R^3$, $R^5$, A, B, E, and Hy are as defined above (in particular with respect to formula (I), (Ia), (II), (III), (IV), (V), (VI), and/or (VIII)) or below, and each of $R^2$ and $R^4$ is independently selected from the group consisting of H, $-P(O)(OR^{11a})_2$, $-(CH_2)_{1-3}-R^{19}$, $-C(=X^a)R^{11a}$, and $-C(=X^a)X^aR^{11a}$, with the proviso that not both of $R^2$ and $R^4$ are H, wherein $R^{11a}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; $R^{19}$ is independently selected from the group consisting of $-OP(O)(OR^{11a})_2$, $-X^aC(=X^a)R^{11a}$, $-X^aC(=X^a)X^aR^{11a}$, and 5-alkyl-2-oxo-1,3-dioxolo-4-yl; $X^a$ is independently selected from O, S, and NH; and the $-(CH_2)_{1-3}-$ group is optionally substituted with one or two independently selected $R^{30}$, wherein $R^{30}$ is as defined herein (preferably, each $R^{30}$ is independently selected from the group consisting of a $1^{st}$ level substituent, a $2^{nd}$ level substituent, and a $3^{rd}$ level substituent as specified herein). In one embodiment of the prodrug form of formula (IXa), (IXb), (IXc), or (IXd), $R^{1a}$, $R^{1b}$, $R^{1c}$, $R^3$, $R^5$, A, B, E, and Hy are as defined above (in particular with respect to formula (I), (Ia), (II), (III), (IV), (V), (VI), and/or (VIII)) or below, and each of $R^2$ and $R^4$ is independently selected from the group consisting of H, $-P(O)(OR^{11a})_2$, $-(CH_2)_{1-3}-R^{19}$, $-C(=O)R^{11a}$, and $-C(=O)OR^{11a}$, with the proviso that not both of $R^2$ and $R^4$ are H, wherein $R^{11a}$ is independently selected from the group consisting of H and $C_{1-6}$ alkyl (preferably $C_{1-3}$ alkyl), wherein the alkyl group is optionally substituted with one or two substituents independently selected from halogen, $-OH$, $-OCH_3$, $-SCH_3$, 2-(N,N-dimethylamino)ethoxy, and $-NH_{2-z}(CH_3)_z$, wherein z is 0, 1, or 2; $R^{19}$ is independently selected from the group consisting of $-OP(O)(OR^{11a})_2$, $-OC(=O)R^{11a}$, $-OC(=O)OR^{11a}$, and 5-($C_{1-3}$ alkyl)-2-oxo-1,3-dioxolo-4-yl; and the $-(CH_2)_{1-3}-$ group is optionally substituted with one or two substituents independently selected from the group consisting of halogen, $-OH$, $-OCH_3$, $-SCH_3$, 2-(N,N-dimethylamino)ethoxy, and $-NH_{2-z}(CH_3)_z$, wherein z is 0, 1, or 2.

For those compounds of the invention having any one of formulas (I), (Ia), (II), (III), (IV), (V), (VI), (VII), (VIII), (IXa), (IXb), (IXc), and (IXd) and bearing one or more hydroxyl (i.e., $-OH$) groups, a further particular prodrug form is that wherein at least one of these two or more hydroxyl groups is derivatized to be a moiety selected from the group consisting of $-OP(O)(OR^{11a})_2$, $-O(CH_2)_{1-3}-R^{19}$, $-OC(=X^a)R^{11a}$, and $-OC(=X^a)X^aR^{11a}$, wherein $R^{11a}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; $R^{19}$ is independently selected from the group consisting of $-OP(O)(OR^{11a})_2$, $-X^aC(=X^a)R^{11a}$, $-X^aC(=X^a)X^aR^{11a}$, and 5-alkyl-2-oxo-1,3-dioxolo-4-yl; $X^a$ is independently selected from O, S, and NH; and the $-(CH_2)_{1-3}-$ group is optionally substituted with one or two independently selected $R^{30}$, wherein $R^{30}$ is as defined herein (preferably, each $R^{30}$ is independently selected from the group consisting of a $1^{st}$ level substituent, a $2^{nd}$ level substituent, and a $3^{rd}$ level substituent as specified herein). In one embodiment of this prodrug form of the compounds of the invention having, the at least one derivatized hydroxyl group is selected from the group consisting of $-OP(O)(OR^{11a})_2$, $-O(CH_2)_{1-3}-R^{19}$, $-OC(=O)R^{11a}$, and $-OC(O)OR^{11a}$, wherein $R^{11a}$ is independently selected from the group consisting of H and $C_{1-6}$ alkyl (preferably $C_{1-3}$ alkyl), wherein the alkyl group is optionally substituted with one or two substituents independently selected from halogen, $-OH$, $-OCH_3$, $-SCH_3$, 2-(N,N-dimethylamino)ethoxy, and $-NH_{2-z}(CH_3)_z$, wherein z is 0, 1, or 2; $R^{19}$ is independently selected from the group consisting of $-OP(O)(OR^{11a})_2$, $-OC(=O)R^{11a}$, $-OC(=O)OR^{11a}$, and 5-($C_{1-3}$ alkyl)-2-oxo-1,3-dioxolo-4-yl; and the $-(CH_2)_{1-3}-$ group is optionally substituted with one or two substituents independently selected from the group consisting of halogen, $-OH$, $-OCH_3$, $-SCH_3$, 2-(N,N-dimethylamino)ethoxy, and $-NH_{2-z}(CH_3)_z$, wherein z is 0, 1, or 2.

In certain embodiments, the invention may relate to a solvate, salt, N-oxide, complex, racemic mixture, diastereomer, enantiomer, tautomer, conformer, isotopically labeled form, or combination thereof, of a prodrug having the formula (IXa), (IXb), (IXc), or (IXd); such as a solvate, salts, complex, racemic mixture, diastereomer, enantiomer, tautomer, conformer, isotopically labeled form, or combination thereof, of such prodrug.

In a one particular embodiment, a compound of the invention is a hydrate, suitably a mono-hydrate or a di-hydrate of a kinase inhibitor as specified under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, N-oxides of $R^{1a}$ and/or $R^6$), complex, polymorph, crystalline form, racemic mixture, diastereomer, enantiomer, tautomer, conformer, isotopically labeled form, prodrug (in particular a prodrug of formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof). In another suitable embodiment, a compound of the invention is a semi-hydrate of such a kinase inhibitor.

A compound of the invention (e.g., as specified under the heading "Compounds") can, in certain embodiments, be in (e.g., provided in) a purified or (e.g., substantially) pure form. For example, the compound may be greater than about 50% pure, such as greater than about 60%, 70% or 80% pure, suitably greater than about 90% pure (in particular, greater than about 95%, 97% 98% and even 99%). That is, in certain of such embodiments such a compound is present together with only a limited amount of impurities (e.g., such as those introduced during manufacturing), such as only small amounts of impurities are present, including embodiments where the compound is present in a from where impurities are substantially absent. The purity (e.g., the absence, or degree of presence of impurities) of the compound can be determined by routine procedures e.g. by HLPC.

In one embodiment, the present invention provides such a compound containing less than about 50%, 40%, 30% and suitably 10% or 5% area by HPLC, preferably less than about 3% and 2% area by HPLC, more preferably less than 1% area by HPLC, of total impurities. The term "% area by HPLC" as used herein refers to the area in an HPLC chromatogram of one or more peaks compared to the total area of all peaks in the HPLC chromatogram expressed in percent of the total area. Further, the purity of the compound may be expressed herein as "HPLC" purity. As such, "HPLC purity", is a calculation of the area under the compound peak divided by the total area under the curve in an HPLC chromatogram. Suitably, the compound contains less than about 10% area by HPLC of total impurities. More preferably, less than about 5% area by HPLC of total impurities.

In a related aspect, and as may be further described, defined, claimed or otherwise disclosed herein, the invention provides one or more containers, wherein the containers (each independently, or all collectively) contain, the kinase inhibitor of the first aspect (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, an N-oxide of $R^{1a}$ and/or $R^6$), complex, polymorph, crystalline form, racemic mixture, diastereomer, enantiomer, tautomer, conformer, isotopically labeled form, prodrug (in particular a prodrug of formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof) in an amount that is more than about 10 mg; in particular, in an amount more than about 50 mg or 100 mg; suitably an amount that is more than about 1 g, 10 g, 50 g or 100 g; or more than about 500 g or 1 Kg.

In a further aspect, the present invention provides a compound of the invention (in particular those specified above with respect to any of formulas (I), (Ia), (II), (III), (IV), (V), (VI), (VII), and (VIII)) for use as medicament, for example for use in therapy. In one embodiment of this aspect, the compound of the invention does not encompass compounds which have formula (I) and belong to one or more of the groups (1), (2), (3), (4) and/or (5) (such as compounds of one or more of the groups (1) (in particular, compounds of group (1) when $R^{1a}$ is 4-(2-hydroxyethyl) piperazin-1-yl), (2) and/or (4) (in particular, compounds 2-[(6-{[3-(1H-imidazol-1-yl)propyl]amino}pyridin-2-yl) amino]-4-methyl-N-[1-(phenylmethyl)-1H-indazol-5-yl]-1, 3-thiazole-5-carboxamide and 2-[(6-{[3-(1H-imidazol-1-yl) propyl]amino}pyridin-2-yl)amino]-N-[1-(phenylmethyl)-1H-indazol-5-yl]-1,3-thiazole-5-carboxamide) specified above. In one embodiment of this aspect, the compound of the invention does not encompass compounds which have formula (Ia) and belong to one or more of the groups (6) (such as, in particular, compounds of group (6)(i) when $R^{1a}$ is 4-(2-hydroxyethyl)piperazin-1-yl), (7) and/or (8) as specified above.

As it is evident from the examples, the inventors have found that the compounds of the invention as well as other structurally similar compounds inhibit one or more protein-tyrosine kinases selected from the group consisting of ABL1/BCR-ABL, SRC, LCK, KIT, FLT3 and their mutants, and/or SIK1, SIK2 and SIK3, and/or PHA2, EPHA4, CSF-R1, HCK and ACK1; and/or NEK11, WEE1, WNK2, Aurora-A, Aurora-B and TBK1. In one embodiment, the compounds of the invention exhibit pharmacological properties (selectivity, bioavailability, toxicity, side effects, dosing, patient compliance, compatibility, stability, half-life, etc.), which are in at least one aspect superior to the pharmacological properties exhibited by dasatinib.

Pharmaceutical Compositions

The compounds described in present invention (in particular those specified above such as those of formula (I), (Ia), (II), (III), (IV), (V), (VI), (VII), or (VIII), particularly those given in Table A and/or Table B) are preferably administered to a patient in need thereof via a pharmaceutical composition. Thus, in a second aspect, the present invention provides a pharmaceutical composition comprising a kinase inhibitor as specified above under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, an N-oxide of $R^{1a}$ and/or $R^6$), complex, polymorph, crystalline form, racemic mixture, diastereomer, enantiomer, tautomer, conformer, isotopically labeled form, prodrug (in particular a prodrug of formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof) and optionally one or more pharmaceutically acceptable excipients.

Thus, in one embodiment the pharmaceutical composition comprises a kinase inhibitor as specified above under the heading "Compounds" and one or more pharmaceutically acceptable excipients. Furthermore, the pharmaceutical composition may further comprise one or more additional therapeutic agents. Thus, in particular embodiments, the pharmaceutical composition comprises (i) a kinase inhibitor as specified above under the heading "Compounds" and one or more additional therapeutic agents; or (ii) a kinase inhibitor as specified above under the heading "Compounds", one or more additional therapeutic agents, and one or more pharmaceutically acceptable excipients.

The term "pharmaceutically acceptable" refers to the non-toxicity of a material which does not interact with the (e.g., therapeutic) action of the active component (e.g., a kinase inhibitor of the invention, either alone or in combination with one or more additional therapeutic agents) of the pharmaceutical composition.

The pharmaceutical composition may be administered to an individual by any route, such as enterally or parenterally.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

The compounds of the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, Berge et al., "Pharmaceutical Salts", 1. Pharm. Sci., 66, pp. 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, stabilizers, emulsifiers, buffers, flavoring agents, colorants, or antioxidants.

The compositions described in the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, e.g., the compound of the present invention, either alone or in combination with one or more additional therapeutic agents, may be coated in a material to protect the active compound(s) from the action of acids and other natural conditions that may inactivate the active compound.

Examples of suitable aqueous and non-aqueous carriers which may be employed in the pharmaceutical compositions according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, vegetable oils (such as olive oil), and injectable organic esters (such as ethyl oleate). Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersions. The use of such media and agents for pharmaceutically active compounds is known in the art. Except insofar as any conventional media or agent is incompatible with the active compound, use thereof in the pharmaceutical compositions according to the present invention is contemplated.

Additional therapeutic agents can be administered together with, before or after the compound of the present invention (in particular that specified above such as those of formula (I), (Ia), (II), (III), (IV), (V), (VI), (VII), or (VIII)) or incorporated into the compositions). In one embodiment, the pharmaceutical composition described herein comprises a kinase inhibitor of the invention as described above (e.g. having the general formula (I), (Ia), (II), (III), (IV), (V), (VI), (VII), or (VIII) or a solvate, salt (in particular a pharmaceutically acceptable salt), N-oxide (in particular, an N-oxide of $R^{1a}$ and/or $R^6$), complex, polymorph, crystalline form, racemic mixture, diastereomer, enantiomer, tautomer, conformer, isotopically labeled form, prodrug (in particular a prodrug of formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination of any of the foregoing), at least one additional therapeutic agent, and one or more pharmaceutically acceptable excipients.

The "additional therapeutic agent" (which in one embodiment is not a kinase inhibitor of formula (I) or (Ia), as specified herein, or in another embodiments may be a different kinase inhibitor of formula (I) or (Ia)) may be selected from any compound which can be used in the treatment of a disorder, disease or condition being a proliferative disorder (e.g., a cancer, such as one described, defined or disclosed elsewhere herein), and/or caused by or associated with: (i) the (e.g., erroneous) expression and/or activity of kinase, such as SRC, ABL/BCR-ABL, LCK, SIK1, SIK2, SIK3, FLT3 and/or KIT; and/or PHA2, EPHA4, CSF-R1, HCK and ACK1; and/or NEK11, WEE1, WNK2, Aurora-A, Aurora-B and TBK1 and/or (ii) cellular resistance to an (eg a cell-mediated) immune response. Examples of suitable additional therapeutic agents are defined or disclosed elsewhere herein, and include an EGFR inhibitor, gemcitabine, docetaxel, and immune checkpoint inhibitor (such as an inhibitor of PD1, PDL1, CTLA-4, LAG3 or IDO1, and in particular an immune checkpoint inhibitor selected from the list consisting of: nivolumab, relatlimab, ipilimumab and BMS-986205), TNF or an agonist of TNFR1- or TNFR2-signalling, adoptive cellular therapy including CAR T cells directed against a tumor antigen, vaccines including dendritic cell—(DC) based vaccination, or an agent that is capable of inducing or induces the exposure of the cells involved with the proliferative disorder to TNF or an agonist of TNFR1-signalling, is administered to the subject. The additional therapeutic agent may induce an additive or synergistic therapeutic effect.

The pharmaceutical composition described herein may comprise, in addition to the kinase inhibitor of the invention, at least one, e.g., 1, 2, 3, 4, 5, 6, 7 or 8, additional therapeutic agents. According to the present teaching, the at least one additional therapeutic agent may be formulated together with the kinase inhibitor of the invention in a single pharmaceutical composition. Alternatively, the pharmaceutical composition may be structured as kit of parts, wherein the kinase inhibitor of the invention is provided in a first formulation and the at least one additional therapeutic agent is provided in a second formulation, i.e., a second pharmaceutical composition. The first and the second pharmaceutical compositions may be combined prior to use. In other words, before administering the pharmaceutical composition, a formulation comprising the additional therapeutic agent may be added to the first pharmaceutical composition comprising the kinase inhibitor of the invention. Alternatively, the present teaching envisages administering the kinase inhibitor of the invention formulated in a first pharmaceutical composition and administering the at least one additional therapeutic agent formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

The compositions may also contain adjuvants such as preservatives, stabilizers, wetting agents, emulsifying agents, pH buffering agents, and dispersing agents. Prevention of the presence of microorganisms may be ensured by sterilization procedures and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the active compounds, which may be used in a suitable hydrated form, and/or the pharmaceutical compositions according to the present invention, are formulated into pharmaceutically acceptable dosage forms by conventional methods known to those of skill in the art (cf., e.g., Remington, "The Science and Practice of Pharmacy" edited by Allen, Loyd V., Jr., 22 nd edition, Pharmaceutical Sciences, September 2012; Ansel et al., "Pharmaceutical Dosage Forms and Drug Delivery Systems", 7th edition, Lippincott Williams & Wilkins Publishers, 1999).

A pharmaceutical composition can be administered by a variety of methods known in the art. As will be appreciated by the skilled artisan, the route and/or mode of administration will vary depending upon the desired results. The pharmaceutical compositions containing one or more active compounds can be prepared with carriers that will protect the one or more active compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such compositions are generally known to those skilled in the art. See, e.g., Sustained and Controlled Release Drug Delivery Systems, J. R. Robinson, ed., Marcel Dekker, Inc., New York, 1978.

To administer a compound of the present invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7: 27(1984)).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms used according to the present invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions according to the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of a compound according to the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound according to the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound according to the present invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/kg and 10 mg/kg (such as between about 2 mg/kg and 5 mg/kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$).

Actual dosage levels of the active ingredients in the pharmaceutical compositions according to the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the (e.g., therapeutically) effective amount of the pharmaceutical composition required. For example, the physician or veterinarian could start with doses of the compounds according to the present invention at levels lower than that required in order to achieve the desired therapeutic effect and gradually increase the dosage until the desired effect is achieved. In general, a suitable daily dose of a composition according to the present invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the (e.g., therapeutically) effective daily dose of a pharmaceutical composition may be administered as two, three, four, five, six or more sub-doses administered separately at appropriate intervals throughout the day, optionally, in unit dosage forms. While it is possible for a compound according to the present invention to be administered alone, it is preferable to administer the compound as a pharmaceutical formulation/composition.

For oral administration, the pharmaceutical composition according to the present invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

In one embodiment, the compound is orally administered in a concentration of, for example, at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight).

In one embodiment, the compound is parenterally administered (e.g., intravenously, intramuscularly, or subcutaneously), in a concentration of, for example, at most 10 mg/kg body weight (such as at most 5 mg/kg body weight, at most 4 mg/kg body weight, at most 3 mg/kg body weight, at most 2 mg/kg body weight, at most 1 mg/kg body weight, at most 0.5 mg/kg body weight, at most 0.4 mg/kg body weight, at most 0.3 mg/kg body weight, at most 0.2 mg/kg body weight, at most 0.1 mg/kg body weight).

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition according to the present invention is conveniently delivered in the form of an aerosol spray presentation from a pressurized pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurized aerosol, the dosage unit can be determined by providing a valve to deliver a metered amount. Capsules and cartridges of, for example, gelatine, for use in an inhaler or insufflator can be formulated containing a powder mix of the pharmaceutical composition according to the present invention and a suitable powder base such as lactose or starch.

The pharmaceutical composition according to the present invention can be formulated for parenteral administration by injection, for example, by bolus injection or continuous infusion. In one embodiment, the compounds or compositions according to the present invention may be administered by slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions according to the present invention are administered by maintenance therapy, such as, e.g., once a week for a period of 6 months or more.

Formulations for injection can be presented in units dosage form (e.g., in phial, in multi-dose container), and with an added preservative. The pharmaceutical composition according to the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Compositions according to the present invention which are suitable for vaginal administration also include pessaries, tampons, creams, gels, pastes, foams or spray formulations containing such carriers as are known in the art to be appropriate. Dosage forms for the topical or transdermal administration of compositions according to the present invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Therapeutic/pharmaceutical compositions can be administered with medical devices known in the art. For example, in a preferred embodiment, a therapeutic/pharmaceutical composition according to the present invention can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,916, which discloses an osmotic drug delivery system.

Many other such implants, delivery systems, and modules are known to those skilled in the art. In certain embodiments, the compounds according to the present invention can be formulated to ensure proper distribution in vivo. For example, the blood-brain barrier (BBB) excludes many highly hydrophilic compounds. To ensure that the compounds according to the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment, the compounds according to the present invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective tumor response.

A "therapeutically effective dosage" for therapy/treatment can also be measured by its ability to stabilize the progression of a condition, disorder or disease. The ability of a compound to inhibit one or more protein kinases or to reduce the viability of cells associated with a proliferative disorder, such as cancer cells can be evaluated by using appropriate in-vitro assays known to the skilled practitioner, such as those described herein (in particular in the Examples below). Alternatively, the properties of a compound described in the present invention can be evaluated by examining the ability of the compound in appropriate animal model systems known to the skilled practitioner such as those described herein (in particular in the Examples below). A therapeutically effective amount of a compound according to the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

The pharmaceutical composition according to the invention can also, if desired, be presented in a pack, or dispenser device which can contain one or more (e.g., unit) dosage forms containing the active compound. The pack can for example comprise metal or plastic foil, such as blister pack. The pack or dispenser device can be accompanied with a leaflet or other information; in particular, that describing (either to the patient and/or the administering physician) salient information or details on the pharmaceutical composition contained in the package, such as how to administer, recommended dosages, safety and/or side-effect information.

In a particular embodiment, a pharmaceutical composition of the invention is formulated for oral administration, and in an alternative particular embodiment, a pharmaceutical composition of the invention is formulated for intravenous administration.

In one embodiment, a pharmaceutical composition of the invention is in unit dose form, and in particular may be in a unit dose form that is formulated for oral administration.

Each of such a unit dose form may comprise (e.g., it may contain) between 1 and 950 mg of the compound, such as the kinase inhibitor of the first aspect (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, an N-oxide of $R^{1a}$ and/or $R^6$), complex, polymorph, crystalline form, racemic mixture, diastereomer, enantiomer, tautomer, conformer, isotopically labeled form, prodrug (in particular a prodrug of formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof). In particular, (e.g., each of) such a unit dose form may comprise (e.g., it may contain) between 2 and 150 mg of such compound; and suitably, between 10 and 150 mg of such compound.

In particular of such embodiments, a pharmaceutical composition of the invention that is in unit dose form (and in particular one be in a unit dose form that is formulated for oral administration) may comprise (e.g., it may contain)—for each unit dose form—about an amount of such compound selected from the list of amounts consisting of: 2 mg, 5 mg, 15 mg, 20 mg, 50 mg, 70 mg, 80 mg, 100 mg and 140 mg; in particular, comprising (e.g., containing) an amount of about 20 mg, 50 mg, 70 mg or 100 mg of a compound of the invention.

In one particular embodiment, the pharmaceutical composition of the invention is (e.g., is formed as) a tablet, caplet or capsule; suitably the pharmaceutical composition of the invention (e.g., a unit dose form thereof) is a caplet. Methods to form (e.g., manufacture) tablets and caplets are, for example, described elsewhere herein.

Suitable excipients for the pharmaceutical compositions of the invention, in particular when formed as a tablet or caplet, include, and particular embodiments of such a pharmaceutical composition of the invention include those that further comprise one or more (e.g., all of) the excipients selected from the list consisting of: lactose (e.g., lactose monohydrate), microcrystalline cellulose, croscarmellose sodium, hydroxypropylcellulose and magnesium stearate.

Therapeutic and Other Applications

In a third aspect, the present application provides a compound as specified above under the heading "Compounds" or a pharmaceutical composition as specified above under the heading "Pharmaceutical compositions" for use as a medicament, for example for use in therapy. In one embodiment of these aspects, the compound of the invention does not encompass compounds which have formula (I) and belong to one or more of the groups (1), (2), (3), (4) and/or (5) (such as compounds of one or more of the groups (1) (in particular, compounds of group (1) when $R^{1a}$ is 4-(2-hydroxyethyl)piperazin-1-yl), (2) and/or (4) (in particular, compounds in particular, compounds 2-[(6-{[3-(1H-imidazol-1-yl)propyl]amino}pyridin-2-yl)amino]-4-methyl-N-[1-(phenylmethyl)-1H-indazol-5-yl]-1,3-thiazole-5-carboxamide and 2-[(6-{[3-(1H-imidazol-1-yl)propyl]amino}pyridin-2-yl)amino]-N-[1-(phenylmethyl)-1H-indazol-5-yl]-1,3-thiazole-5-carboxamide) specified above under the heading "Compounds". In one embodiment of these aspects, the compound of the invention does not encompass compounds which have formula (Ia) and belong to one or more of the groups (6) (such as, in particular, compounds of group (6)(i) when $R^{1a}$ is 4-(2-hydroxyethyl)piperazin-1-yl), (7) and/or (8) as specified above under the heading "Compounds".

It is contemplated that a compound as specified above under the heading "Compounds" may be used for the inhibition of: (i) a kinase, such as one described herein, in particular SRC, ABL, BCR-ABL, LCK, SIK1, SIK2, SIK3, FLT3 and/or KIT, and/or PHA2, EPHA4, CSF-R1, HCK and ACK1, and/or NEK11, WEE1, WNK2, Aurora-A, Aurora-B and TBK1; and/or (ii) cellular resistance to an (e.g., a cell-mediated) immune response. For example, the compound can be used in a method for the treatment of a disease, disorder or condition in an individual (in particular a human patient), wherein the disease or condition is associated with such kinase.

The compounds of the invention may be used for treatment alone or in conjunction with one or more additional therapeutic agents, for example in combination with those that are defined or disclosed elsewhere herein, and that include an EGFR inhibitor, gemcitabine, docetaxel, and immune checkpoint inhibitor (such as an inhibitor of PD1, PDLL, CTLA-4, LAG3 or IDO1, and in particular an immune checkpoint inhibitor selected from the list consisting of: nivolumab, relatlimab, ipilimumab and BMS-986205), TNF or an agonist of TNFR1- or TNFR2-signalling, adoptive cellular therapy including CAR T cells directed against a tumor antigen, vaccines including dendritic cell—(DC) based vaccination, or an agent that is capable of inducing or induces the exposure of the cells involved with the proliferative disorder to TNF or an agonist of TNFR1-signalling, is administered to the subject.

Treatment including or utilising such compounds may be provided at home, the doctor's office, a clinic, a hospital's outpatient department, or a hospital. Treatment generally begins under medical supervision so that medical personnel can observe the treatment's effects closely and make any adjustments that are needed. The duration of the treatment depends on the age and condition of the patient, as well as how the patient responds to the treatment.

A person having a greater risk of developing a condition, disorder or disease may receive prophylactic treatment to inhibit or delay symptoms of the condition, disorder or disease.

The term "treatment" is known to the person of ordinary skill, and includes the application or administration of a therapeutic agent (e.g., a pharmaceutical composition containing said agent) or procedure to a patient or application or administration of a therapeutic agent (e.g., a pharmaceutical composition containing said agent) or procedure to a cell, cell culture, cell line, sample, tissue or organ isolated from a patient, who has a condition, disorder or disease, a symptom of the condition, disorder or disease or a predisposition toward a condition, disorder or disease, with the purpose to cure, heal, alleviate, relieve, alter, remedy, ameliorate, improve, affect or prevent the condition, disorder or disease, the symptoms of the condition, disorder or disease or the predisposition toward the condition, disorder or disease. Hence, the term "treatment" can include prophylactic treatment of a condition, disorder or disease, or the symptom of a condition, disorder or disease. A therapeutic agent, when used in treatment, includes the kinase inhibitors of the invention and includes, but is not limited to, additional therapeutic agents that may be small molecules, peptides, peptidomimetics, polypeptides/proteins, antibodies, nucleotides such as DNA or RNA, cells, viruses, ribozymes, siRNA, and antisense oligonucleotides.

Accordingly, in one fourth aspect, and as may be further described, defined, claimed or otherwise disclosed herein, the present invention relates to a compound as specified under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, N-oxides of $R^{1a}$ and/or $R^6$), complex, polymorph, crystalline form, racemic mixture, diastereomer, enantiomer, tautomer, conformer, isotopically labeled form, prodrug (in particular a prodrug having formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof) for use in a treatment of a proliferative disorder in a subject.

In another fourth aspect, and as may be further described, defined, claimed or otherwise disclosed herein, the present invention relates to a pharmaceutical composition as described above (e.g., one comprising a compound as specified under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, N-oxides of $R^{1a}$ and/or $R^6$), complex, polymorph, crystalline form, racemic mixture, diastereomer, enantiomer, tautomer, conformer, isotopically labeled form, prodrug (in particular a prodrug having formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof)) for use in a treatment of a proliferative disorder in a subject.

In a related fourth aspect, and as may be further described, defined, claimed or otherwise disclosed herein, the present invention relates to a method for the treatment of a proliferative disorder in a subject, comprising administering to the subject (e.g., a therapeutically effective amount of): (X) a compound as specified under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, N-oxides of $R^{1a}$ and/or $R^6$), complex, polymorph, crystalline form, racemic mixture, diastereomer, enantiomer, tautomer, conformer, isotopically labeled form, prodrug (in particular a prodrug having formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof); or (Y) a pharmaceutical composition as described above (e.g., one comprising a compound as specified under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, N-oxides of $R^{1a}$ and/or $R^6$), complex, polymorph, crystalline form, racemic mixture, diastereomer, enantiomer, tautomer, conformer, isotopically labeled form, prodrug (in particular a prodrug having formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof)).

In another related fourth aspect, and as may be further described, defined, claimed or otherwise disclosed herein, the present invention relates to a use of a compound as specified under the heading "Compounds" (e.g., a kinase inhibitor having the general formula (I), (Ia), (II), (III), (IV), (V), (VI), (VII), or (VIII), or a solvate, salt (in particular a pharmaceutically acceptable salt), N-oxide (in particular, N-oxides of $R^{1a}$ and/or $R^6$), complex, polymorph, crystalline form, racemic mixture, diastereomer, enantiomer, tautomer, conformer, isotopically labeled form, prodrug (in particular a prodrug having formula (IXa), (IXb), (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof)) for the manufacture of a medicament for the treatment of a proliferative disorder in a subject.

In such fourth aspects, the treatment of such use or method comprises administering to the subject (e.g., a therapeutically effective amount of) a compound or pharmaceutical composition of the invention.

In one particular embodiment of such aspect, the subject is a human, suitably an adult human. For example, a human that is 18 (or 16) years or older, such as a human between the ages of about 18 (or 16) and 90, or between 18 (or 16) and 80. In certain of such embodiments, the adult human is about 20 or older, 30 or older, 35 or older, 40 or older, 45 or older, 50 or older or 55 or older. In more particular of such embodiments, the adult human is a young adult (such as between about 18 (or 16) and 45 (or 40), or between about 30 and 45 (or 40)), is middle aged (such as between about 45 (or 40) and 65 (or 60), or between about 45 (or 40)) and 55 (or 50), or between about 55 (or 50) and 65 (or 60), or is elderly (such as being between about 60 and 90 (or older, such as 92, 95 or 98), between about 65 and 85 or between about 70 and 88).

As an alternative to such embodiments, the subject treated is a paediatric human such as being younger than about 18 (or 16). For example, such a human may be between about 3 and 18 (or 16), such as between about 5 and 16 or between about 10 and 16 or 12 and 17. The paediatric human may be an infant (such as between about two months of age to about 2 years or age), a toddler (such as between about 2 years to about 4 years), an early child (such as between about 4 years and about 9 years), a preadolescent (such as between about 9 years and about 12 or 13 (or 11 or 14) years) or an adolescent (such as between about 12 or 13 (or 11 or 14) years) years and about 15 (or 16 or 17)).

In one embodiment of such aspect, the treatment comprises administering to an adult human subject in need thereof an amount of a compound of the invention (for example, as comprised in a pharmaceutical composition) of less than about 140 mg daily. For example, optionally, where the proliferative disorder is not (e.g., the subject suffers from a proliferative disorder that is not) chronic phase Ph+ CML. In an alternative embodiment of such aspect, the treatment comprises administering to an adult human subject in need thereof an amount of such compound (for example, as comprised in a pharmaceutical composition) of more than about 140 mg daily, such as more than 150 mg daily.

In another embodiment of such aspect, the treatment comprises administering to an adult human subject in need thereof an amount of a compound of the invention (for example, as comprised in a pharmaceutical composition) of less than about 100 mg daily. For example, optionally, where the proliferative disorder is (e.g., the subject suffers from) chronic phase Ph+ CML. In an alternative embodiment of such aspect, the treatment comprises administering to an adult human subject in need thereof an amount of such compound (for example, as comprised in a pharmaceutical composition) of more than about 100 mg daily, such as more than 120 mg daily.

In one alternative embodiment, the treatment comprises administering to a paediatric human subject in need thereof an amount of a compound of the invention of:
  less than about 40 mg daily for paediatric patients with a body weight of 10 kg to less than 20 kg;
  less than about 60 mg daily for paediatric patients with a body weight of 20 kg to less than 30 kg;
  less than about 70 mg daily for paediatric patients with a body weight of 30 kg to less than 45 kg; or
  less than about 100 mg daily for paediatric patients with a body weight of at least 45 kg.

In one further alternative embodiment, the treatment comprises administering to a paediatric human subject in need thereof an amount of a compound of the invention of:
  greater than about 40 mg daily for paediatric patients with a body weight of 10 kg to less than 20 kg;
  greater than about 60 mg daily for paediatric patients with a body weight of 20 kg to less than 30 kg;
  greater than about 70 mg daily for paediatric patients with a body weight of 30 kg to less than 45 kg; or
  greater than about 100 mg daily for paediatric patients with a body weight of at least 45 kg.

In respect of those embodiments where an amount of such compound is (e.g. to be) administered to the human subject, such amount may be administered less frequently than daily. For example, a given amount of "less than 40 mg daily", may be achieved by administering, for example, 35, 30 or 20 mg each day, or 75, 65, or 40 mg once every two days (or less frequently).

In a particular embodiment, upon (or after) such administration of the (eg therapeutically effective) amount of a compound of the invention the subject is less likely to (eg, does not) have (or suffer from) an adverse reaction, such myelosuppression.

In one of such particular embodiments, upon (or after) such administration of the (eg therapeutically effective) amount of the compound to the subject is less likely to (eg, does not) have (or suffer from) a non-haematological adverse reaction, such as a cardiological adverse reaction.

In more particular of such embodiments, upon (or after) such administration of the (eg therapeutically effective) amount of the compound, to the subject is less likely to (eg, does not) have (or suffer) QT-prolongation.

In one embodiment, the subject is characterised by not concomitantly using a strong CYP3A4 inhibitor. For example, is not concomitantly using ketoconazole, itraconazole, erythromycin, clarithromycin, ritonavir, telithromycin, or ingests grapefruit juice.

The disease, disorder or a condition, in the context of the herein described invention, is, in certain embodiments, a proliferative disorder (including a condition or symptom associated with such disorder).

A "proliferative disorder" refers to a disorder characterised by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "proliferative disorder" is neoplasm or tumour, which is an abnormal growth of tissue or cells. Cancer is art understood, and includes any of various malignant neoplasms characterised by the proliferation of cells that have the capability to invade surrounding tissue and/or metastasise to new colonisation sites. Proliferative disorders include cancer, atherosclerosis, rheumatoid arthritis, idiopathic pulmonary fibrosis and cirrhosis of the liver. Non-cancerous proliferative disorders also include hyperproliferation of cells in the skin such as psoriasis and its varied clinical forms, Reiter's syndrome, *Pityriasis rubra* pilaris, and hyperproliferative variants of disorders of keratinisation (e.g., actinic keratosis, senile keratosis), scleroderma, and the like.

In more particular embodiments, the proliferative disorder is a cancer or tumour, in particular a solid tumour (including a condition or symptom associated with such cancer or tumour). Such proliferative disorders including but not limited to head and neck cancer, squamous cell carcinoma, multiple myeloma, solitary plasmacytoma, renal cell cancer, retinoblastoma, germ cell tumours, hepatoblastoma, hepatocellular carcinoma, melanoma, rhabdoid tumour of the kidney, Ewing Sarcoma, chondrosarcoma, any haemotological malignancy (e.g., chronic lymphoblastic leukemia, chronic myelomonocytic leukemia, acute lymphoblastic leukemia, acute lymphocytic leukemia, acute myelogenous leukemia, acute myeloblasts leukemia, chronic myeloblastic leukemia, Hodgkin's disease, non-Hodgkin's lymphoma, chronic lymphocytic leukemia, chronic myelogenous leukemia, myelodysplastic syndrome, hairy cell leukemia, mast cell leukemia, mast cell neoplasm, follicular lymphoma, diffuse large cell lymphoma, mantle cell lymphoma, marginal zone lymphoma, Burkitt Lymphoma, mycosis fungoides, seary syndrome, cutaneous T-cell lymphoma, peripheral T cell lymphoma, chronic myeloproliferative disorders, myelofibrosis, myeloid metaplasia, systemic mastocytosis), and central nervous system tumours (eg, brain cancer, glioblastoma, non-glioblastoma brain cancer, meningioma, pituitary adenoma, vestibular schwannoma, a primitive neuroectodermal tumour, medulloblastoma, astrocytoma, anaplastic astrocytoma, oligodendroglioma, ependymoma and choroid plexus papilloma), myeloproliferative disorders (eg, polycythemia vera, thrombocythemia, idiopathic myelfibrosis), soft tissue sarcoma, thyroid cancer, endometrial cancer, carcinoid cancer, or liver cancer.

In a particular embodiment, the various aspects of the invention relate to (for example the compounds or the pharmaceutical compositions of the invention are used in) treatments for proliferative disorders that include those described herein. Accordingly, in in such embodiments the proliferative disorder may be a cancer or tumour.

In one particular embodiment, the cancer is a hematopoietic or lymphoid cancer, and in one such embodiment, the proliferative disorder is (eg, the subject suffers from, or is suspected of suffering from) a Philadelphia chromosome-positive leukaemia; for example, Philadelphia chromosome-positive chronic myeloid leukaemia (Ph+ CML) or Philadelphia chromosome-positive acute lymphoblastic leukaemia (Ph+ ALL).

In a certain embodiment, the proliferative disorder is (eg, the subject (eg an adult human subject) suffers from, or is suspected of suffering from):
  newly diagnosed (Ph+ CML) in the chronic phase;
  chronic, accelerated or blast phase CML with resistance or intolerance to prior therapy including imatinib (eg, imatinib mesilate); or
  Ph+ acute lymphoblastic leukaemia (ALL) and lymphoid blast CML with resistance or intolerance to prior therapy.

In another certain embodiment, the subject is a paediatric human and proliferative disorder is (eg, the subject suffers from, or is suspected of suffering from):
  newly diagnosed Ph+ CML in chronic phase (Ph+ CML-CP) or Ph+ CML-CP resistant or intolerant to prior therapy including imatinib.

In another particular embodiment, the cancer is a solid tumour, and in one such embodiment, the proliferative disorder is (eg, the subject suffers from, or is suspected of suffering from) a solid tumour being one of those described elsewhere herein, such as pancreatic cancer, breast cancer, lung, prostate, melanoma, ovarian cancer, oesophageal cancer, sarcoma and colorectal cancer. In a certain of such embodiments, the proliferative disorder is (eg, the subject suffers from. or is suspected of suffering from) pancreatic cancer; in another of such embodiments, the proliferative disorder is (eg, the subject suffers from, or is suspected of suffering from) prostate cancer; and in yet another of such embodiments, the proliferative disorder is (eg, the subject suffers from, or is suspected of suffering from) lung cancer (eg, non-small cell lung cancer).

As described elsewhere, a compound (or pharmaceutical composition) of the invention may be administered to the subject (eg, as a combination therapy or regimen) with another medical procedure (eg, an additional therapeutic agent, such as described elsewhere herein, surgery or radiotherapy). Then such combination treatment regimen may comprise embodiments where such exposures/administrations are concomitant. In alternative embodiments such administrations may be sequential; in particular those embodiments where a compound (or pharmaceutical composition) of the invention is administered before such other procedure. For example the compound (or pharmaceutical composition) may be sequentially administered within about 14 days of (eg before) the other procedure, such as within about 10 days, 7 days, 5 days, 2 days or 1 day of (eg before) the other procedure; and further including where the compound (or pharmaceutical composition) may be sequentially administered within about 48 hours, 24 hours, 12 hours, 8 hours, 6 hours, 4 hours, 2 hours, 1 hours, 30 mins, 15 mins or 5 mins of (eg before) the other procedure.

Such combination regimens can include the (eg further) administration to the subject of:
  an EGFR inhibitor and/or gemcitabine—in particular when the proliferative disorder is (eg, the subject suffers from, or is suspected of suffering from) pancreatic cancer;
  docetaxel—in particular when the proliferative disorder is (eg, the subject suffers from, or is suspected of suffering from) prostate cancer; and/or
  an immune checkpoint inhibitor—in particular when the proliferative disorder is (eg, the subject suffers from, or is suspected of suffering from) lung cancer, such as non-small cell lung cancer.

Exemplary immune checkpoint inhibitor that may be comprise such combination therapy or regimen are described elsewhere, and include an antibody or small-molecule inhibitor of PD1, PDL1, CTLA-4, LAG3 or IDO1, and in particular such an immune checkpoint inhibitor may be one selected from the list consisting of: nivolumab, relatlimab, ipilimumab and BMS-986205, in particular nivolumab.

In other embodiments, the combination regimens can include the (eg further) administration to the subject of:
  an immune-activator (eg, agonist) antibody, such as an antibody against OX40 (eg, Yang et al 2012, Blood 120:4533), 41BB, CD40 or ICOS (eg, Deng et al 2004, Hybrid Hybridomics 23:176), in particular those that increase TNF levels by stimulated/stimulating T cells; and/or dendritic cell—(DC) based vaccination (eg, Lowe et al 2014, Oncoimmunology 3:e27589).

In one particular embodiment, the proliferative disorder (eg, in the subject) has progressed on (eg despite) standard therapy, or in anther embodiment, the subject may be unable to receive standard therapy, for example as the subject is intolerant thereto. In either of such embodiments, the subject may be so characterised (eg, stratified) as having progressed on standard therapy or being unable to receive (eg, is intolerant to) standard therapy.

As examples of standard therapy, may be imatinib (eg, for CML or ALL), docetaxel (eg for prostate cancer) or immunotherapy such as an immune checkpoint inhibitor described herein (eg, for melanoma or lung cancer).

Sensitisation to Immune Responses and Inhibition of Kinases

The compounds of the invention can sensitise cells involved with a proliferative disorder to a cell-mediated immune response.

Accordingly, in one embodiment, a treatment comprising administering a compound (or a pharmaceutical composition) of the invention to the subject involves (eg, is mediated, is or supported) sensitising cells involved with the proliferative disorder to a cell-mediated immune response.

In an alternative embodiment, a treatment comprising administering a compound (or a pharmaceutical composition) of the invention to the subject involves (eg, is mediated, is or supported by) inhibiting a kinase involved in resistance to a cell-mediated immune response, such as inhibiting SIK3.

In a related embodiment, a treatment comprising administering a compound (or a pharmaceutical composition) of the invention to the subject involves (eg, is mediated, is or supported by) inhibiting a kinase involved in resistance to a cell-mediated immune response, such as inhibiting SIK3, and (for example, thereby) sensitising cells involved with the proliferative disorder to a cell-mediated immune response.

In a further aspect, and as may be further described, defined, claimed or otherwise disclosed herein, the invention relates to a method for the sensitisation of cells involved with a proliferative disorder to a cell-mediated immune response in the treatment of the proliferative disorder in a subject, the method comprising administering a compound (or a pharmaceutical composition) of the invention to the subject; and in another further aspect, and as may be further described, defined, claimed or otherwise disclosed herein, the invention relates to a method for the inhibition of a kinase involved in resistance to a cell-mediated immune response, such as inhibiting, in the treatment of a proliferative disorder in a subject, the method comprising administering a compound (or a pharmaceutical composition) of the invention to the subject.

In a related further aspect, and as may be further described, defined, claimed or otherwise disclosed herein, the invention relates to a compound (or a pharmaceutical composition) of the invention for use as a medicament for: (i) sensitising cells involved with a proliferative disorder to a cell-mediated immune response; and/or (ii) inhibiting a kinase involved in resistance to a cell-mediated immune response, such as inhibiting SIK.

In yet a related further aspect, and as may be further described, defined, claimed or otherwise disclosed herein, the invention relates to a compound (or a pharmaceutical composition) of the invention for use as a medicament (eg an immuno-oncology medicament) sensitising cells involved with a proliferative disorder (such as a tumour or cancer) to a cell-mediated immune response, for example sensitising cells involved with a proliferative disorder to killing (cell-death) that may be induced by the cell-mediated immune response. An "immune-oncology" medicament is one that would be recognised by the person of ordinary skill, and includes a medicament that is intended to (eg, specifically designed to) enhance one or more components of the immune system of an organism (such as a human) towards cancerous or tumourous cells present in such organism. An immune-oncology medicament may be one (eg an antibody) that binds to an extrinsic immune (inhibitory) checkpoint molecule (such as one described elsewhere herein) and that (eg directly) suppresses T cell function against the cancerous or tumourous cells, or an immune-oncology medicament may be one that inhibits an immune regulator (such as SIK3, as in the present invention) that is intrinsic to the cancerous or tumourous cells where such intrinsic immune regulator does not actively (eg directly) suppress T cells but rather protects the tumour or cancer cells from an immune response via a resistance mechanism.

In particular embodiments of such aspects, the cells involved with a proliferative disorder may be sensitised to killing (cell-death) by (such as induced by) the cell-mediated immune response.

"Salt-inducible kinase 3" or "SIK3" (synonyms QSK and KIAA0999) is a member of a subfamily of serine/threonine protein kinases including SIK1, SIK2, and SIK3 that belong to an AMP-activated protein kinase (AMPK) family. A SIK3 protein in context of the invention is, typically, a protein kinase. Pertinent information on the human SIK3 protein is accessible on UniProt: Q9Y2K2 (Entry version 138 of 15 Mar. 2017) and a SIK3 protein in context of the invention has, preferably, an amino acid sequence shown in SIK3, Entry version 138 of 15 Mar. 2017 or Entry version 144 of 28 Mar. 2018, which sequences are incorporated herein by reference. SIK3 is a cytoplasmatic protein with serine/threonine kinase activity which is regulated through phosphorylation of a conserved threonine residue (position 163) in the T-loop of the kinase domain by the LKB1 complex; a phosphorylation which is reported as essential for catalytic activity of SIK3 (Lizcano, J. M. et al.; EMBO J. 23, 833-843 (2004)). For the purposes of the herein disclosed invention the term "phosphorylated SIK3" shall denote a SIK3 protein that is phosphorylated substantially as SIK3 protein can be (eg is) phosphorylated by LKB1, wherein preferably such phosphorylated SIK3 comprising a phosphor-threonine at amino acid position 163. A phosphorylated SIK3 in context of the invention is an SIK3 protein that is activated in its cell-biological context. At least four protein isoforms (SIK3-001 to SIK3-004) generated by alternative splicing of the SIK3 gene product are known. The human SIK3 gene is located at chromosomal position 11q23.3 (HGNC gene Symbol Acc: HGNC: 29165), and is conserved in many species such as in chimpanzee, Rhesus monkey, dog, cow, mouse, rat, chicken, zebrafish, and frog. The term SIK3 in some embodiments of the invention may also pertain to variants of the human SIK3 protein having an amino acid sequence that is substantially identical to, or of at least 80%, preferably 85%, more preferably 90, 95, 96, 97, 98, 99, or 100% sequence identity to, the amino acid sequence of SIK3 as described above, as determined using, e.g., the "Blast 2 sequences" algorithm described by Tatusova & Madden 1999 (FEMS Microbiol Lett 174: 247-250), and which (preferably) retain biological activity identical or substantially identical to the respective reference SIK3 (eg to phosphorylate one or more class II (eg IIa) HDACs, such as HDAC4). Preferred variants of SIK3 protein comprise sequence variants thereof due to sequence polymorphism between and within populations of the respective species, as well as mutations compared to the wild-type sequence of SIK3 which are located in or in close proximity to the activity loop or activation loop (T-loop) of SIK3. A preferred variant of SIK3 protein is a SIK3 T163 mutation, such as a mutation affecting the activation of SIK3. In preferred embodiments a SIK3 protein of the invention is not a SIK1 (synonyms: SIK and SNF1LK) protein and/or is not a SIK2 (synonyms: QIK, KIAA0781 and SNF1LK2) protein. The amino acid sequence of human SIK1 (UniProt: P57059; entry version 168 of 15 Mar. 2017) and human SIK2 (UniProt: Q9HOK1; entry version 153 of 15 Mar. 2017) are incorporated herein by reference. The term SIK3 can mean, as applicable to the context (if not more specifically indicated), a SIK3 protein (such as one described above) or an mRNA molecule encoding such a SIK3 protein. The analogous meaning with respect of "SIK1" and "SIK2" is to be understood.

A compound being an "inhibitor of SIK3" (or "SIK3 inhibitor") is any moiety that inhibits SIK3, which can mean inhibition of the activity of SIK3, especially of protein of SIK3, and in particular of phosphorylated SIK3. A SIK3 inhibitor may impair (eg, induces a decrease or reduction in) the efficiency, effectiveness, amount or rate of one or more activities of SIK3, such as one or more of those activities described herein, for example, the activity of SIK3 to phosphorylate class II (eg IIa) HDACs (eg HDAC4) and/or to sensitise a cell involved with a proliferative disorder to a cell-mediated immune response.

Such a SIK3 inhibiting moiety can act directly, for example, by binding to SIK3 and decreasing the amount or rate of one or more of the properties of SIK3 such as its function, in particular its ability to act as a kinase (eg to phosphorylate HDAC4), for example by reducing the activity of phosphorylated SIK3 in the cell.

Compounds being SIK3 inhibitors are described elsewhere herein, including those as may be characterised by the applicable functional and/or structural features set out herein.

In preferred embodiments, a "subject", in particular, is also meant to include all mammals, including without limitation humans, but also non-human primates such as cynomolgus monkeys. It also includes dogs, cats, horses, sheep, goats, cows, rabbits, pigs and rodents (such as mice and rats). It will be appreciated that a particularly preferred subject according to the invention is a human subject, such as a human suffering from (or at risk of suffering from) a disorder, disease or condition, for example a human patient.

As used herein, "therapy" is synonymous with treating a disease, disorder or condition, which includes reducing symptoms of the disease, disorder or condition, inhibiting progression of the disease, disorder or condition, causing regression of the disease, disorder or condition and/or curing the disease, disorder or condition.

In preferred embodiments, a "treatment" in the present invention, and in particular, is also meant to include therapy, e.g. therapeutic treatment, as well as prophylactic or suppressive measures for a disease (or disorder or condition). Thus, for example, successful administration of a compound (or pharmaceutical composition) of the invention prior to onset of the disease results in treatment of the disease. "Treatment" also encompasses administration of a compound (or pharmaceutical composition) of the invention after the appearance of the disease in order to ameliorate or eradicate the disease (or symptoms thereof). Administration of a compound (or pharmaceutical composition) of the invention after onset and after clinical symptoms, with possible abatement of clinical symptoms and perhaps amelioration of the disease, also comprises treatment of the disease. Those "in need of treatment" include subjects (such as a human subject) already having the disease, disorder or condition, as well as those prone to or suspected of having the disease, disorder or condition, including those in which the disease, disorder or condition is to be prevented.

The cell that is sensitised to the cell-mediated immune response is, suitably, one involved with the proliferative disorder (eg, a cell associated with the proliferative disorder), which in certain embodiments such cell is one involved in the proliferative disorder (eg, a cell that is abnormally proliferating, such as one that is over-proliferating). For example, such cell may be a cell characterised by loss of normal controls that affect its growth and cell division, such as a cell of a neoplasm or tumour. In particular embodiments, such cell may be a cancerous cell or one that is derived form or is a cell of a cancer or tumour. In other embodiments, such cell may be skin cell, such as one showing hyperproliferation such as one involved in psoriasis, Reiter's syndrome, *pityriasis rubra* pilaris or scleroderma.

A cell may be "involved with a proliferative disorder" if, for example, it is associated therewith, such as it being a causative factor in such proliferative disorder or if it is affected by such proliferative disorder. In particular a cell is "involved with a proliferative disorder" if the cell is characterised by an abnormal proliferation such as abnormal cell growth or cell division, and if the abnormal cell growth or cell division is part of the pathology of, or causative for, the proliferative disease. A cell "involved with a proliferative disorder", in those embodiments wherein the proliferative disorder is a tumour or cancer, can as a non-limiting example, be a tumour (or cancer) cell, or a cell of derived from (tissue) of such tumour or cancer; in particular of a solid tumour.

In certain embodiments, a compound of the invention may inhibit SIK3 in the cell involved with the proliferative disorder (eg the tumour cell). In particular of such embodiments, the compound may inhibit SIK3 in such cell preferentially to inhibiting SIK1 and/or SIK2 in such cell; and/or may inhibit SIK3 in such cell preferentially to inhibiting SIK1 and/or SIK2 and/or SIK3 in one or more types of immune cells. For example, a compound of the invention may inhibit SIK3 in the cell involved with the proliferative disorder (eg the tumour cell) preferentially to inhibiting SIK1 and/or SIK2 and/or SIK3 in macrophages and/or dendritic cells (in particular, those capable of or producing IL-10).

A compound (or pharmaceutical composition) of the invention may be administered to the subject, in particular in an amount (such as a dose) that is effective to, inhibit SIK3 and/or that is effective to sensitise the cells involved with the proliferative disorder to the cell-mediated immune response. Suitable amounts, formulations and means for such administration are described elsewhere herein.

In particular embodiments, a compound (or pharmaceutical composition) of the invention is administered in an amount (such as a therapeutically effective amount) that is effective to reduce activity of SIK3, preferably of SIK3 in (of) the cells involved with the proliferative disorder. In such embodiments, a "therapeutically effective amount" of the compound (or pharmaceutical composition) can be an amount that is capable to reduce the activity of the SIK3 to an applicable level, but that does not lead to significant (eg intolerable) side effects or over-dosage in respect of other activities of the compound (or pharmaceutical composition).

Preferably, the activity of SIK3 is effectively inhibited (reduced), preferably referring to the SIK3 kinase in (of) the cells involved with a proliferative disorder. For example, an "effective" inhibition (or reduction) may include one where the activity is lowered by a degree (or to a level) that has a physiological effect (eg to a therapeutically effective level), such as a reduction by about 10%, 20%, 50%, or more than 50% such as 70% or 90% of activity of the respective kinase. In respect of SIK3, one of such reductions may be desirable to elicit a therapeutic response.

The term "immune cell" is art recognised to describe any cell of an organism involved in the immune system of such organism, in particular of a mammal such as a human. Leukocytes (white blood cells) are immune cells that are involved in the innate immune system, and the cells of the adaptive immune system are special types of leukocytes, known as lymphocytes. B cells and T cells are the major types of lymphocytes and are derived from hematopoietic stem cells in the bone marrow. B cells are involved in the humoral immune response, whereas T cells are involved in cell-mediated immune response. In preferred embodiments of the invention, the immune cell can be a myeloid cell eg a T cell, and in particular (such as when an increase in cell-mediated immune response is required, such as to treat a cancer) the T cell can be a cytotoxic T cell (also known as TC, cytotoxic T lymphocyte, CTL, T-killer cell, cytolytic T cell, CD8+ T-cell or killer T cell). A CTL is a T-cell that is involved in the killing of cancer cells, cells that are infected (particularly with viruses), or cells that are damaged in other ways. Other preferred immune cells for such embodiments can include Tumour-Infiltrating Lymphocytes (TILs). TILs are white blood cells that have left the bloodstream and migrated into a tumour. Typically, TILs are a mix of different types of cells (eg, T cells, B cells, NK cells, macrophages) in variable proportions, T cells being the most abundant cells. TILs can often be found in the stroma and within the tumour itself, and are implicated in killing tumour cells. The presence of lymphocytes in tumours is often associated with better clinical outcomes.

The term "cell-mediated immune response", as used herein, may include, but is not limited to, a response in a host organism involving, utilising, and/or promoting any one or combinations of T cell maturation, proliferation, activation, migration, infiltration and/or differentiation, and/or the activation/modulation/migration/infiltration of a macrophage, a natural killer cell, a T lymphocyte (or T cell), a helper T lymphocyte, a memory T lymphocyte, a suppressor T lymphocyte, a regulator T lymphocyte, and/or a cytotoxic T lymphocyte (CTL), and/or the production, release, and/or effect of one or more cell-secretable or cell-secreted factor such as a cytokine or autocoid (in particular a pro-inflammatory cytokine such as TNF), and/or one or more components of any of such processes (such as a cytokine or autocoid, particular a pro-inflammatory cytokine such as TNF). The term "cell-mediated immune response," as used herein, may include a cellular response involving a genetically engineered, in-vitro cultured, autologous, heterologous, modified, and/or transferred T lymphocyte, or it may include a cell-secretable or cell-secreted factor (such as a cytokine or autocoid, in particular a pro-inflammatory cytokine such as TNF) produced by genetic engineering. A cell-mediated immune response is preferably not a humoral immune response, such as an immune response involving the release of antibodies. In certain embodiments, in particular when the proliferative disorder is a cancer or tumour, the cell-mediated immune response is an anti-tumour cell-mediated immune response. For example, one that leads to a reduction in tumour (cell) growth, such as a cytotoxic cell-mediated immune response (such as a cytotoxic T cell and/or TNF exposure) that kills cells of the cancer or tumour.

In certain embodiments, the cell-mediated immune response may be mediated by a cell, such as an immune cell, capable of secreting (eg secreting) pro-inflammatory cytokine, such as one selected from the group consisting of: interleukin-1 (IL-1), IL-8 and IL-12, tumour necrosis factor (TNF), interferon gamma (IFN-gamma), and granulocyte-macrophage colony stimulating factor. In particular of such embodiments, the pro-inflammatory cytokine is tumour necrosis factor (TNF) [alpha].

In other embodiments, the cell-mediated immune response may a cell-secretable or cell-secreted factor (such as a cytokine or autocoid), in particular one secretable or secreted by an immune cell. In particular of such embodiments, the cell-mediated immune response is a pro-inflammatory cytokine, in particular tumour necrosis factor (TNF).

The terms "sensitising", "sensitisation" and "to sensitise" (and the like), as used herein in the context of cell(s) being sensitised to a cell-mediated immune response, will be understood by the person of ordinary skill, and include the meaning that such cells can exhibit an increased susceptibility to one or more effect (eg a treatment effect) that the cell-mediated immune response may have on such cells. In particular, cells that are so sensitised may, when in the presence of (eg exposed to) a cell-mediated immune response, be killed more easily (such as more rapidly, a greater proportion of cells dying or being killed and/or upon a lower amount or exposure of the cell-mediated immune response) than analogous cells that have not been so "sensitised". For example, cell(s) so sensitised may be induced into cell-death (eg apoptosis) upon exposure to a lower number of T cells or to a lower concentration of TNF (such as about 10%, 20%, 30% 40%, 50% or more than 50% fewer T cells or lower concentration of TNF). Methods to determine whether such cells have been sensitised (and by which degree) to cell-mediated immune responses are described herein, such as in the examples. Accordingly, in certain embodiments of the present invention, cells involved with the proliferative disorder may be sensitised to cell-death/killing (eg by entry into apoptosis) by a cell-mediated immune response (such as CTL or a proinflammatory cytokine eg TNF).

The terms "tumour necrosis factor" and "TNF" (previously and hence alternatively known as tumour necrosis factor alpha and TNF-alpha) shall, in the context of the herein disclosed invention, be understood to refer to any proteins know under these denotations in the art. In particular, the term TNF encompasses endogenous TNF of any organism where such is present, and preferably of animals or mammals, such as humans. By means of example and not limitation, human TNF may encompass endogenous proteins as disclosed in inter alia Pennica et al. 1984 (Nature 312: 724-9) and in the UniProtKB/Swiss-Prot database with the entry No P01375 (for example, entry version 224 of 15 Mar. 2017), as well as any sequence variants thereof due to normal sequence polymorphism between and within human populations. By means of further non-limiting examples, the term may encompass endogenous TNF proteins as annotated in the UniProtKB/Swiss-Prot database for bovine (Q06599), dog (P51742), goat (P13296), guinea pig (P51435), cat (P19101), horse (P29553), mouse (P06804), chimp (Q8HZD9), pig (P23563), rabbit (P04924), rat (P16599) and others, as well as any sequence variants thereof due to sequence polymorphism between and within populations of each respective species. Further, the term TNF particularly encompasses the soluble, secreted cytokine form of TNF, including monomeric as well as, preferably, the typically more active trimeric forms thereof (see, e.g., Smith & Baglioni 1987. J Biol Chem 262: 6951-4). The primary amino acid sequences of soluble forms of endogenous TNF are indicated in the above mentioned UniProtKB/Swiss-Prot database entries for the respective exemplified organisms. In addition, the term TNF may also encompass membrane-bound forms of TNF expressed on the surface of some cell types (see, e.g., Kriegler et al. 1988. Cell 53: 45-53). Further, the term TNF may also encompass synthetic or recombinant proteins whose primary amino acid sequence is identical or substantially identical ("substantially identical", as used throughout this specification, generally refers to ≥80%, e.g., ≥85%, preferably ≥90%, more preferably ≥95%, even more preferably 98% or 99% sequence identity) to the sequence of an endogenous TNF, as determined using, e.g., the "Blast 2 sequences" algorithm described by Tatusova & Madden 1999 (FEMS Microbiol Lett 174: 247-250), and which (preferably) retain biological activity identical or substantially identical to the respective endogenous TNF, as determined using, e.g., the cytotoxicity tests described by Flick & Gifford 1984 (J Immunol Methods 68: 167-75). As will appear from the context of aspects and embodiments of the present invention, the term TNF may, in particular, refer herein to endogenous TNF, soluble and/or membrane bound, preferably soluble, produced by cells, tissues, organs or organisms, preferably human. Nevertheless, also envisioned by the term "TNF" are exogenous forms of tumour necrosis factor, in particular those produced by recombinant technologies and, in certain embodiments, may be administered to subjects, or exposed to or contacted with cells in various aspects and embodiments of the invention. In certain of such embodiments, the TNF may be a recombinant TNF used as a therapeutic, such as tasonermin (BEROMUN).

In certain embodiments, the cell-mediated immune response can be mediated by a pro-inflammatory cytokine-secreting cell, such as a lymphocyte (eg a T cell), in particular a cytotoxic T lymphocyte (CTL).

In particular embodiments, the cell-mediated immune response may induce killing (eg cell-death, such via apoptosis) of cells involved with the proliferative disorder. For example, the treatment (method) may comprise (eg may involve) that (or be mediated by) the cell-mediated immune response induces such killing of cells involved with the proliferative disorder.

The cells involved with the proliferative disorder may be killed (eg induced into cell death) by one or more cytotoxic processes, in particular those that are endogenous to such cell such as programmed cell death (PCD). Cell death processes may include, but are not limited to, necrosis (in particular necroptosis), apoptosis, anoikis, autophagy, ferroptosis, mitotic catastrophe and activation-induced cell death. In certain preferred embodiments, the cells involved with the proliferative disorder (eg the tumour cells) are induced into apoptosis by the cell-mediated immune response (eg by TNF). In a further embodiment, a compound (or pharmaceutical composition) of the invention is administered to not kill such cells in the absence of the cell-mediated immune response (eg in the absence of TNF). In particular of such further embodiments, the compound (or pharmaceutical composition) may be administered in an amount (eg in a dose) that is not effective to kill such cells in the absence of the cell-mediated immune response. The examples herein, describe various assays by which an amount of a compound (or pharmaceutical composition) of the invention may be determined that is effective to kill such cells only, or preferentially, in the presence of the cell-mediated immune response.

In other particular embodiments, the cell-mediated immune response may involve at least one immune cell effector molecule, in particular an effector molecule that is secretable or secreted by an immune cell. In particular of such embodiments, the effector molecule can be a pro-inflammatory cytokine, preferably tumour necrosis factor (TNF).

In certain embodiments, the effector molecule is not a cell effector molecule selected from Fas ligand (FasL or CD95L) and TNF-related apoptosis-inducing ligand (TRAIL, CD253 or TNFSF10).

In particular embodiments of the invention, a compound (or pharmaceutical composition) of the invention may be administered to the subject (eg in an amount or dose effective) with the intent to (or so as to) (effectively) sensitise cells involved with the proliferative disorder to killing induced by TNF. For example, the compound (or pharmaceutical composition) may be administered in a therapeutically effective amount, such as an amount effective to sensitise the cells involved with the proliferative disorder to killing (cell-death) induced by TNF.

For example, a compound (or pharmaceutical composition) of the invention may be administered to the subject (for example, in an amount or dose effective) to induce apoptosis of such cells mediated by TNF, such as when such cells are in the presence of or contacted with TNF. In further embodiments, the a compound (or pharmaceutical composition) of the invention may be administered to the subject (eg in an amount or dose effective) to induce a reduced amount of cytotoxicity (eg apoptosis)—such as to not induce killing (eg apoptosis) of such cells—in the absence of TNF; for example the compound (or pharmaceutical composition) may be administered in an amount or dose that is—not as effective in cytotoxicity (eg apoptosis)—such as being not effective to induce such killing—in the absence of TNF.

TNF can induce pro-apoptotic processes via binding to and/or signalling via tumour necrosis factor receptor 1 (TNFR1) and or tumour necrosis factor receptor 2 (TNFR2). Accordingly, in certain embodiments a compound (or pharmaceutical composition) of the invention may be administered to the subject (eg in an amount or dose effective) to (effectively) sensitise cells involved with the proliferative disorder to apoptosis mediated by tumour necrosis factor receptor 1 (TNFR1) signalling and/or tumour necrosis factor receptor 2 (TNFR2) signalling. Preferably, the compound (or pharmaceutical composition) can be administered to the subject (eg in an amount or dose effective) to (effectively) sensitise cells involved with the proliferative disorder to apoptosis mediated thereby in particular mediated by TNFR1. For example, the compound (or pharmaceutical composition) may be administered in a therapeutically effective amount that is effective to mediate TNFR1- and/or TNFR2-signalling, and/or apoptosis mediated thereby.

For example in certain embodiments, a compound (or pharmaceutical composition) of the invention may be administered (eg in an amount or dose effective) to induce apoptosis of such cells by TNFR1 and/or TNFR2 signalling, such as upon active TNFR1 signalling. In particular of such embodiments, the compound (or pharmaceutical composition) may be administered to the subject (eg in an amount or dose, such as a therapeutically effective amount) to (effectively) induce a reduced amount of cytotoxicity (eg apoptosis)—such as to not induce apoptosis of such cells—in the absence of TNFR1 and/or TNFR2 signalling, such as in the absence of active TNFR1 signalling. For example, the compound (or pharmaceutical composition) may be administered in an amount or does that is not as effective in cytotoxicity (eg apoptosis)—such as being not effective to induce such apoptosis—in the absence of such signalling.

Therefore, in certain embodiments, a compound (or pharmaceutical composition) of the invention may be administered to the subject (eg in an amount or dose) to induce a reduced amount of cytotoxicity (eg apoptosis)—such as to not be cytotoxic—to cells involved with the proliferative disorder in the absence of the cell-mediated immune response.

In particular embodiments, a compound (or pharmaceutical composition) of the invention may be continued to be administered to the subject even if the tumour of the subject is increased in size during treatment. Without being bound to theory, even if an increase in tumour size is observed during such treatment, this may indicate an (enhanced) immune reaction against cells of the tumour (eg, the cells have become sensitised to the cell-mediated immune response; and the tumour is increasing in size because of such immune response), and hence the administration of the compound (or pharmaceutical composition) can, in such embodiments, continued to be administered so as to maintain such sensitivity and associated (enhanced) immune reaction.

As described in PCT/EP2018/060172, the inhibition of SIK3 is associated with a number of key biological processes or phenotypes, including those surprisingly involved in the control and/or triggering of cytotoxic process innate to cells, such as apoptosis. For example, tumour cells can be sensitised to the apoptotic/cytotoxic effects of TNF by the inhibition of SIK3, acting through pathways and components thereof including liver kinase B1 (LKB1, STK11 or NY-REN-19), histone deacetylase 4 (HDAC4), nuclear factor kappa-light-chain-enhancer of activated B cells (NF-kappaB), and pro-apoptotic genes regulated by NF-kappaB such as Caspase 8 and Caspase 9. Also c-Jun N-terminal kinase (JNK) is a signalling component associated with sensitisation to the apoptotic/cytotoxic effects of TNF by the inhibition of SIK3.

The term "associated with", in the context of this embodiment (and other embodiments, where applicable) can mean that two components, variables, effects or phenotypes are interrelated with each other, and/or that they are related to (eg correlated to) each other, and/or that there is a causative link between a first and a second component, variable, effect or phenotype (such as the second is in response to the first, the second is a consequence of the first, or the second is caused by the first).

Accordingly, in one such embodiment, administration of a compound (or pharmaceutical composition) of the invention can associate with impairment of NF-kappaB activity (eg, by an enhancement or increase in translocation of NF-kappaB out of the nucleus) in cells involved with the proliferative disorder.

In particular of such embodiments, such impairment of NF-kappaB activity (eg, by an enhancement or translocation of NF-kappaB out of the nucleus) may be associated with (activated) TNF- and/or TNFR1-mediated signalling (or TNFR2-mediated signalling) in such cells.

In certain embodiments, a compound (or pharmaceutical composition) of the invention may be administered to the subject (eg in an amount or dose effective) to impair or inhibit NF-kappaB activity in the cells involved with the proliferative disorder, for example to enhance or increase translocation of NF-kappaB out of the nucleus of such cells. For example, the compound (or pharmaceutical composition) may be administered to the subject in a (eg, therapeutically effective) amount being effective to (effectively) impair NF-kappaB activity in cells involved with the proliferative disorder, in particular in an amount effective to (effectively) enhance or increase translocation of NF-kappaB out of the nucleus of the cells involved with the proliferative disorder.

In alternative or further embodiments, administration of a compound (or pharmaceutical composition) of the invention may be associated with an increase in (eg, the compound (or pharmaceutical composition) is administered, such as in an amount or dose effective, to increase) activity of class II (eg IIa) HDACs, eg HDAC4, in the cells involved with the proliferative disorder, for example its translocation or localisation to or its activity in the nucleus of such cells; and in particular upon TNF- and/or TNFR1-mediated signalling (or TNFR2-mediated signalling) in such cells.

In other alternative or further embodiments, administration of a compound (or pharmaceutical composition) of the invention may be associated with de-acylation of nuclear NF-kappaB (eg de-acylation at its p65 subunit) and/or decreased transactivation of one or more anti-apoptotic factors, in particular upon TNF- and/or TNFR1-mediated signalling (or TNFR2-mediated signalling) in the cells involved with the proliferative disorder. For example, the compound (or pharmaceutical composition) may be administered (such as in an amount or dose effective) to cause de-acylation of nuclear NF-kappaB (eg at its p65 subunit) and/or decreased transactivation of one or more anti-apoptotic factors.

In another alternative or further embodiment, administration of a compound (or pharmaceutical composition) of the invention may be associated with an increase in (eg the compound (or pharmaceutical composition) is administered, such as in an amount or dose effective, to increase) cleavage of Caspase 8 and/or Caspase 9 in the cells involved with the proliferative disorder, in particular upon TNF- and/or TNFR1-mediated (or TNFR2-mediated signalling) signalling in such cells.

In yet other alternative or further embodiments, administration of a compound (or pharmaceutical composition) of the invention may be associated with a reduction in the transcription of one or more anti-apoptotic factors, in particular upon TNF- and/or TNFR1-mediated signalling (or TNFR2-mediated signalling) in the cells involved with the proliferative disorder, for example the reduction of the transcription of one or more NF-kappaB target genes in such cells. In particular, the compound (or pharmaceutical composition) may be administered (eg in an amount dose effective) to reduce the transcription of one or more such anti-apoptotic factors, in particular upon TNF- and/or TNFR1-mediated signalling (or TNFR2-mediated signalling) in the cells involved with the proliferative disorder.

In one embodiment the administration of a compound (or pharmaceutical composition) of the invention may be associated with an increase in (eg the compound (or pharmaceutical composition) is administered, such as in an amount or dose effective, to increase) JNK activation (such as by phosphorylation) in the cells involved with the proliferative disorder, in particular upon TNF- and/or TNFR1-mediated signalling (or TNFR2-mediated signalling) in such cells.

In another embodiment, administration of a compound (or pharmaceutical composition) of the invention may not be associated with a significant change in CREB-pathways signalling and/or a significant change gene expression mediated by CREB and/or CREB-regulation.

In a particular embodiment, the TNF- (TNFR2-) and/or TNFR1-mediated signalling in the cells involved with the proliferative disorder may be associated with increased levels of pLKB1 in such cells.

As will now be apparent to the person of ordinary skill given knowledge of the present invention, the treatment aspects of the invention may further comprise a step of administering one or more other moieties that appropriately modify the expression, activity, function or stability of one or more these other pathway components described above, so as to additively or synergistically contribute to the treatment effect. For example, in one such embodiment, a treatment aspect of the invention may further comprise a step of administering an inhibitor of LKB1. In another of such embodiments, a treatment aspect of the invention may further comprise a step of administering a compound of the invention that promotes, enhances or increases one or more class II (eg IIa) HDACs (histone deacetylases), such as HDAC4, in the nucleus of the cells involved with the proliferative disorder. In yet another of such embodiments, a treatment aspect of the invention may further comprise a step of administering an inhibitor of NF-kappaB (activation). The invention also envisions that combinations of two or more such other moieties may be used in a treatment together with a compound (or pharmaceutical composition) of the invention and/or using other (eg anti-cancer) therapeutically active agents (such as an additional therapeutic agent as described elsewhere herein) together with the compound (or pharmaceutical composition).

In a further aspect, and as may be further described, defined, claimed or otherwise disclosed herein, the invention relates to a method for the sensitisation of cells involved with a proliferative disorder to a cell-mediated immune response, the method comprising exposing (eg contacting) the cells involved with a proliferative disorder to a compound (or pharmaceutical composition) of the invention. Such a method may, typically, be practiced as an in-vitro and/or ex-vivo method.

In a particular embodiment, the cell-mediated immune response comprises killing the cells involved with a proliferative disorder, such as where said killing involves (eg, is mediated, is or supported by) TNF, TNFR2- and/or TNFR1-mediated signalling. For example, the killing of such cells may involve apoptosis of such cells induced by TNF, TNFR2- and/or TNFR1-mediated signalling. Within this and the other applicable embodiments of the various aspects of the invention, TNFR2- and/or TNFR1-mediated signalling may be triggered (eg activated) by any appropriate triggering molecule, such as TNF, a variant of TNF and or a TNFR2 or TNFR1 agonist; in particular by exposing (eg by contacting) the cells associated with the proliferative disorder to the triggering molecule (eg TNF, TNF variant or TNFR1 agonist). Such exposure can lead to the triggering molecule (eg TNF, TNF variant or TNFR1 agonist) binding to TNFR2 and/or TNFR1 and, in particular the triggering (eg activation) of TNFR1 signalling.

In a yet further aspect, and as may be further described, defined, claimed or otherwise disclosed herein, the invention relates to a method for the killing of cells involved with a proliferative disorder, the method comprising exposing (eg contacting) the cell involved with the proliferative disorder to: (i) TNF, a TNF variant and/or an agonist of TNFR1- or TNFR2-signalling (preferably, TNFR1-signalling); and exposing (eg contacting) the cells involved with the proliferative disorder to (ii) a compound (or pharmaceutical composition) of the invention. As will be appreciated by the person or ordinary skill, such a method may, typically, be practiced as an in-vitro and/or ex-vivo method.

In a related aspect, the invention relates to a compound (or pharmaceutical composition) of the invention for use in the treatment of a proliferative disease involving the killing of a cell involved with the proliferative disorder, the treatment comprising exposing such cell to: (i) TNF, a TNF variant and/or a TNFR1 or TNFR2 agonist; and (ii) a compound (or pharmaceutical composition) of the invention.

In particular embodiments of such aspects, the killing of the cell involved with the proliferative disorder is mediated by sensitising such cell to a cell-mediated immune response, in particular by inducing sensitivity to apoptosis of such cell that involves (eg, is mediated, is or supported by) TNF, TNFR2 and/or TNFR1-mediated signalling.

The cell(s) involved with the proliferative disorder may be exposed to the TNF, a TNF variant and/or a TNFR1 or TNFR2 agonist by contacting the cell to such triggering molecule; and/or such cell(s) may be exposed to a compound (or pharmaceutical composition) of the invention by contacting (or introducing into) such cell(s) with a compound (or pharmaceutical composition) of the invention. The amounts (or dose) of (i) TNF, a TNF variant and/or a TNFR1 or TNFR2 agonist; and/or (ii) a compound (or pharmaceutical composition) of the invention are, typically, effective amounts; that is amounts (or doses) that are effective in, for example, sensitising the cell(s) to (such as killing such cell(s) by) apoptosis induced by TNF, TNFR2 and/or TNFR1-mediated signalling. Elsewhere are disclosed suitable amounts of these active agents (or ways to determine them) that may be incorporated in these aspects of the invention; as are further particular characteristics of the compound (or pharmaceutical composition) of the invention. Accordingly, in certain embodiments: (i) TNF, a TNF variant and/or a TNFR1 or TNFR2 agonist; and (ii) a compound (or pharmaceutical composition) of the invention, can be administered to a subject suffering from the proliferative disorder (eg, the treatment can comprise the administration of: (i) TNF, a TNF variant and/or a TNFR1 or TNFR2 agonist; and (ii) a compound (or pharmaceutical composition) of the invention, can be administered to the subject).

The cell(s) involved with the proliferative disorder may be one as described elsewhere herein, and in particular such cell(s) may be cancerous or tumour cell. For example, such cell(s) may be one that is of, or derived from, a solid tumour.

In certain embodiments of these aspects, the method is an in vitro (and/or ex-vivo) method. In alternative embodiments of such methods, the cell(s) involved with the proliferative disorder (such as tumour cells) is present in such subject, in particular in a subject in need of treatment thereof.

In further embodiments of the methods of these aspects, the (treatment) effect of such method (eg, on the cell(s) involved with the proliferative disorder) can be mediated by (eg, the treatment may comprise, involve or be mediated by) inhibiting SIK3; in particular, by inhibiting the function and/or activity of SIK3 protein (eg, of phosphorylated SIK3 protein, and/or as described elsewhere herein). In particular, in such embodiments, the SIK3 activity is (eg, effectively) reduced, such as reduced to a therapeutically effective level.

In certain embodiments of such methods, in the absence of (eg such effective amount or dose of) a compound (or pharmaceutical composition) of the invention, the cell(s) involved with the proliferative disorder (such as the tumour cell(s)) are not killed or induced to enter apoptosis (for example, they proliferate) upon TNF, TNFR2- and/or TNFR1-mediated signalling and/or exposure to (eg, the effective amount or dose of) TNF, TNF variant, TNFR2 or TNFR1 agonist.

As described above, in certain embodiments of these methods, a compound (or pharmaceutical composition) of the invention may inhibit SIK3 in (of) the cell(s) involved with the proliferative disorder (eg tumour cells). In particular of such embodiments, the compound (or pharmaceutical composition) may inhibit SIK3 in (of) such cell(s) preferentially to inhibiting SIK1 and/or SIK2 in (of) such cell; and/or may inhibit SIK3 in such cell preferentially to inhibiting SIK1 and/or SIK2 and/or SIK3 in (of) one or more types of immune cells. For example, a compound (or pharmaceutical composition) of the invention may inhibit SIK3 in (of) the cell(s) involved with the proliferative disorder (eg tumour cells) preferentially to inhibiting SIK1 and/or SIK2 and/or SIK3 in (of) macrophages and/or dendritic cells (in particular, those capable of or producing IL-10). In particular embodiments, the (treatment) effect is mediated by (eg, the treatment comprises, involves, is by or is mediated by) inhibition of SIK3 in (of) the cell(s) involved with the proliferative disorder (eg a tumour cell); and in further of such embodiments, the (treatment) effect is not mediated by (or the effect is mediated by not) (eg, the treatment does not comprise, involve or is not mediated by) inhibiting SIK2, in particular SIK2 in/of other cells (such as those involved with the proliferative disorder or immune cells), and/or the (treatment) effect is not mediated by (or the effect is mediated by not) inhibiting SIK1 (eg, the treatment does not comprise, involve or is not mediated by inhibiting SIK1), in particular SIK1 in/of other cells (such as those involved with the proliferative disorder or immune cells).

Accordingly, in one embodiment, the SIK3 of (eg, in) the cell(s) involved with the proliferative disorder is inhibited (eg, by a compound or pharmaceutical composition of the invention). In another (or further) embodiment, another kinase (eg SIK2, in particular SIK2) of (eg in) immune cells—such as CTLs—is inhibited to a lesser extent than SIK3 (eg in the cell(s) involved with the proliferative disorder). In yet another (or further) embodiment SIK1, in particular SIK1 of (eg in) immune cells—such as CTLs—is inhibited to a lesser extent than such SIK3.

In certain of such embodiments, one or more of the kinases selected from the list consisting of: SIK3, SIK1, SIK2, JAK1, RET, ERBB4 PDGFR-alpha, and EPHB2, is inhibited (eg, by a compound or pharmaceutical composition of the invention) to a lesser extent than one or more of the kinases selected from the list consisting of: ABL1, SRC, BCR-ABL, LCK, LYN, YES, FYN, KIT and FLT3.

In certain of such embodiments, one or more of the kinases selected from the list consisting of: PDGFR-alpha, TGFB-R1, B-RA, p38-beta, ACV-R1, BMPR1A and RET, is inhibited (eg, by a compound or pharmaceutical composition of the invention) to a lesser extent than one or more of the kinases selected from the list consisting of: EPHA2, EPHA4, CSF1-R, HCK and ACK1.

In certain of such embodiments, one or more of the kinases selected from the list consisting of: NEK11, WEE1, WNK2, Aurora-A, Aurora-B and TBK1, is inhibited (eg, by a compound or pharmaceutical composition of the invention) to a lesser extent than one or more of the kinases selected from the list consisting of: ABL1, SRC, BCR-ABL, LCK, LYN, YES, FYN and KIT.

A given kinase (such as SIK1 or SIK2) may be inhibited to a "lesser extent" than another kinase (such as SIK3) if, for example, the other kinase (such as SIK3) is inhibited by an amount greater than about 2 fold more than the given kinase, such as by an amount greater than about 5, 10, 20, 50, 75 or 100-fold more than the given kinase. In particular, the other kinase (such as SIK3) may be inhibited by an amount between about 5 and 20 fold, 20 and 50 or 50 and 100 fold more than the given kinase. For example, the SIK3 (ie, the other kinase) may be inhibited between about 20 and 50 fold more than SIK1 and/or SIK2 (ie, a given kinase). By way of example, a compound (or pharmaceutical composition) of the invention may inhibit the other kinase (eg SIK3) by 80% (ie, to have only 20% of its uninhibited activity) but inhibit the given kinase (eg SIK1) by only 4% and SIK2 by only 8%. Accordingly, the other kinase (eg SIK3) is inhibited about 20-fold more than the given kinase (eg SIK1) and 10-fold more than another given kinase (eg SIK2). In particular embodiments, the other kinase (eg SIK3) may be inhibited to about the same extent as eg SIK1 (eg between about 2 to 53 fold of each other), and eg SIK2 is inhibited to a lesser extent that either (or both) of eg SIK3 and SIK1: For example, in such embodiments, eg SIK3 and SIK1 are inhibited by between about a 20 and 50 fold more than eg SIK2 (eg in immune cells) is inhibited.

The compounds of the invention are shown to be potent inhibitors of one or more kinases (as shown in the Examples, and in particular by FIG. 3). In particular, any of (or any combination of) those kinases in FIG. 3 having a residual activity of between about 50% and about 25%, or less than about 25% residual activity (and particular, those having a residual activity of less than about 10%), are considered, in certain embodiments to be "key-kinases" that are inhibited by the respective compounds of the invention. Mutants of such kinases are also considered therein. As particular examples, the key-kinases include one or more kinases selected from the list consisting of: SIK1, SIK2, SIK3, ABL1/BCR-ABL, SRC, FLT3, KIT, YES, LYN, FYN and LCK; and/or EPHA2, EPHA4, CSF1-R, HCK, ACK1; and/or PDGFR-alpha, TGFB-R1, B-RAF and/or p38-beta; and/or ACV-R1 and/or BMPR1A; and/or RET; and/or NEK11, WEE1 and/or WNK2; and/or Aurora-A and/or Aurora-B; and/or TBK1; in particular, ABL1/BCR-ABL, ABL1/BCR-ABL and FLT3.

The inventors find that the compounds of the invention inhibit a different set of kinases and/or each to a different degree compared to other kinase inhibitors. For example, compounds B3 and A8 are equivalent inhibitors of ABL1 and SRC (and of mutants of ABL1). However, as shown in the Examples, they inhibit SIK1, SIK2, SIK3, and in particular FLT3, KIT and SYK to different degrees.

Also shown in the examples, are that the compounds of the invention are more selective for ABL1 and (in particular) for SRC kinases than dasatinib, and that this selectivity also applies within the class of protein-tyrosine kinases.

Compounds that inhibit different kinases and/or kinases to different degrees will have different properties in vivo, and can be used for different medical indications, or for the same medical indications but showing different properties in terms of efficacy and side-effects. As will be appreciated, compounds with different specificity to kinases can have surprisingly different properties and applications.

Accordingly, in one embodiment, the treatment comprises (eg, involves, is by or is mediated by) inhibition of one or more of the key-kinases (eg of ABL1 and/or SRC kinase, and/or LCK). In particular of such embodiments, the treatment comprises (eg, involves, is by or is mediated by) inhibition of such key-kinase(s) more than comprising (eg, involving, is or is mediated by) inhibition of one or more of the other key-kinases (eg SIK3 and/or SIK1 and/or SIK2).

For example, the treatment can involve inhibiting ABL1 and/or SRC kinase, and/or one or more kinases selected from the list consisting of: BCR-ABL, LCK, LYN, YES, FYN and KIT.

In a particular (alternative or additional) embodiment, the treatment does not comprise (eg, does not involve, is not or is not mediated by) inhibition of one or more of the key-kinases. In particular of such embodiments, the treatment does not comprise (eg, does not involve, is not or is not mediated by) inhibition of SIK3, and/or the treatment does not comprise (eg, does not involve, is not or is not mediated by) inhibition of SIK1 and/or SIK2.

In further embodiments, the treatment may not comprise (eg, may not involve, is not or is not mediated by) inhibition of one or more of following kinases: JAK1, RET, ERBB4, PDGFR-alpha or EPHB2.

In another particular (alternative or additional) embodiment, the treatment does not comprise (eg, does not involve, is not or is not mediated by) inhibition of SYK. For example, compound B3 inhibits SYK with an IC50 of over 25 uM, while compound A8 has an IC50 for SYK of less than 5 uM.

In yet another particular (alternative or additional) embodiment, the treatment comprises (eg, involves, is by or is mediated by) inhibition of KIT. For example, compound B3 inhibits KIT with an IC50 of less than 50 nM, and compound A8 has an IC50 for KIT also of less than 50 nM.

In one further particular (alternative or additional) embodiment, the treatment comprises (eg, involves, is by or is mediated by) inhibition of FLT3. For example, compound B3 inhibits FLT3 with an IC50 of less than 10 uM, while compound A8 has an IC50 for FLT3 of greater than 25 uM.

Indeed, in a certain particular (alternative or additional) embodiment, the treatment comprises (eg, involves, is by or is mediated by) inhibition of both KIT and FLT3; for example, by administration of compound B3 to the subject, and for example, the treatment comprises (eg, involves, is by or is mediated by) inhibition of ABL1, SRC and/or SIK3.

In one further embodiment, the treatment comprises (eg, involves, is by or is mediated by) inhibition of a mutant of either ABL1 or KIT kinase; such as the inhibition of BCR-ABL, or another mutant of ABL1, such as one selected from the list consisting of: G250E, Q252H, Y253F, E255K, F317I, M351T and H396P.

As described elsewhere herein, in one (alternative or additional) embodiment, compounds of the invention sensitise (eg, the treatment comprises, involves, is by or is mediated by sensitisation of) cells involved with a proliferative disorder to a cell-mediated immune response (such as TNF). However, in an alterative (alternative or additional) embodiment, the compounds do not sensitise (eg, the treatment does not comprise, involve, is not by or is not mediated by sensitisation of) cells involved with a proliferative disorder to a cell-mediated immune response (such as TNF).

In contrast to other studies using kinase (eg SIK) inhibitors, treatment with a compound (or pharmaceutical composition) of the invention in accordance with the present invention, in certain embodiments, may not be associated with an (effective) increase in the production of one or more anti-inflammatory cytokines (for example the anti-inflammatory cytokine may be one selected from the list consisting of: IL-Ira, IL-4, IL-10, IL-11, IL-13 and TGF-beta), and in particular may not be associated with an (effective) increase in the production of IL-10. Correspondingly, in other or further embodiments, treatment with a compound (or pharmaceutical composition) of the invention in accordance with the present invention may not be associated with an (effective) decrease in the production of one or more pro-inflammatory cytokines; for example, one selected from the list consisting of: IL-1-beta, IL-6, IL-12 and TNF, IFN-gamma and granulocyte-macrophage colony stimulating factor, and in particular embodiments may not be associated with an (effective) decrease in the production of TNF. Accordingly, in certain embodiments, a compound (or pharmaceutical composition) of the invention may be administered to a subject in: (i) a (therapeutically effective) amount NOT effective to (effectively) increase the production of one or more (eg such) anti-inflammatory cytokines; and/or (ii) in a (therapeutically effective) amount NOT effective to (effectively) decrease the production of one or more (eg such) pro-inflammatory cytokines.

Certain cells involved with the proliferative disorder (eg tumour cells) may, in certain embodiments, be expected to be more susceptible to the sensitising effects of a compound (or pharmaceutical composition) of the invention in the various aspects of the invention. For example, such cells may be those that exhibit (eg are subject to) activation of TNFR2 and/or TNFR1 signalling, in particular an activated TNFR1. In certain embodiments, such cells are those that express TNFR2 and/or TNFR1, in particular tumour cells that express TNFR1. Accordingly, in certain embodiments, such cells are distinguished or characterised by activated TNFR1- and/or TNFR2-signalling (or the subject is distinguished or characterised by having cells involved with the proliferative disorder—eg tumour cells—that are so distinguished or characterised). The person of ordinary skill will know techniques for determining the status of TNFR1- and/or TNFR2-activation in such cells (such as of the subject). For example, by detecting or monitoring one or more down-stream protein in the TNFR1- and/or TNFR2-signalling pathways. Such proteins are described elsewhere herein, and include NF-kappaB and/or HDAC4.

In one related aspect, the invention relates to a method for the treatment of a proliferative disorder (such as a tumour) in a subject, the (treatment) method comprising administering a compound (or pharmaceutical composition) of the invention to the subject, by inhibiting a kinase/key-kinase (eg SIK3), wherein cells involved with the proliferative disorder are characterised by (eg exhibit or are subject to) activated TNFR2 and/or TNFR1 signalling (eg activated TNFR1 signalling). In another related aspect, the invention relates to a compound (or pharmaceutical composition) of the invention for use in the treatment of a proliferative disorder, wherein cells involved with the proliferative disorder are distinguished or characterised by (eg exhibit or are subject to) activated TNFR2 and/or TNFR1 signalling (eg activated TNFR1 signalling).

In certain embodiments of the various aspects of the invention, cells involved with the proliferative disorder are those exposed to an appropriate triggering or activating molecule, such as TNF, a variant of TNF and or an agonist of TNFR2- or TNFR1-signalling (preferably, an agonist of TNFR1-signalling), in particular are exposed to an effective amount of such triggering or activating molecule.

In particular embodiments, when the triggering or activating molecule is TNF, it is human TNF. In certain of such embodiments, the TNF is recombinant human TNF (rHuTNF). However, in other embodiments the TNF is endogenous TNF, such as that is produced by or otherwise present in the subject (eg the human patient).

Studies have shown that plasma TNF levels are elevated in numerous types of cancers, including in ovarian cancer (Dobrzycka et al 2009, Eur Cytokine Netw 20:131), and that for example, the upper normal limit of total TNF in healthy subjects is 1.8 pg/mL, as measured using a Quantikine human TNF-alpha Immunoassay PDTA00C. In other cancers and assays (eg, TNF-alpha-EASIA Kit, DIAsource), the TNF plasma levels of oesophageal cancer patients and the control group were 12.35±9.69 and 4.62±3.06 pg/mL, respectively (Aydin et al 2012, Turk J Med Sci 42:762). Accordingly, in other embodiments the cells involved with the proliferative disorder are (for example a tumour is) one present in a subject having a plasma concentration of TNF greater than about 1.5, 2.5 or 4 pg/mL, such as greater than about 5 pg/mL, and in particular greater than about 10 pg/mL (for example, as measured by a Quantikine human TNF-alpha Immunoassay PDTA00C or a TNF-alpha-ELISA Kit, DIAsource).

Accordingly, in one particular embodiment, the subject involved in the treatment methods of the invention may have (that is, such a subject can be distinguished by, such as distinguished as one suitable for the therapeutic methods of the present invention, by showing, possessing or displaying) a plasma concentration of TNF greater than about 2 pg/mL or greater than about 5 pg/mL (eg, the cells involved with the proliferative disorder are one present in a subject having a plasma concentration of TNF greater than about 2 pg/mL or 5 pg/mL).

Indeed, in those embodiments where the proliferative disorder is a tumour, then the intratumoural concentration of TNF may be a characterisation of the tumour, such as when the tumour is a solid tumour and accessible for biopsy (Reissfelder et al 2015, J Clin Inv 125:739). For example, a tumour (such as a solid tumour eg colorectal cancer) can, in some embodiments of the invention, have an intratumoural concentration (eg, within the tumour tissue) of TNF that is greater than about 0.2, 0.5 or 1 pg/mL, such as greater than about 2 pg/mL, and in particular greater than about 5 pg/mL (for example, as measured by a Quantikine human TNF-alpha Immunoassay).

Accordingly, in such embodiments when the proliferative disorder is a tumour (eg a solid tumour), then the solid tumour (eg, within the subject) may have (that is, such a subject can be distinguished by, such as distinguished as one suitable for the therapeutic methods of the present invention, by showing, possessing or displaying) an intratumoural concentration of TNF greater than (about) 0.5 pg/mL or greater than about 1 pg/mL.

Accordingly, in a related aspect, the invention can relate to a method for the treatment of a proliferative disorder (or a compound (or pharmaceutical composition) of the invention for use in such a treatment) in a subject distinguished by having: (i) a plasma concentration of TNF greater than about 2 pg/mL (preferably greater than about 5 pg/mL); and/or (ii) an intratumoural concentration of TNF greater than about 0.5 pg/mL preferably greater than about 1 pg/mL), the treatment method comprising administering a compound (or pharmaceutical composition) of the invention to the subject, wherein the compound (or pharmaceutical composition): (a) inhibits a kinase/key-kinase (eg SIK3) in cells involved with the proliferative disorder; and/or (b) sensitises cells in the subject involved with the proliferative disorder to a cell-mediated immune response.

In particular of such embodiments, the amount (or dose) of a compound (or pharmaceutical composition) of the invention that is exposed to cells involved with the proliferative disorder, or that is administered to the subject, is related to (eg correlated to) the plasma or intratumoural concentration of TNF, wherein a greater amount (or dose) of the compound (or pharmaceutical composition) is exposed to such cells (or administered to such subject) in those cases of a greater plasma or intratumoural concentration of TNF.

In other or further embodiments, the tumour may be present in a subject having tumour-reactive T-cells in peripheral blood or bone marrow, for example as may be determined by IFN-gamma ELISPOT. In yet other or further embodiments, the tumour shows infiltration by Tregs, CD4+ Tconv and/or CD8+ T cells.

In other embodiments, the cells involved with the proliferative disorder comprises a single nucleotide polymorphism (SNP) in the promoter region of TNF associated with increased expression of TNF and cancer sensitivity, for example with an AA or GA genotype at the −308G/A SNP in the promoter region of TNF; and in alternative embodiments the tumour does not comprise a SNP associated with decreased expression of TNF and reduced cancer risk, such as does not comprise an AA or GA genotype at the −238G/A SNP or a −857T allele, in each case in the promoter region of TNF (Wang and Lin 2008, Acta Pharmacol Sin 28:1275).

The invention hereby provides alternative combination treatment regimens based on the surprising finding of the inventors that inhibition of one or more kinase, such a one or more key-kinases, (eg SIK3) by compounds of the invention can influence the sensitivity of a cell towards the apoptotic/cytotoxic effects of TNF. Accordingly, in a fifth aspect, and as may be further described, defined, claimed or otherwise disclosed herein, the invention relates to a method for the treatment of a proliferative disorder in a subject, the method comprising exposing (eg contacting) cells involved with the proliferative disorder in the subject to: (i) TNF, a TNF variant and/or an agonist of TNFR2- or TNFR1-signalling; and exposing (eg contacting) the cells involved with the proliferative disorder in the subject to (ii) a compound (or pharmaceutical composition) of the invention. In certain embodiments, step (i) of such method does not comprise exposing (eg contacting) cells involved with the proliferative disorder in the subject to a TNF variant.

In certain embodiments, the proliferative disorder and/or such cells are those of the tumour, and in other embodiments, component (i) is TNF, in particular human TNF (such as rHuTNF); and/or component (i) is an agonist of TNFR1-signalling.

In particular embodiments, the method comprises (eg the treatment comprises, involves, is by or is mediated by) increasing the amount of TNF exposed to the cells involved with the proliferative disorder in the subject.

In certain embodiments of such aspects, the treatment may comprise (eg, involves, is by or is mediated by) increasing TNFR1- and/or TNFR2-signalling in (of) the cells involved with the proliferative disorder in the subject. Accordingly, in a related aspect the invention relates to a method for the treatment of a proliferative disorder in a subject, the method comprising: (i) increasing TNFR1- and/or TNFR2-signalling in (of) the cells involved with the proliferative disorder; and (ii) exposing (eg contacting) the cells involved with the proliferative disorder in the subject to a compound (or pharmaceutical composition) of the invention.

In particular the method can, for example, be effected though the consequence(s) of inhibition of a kinase (eg a key-kinase such as SIK3) (such as inhibition of the function and/or activity of phosphorylated SIK3), in particular in combination with the consequence(s) of activation of TNFR1- and/or TNFR2-signalling, such as upon binding of the TNF, TNF variant and/or TNFR1 agonist to TNFR1 or TNFR2.

Accordingly, the treatment effect can, in certain embodiments, involve, or be mediated (eg, caused) by, inhibiting a kinase (eg a key-kinase, such as SIK3), and/or by sensitising the cells involved with the proliferative disorder to the cytotoxic (eg apoptotic) effects of TNFR1- or TNFR2-signalling. In particular of such embodiments, the kinase/key-kinase activity may be (effectively) reduced, such as to a therapeutically effective level.

As described above, herein are also envisioned embodiments wherein a kinase, such as a key-kinase (eg SIK3) in the tumour cells is inhibited and, optionally, where one or more other kinase/key-kinase (eg SIK2 and/or SIK1) are inhibited to a lesser extent, such as such other kinase (eg SIK2 or SIK1) of immune cells.

Also as described above, herein are also envisioned embodiments wherein the treatment comprises, involves, is by or is mediated by (eg, a compound (or pharmaceutical composition) of the invention is administered in an amount, such as a therapeutically effective amount that is effective to) inhibition of a kinase/key-kinase activity such that it is (eg, effectively) reduced, such as reduced to a therapeutically effective level.

In certain embodiments of such aspect, the subject can be administered a compound (or pharmaceutical composition) of the invention and/or can be administered (the) TNF, an (the) TNF variant or an (the) agonist of TNFR1- or TNFR2-signalling.

In such embodiments, a compound (or pharmaceutical composition) of the invention and the TNF, TNF variant or TNFR1 or TNFR2 agonist can be exposed to (for example administered in) an effective amount (or dose), including in formulations or administrative routes as described elsewhere herein. In particular are envisioned embodiments where the TNF, TNF variant or TNFR1 or TNFR2 agonist is encapsulated as a liposomal or other nanoparticle formulation.

When the TNF, TNF variant or TNFR1 or TNFR2 agonist is exposed/administered and a compound (or pharmaceutical composition) of the invention is exposed/administered, then such combination treatment regimen may comprise embodiments where such exposures/administrations are concomitant. In alternative embodiments such exposures/administrations may be sequential; in particular those embodiments where a compound (or pharmaceutical composition) of the invention is exposed/administered before the TNF, TNF variant or TNFR1 or TNFR2 agonist is exposed/administered. For example a compound (or pharmaceutical composition) of the invention may be sequentially exposed/administered within about 14 days of (eg before) the other component, such as within about 10 days, 7 days, 5 days, 2 days or 1 day of (eg before) the other component; and further including where the compound (or pharmaceutical composition) may be sequentially exposed/administered within about 48 hours, 24 hours, 12 hours, 8 hours, 6 hours, 4 hours, 2 hours, 1 hours, 30 mins, 15 mins or 5 mins of (eg before) the other component.

The TNF or the TNF variant or TNFR1 or TNFR2 agonist may be administered via conventional routes, such as s.c., i.v. or i.m., and on certain embodiments may be administered intratumourally or by isolated limb perfusion (ILP), such as isolated hepatic perfusion (IHP); and/or may be so administered (in particular, rHuTNF may be so administered) at a dose of between about 5 and 500 µg/m$^2$/day. For example, TNF may be administered between about 25 and 250 µg/m$^2$/day, such as between about 50 and 150 µg/m$^2$/day or between about 75 and 100 µg/m$^2$/day; or wherein TNF is administered up to a MTD of about 50 and 75 µg/m$^2$/day when administered s.c. or up to a MTD of about 150 and 200 µg/m$^2$/day when administered i.v. or i.m. Accordingly, in particular of such embodiments, TNF can be administered to the subject at a dose of between about 5 and 500 µg/m$^2$/day, in particular between about 20 and 200 µg/m$^2$/day.

In particular embodiments a variant of TNF, such as a TNF variant having higher anti-tumour activity and lower systemic toxicity that rHuTNF may be exposed/administered. For example, the TNF variant may be one selected from the group consisting of: (i) a −K90R variant of TNF; (ii) a tumour-homing peptide conjugated to TNF; and (iii) a TNF-antibody conjugate.

In those embodiments of the invention involving a TNF variant, it may be a variant form of TNF having higher cytotoxic activity and lower systemic toxicity.

In other embodiments a TNFR1 or TNFR2 agonist, such as the anti-TNFR1 monoclonal antibody htr-9 (Ferrero et al 2001, Am J Physiol Cell Physiol 281:$C_{1173}$) may be exposed/administered, and in other embodiments lymphotoxin-alpha (Etemadi et al 2013, FEBS J 280:5283) or a variant thereof may be exposed/administered.

In alternative embodiments, cells involved with the proliferative disorder (eg tumour cells) may be exposed to TNF (or increased TNFR1- and/or TNFR2-signalling) through the administration of an agent (eg to a subject harbouring such cell) that can lead to the exposure of such cells to (eg endogenous) TNF, or to another triggering molecule such as a variant of TNF or a TNFR1 or TNFR2 agonist. Such an agent may, for example, be one that is capable of inducing (eg induces) the exposure of such cells to (eg an elevated level of) TNF, in particular an agent that induces the exposure of such cells to TNF levels, such as to an effective amount of (eg endogenous) TNF, for example levels of plasma or intratumoural TNF that are greater than one or those levels described elsewhere herein.

Accordingly, the invention includes those embodiments wherein the subject is administered an agent that is capable of inducing (eg induces) the exposure of the cells involved with the proliferative disorder to (the) TNF, an (the) TNF variant or an (the) agonist of TNFR1- or TNFR2-signalling. The invention also includes those embodiments wherein the subject gets administered an agent that is capable of increasing TNFR1-signalling (and/or TNFR2-signalling) of, and/or increasing the amount of TNF exposed to, cells involved with the proliferative disorder in the subject.

In certain of such embodiments, the agent is a virus, in particular one that has been engineered to produce a triggering molecule being TNF, a TNF variant or the TNFR1 or TNFR2 agonist (especially, a virus engineered to produce human TNF). Further of such embodiments include those where such virus preferentially infects the cell(s) involved with the proliferative disorder (eg tumour cells) and/or preferentially produces the triggering molecule in the context of (eg when it infects) such cells. As will now be apparent, the administration of such a virus can lead to the exposure of the cell(s) involved with the proliferative disorder to such triggering molecule, and in particular to an effective amount of such a triggering molecule such as TNF.

Accordingly, in certain of such methods, the agent may be a virus that is capable of inducing (eg induces) the exposure of the cell(s) involved with the proliferative disorder the TNF, TNF variant or agonist of TNFR1- or TNFR2-signalling.

Such a virus may be any that is suitable for inducing the exposure of the triggering molecule, and in particular may be a recombinant virus; for example one engineered to infect tumour cells and/or to express TNF (eg after infecting a tumour cell). Examples of virus that may be so engineered include oncolytic viruses (eg, those based on an adenovirus, HSV, vaccinia virus, vesicular stomatitis virus or Newcastle disease virus), such as intratumoural injection of adenovirus vectors to increase plasma levels of pro-inflammatory cytokines and chemokines, including TNF (Bernt et al 2005, Cancer Res 65:4343). In particular of such embodiments, the oncolytic virus may be one based on a DNA virus described in Table 1 of Kaufman et al 2015 (Nature Rev Drug Disc 14:642), one based on an RNA virus described in Table 2 of Kaufman et al 2015, preferably, is an oncolytic virus described in Table 3 of Kaufman et al 2015 as being in clinical trials.

In other of such embodiments, the agent that is administered (and that consequentially leads to exposure of the cells involved with the proliferative disorder to a triggering molecule being TNF, a TNF variant or a TNFR1 or TNFR2 agonist) is an immune cell. In certain of such embodiments, the immune cell may not be an IL10-producing macrophage, for example the immune cells can be a pro-inflammatory immune cell. In particular of such embodiments, the immune cell that is administered may be a lymphoid cell, eg a T cell or a natural killer (NK) cell, for example such a cell that produces TNF.

When administered as an agent in such embodiments of the invention, the immune cell may be administered via adoptive cell transfer (ACT); meaning the transfer of the immune cell into the subject (eg, by infusion or other delivery techniques). Such process is, typically, conducted with the goal of improving immune functionality and characteristics in the subject, and while conventionally the transferred immune cells will have originated from the same subject, they may alternatively have been derived from another (suitable) individual.

When used in this embodiment of the invention, the immune cells may be T cells extracted from the subject, genetically modified and cultured in vitro and returned to the same subject, such as in a therapeutic method of the invention. Such genetic modification can include those that enhance the specificity or targeting of the immune cell, such as the targeting of the immune cell (eg increasing its specificity) to the cell(s) involved with the proliferative disorder (eg a tumour cell). For example, a T cell that is used in such embodiments may be modified to alter the specificity of the T cell receptor (TCR) or to introduce antibody-like recognition in chimeric antigen receptors (CARs). CAR immune cells, in particular, are envisioned for use in such embodiments. CAR immune cells are immune cells displaying engineered receptors, which graft an arbitrary specificity (eg to a tumour cell) onto an immune effector cell (eg a T cell). Typically, these receptors are used to graft the specificity of a monoclonal antibody onto a T cell; with transfer of their coding sequence facilitated by retroviral vectors. CAR T cells are a promising therapy for cancer (Song et al 2015, Oncotarget. 6:21533): using ACT, T cells are removed from an individual (typically the subject) and modified so that they express receptors specific to the patient's particular cancer. These T cells, which can then recognise the subject's cancer cells, are (re)introduced into the subject, leading to exposure of TNF (eg produced by the CAR T cells) to the tumour cells and hence killing of such cells, in particular such cells that are sensitised to such TNF-mediate cytotoxicity by exposure to (eg following administration to the subject of) a compound (or pharmaceutical composition) of the invention. Accordingly, in particular of such embodiments, the immune cells can be a CAR T cell, such as one engineered to have increased specificity to the subject's cells that are involved with the proliferative disorder (such as tumour cells).

In alternative embodiments, the exposure of the cells involved with the proliferative disorder to TNF (eg endogenous TNF) may be induced by other means or procedures. Accordingly, in such embodiments, the exposure of the cells involved with the proliferative disorder to (eg an effective amount of) TNF can be induced by (and/or the increase in TNFR1-signalling (and/or TNFR2-signalling) in/of the cells involved with the proliferative disorder is induced by) a pharmaceutical, therapeutic or other procedure that increases the amount of TNF in the plasma of the subject and/or in the environment of such cells.

In certain embodiments, such induced exposure to TNF may be brought about by the administration of a cancer immunotherapy.

In one example, such induced exposure to TNF is brought about by an anti-tumour vaccine (eg, a cancer vaccine). Such cancer vaccines include those whereby antigens (eg, those specific to or preferentially expressed by cancer cells) are directly or indirectly introduced into the subject so as to raise or increase an immune response (typically, an adaptive immune response) in the subject that is envisioned to be (more) specific to the cancer cell. Cancer vaccine may comprise, for example, attenuated viruses, in particular for use against cancers such as cervical or liver cancers that are caused by such virus (eg HPV or HBV). Cancer vaccines can alternatively represent individual (or combinations) of particular tumour antigens (eg, those specific to or preferentially expressed by cancer cells), such as tumour-associated antigens (TAAs) that are used to immunise the subject so as to also raise or increase the immune response in the subject. The cancer vaccine may comprise recombinant protein representing (eg a peptide from) the TAA(s), or may be a tumour specific carbohydrate antigen, and hence are directly introduced into the subject upon administration. The cancer vaccine may, alternatively, comprise a nucleic acid (such as DNA or mRNA) than encodes the protein (or peptide) TAA, and upon administration of the nucleic acid vaccine into the subject, the encoded TAA is expressed by cellular targets in the subject, and hence are indirectly introduced into the subject. TAAs may be divided into two categories: shared tumour antigens; and unique tumour antigens. Shared antigens are expressed by many tumours. Unique tumour antigens result from mutations induced through physical or chemical carcinogens (also known as neoantigens); they are therefore expressed only by individual tumours. The person of ordinary skill will be aware of examples of cancer vaccines in clinical trials, or approved for use, and include PROSTVAC (Bavarian Nordic), PROVENGE (Dendreon) and CV9104 (CureVac), as well as being aware of various TAAs (including neoantigens) and approaches by such tumour antigens may be utilised in cancer vaccines. As further examples: (1) immunisation with recipient-derived clonal myeloma immunoglobulin, idiotype (Id), as a tumour antigen, conjugated with keyhole limpet hemocyanin (KLH) has been shown to produce substantial amount or pro-inflammatory cytokines including TNF (Foglietta et al 2013, Bone Marrow Transplant 48: 269); and (2) a synthetic micro-consensus SynCon DNA vaccine of WT1 antigens induced new, neo-antigen-like responses that were superior to those induced by native WT1 DNA immunogens, such as strong CD4 and CD8 T cell responses (including IFN-gamma, CD107a, and TNF responses).

In another example, such induced exposure to TNF may be brought about by the administration of a ligand (such as an antibody, eg, a monoclonal antibody), for example one that binds to the surface of the cell(s) involved with the proliferative disorder (such as a tumour cell), for example by binding to a TAA or a receptor on the surface of such cell. Cell surface receptors are common targets for such ligand (antibody) therapies and include CD52 and CD20. Once bound to such a cancer antigen, the eg antibodies can induce antibody-dependent cell-mediated cytotoxicity, activate the complement system, or prevent a receptor from interacting with its ligand, all of which can lead to cell death. Approved such ligands that are antibodies include alemtuzumab, ofatumumab and rituximab. In certain embodiments, such ligands used in combination with a compound (or pharmaceutical composition) of the invention can include those that activate T cells or other cell-mediated immune response. For example: (1) anti-CD137 monoclonal antibodies can dramatically promote proliferation of cytokine-induced killer (CIK) cells and expression of TNF (Zhu et al 2009, Biomed Pharmacother 63:509); (2) an agonist anti-OX40 monoclonal antibody can enhance antitumour immune response by augmenting T-cell differentiation (Redmond et al 2014, Cancer Immunol Res. 2014, 2:142); and (3) an anti-ICOS antibody that activates T cells (eg Deng et al 2004, Hybrid Hybridomics 23:176).

In yet another example, the ligand that is administered to the subject is one that binds to an immune (inhibitory) checkpoint molecule. For example, such checkpoint molecule may be one selected from the group consisting of: A2AR, B7-H3, B7-H4, CTLA-4, IDO, KIR, LAG3, PD-1 (or one of its ligands PD-L1 and PD-L2), TIM-3 (or its ligand galectin-9), TIGIT and VISTA. In particular of such embodiments, the ligand binds to a checkpoint molecule selected from: CTLA-4, PD-1 and PD-L1. In other more particular embodiments, the ligand is an antibody selected from the group consisting of: ipilimumab, nivolumab, pembrolizumab, BGB-A317, atezolizumab, avelumab and durvaluma; in particular an antibody selected from the group consisting of: ipilimumab (YERVOY), nivolumab (OPDIVO), pembrolizumab (KEYTRUDA) and atezolizumab (TECENTRIQ). In other embodiments, the ligand that binds to a immune (inhibitory) checkpoint molecule may be a non-antibody peptide, such as a high-affinity PD-1 variant (eg, Maute et al, 2015; PNAS 112:E6506), a peptide targeting the immune checkpoint molecule (such as AUNP-12 of Aurigene Discovery Technologies, US 2011/0318373) or a D peptide blocking an interaction between immune checkpoint molecule (such as the PDL1-PD1 interaction and (D) PPA-1, Chang et al, 2015; Anyeg Chem Int 54:11760). In yet other embodiments, the ligand that binds to an immune (inhibitory) checkpoint molecule may be a small molecule, such as the PDL1-targeting BMS-202 or BMS-8 (Zak et al 2016; Oncotarget 7:30323), the inhibitors of PDL1/D1 known as BMS-1001 or BMS-1166 (Skalniak et al, 2017; Oncotarget 8:72167), the PDL1 and VISTA antagonist CA-170 of Curis/Aurigen undergoing phase 1 trials (Powderly et al, Ann Onc 28: Issue suppl 5, mdx376.007) or CA-327 of Curis/Aurigen which targets PDL1 and TIM3.

In yet another particular embodiments, such induced exposure to TNF may be brought about by radiotherapy.

Radiotherapy is a method of locoregional treatment of cancers or tumours, using radiation to destroy the cancer cells by blocking their ability to multiply and/or to stimulate an immune reaction against them (such one raised as a response to the presence of dead or dying cancer cells). Radiotherapy, in the context of the present invention, consists—in particular—of the therapeutic use of ionising radiation. Said radiotherapy and the associated ionising radiation are those commonly used and known to those skilled in the art. Radiotherapy includes in particular the use of ionizing radiation, for example gamma-rays, X-rays and/or radiation emanating from radioisotopes. In the context of the present invention, it is more particularly X-ray radiation. The radiotherapy may be administered in fractionated form during one or more cycles, such as a cycle that can range from 1 to 4 weeks, more particularly 3 weeks. The cycle defines the interval between the beginning and the end of an administration scheme. When the cycle takes three weeks, radiotherapy can be administered over three weeks, with one week between. The radiotherapy may in particular be administered at a rate of one daily irradiation, 5 days out of 7, for the desired number of weeks. The amount of radiation used in (photon) radiation therapy is measured in gray (Gy), and varies depending on the type and stage of cancer being treated. For curative cases, the typical dose for a solid epithelial tumour ranges from 60 to 80 Gy, while lymphomas are treated with 20 to 40 Gy.

When a compound (or pharmaceutical composition) of the invention is used in combinations treatments together with any of such other procedures (eg, the other agent, the cancer immunotherapy, the cancer vaccine, the antibody or the radiotherapy, in each case as described herein), then such combination treatment regimen may comprise embodiments where such exposures/administrations are concomitant. In alternative embodiments such administrations may be sequential; in particular those embodiments where the compound (or pharmaceutical composition) is administered before such other procedure. For example a compound (or pharmaceutical composition) of the invention may be sequentially administered within about 14 days of (eg before) the other procedure, such as within about 10 days, 7 days, 5 days, 2 days or 1 day of (eg before) the other procedure; and further including where the compound (or pharmaceutical composition) may be sequentially administered within about 48 hours, 24 hours, 12 hours, 8 hours, 6 hours, 4 hours, 2 hours, 1 hours, 30 mins, 15 mins or 5 mins of (eg before) the other procedure.

Without being bound to theory, administration of a compound (or pharmaceutical composition) of the invention (and hence inhibition of the expression, amount, function, activity or stability of a kinase/key-kinase such as SIK3, eg in a tumour cell) prior to administration of the TNF, TNF variant or TNFR1 or TNFR2 agonist, or prior to administration of such other procedures (eg, the other agent, the cancer immunotherapy, the cancer vaccine, the antibody or the radiotherapy, is foreseen to be particularly effective in sensitising the cells involved with the proliferative disorder to the cytotoxic effects of the cell-mediated immune response.

As described above, existing therapies (or those under clinical trials) involving administration of TNF and/or use of anti-TNF molecules suffer certain known disadvantages; and particular side effects. The present invention provides methods that may be used to mitigate (or reduce) such disadvantages and/or particular side effects.

In a sixth aspect, and as may be further described, defined, claimed or otherwise disclosed herein, the invention relates to a method for the increase of the therapeutic index of treatment with TNF in a subject being treated therewith for a proliferative disorder (eg a cancer disease or a tumour), the method comprising administering a compound (or pharmaceutical composition) of the invention to the subject.

In a related aspect, the invention relates to a method for supporting TNF therapy in a subject suffering from a proliferative disorder (eg a cancer disease or a tumour), the method comprising administering a compound (or pharmaceutical composition) of the invention to the subject.

In a seventh aspect, and as may be further described, defined, claimed or otherwise disclosed herein, the invention relates to a method for the sensitisation of a subject suffering from a proliferative disorder (eg a cancer disease or tumour) to a therapy involving the administration of TNF to the subject, the method comprising administering a compound (or pharmaceutical composition) of the invention to the subject.

The term "sensitisation" (and the like), as used herein in the context of a subject being sensitised to a therapy (eg one involving the administration of TNF), will be understood by the person of ordinary skill, and includes the meaning that the subject increases susceptibility to one or more (treatment) effect—in particular an efficacy effect—that such therapy may have on the subject. In particular, a subject that is so sensitised may, when undergoing such therapy, show an increased response (such as more rapidly, a greater degree of response and/or upon a lower amount or exposure of such therapy) than an analogous subject that have not been so "sensitised".

In an eighth aspect, and as may be further described, defined, claimed or otherwise disclosed herein, the invention relates to a method for the reduction in risk of (developing) a haematological proliferative disorder (eg, as a secondary disorder) in a subject being treated with an anti-TNF agent, the method comprising administering a compound (or pharmaceutical composition) of the invention to the subject. For example, such aspect may alternatively, be considered as a method for the prevention of a haematological proliferative disorder (as a secondary disorder) in a subject being treated with an anti-TNF agent, the method comprising administering a compound (or pharmaceutical composition) of the invention to the subject.

This aspect of the invention is based on the observation as described above, that there are reports of patients receiving anti-TNF biologics developing lymphomas and other haematological malignancies. Indeed, such disorders are typically described in package leaflets/prescribing information as possible (but rare) side-effects of treatment with anti-TNF agents. As a direct consequence of the perceived increase in haematological malignancy and widespread use of these and other immunosuppressive agents, the WHO classification of tumours now includes the category "iatrogenic immunodeficiency-associated lymphoproliferative disease".

Therefore, typically in such aspects, the subject is being treated with the anti-TNF agent for an indication other than a proliferative disorder, and in particular of such embodiments the subject does not—upon commencement of the anti-TNF treatment—suffer from a haematological proliferative disorder. Indeed, typically the subject would suffer from, and/or is being treated with the anti-TNF agent for an autoimmune disorder; preferably an autoimmune disorder selected from the group consisting of: rheumatoid arthritis, psoriatic arthritis, ankylosing spondylitis, plaque psoriasis, inflammatory bowel disease, ulcerative colitis, Crohn's Disease, psoriasis, hidradenitis suppurativa and refractory asthma; such as one selected from the group consisting of: rheumatoid arthritis, psoriatic arthritis, ankylosing spondylitis, plaque psoriasis and Crohn's Disease; and in particular rheumatoid arthritis.

In certain embodiments, the anti-TNF agent is one selected from a list consisting of: infliximab, adalimumab, golimumab, humicade, etanercept, onercept and certolizumab pegol, in particular infliximab or humicade.

In certain embodiments, the haematological malignancies proliferative disorder may be a lymphoproliferative disease, in particular an iatrogenic immunodeficiency-associated lymphoproliferative disease.

In certain embodiments of such sixth to eighth aspects, the (treatment) effect (eg the increase in therapeutic index, sensitisation of a subject or reduction in risk) is mediated by (eg, the treatment comprises, is by, is mediated by or involves): (i) inhibiting a kinase (eg a key-kinase such as SIK3) (such as by the inhibition of the function and/or activity of phosphorylated SIK3), in particular by inhibiting such a kinase (eg a key-kinase) in cells involved with the proliferative disorder; and/or (ii) sensitising such cells to the killing (apoptotic/cytotoxic) effects of TNF. In further embodiments, the (treatment) effect may not be mediated by (eg, the treatment may not comprise or involve) inhibiting one or more other key-kinases (eg, ABL1 and/or SRC, or SIK2 and/or SIK1), in particular not mediated by (eg, the treatment does not comprise or involve) inhibiting or more other key-kinases (eg SIK2 and/or SIK1 (and/or SIK3) in immune cells.

Pre-Clinical and Clinical Testing

In certain embodiments, the subject is a human volunteer; for example one that has chosen (eg consented) to be administered a compound (or pharmaceutical composition) of the invention for a clinical trial or other experimental use of the compound. In another embodiment, the subject is a laboratory animal, in particular an animal selected from the group consisting of: mouse, rat, rabbit, pig and monkey.

In such (eg experimental treatment) embodiments, a plurality of such subjects can be treated; in particular 5 or more subjects, such as between about 5 and 20, 10 and 50, 25 and 200, or 75 and 250 subjects, or more than about 250 subjects.

Such experimental (or clinical trial) treatments may comprise: (i) the administration to at least one of such subjects of one dosage of a compound of the invention and/or one formulation of a pharmaceutical composition of the invention; and (ii) the administration to at least one other of such subjects of a different dosage of the compound and/or a different formulation of the pharmaceutical composition.

In further of such embodiments, such experimental (or clinical trial) treatments may comprise: (i) the administration to at least one of such subjects of one dosage of a compound of the invention and/or one formulation of the pharmaceutical composition of the invention; and (ii) the administration to at least one other of such subjects of either: (a) a placebo; or (b) the dosage of the compound and/or the formulation of the pharmaceutical composition of the subject(s) of (i) as well as an additional pharmaceutical, therapeutic or other procedure.

The term "placebo" will be art recognised, and includes a substance or treatment of no intended therapeutic value. In such embodiments, the placebo can be made to resemble the other administration so that it functions as a control, such as in a blinded trial.

In certain of such embodiments, such experimental (or clinical trial) treatment is specifically designed for the investigation and/or determination of a therapeutically effective dosage of a compound of the invention and/or the identification of a therapeutically effective formulation of a pharmaceutical composition of the invention.

Diagnosis

In a ninth aspect, the invention relates to a method of diagnosing and treating a disease, disorder or condition characterised by the presence of or an amount of, and/or characterised by (eg aberrant) expression or activity of, one or more applicable biomarkers (such as a kinase) in a subject, such as a human patient, comprising:

detecting one or more such applicable biomarkers in a biological sample from said subject, thereby diagnosing if the subject is suffering (or is likely to suffer) from such a disease, disorder or condition; and administering an effective amount of a compound of the invention (and/or a pharmaceutical composition comprising such compound) to the so diagnosed subject, in particular practicing a treatment method of the invention on the subject.

In one of such embodiments, the disease, disorder or condition is a proliferative disorder, such as one disclosed elsewhere herein (eg a tumour or cancer).

The term "applicable biomarker" means any one (or more) of the genes expressed by the cell involved with the proliferative disorder that are involved in the (eg kinase/key-kinase mediated) cellular resistance against an immune response (eg a cell-mediated immune response such as TNF). Such genes include: (X) one or more kinase, in particular one or more key-kinase as described herein, such as SIK1, SIK2, SIK3, ABL1 (BCR-ABL), SRC, FLT3, KIT, YES, LYN, FYN and LCK; in particular, ABL1 (BCR-ABL), ABL1 (BCR-ABL) and FLT3 and, in particular, phosphorylated SIK3; (Y) a mutant of a kinase, such as a mutant ABL1 kinase (eg BCR-ABL) or a mutant of KIT kinase; and/or (Z) one or more of (a) to (f) below):

(a) TNFR1 (or TNFR2), such as the presence of (or an amount of) or expression and/or activity of TNFR1 (or TNFR2), in particular TNFR1;
  (b) LKB1, such as the presence of (or an amount of) or expression and/or activity of LKB1, in particular increased amount or activity of LKB1 or pLKB1;
  (c) one or more class II (eg IIa) HDACs, eg HDAC4, such as the presence of (or an amount of) or expression and/or activity of such HDAC, in particular increased amount or activity of such HDAC or pHDAC, especially in the cytoplasm of cells of the tumour;
  (d) Expression of NF-kappa-B, in particular, constitutive expression of NF-kappa-B;
  (e) NF-kappa-B, such as the presence of (or an amount of) or expression and/or activity of NF-kappa-B, in particular increased amount or activity of NF-kappa-B or acetylated NF-kappa-B, especially in the nucleus of cells of the tumour; and/or
  (f) one or more anti-apoptotic genes, such as the presence of (or an amount of) or expression and/or activity of one or more anti-apoptotic genes, in particular one or more of such genes under transcriptional control by NF-kappa-B.

In certain embodiments, the applicable biomarker is one or more key-kinases selected from the list consisting of: EPHA2, EPHA4, CSF1-R, HCK, ACK1; and/or PDGFR-alpha, TGFB-R1, B-RAF and/or p38-beta; and/or ACV-R1 and/or BMPR1A; and/or RET; and/or NEK11, WEE1 and/or WNK2; and/or Aurora-A and/or Aurora-B; and/or TBK1.

Further embodiments of the administering (or treatment) step of this method of diagnosis and treatment are described in more details elsewhere; as are particular embodiments of the methods of the detection, determination or diagnostic method step of this method. Particular of such embodiments include those where the amount of a compound (and/or pharmaceutical composition) of the invention administered to the subject is correlated to the plasma or intratumoural concentration of TNF (in the subject), wherein a greater amount (or dose) of the compound (and/or pharmaceutical composition) administered to such subject in those cases of a greater plasma or intratumoural concentration of TNF.

In certain embodiments, a biological sample will (preferably) comprise cells or tissue of the subject, or an extract of such cells or tissue, in particular where such cells are those (usually, typically; or in the case or a specific subject as suspected to be) involved with the proliferative disorder (eg tumour cells such as cells of a solid tumour). The tumour or cell thereof, may be one of, or derived from, one of the tumours described elsewhere herein.

In particular embodiments of such aspect, the method will also comprise a step of:

providing (such as by obtaining) the biological sample from the subject, in particular where such step is conducted prior to the detection step.

In particular embodiments, such detection and/or determination methods can be practiced as a method of diagnosis, such as a method of diagnosis whether a mammalian subject (such as a human subject or patient) has a disease, disorder or condition, in particular (the presence of) a proliferative disorder such as a cancer or tumour (or has a risk of developing such a disease, disorder or condition) that is associated with cellular resistance against a cell-mediated immune response and/or that is associated with (eg aberrant) expression or activity of the applicable biomarker (eg SIK3); in particular a (solid) tumour, such as one having cellular resistance against a cell-mediated immune response.

In certain embodiments of these detection, determination and/or diagnostic methods, the cellular resistance against a cell-mediated immune response is cellular resistance against a T cell-mediated immune response, in particular cellular resistance to the killing (apoptotic/cytotoxic) effect of TNF and/or of TNFR1 or TNFR2 signalling.

Accordingly, particular embodiments of these detection and/or diagnostic methods may also comprise a step of determining the presence or amount of TNF in the sample, wherein the presence of (or an amount of) TNF in the sample indicates a/the proliferative disorder (or a/the risk of developing a proliferative disorder) that is associated with cellular resistance against the cell-mediated immune response, and/or associated with (aberrant) expression or activity of the kinase (eg SIK3), in the subject. In particular of such embodiments, amount of TNF in the sample is determined qualitatively. Preferably, the subject is distinguished as having: (i) a plasma concentration of TNF greater than about 2 pg/mL or 5 pg/mL in a plasma sample from the subject; and/or (ii) an intratumoural concentration of TNF greater than about 0.5 pg/mL or 1 pg/mL from a tissue sample from the subject, indicates the (presence of the proliferative disorder or a risk of developing the proliferative disorder that is associated with cellular resistance against the cell-mediated immune response, and/or associated with expression or activity of the kinase (eg SIK3), in the subject.

Methodologies to determine the presence or amount of TNF in a sample are described elsewhere herein (in particular, quantitative detection of TNF using ELISA assays such as a Quantitkine TNF-alpha Immunoassay; as are amounts of TNF that, if are exceeded by the TNF present in the sample, indicate that a proliferative disorder associated with cellular resistance against the cell-mediated immune response, and/or associated with (aberrant) expression or activity of the kinase (eg SIK3), in the subject.

In certain embodiments, the biological sample is one obtained from a mammalian subject like a human patient. The term "biological sample" is used in its broadest sense and can refer to a bodily sample obtained from the subject (eg, a human patient). For example, the biological sample can include a clinical sample, ie, a sample derived from a subject. Such samples can include, but are not limited to: peripheral bodily fluids, which may or may not contain cells, eg, blood, urine, plasma, mucous, bile pancreatic juice, supernatant fluid, and serum; tissue or fine needle biopsy samples; tumour biopsy samples or sections (or cells thereof), and archival samples with known diagnosis, treatment and/or outcome history. Biological samples may also include sections of tissues, such as frozen sections taken for histological purposes. The term "biological sample" can also encompass any material derived by processing the sample. Derived materials can include, but are not limited to, cells (or their progeny) isolated from the biological sample, nucleic acids and/or proteins extracted from the sample. Processing of the biological sample may involve one or more of: filtration, distillation, extraction, amplification, concentration, fixation, inactivation of interfering components, addition of reagents, and the like.

In some embodiments, these detection, determination and/or diagnostic methods may be a computer-implemented method, or one that is assisted or supported by a computer. In some embodiments, information reflecting the presence or an amount of the applicable biomarker (eg, a key-kinase such as ABL1/BCR-ABL, SRC and/or SIK3) to be determined (or activity thereof) in a sample is obtained by at least one processor, and/or information reflecting the presence or an amount of such marker (or activity thereof) in a sample is provided in user readable format by another processor. The one or more processors may be coupled to random access memory operating under control of or in conjunction with a computer operating system. The processors may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processors may communicate with data storage devices, such as a database stored on a hard drive or drive array, to access or store program instructions other data. Processors may further communicate via a network interface, which in turn may communicate via the one or more networks, such as the Internet or other public or private networks, such that a query or other request may be received from a client, or other device or service. In some embodiments, the computer-implemented method of detecting the presence or an amount of the applicable biomarker (or activity thereof) in a sample is provided as a kit.

Such detection, determination and/or diagnosis methods can be conducted as an in-vitro (eg ex-vivo) method, and can be, for example, practiced using the kit of the present invention (or components thereof). An in-vitro method may use, involve or be practised on immortalised cell lines (such as those replicated, cultured or indefinitely maintained outside of the body of an animal or human), or it may be use, involve or be practised in-vitro using cells (such as primary cells) directly or freshly obtained from the body of an animal of human (eg, practised as a so-called "ex-vivo" method).

In some embodiments of these detection, determination and/or diagnosis methods, the biological sample is a tissue sample from the subject, such as a sample of a tumour or a cancer from the subject. As described above, such tissue sample may be a biopsy sample of the tumour or a cancer such as a needle biopsy sample, or a tumour biopsy section or an archival sample thereof. Such a tissue sample may comprise living, dead or fixed cells, such as from the tumour or a cancer, and such cells may be suspected of expressing (e.g. aberrantly or localised) the applicable biomarker to be determined.

In some embodiments, determination and/or diagnosis method of the invention can comprise, such as in a further step, comparing the detected amount (or activity of) of (eg protein or mRNA of) the applicable biomarker (eg the kinase/key-kinase such as SIK3, and in particular phosphorylated SIK3) with a standard or cut-off value; wherein a detected amount greater than the standard or cut-off value indicates a phenotype (or a risk of developing a phenotype) that is associated with cellular resistance against the cell-mediated immune response in the subject and/or is associated with is associated with (aberrant) expression or activity of the kinase/key-kinase (eg SIK3) in the subject. Such a standard or cut-off value may be determined from the use of a control assay, or may be pre-determined from one or more values obtained from a study or a plurality of samples having known phenotypes. For example, a cut-off value for a diagnostic test may be determined by the analysis of samples taken from patients in the context of a controlled clinical study, and determination of a cut-off depending on the desired (or obtained) sensitivity and/or specificity of the test.

The applicable biomarker can, in certain embodiments, be detected by detecting protein of the applicable biomarker, or by detecting mRNA that encodes protein of the applicable biomarker. Methods to detect proteins (eg antibody detection, in particular by immunohistochemistry) and mRNA (eg by hybridisation, qPCR or sequencing) are well known.

Examples of methods useful in the detection of (such as the presence or absence of, or an amount of) the applicable biomarker (such as the kinase/key-kinase eg SIK3, and in particular phosphorylated SIK3) include immunoassays, such as the enzyme linked immunosorbent assay (ELISA) and the radioimmunoassay (RIA), which employ an antigen binding protein ("ABP") such as an antibody or an antigen-binding fragment thereof, that specifically binds to such applicable biomarker.

Intermediates Synthesis Manufacturing and Other Aspects

The compounds disclosed herein can be prepared as described below or prepared by methods analogous thereto, which are readily known and available to one of ordinary skill in the art of organic synthesis.

In a tenth aspect, the invention relates to the use of a compound (eg, an intermediate) to prepare a compound of the invention (eg, to prepare a compound of formula (I), (Ia), (II), (III), (IV), (V), (VI), (VII) or (VIII), or a solvate, salt (in particular a pharmaceutically acceptable salt), N-oxide (in particular, an N-oxide of $R^{1a}$ and/or $R^6$), complex, polymorph, crystalline form, racemic mixture, diastereomer, enantiomer, tautomer, conformer, isotopically labeled form, prodrug (in particular a prodrug having formula (IXa), (IXb) (IXc), or (IXd) and/or having at least one derivatized hydroxyl group, as specified above, or a solvate, salt, N-oxide, complex, polymorph, crystalline form, racemic mixture, diastereomer, enantiomer, tautomer, conformer, isotopically labeled form or combination thereof), or combination thereof), wherein the compound (eg the intermediate) comprises a substructure of $R^6$ or $R^{1a}$, or comprises the following substructure:

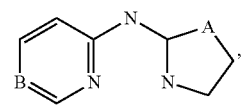

wherein, $R^6$, $R^{1a}$, A and B are as defined anywhere herein.

In particular of such embodiments, the compound (eg the intermediate) is not compound B3.

In a certain of such embodiment, the compound (eg the intermediate) is 2-bromo-4-chloropyridin-3-amine (Compound IaB3) or is 4-chloro-2-methylpyridin-3-amine (Compound IbB3).

In another certain of such embodiment, the compound (eg the intermediate) is selected from the list consisting of: 2,4-dimethylpyridin-3-amine, 3-methylpyridin-2-amine, 4-bromo-2-methylpyridin-3-amine, 3-chloro-5-methylpyridin-4-amine, 3,5-dimethylpyridin-4-amine, 2-methylpyridin-3-amine, 2-chloro-4-methylthiophen-3-amine, 1,3,5-trimethyl-1H-pyrazol-4-amine, 3,5-dimethylisoxazol-4-amine, quinuclidine-3-amine and 2-ethyl-4-methylpyridin-3-amine.

In another certain of such embodiment, the compound (eg the intermediate) is selected from the group consisting of a compound (eg an intermediate) having a structure of formula (I), (Ia), (II), (III), (IV), (V), (VI), (VII) or (VIII), wherein R1a is a leaving group, such as a halogen, preferably Cl.

In a related aspect, the invention also relates to (the composition of matter of) a compound (eg an intermediate) being 2-bromo-4-chloropyridin-3-amine or 4-chloro-2-methylpyridin-3-amine, in particular wherein such compound (eg the intermediate) is in an amount of greater than about 1 g or 10 g, such as greater than about 100 g, and/or is in purified form (eg, as defined elsewhere herein).

In an eleventh aspect, the invention relates to a method for preparing a compound of the invention (eg, a compound of formula (I), (Ia), (II), (III), (IV), (V), (VI), (VII) or (VIII)) that is in a (eg substantially) purified form, the method comprising the steps:
    providing the compound (eg C2, C, C7, C8, C9 or C12) in admixture with one or more impurities; and
    removing at least a fraction of the impurities from the admixture.

In certain embodiments of such aspect, suitable methods to remove a fraction of the impurities are well known and include eg column chromatography, selective precipitation, trituration and elution of impurities with a suitable solvent in which the desired compound is not soluble, etc.

The fraction of impurities removed may be such that the compound is prepared in substantially pure form; that is, for example, in a percentage purity as described above.

In other embodiments, the admixture of provided by synthesising an impure form of the compound.

In a twelfth aspect, the invention also relates to a method for manufacturing a pharmaceutical composition comprising the step of formulating a compound of the invention (eg a compound of formula (I), (Ia), (II), (III), (IV), (V), (VI), (VII) or (VIII)) together with a pharmaceutically acceptable excipient (such as one described elsewhere herein, such as a pharmaceutically acceptable stabiliser of carrier).

In a particular of such embodiments, the pharmaceutical composition is manufactured in an amount that is greater than about 10 g; such as greater than about 100 g, and suitably greater than about 1 Kg (or greater than 10 Kg).

In one embodiment of such aspect, the pharmaceutical composition is manufactured in unit dose form.

In certain of such embodiments, the pharmaceutical composition is formed as a tablet, caplet or capsule; in particular as a tablet or capsule.

In a further of such embodiments, the pharmaceutical composition is formed as a film-coated tablet, or as a film-coated caplet. For example, the method may comprise a further step of coating a tablet or caplet with a film, in particular with a pharmaceutical effective film-coating.

In a thirteenth aspect, the invention also relates to a method of preparing a pharmaceutical package, comprising the steps:
    inserting into packaging a pharmaceutical composition of the invention, thereby forming a package containing the pharmaceutical composition; and optionally,
    inserting into the package a leaflet describing prescribing information for the pharmaceutical composition.

In one of such embodiments, the pharmaceutical composition is in finished pharmaceutical form; for example, that is in the form that would be administered (or finally prepared to be administered) to a subject.

The packaging can be primary and/or secondary packaging. For example, the primary packaging may be a glass vial or a blister strip. Typical (but non-limiting) secondary packaging can be a box or carton, which in certain embodiments may be marked with the name, strength and/or brand of the pharmaceutical composition it contains.

The packaging may further comprise a leaflet or other information. In particular, that describing (either to the patient and/or the administering physician) salient information or details on the pharmaceutical composition contained in the package, such as how to administer, recommended dosages, safety and/or side-effect information.

In a fourteenth aspect, the invention also relates to a pharmaceutical package containing a pharmaceutical composition of the invention; preferably, wherein the pharmaceutical composition is in finished pharmaceutical form. In certain embodiments of such aspect, the pharmaceutical package may further containing a leaflet describing prescribing information for the pharmaceutical composition.

In a fifteenth aspect, the invention also relates to a method of delivering a pharmaceutical composition or pharmaceutical package of the invention from a first location to a second location, the method comprising the steps:
    receiving at a first location a request from a second location for the delivery of an amount of the pharmaceutical composition or the pharmaceutical package; and
    delivering at least a portion of (preferably, all of) the requested amount from the first location to the second location in one or more deliveries,
wherein first location and the second location are separated by a distance of greater than about 10 m, and one or more of the deliveries is/are transported for at least part of the distance between the first location to the second location by wheeled transporters.

In embodiments of such aspect, the requests may be sent, transmitted and/or received by electronic methods, such as telephone, email or other computer message or signal.

The distance between the two locations is greater than about 10 m, such as more than about 100 m or more than about 1 Km, In particular embodiments, the distance between the first location and the second location is more than about 10 Km, such as more than about 100 Km or 1,000 Km.

A technical unit, being a wheeled transporter, is used to transport the pharmaceutical composition or the pharmaceutical package for at least a portion of the distance between the two locations. For example, for a short distance, the pharmaceutical composition or pharmaceutical package may be first carried by foot from a storage shelf and then placed on a wheeled trolley to transport to another room or part of a hospital.

In other embodiments, the wheeled transporter may be a vehicle (such a van or lorry) that transports the pharmaceutical composition or pharmaceutical package for, eg longer, distances. For example, a van may be used to transport the pharmaceutical composition or pharmaceutical package between locations that are more than about 10 Km apart. Alternatively, a bicycle (or motorbike) may be used to transport the pharmaceutical composition or pharmaceutical package between locations that are less than about 10 Km apart. However, even if the pharmaceutical composition or pharmaceutical package is transported longer distances (eg from one country or continent to another), such as greater than about 100 Km, and are taken for much of that distance by eg plane or ship, then it would be envisioned that the pharmaceutical composition or pharmaceutical package would still be transported to the departure airport or port (and/or from the airport or port) by a wheeled transporter such as van or lorry, or at the port or airport in a shipping container on a trailer.

In view of the above, it will be appreciated that the present invention also relates to the following itemised embodiments:

1. A compound selected from the group consisting of a kinase inhibitor of the formula:

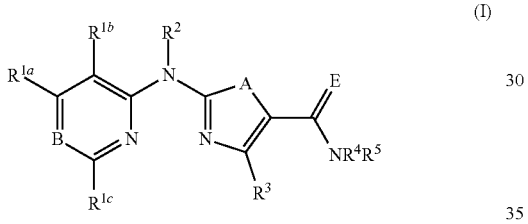

(I)

and solvates, salts, N-oxides, complexes, polymorphs, crystalline forms, racemic mixtures, diastereomers, enantiomers, tautomers, conformers, isotopically labeled forms, prodrugs, and combinations thereof;

wherein:

$R^{1a}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

each of R$^{1b}$ and R$^{1c}$ is independently selected from the group consisting of H, C$_{1-6}$ alkyl, C$_{2-6}$ alkenyl, C$_{2-6}$ alkynyl, C$_{3-7}$ cycloalkyl, C$_{6-10}$ aryl, 3- to 7-membered heteroaryl, 3- to 7-membered heterocyclyl, —O(CH$_2$)$_{0-2}$(C$_{3-7}$ cycloalkyl), —O(CH$_2$)$_{0-2}$(C$_{6-10}$ aryl), —O(CH$_2$)$_{0-2}$(3- to 7-membered heteroaryl), —O(CH$_2$)$_{0-2}$(3- to 7-membered heterocyclyl), —NH(CH$_2$)$_{0-2}$(C$_{3-7}$ cycloalkyl), —NH(CH$_2$)$_{0-2}$(C$_{6-10}$ aryl), —NH(CH$_2$)$_{0-2}$(3- to 7-membered heteroaryl), —NH(CH$_2$)$_{0-2}$(3- to 7-membered heterocyclyl), halogen, —CF$_3$, —CN, azido, —NO$_2$, —OH, —O(C$_{1-6}$ alkyl), —OCF$_3$, —S(C$_{1-6}$ alkyl), —NH$_2$, —NH(C$_{1-6}$ alkyl), —N(C$_{1-6}$ alkyl)$_2$, —NHS(O)$_2$(C$_{1-6}$ alkyl), —S(O)$_2$NH$_{2-z}$(C$_{1-6}$ alkyl)$_z$, —C(=O)(C$_{1-6}$ alkyl), —C(=O)OH, —C(=O)O(C$_{1-6}$ alkyl), —C(=O)NH$_{2-z}$(C$_{1-6}$ alkyl)$_z$, —NHC(=O)(C$_{1-6}$ alkyl), —NHC(=NH)NH$_{z-2}$(C$_{1-6}$ alkyl)$_z$, and —N(C$_{1-6}$ alkyl)C(=NH)NH$_{2-z}$(C$_{1-6}$ alkyl)$_z$, wherein z is 0, 1, or 2 and each of the C$_{1-6}$ alkyl, C$_{2-6}$ alkenyl, C$_{2-6}$ alkynyl, C$_{3-7}$ cycloalkyl, C$_{6-10}$ aryl, 3- to 7-membered heteroaryl, and 3- to 7-membered heterocyclyl groups is optionally substituted with one, two, or three moieties independently selected from the group consisting of —OH, methyl, ethyl, —OCH$_3$, —SCH$_3$, and —NH$_{2-z}$(CH$_3$)$_z$; R$^2$ is H;

R$^3$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

R$^4$ is H;

R$^5$ is -L-R$^6$;

L is selected from the group consisting of a bond, C$_{1-6}$ alkylene, C$_{2-6}$ alkenylene, C$_{2-6}$ alkynylene, and —(CH$_2$)$_m$—[Y—(CH$_2$)$_n$]$_o$—, wherein m is an integer between 1 and 6, n is an integer between 0 and 3, o is an integer between 1 and 3, wherein if n is 0 then o is 1; Y is independently selected from O, S, and —N(R$^{13}$)—; and each of the C$_{1-6}$ alkylene, C$_{2-6}$ alkenylene, C$_{2-6}$ alkynylene, —(CH$_2$)$_m$—, and —(CH$_2$)$_n$— groups is optionally substituted with one or two independently selected R$^{30}$;

R$^6$ is heteroaryl or heterocyclyl each of which is optionally substituted with one or more independently selected R$^7$;

R$^7$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, and/or any two R$^7$ which are bound to the same atom of R$^6$ being a heterocyclyl group may join together to form =O, wherein each of the alkyl, alkenyl, alkynyl, cycloalkyl, aryl, heterocyclyl, and heteroaryl groups is optionally substituted with one or more independently selected R$^{30}$;

A is selected from the group consisting of S, O, NR$^8$, and C(R$^9$)$_2$;

R$^8$ is selected from the group consisting of H, alkyl, alkenyl, alkynyl, cycloalkyl, aryl, heterocyclyl, and heteroaryl, wherein each of the alkyl, alkenyl, alkynyl, cycloalkyl, aryl, heterocyclyl, and heteroaryl groups is optionally substituted with one or more independently selected R$^{30}$;

R$^9$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

X is independently selected from the group consisting of O, S, and N(R$^{14}$);

E is O or S;

B is N or CR$^{1d}$;

R$^{1d}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

R$^{11}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected R$^{30}$;

each of R$^{12}$ and R$^{13}$ is independently selected from the group consisting of H, alkyl, alkenyl, alkynyl, cycloalkyl, aryl, heteroaryl, and heterocyclyl, or R$^{12}$ and R$^{13}$ may join together with the nitrogen atom to which they are attached to form the group —N=CR$^5$R$^{16}$, wherein each of the alkyl, alkenyl, alkynyl, cycloalkyl, aryl, heteroaryl, and heterocyclyl groups is optionally substituted with one or more independently selected R$^{30}$;

R$^{14}$ is independently selected from the group consisting of H, alkyl, alkenyl, alkynyl, cycloalkyl, aryl, heteroaryl, heterocyclyl, and —OR$^{11}$, wherein each of the alkyl, alkenyl, alkynyl, cycloalkyl, aryl, heteroaryl, and heterocyclyl groups is optionally substituted with one or more independently selected R$^{30}$;

each of R$^{15}$ and R$^{16}$ is independently selected from the group consisting of H, alkyl, alkenyl, alkynyl, cycloalkyl, aryl, heteroaryl, heterocyclyl, and —NH$_y$R$^{20}{}_{2-y}$, or R$^{15}$ and R$^{16}$ may join together with the atom to which they are attached to form a ring which is optionally substituted with one or more independently selected R$^{30}$, wherein each of the alkyl, alkenyl, alkynyl, cycloalkyl, aryl, heteroaryl, and heterocyclyl groups is optionally substituted with one or more independently selected R$^{30}$;

y is an integer from 0 to 2;

R$^{20}$ is independently selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected R$^{30}$; and R$^{30}$ is a 1$^{st}$ level substituent and is, in each case, independently selected from the group consisting of alkyl, alkenyl, alkynyl, cycloalkyl, aryl, heteroaryl, heterocyclyl, halogen, —CN, azido, —NO$_2$, —OR$^{71}$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$R$^{71}$, —NR$^{71}$S(O)$_{1-2}$OR$^{71}$, —NR$^{71}$S(O)$_{1-2}$N(R$^{72}$)(R$^{73}$), —OP(O)(OR$^{71}$)$_2$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two R$^{30}$ which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups being a 1$^{st}$ level substituent is optionally substituted by one or more 2$^{nd}$ level substituents, wherein said 2$^{nd}$ level substituent is, in each case, independently selected from the group consisting of C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —S(O)$_{0-2}$R$^{81}$, —S(O)$_{1-2}$OR$^{81}$, —OS(O)$_{1-2}$R$^{81}$, —OS(O)$_{1-2}$OR$^{81}$, —S(O)$_{1-2}$N(R$^{82}$)(R$^{83}$), —OS(O)$_{1-2}$N(R$^{82}$)(R$^{83}$), —N(R$^{81}$)S(O)$_{1-2}$R$^{81}$, —NR$^{8'}$S(O)$_{1-2}$OR$^{81}$, —NR$^{81}$S(O)$_{1-2}$N(R$^{82}$)(R$^{83}$), —OP(O)(OR$^{81}$)$_2$, —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two 2$^{nd}$ level substituents which are bound to the same carbon atom of a cycloalkyl or heterocyclyl group being a 1$^{st}$ level substituent may join together to form =X$^2$, wherein each of the C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl groups being a 2$^{nd}$ level substituent is optionally substituted with one or more 3$^{rd}$ level substituents, wherein said 3$^{rd}$ level substituent is, in each case, independently selected from the group consisting of C$_{1-3}$ alkyl, halogen, —CF$_3$, —CN, azido, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-2}$(C$_{1-3}$ alkyl)$_z$, and —N(C$_{1-3}$ alkyl)C(=NH)NH$_{2-z}$(C$_{1-3}$ alkyl)$_z$, wherein each z is independently 0, 1, or 2 and each C$_{1-3}$ alkyl is independently methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N(C$_{1-3}$ alkyl);

wherein each of R$^{71}$, R$^{72}$, and R$^{73}$ is independently selected from the group consisting of H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents independently selected from the group consisting of C$_{1-3}$ alkyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein each z is independently 0, 1, or 2 and each $C_{1-3}$ alkyl is independently methyl, ethyl, propyl or isopropyl;

each of $R^{81}$, $R^{82}$, and $R^{83}$ is independently selected from the group consisting of H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents independently selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-2}$($C_{1-3}$ alkyl)$_z$, and —N($C_{1-3}$ alkyl)C(=NH)NH$_{2-z}$($C_{1-3}$ alkyl)$_z$, wherein each z is independently 0, 1, or 2 and each $C_{1-3}$ alkyl is independently methyl, ethyl, propyl or isopropyl; and each of $X^1$ and $X^2$ is independently selected from O, S, and N($R^{84}$), wherein $R^{84}$ is H or $C_{1-3}$ alkyl; with the proviso that
(1) when $R^{1a}$ is 4-(2-hydroxyethyl)piperazin-1-yl or Cl; $R^{1b}$ is H; $R^{1c}$ is methyl; B is N; E is O; $R^3$ is H; A is S; and L is a bond; then $R^6$ is not 4-chloro-2-methylpyridin-3-yl;
(2) when $R^{1a}$ is methoxy; $R^{1b}$ is H; $R^{1c}$ is methoxy; B is N; E is O; $R^3$ is H; A is S; and L is a bond; then $R^6$ is not 2,2-difluoro-5H-1,3-dioxolo[4,5-f]benzimidazol-6-yl;
(3) when $R^3$ is H; A is S; L is a bond; $R^6$ is 1-methyl-4-piperidinyl; $R^{1b}$ is H; B is N; E is O; and
  (i) $R^{1a}$ is methyl; then $R^{1c}$ is not N-tert-butoxycarbonylpiperidin-4-yl; or
  (ii) $R^{1c}$ is methyl; then $R^{1a}$ is not N-tert-butoxycarbonylpiperidin-4-yl or N-tert-butoxycarbonylpiperidin-3-yl;
(4) when E is O; B is $CR^{1d}$ and $R^{1d}$ is either H, F, Cl or Br, then $R^{1a}$ is not H; and
(5) when $R^{1a}$ is methyl; each of $R^{1b}$ and $R^{1c}$ is H; B is CH; E is O; A is S; and $R^3$ is methyl; then $R^5$ is not 1,3-benzodioxol-5-ylmethyl, 2-furanylmethyl, 1,3-benzodioxol-5-yl, 2-(2-thienyl)ethyl, 2-(4-morpholinyl)ethyl, 2-(2-pyridinyl)ethyl, 2-pyridinylmethyl, or tetrahydro-2-furanylmethyl.

2. The compound of item 1, wherein $R^6$ is a 3- to 10-membered heteroaryl or a 3- to 10-membered heterocyclyl, each of which is optionally substituted with one, two, or three independently selected $R^7$.

3. The compound of item 1 or 2, wherein $R^6$ is a mono- or bicyclic heteroaryl or a mono- or bicyclic heterocyclyl, each of which is optionally substituted with one, two, or three independently selected $R^7$.

4. The compound of any one of items 1-3, wherein $R^6$ is selected from the group consisting of a 5- to 6-membered monocyclic heteroaryl, a 4- to 6-membered monocyclic heterocyclyl, a 7- to 9-membered bicyclic heteroaryl, and a 7- to 9-membered bicyclic heterocyclyl, each of which is optionally substituted with one, two, or three independently selected $R^7$.

5. The compound of any one of items 1-4, wherein $R^6$ is selected from the group consisting of pyridinyl, thienyl, pyridazinyl, furanyl, pyrrolyl, pyrazolyl, oxazolyl, isoxazolyl, oxadiazolyl, imidazoimidazolyl, indolyl, naphthyridinyl, thienopyridinyl, tetrahydropyranyl, piperidinyl, pyrrolidinyl, azetidinyl, azabicycloheptanyl, azabicyclooctanyl, azapentacyclooctanyl, piperazinyl, morpholinyl, and tetrahydrothiophenyl, each of which is optionally substituted with one, two, or three independently selected $R^7$, preferably $R^6$ is selected from the group consisting of pyridinyl, thienyl, pyrazolyl, isoxazolyl, pyrrolyl, piperidinyl, pyrrolidinyl, azetidinyl, and azabicyclooctanyl, each of which is optionally substituted with one, two, or three independently selected $R^7$.

5a. The compound of any one of items 1-4, wherein $R^6$ is a 5- to 6-membered monocyclic heteroaryl optionally substituted with one, two, or three independently selected $R^7$.

5b. The compound of any one of items 1-4, wherein $R^6$ is a 7- to 9-membered bicyclic heterocyclyl optionally substituted with one, two, or three independently selected $R^7$.

6. The compound of any one of items 1-5b, wherein $R^7$ is independently selected from the group consisting of $C_{1-6}$ alkyl, $C_{2-6}$ alkenyl, $C_{2-6}$ alkynyl, halogen, —CN, —O($C_{1-6}$ alkyl), —NH($C_{1-6}$ alkyl), —N($C_{1-6}$ alkyl)$_2$, —NHS(O)$_{1-2}$($C_{1-6}$ alkyl), —NHS(O)$_{1-20}$($C_{1-6}$ alkyl), —C(=O)($C_{1-6}$ alkyl), and —OC(=O)($C_{1-6}$ alkyl), and/or any two $R^7$ which are bound to the same atom of $R^6$ being a heterocyclyl group may join together to form =O, wherein each of the $C_{1-6}$ alkyl, $C_{2-6}$ alkenyl, and $C_{2-6}$ alkynyl groups is optionally substituted with one or more independently selected $R^{30}$.

7. The compound of any one of items 1-6, wherein $R^7$ is independently selected from the group consisting of $C_{1-3}$ alkyl, halogen, —CN, —O($C_{1-3}$ alkyl), —NH($C_{1-3}$ alkyl), and —N($C_{1-3}$ alkyl)$_2$, and/or any two $R^7$ which are bound to the same atom of $R^6$ being a heterocyclyl group may join together to form =O, wherein each of the $C_{1-3}$ alkyl groups is optionally substituted with one or more independently selected $R^{30}$.

7a. The compound of any one of items 1-7, wherein $R^7$ is independently selected from the group consisting of halogen and $C_{1-2}$ alkyl, wherein the $C_{1-2}$ alkyl groups is optionally substituted with one, two, or three independently selected $R^{30}$.

7b. The compound of any one of items 1-7a, wherein $R^7$ is independently selected from the group consisting of Cl, Br, and methyl.

8. The compound of any one of items 1-7b, wherein one $R^7$ group is bound to a ring atom of $R^6$ at position 2 relative to the ring atom by which $R^6$ is bound to the remainder of the compound.

9. The compound of any one of items 1-8, wherein $R^6$ is selected from the following formulas:

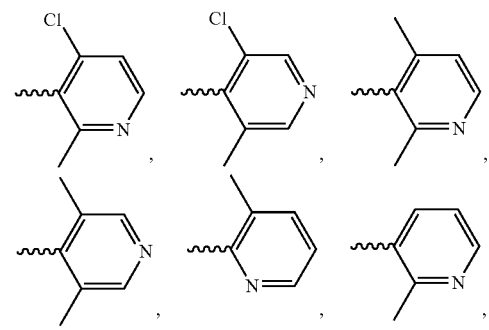

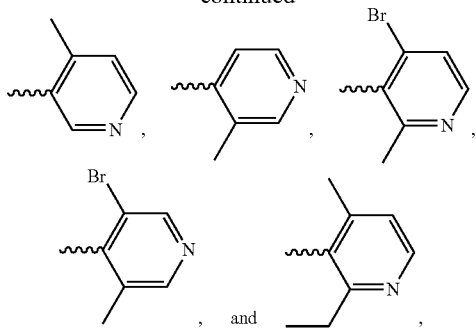

wherein ⌇⌇⌇ represents the bond by which R⁶ is bound to the remainder of the compound.

10. The compound of any one of items 1-8, wherein R⁶ is selected from the following formulas:

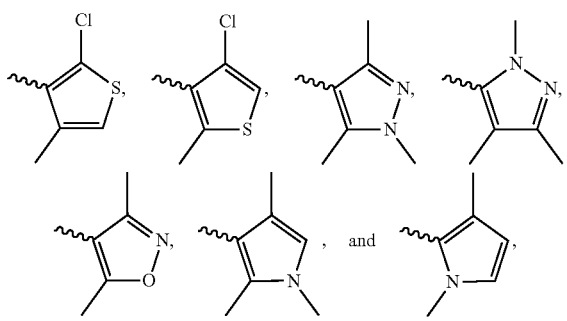

wherein ⌇⌇⌇ represents the bond by which R⁶ is bound to the remainder of the compound.

11. The compound of any one of items 1-8, wherein R⁶ is selected from the following formulas:

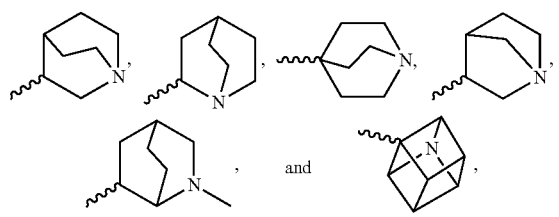

wherein ⌇⌇⌇ represents the bond by which R⁶ is bound to the remainder of the compound.

12. The compound of any one of items 1-11, wherein L is selected from the group consisting of a bond, $C_{1-6}$ alkylene, $C_{2-6}$ alkenylene, $C_{2-6}$ alkynylene, and —$(CH_2)_m$—[Y—$(CH_2)_n$]$_o$—, wherein m is 1, 2, or 3, n is 0, 1, or 2, o is 1, 2, or 3, wherein if n is 0 then o is 1; Y is independently selected from O, S, and NH, wherein each of the $C_{1-6}$ alkylene, $C_{2-6}$ alkenylene, $C_{2-6}$ alkynylene, —$(CH_2)_m$—, and —$(CH_2)_n$— groups is optionally substituted with one or more independently selected $R^{30}$.

13. The compound of any one of items 1-12, wherein L is selected from the group consisting of a bond; $C_1$ alkylene, optionally substituted with one $R^{30}$; $C_2$ alkylene (in particular 1,2-ethylene or 1,1-ethylene), optionally substituted with one $R^{30}$; $C_3$ alkylene (in particular trimethylene), optionally substituted with one $R^{30}$; $C_4$ alkylene (in particular tetramethylene or 2,4-butandiyl), optionally substituted with one $R^{30}$; —$(CH_2)_mO$—; and —$(CH_2)_mNH$—, wherein m is 1, 2, or 3.

14. The compound of any one of items 1-13, wherein L is a bond.

15. The compound of any one of items 1-14, wherein $R^{1a}$ is selected from the group consisting of alkyl, —O(alkyl), —S(alkyl), —NH(alkyl), —N(alkyl)$_2$, and heterocyclyl, wherein each of the alkyl and heterocyclyl groups is optionally substituted with one or more independently selected $R^{30}$.

16. The compound of any one of items 1-15, wherein $R^{1a}$ is selected from the group consisting of $C_{1-3}$ alkyl, —O($C_{1-3}$ alkyl), —S($C_{1-3}$ alkyl), —NH($C_{1-3}$ alkyl), —N($C_{1-3}$ alkyl)$_2$, and 3- to 7-membered heterocyclyl, wherein the 3- to 7-membered heterocyclyl group is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)($C_{1-3}$ alkyl), —$(CH_2)_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2.

17. The compound of any one of items 1-16, wherein $R^{1a}$ is selected from the group consisting of $C_{1-3}$ alkyl, —O($C_{1-3}$ alkyl), —S($C_{1-3}$ alkyl), —NH($C_{1-3}$ alkyl), piperazinyl, morpholinyl, piperidinyl, and pyrrolidinyl, wherein each of the piperazinyl, morpholinyl, piperidinyl, and pyrrolidinyl groups is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)($C_{1-3}$ alkyl), —$(CH_2)_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2.

18. The compound of any one of items 1-17, wherein $R^{1a}$ is selected from the group consisting of —NH($C_1$-3 alkyl) piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the $C_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2.

19. The compound of any one of items 1-18, wherein $R^{1a}$ is selected from the group consisting of 4-(2-hydroxyethyl)piperazinyl, 4-methylpiperazinyl, 4-acetylpiperazinyl, (2-hydroxyethyl)amino, 4-aminopiperidinyl, 4-(4-methylpiperazinyl)piperidinyl, 4-carboxymethylpiperazinyl, and 3-hydroxypyrrolidinyl.

19a. The compound of any one of items 1-19, wherein $R^{1a}$ is selected from the group consisting of 4-(2-hydroxyethyl)piperazinyl, 4-methylpiperazinyl, 4-acetylpiperazinyl, and (2-hydroxyethyl)amino.

20. The compound of any one of items 1-19a, wherein each of $R^{1b}$ and $R^{1c}$ is independently selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, phenyl, pyridinyl, pyrazolyl, phenoxy, pyridinyloxy, imidazolylamino, and tetrahydrofuranylmethoxy, wherein z is 0, 1, or 2; and each of the phenyl, pyridinyl, pyrazolyl, phenoxy, pyridinyloxy, imidazolylamino, and tetrahydrofuranylmethoxy groups is optionally substituted with one, two or three moieties independently selected from methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, and —NH$_{2-z}$(CH$_3$)$_z$, wherein z is 0, 1, or 2.

21. The compound of any one of items 1-20, wherein at least one of $R^{1b}$ and $R^{1c}$ is selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, and phenyl, wherein z is 0, 1, or 2.

22. The compound of any one of items 1-21, wherein $R^{1b}$ is methyl, ethyl, propyl, or isopropyl, preferably methyl; and $R^{1c}$ is H.

23. The compound of any one of items 1-21, wherein $R^{1b}$ is H; and $R^{1c}$ is methyl, ethyl, propyl, isopropyl, or phenyl, preferably methyl.

24. The compound of any one of items 1-23, wherein A is selected from the group consisting of S, O, NH, N(C$_{1-6}$ alkyl), and C(C$_{1-6}$ alkyl)$_2$.

25. The compound of any one of items 1-24, wherein A is S, O, or N(CH$_3$)$_2$.

26. The compound of any one of items 1-25, wherein A is S.

27. The compound of any one of items 1-26, wherein B is N or CR$^{1d}$, wherein R$^{1d}$ is selected from the group consisting of C$_{1-3}$ alkyl, halogen, —O(C$_{1-3}$ alkyl), —S(C$_{1-3}$ alkyl), —NH(C$_{1-3}$ alkyl), and —N(C$_{1-3}$ alkyl)$_2$, wherein each of the C$_{1-3}$ alkyl groups is optionally substituted with one or two moieties independently selected from the group consisting of halogen, —OH, —OCH$_3$, —SCH, and —NH$_{2-z}$(CH$_3$)$_z$, wherein z is 0, 1, or 2.

28. The compound of any one of items 1-26, wherein B is N.

29. The compound of any one of items 1-28, wherein E is O.

30. The compound of any one of items 1-29, wherein $R^3$ is selected from the group consisting of H, C$_{1-6}$ alkyl, C$_2$-6 alkenyl, C$_{2-6}$ alkynyl, C$_{3-6}$ cycloalkyl, phenyl, halogen, —CN, azido, —NO$_2$, —O(C$_{1-6}$ alkyl), —OCF$_3$, —S(C$_{1-6}$ alkyl), —NH$_2$, —NH(C$_{1-6}$ alkyl), —N(C$_{1-6}$ alkyl)$_2$, —NHS(O)$_2$(C$_{1-6}$ alkyl), —S(O)$_2$NH$_{2-z}$(C$_{1-6}$ alkyl)$_z$, —C(=O)(C$_{1-6}$ alkyl), —C(=O)OH, —C(=O)O(C$_{1-6}$ alkyl), —C(=O)NH$_{2-z}$(C$_{1-6}$ alkyl)$_z$, —NHC(=O)(C$_{1-6}$ alkyl), —NHC(=NH)NH$_{z-2}$(C$_{1-6}$ alkyl)$_z$, and —N(C$_{1-6}$ alkyl)C(=NH)NH$_{2-z}$(C$_{1-6}$ alkyl)$_z$, wherein z is 0, 1, or 2 and wherein each of the C$_{1-6}$ alkyl, C$_{2-6}$ alkenyl, C$_{2-6}$ alkynyl, C$_{3-6}$ cycloalkyl, and phenyl groups is optionally substituted with one or more independently selected $R^{30}$.

31. The compound of any one of items 1-30, wherein $R^3$ is selected from the group consisting of H, C$_{1-4}$ alkyl, C$_{3-6}$ cycloalkyl, phenyl, halogen, —CN, —O(C$_{1-4}$ alkyl), —OCF$_3$, —S(C$_{1-4}$ alkyl), —NH$_2$, —NH(Cia alkyl), —N(C$_{1-4}$ alkyl)$_2$, —C(=O)(C$_{1-4}$ alkyl), —C(=O)OH, —C(=O)O(C$_{1-4}$ alkyl), —C(=O)NH$_{2-z}$ (C$_{1-4}$ alkyl)$_z$, —NHC(=O)(C$_{1-4}$ alkyl), —NHC(=NH)NH$_{z-2}$(Cia alkyl)$_z$, and —N(Cia alkyl)C(=NH)NH$_{2-z}$(C$_{1-4}$ alkyl)$_z$, wherein the phenyl group is optionally substituted with one, two or groups independently selected from the group consisting of halogen, methyl, isopropyl, —CN, —CF$_3$, —OCF$_3$, —OH, —NH$_2$, —NH(C$_{1-3}$ alkyl), —N(C$_{1-3}$ alkyl)$_2$, —NHC(=O)(C$_{1-3}$ alkyl), —C(=O)NH$_{2-z}$(C$_{1-3}$ alkyl)$_z$, —(CH$_2$)$_{1-3}$NH$_2$, —(CH$_2$)$_{1-3}$NH(C$_{1-3}$ alkyl), —(CH$_2$)$_{1-3}$N(C$_{1-3}$ alkyl)$_2$, —(CH$_2$)$_{1-30}$H, and —(CH$_2$)$_{1-30}$(C$_{1-3}$ alkyl); and wherein z is 0, 1, or 2.

32. The compound of any one of items 1-31, wherein $R^3$ is selected from the group consisting of H, methyl, ethyl, propyl, isopropyl, phenyl, and halogen.

33. The compound of any one of items 1-32, wherein $R^3$ is H.

34. The compound of any one of items 1-33, selected from the group consisting of:

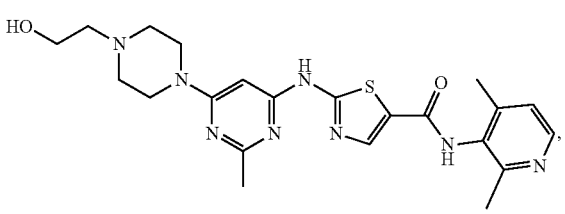

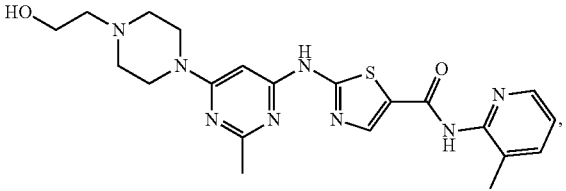

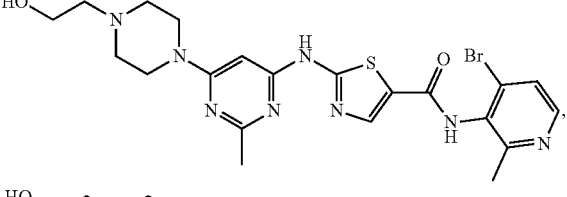

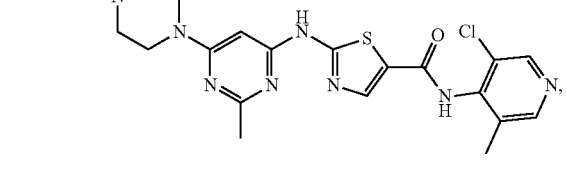

-continued

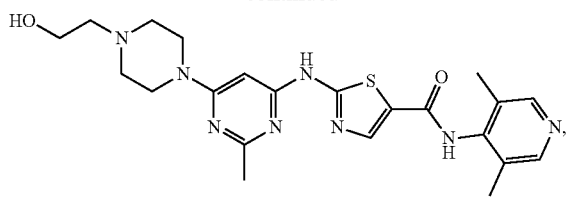

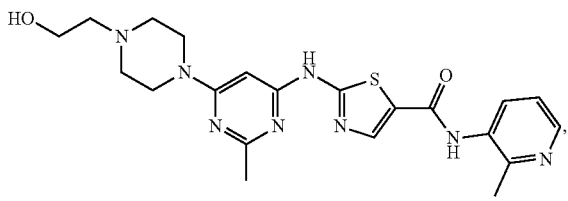

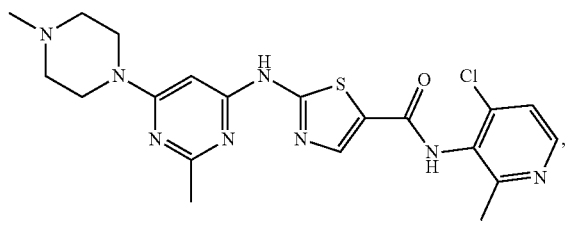

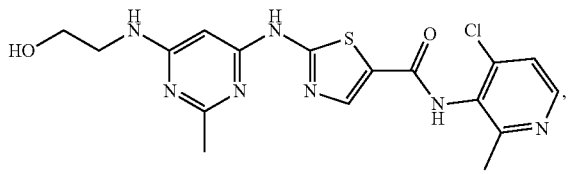

and

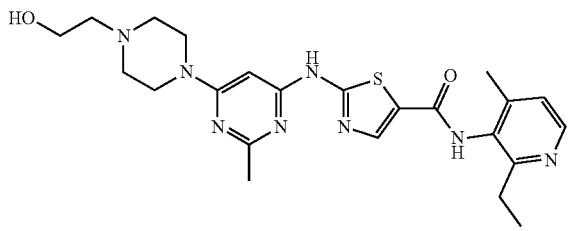

and solvates, salts, N-oxides, complexes, polymorphs, crystalline forms, tautomers, conformers, isotopically labeled forms, prodrugs, and combinations thereof.

35. The compound of any one of items 1-33, selected from the group consisting of:

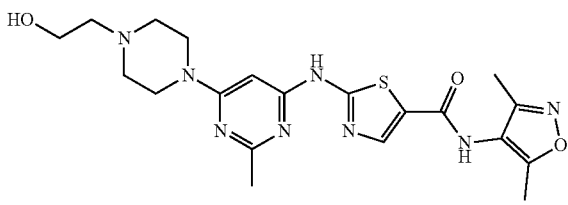 [SMILES: Cc1nc(Nc2ncc(C(=O)Nc3c(C)noc3C)s2)cc(N2CCN(CCO)CC2)n1]

and solvates, salts, N-oxides, complexes, polymorphs, crystalline forms, tautomers, conformers, isotopically labeled forms, prodrugs, and combinations thereof.

36. The compound of any one of items 1-33, selected from the group consisting of:

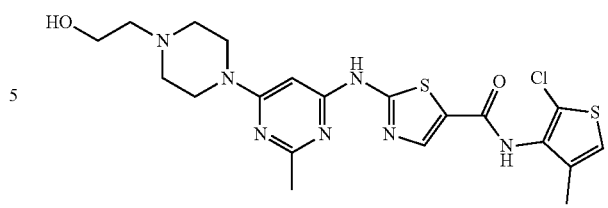

and solvates, salts, N-oxides, complexes, polymorphs, crystalline forms, tautomers, conformers, isotopically labeled forms, prodrugs, and combinations thereof.

37. The compound of any one of items 1-33, selected from the group consisting of:

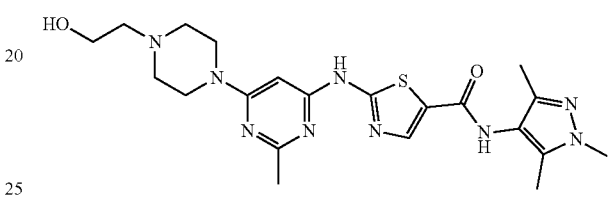

and solvates, salts, N-oxides, complexes, polymorphs, crystalline forms, tautomers, conformers, isotopically labeled forms, prodrugs, and combinations thereof.

38. The compound of any one of items 1-33, selected from the group consisting of:

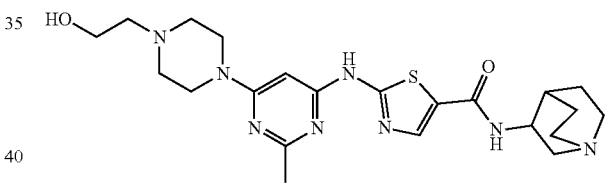

and solvates, salts, N-oxides, complexes, polymorphs, crystalline forms, racemic mixtures, diastereomers, enantiomers, tautomers, conformers, isotopically labeled forms, prodrugs, and combinations thereof.

38a. The compound of any one of items 1-33, selected from the group consisting of:

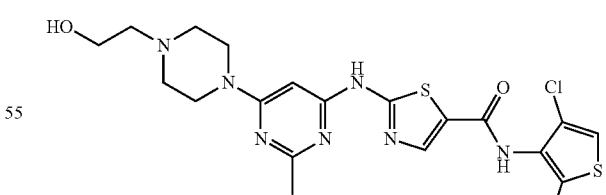

and solvates, salts, N-oxides, complexes, polymorphs, crystalline forms, racemic mixtures, diastereomers, enantiomers, tautomers, conformers, isotopically labeled forms, prodrugs, and combinations thereof.

38b. The compound of any one of items 1-33, selected from the group consisting of:

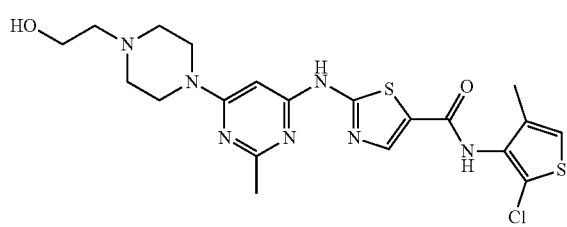 [SMILES: Cc1nc(Nc2ncc(C(=O)Nc3c(C)csc3Cl)s2)cc(N2CCN(CCO)CC2)n1]
and solvates, salts, N-oxides, complexes, polymorphs, crystalline forms, racemic mixtures, diastereomers, enantiomers, tautomers, conformers, isotopically labeled forms, prodrugs, and combinations thereof.
38c. The compound of any one of items 1-33, selected from the group consisting of:
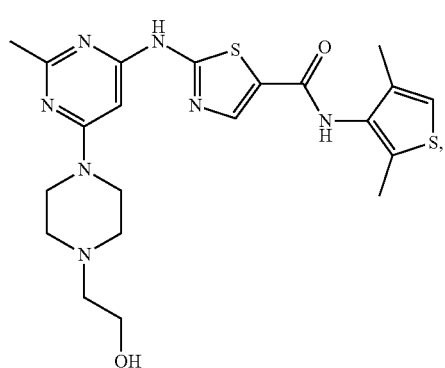
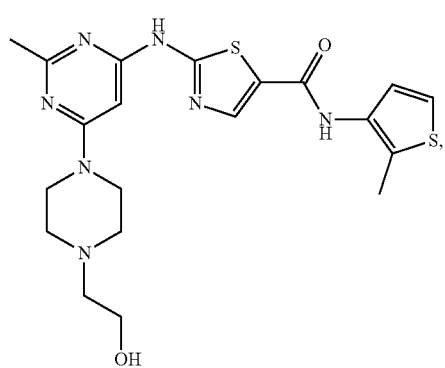
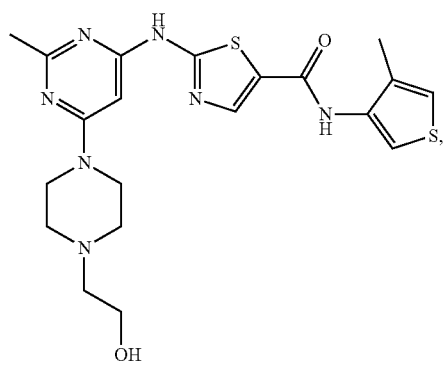
-continued
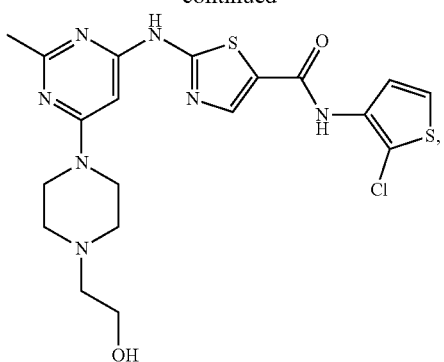
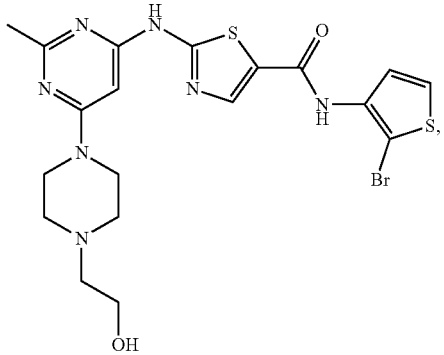
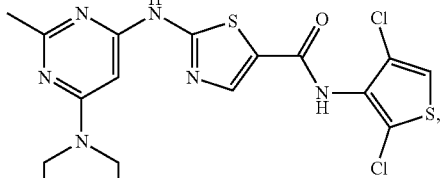
and
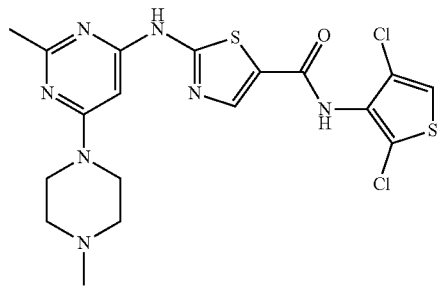

and solvates, salts, N-oxides, complexes, polymorphs, crystalline forms, racemic mixtures, diastereomers, enantiomers, tautomers, conformers, isotopically labeled forms, prodrugs, and combinations thereof.

39. The compound of any one of items 1 to 38, or of any one of items 38a to 38c, in substantially pure form, in particular in greater than about 90%, 95%, 98% or 99% pure form.
40. The compound of any one of items 1 to 38 and 39, or of any one of items 38a to 38c, as a hydrate.
41. One or more containers containing, each independently or all collectively, more than about 10 g or 50 g of the compound of any one of items 1 to 38, 39 and 40, or of any one of items 38a to 38c, suitably containing more than about 100 g of such compound, more suitably containing more than about 500 g of such compound.
42. A pharmaceutical composition comprising the compound of any one of items 1 to 38, 39 and 40, or of any one of items 38a to 38c, and optionally further comprising a pharmaceutically acceptable excipient.
43. The pharmaceutical composition of item 42 formulated for oral administration.
44. The pharmaceutical composition of item 42 or 43 in unit dose form.
45. The pharmaceutical composition of item 44, comprising between 1 and 950 mg of the compound per unit dose form.
46. The pharmaceutical composition of item 45, comprising between 2 and 150 mg of the compound per unit dose form.
47. The pharmaceutical composition of item 45, comprising between 10 and 150 mg of the compound per unit dose form.
48. The pharmaceutical composition of item 45 or 46, comprising about an amount of the compound per unit dose form selected from the list of amounts consisting of: 2 mg, 5 mg, 15 mg, 20 mg, 50 mg, 70 mg, 80 mg, 100 mg and 140 mg.
49. The pharmaceutical composition of any one of items 42 to 48 in unit dose form, wherein the unit dose form is a tablet, caplet or capsule.
50. The pharmaceutical composition of any one of items 42 to 49, further comprising one or more, preferably all, of the excipients selected from the list consisting of: lactose, microcrystalline cellulose, croscarmellose sodium, hydroxypropylcellulose and magnesium stearate.
51. The pharmaceutical composition of any one of items 44 to 50, wherein the unit dose form is a film-coated a table or a film-coated caplet.
52. The pharmaceutical composition of item 51, wherein the film-coating comprises one or more, preferably all, of the excipients selected from the list consisting of: hypromellose, titanium dioxide and macrogol 400.
53. The compound of any one of items 1 to 38, 39 and 40, or of any one of items 38a to 38c, or the pharmaceutical composition of any one of items 42 to 52, for use in therapy.
54. A compound or a pharmaceutical composition for use in a treatment of a proliferative disorder in a subject, the treatment comprising administering the compound or the pharmaceutical composition to the subject, wherein, the compound is a compound of any one of items 1 to 38, 39 and 40, or any one of items 38a to 38c, or the pharmaceutical composition is a pharmaceutical composition of any one of items 42 to 52.
55. The compound or pharmaceutical composition for use of item 53 or 54, wherein the subject is an adult human; suitably, wherein the adult human is about 30 or older; in particular wherein the adult human is a young adult, is middle aged or is elderly.
56. The compound or pharmaceutical composition for use of item 53 or 54, wherein the subject is a paediatric human, suitably, wherein the paediatric human is younger than about 16; in particular wherein the paediatric human is an adolescent a preadolescent, an early child, a toddler or an infant.
57. The compound or pharmaceutical composition for use of any one of items 53 to 56, wherein the treatment does not involve inhibiting SIK3 kinase.
58. The compound or pharmaceutical composition for use of any one of items 53 to 57, wherein the treatment:
    does not involve inhibiting SIK3 kinase;
    does not involve inhibiting SIK1 and/or SIK2 kinases;
    does not involve inhibiting JAK1 kinase;
    does not involve inhibiting RET kinase;
    does not involve inhibiting ERBB4 kinase;
    does not involve inhibiting PDGFR-alpha kinase and/or
    does not involve inhibiting EPHB2 kinase.
59. The compound or pharmaceutical composition for use of any one of items 53 to 58, wherein the treatment:
    does not involve inhibiting PDGFR-alpha kinase;
    does not involve inhibiting TGFB-R1, B-RAF and/or p38-beta kinase;
    does not involve inhibiting ACV-R1 and/or BMPR1A kinase; and/or
    does not involve inhibiting RET kinase.
60. The compound or pharmaceutical composition for use of any one of items 53 to 59, wherein the does not involve sensitising cells involved with the proliferative disorder to a cell-mediated immune response.
61. The compound or pharmaceutical composition for use of any one of items 53 to 60, wherein the treatment:
    involves inhibiting ABL1 and/or SRC kinase;
    involves inhibiting BCR-ABL kinase;
    involves inhibiting LCK kinase;
    involves inhibiting LYN kinase
    involves inhibiting YES kinase;
    involves inhibiting FYN kinase; and/or
    involves inhibiting KIT kinase.
62. The compound or pharmaceutical composition for use of any one of items 53 to 61, wherein the treatment:
    involves inhibiting EPHA2 kinase;
    involves inhibiting EPHA4 kinase;
    involves inhibiting CSF1-R kinase;
    involves inhibiting HCK kinase; and/or
    involves inhibiting ACK1 kinase.
63. The compound or pharmaceutical composition for use of any one of items 53 to 62, wherein the treatment involves inhibiting ABL1 and/or SRC kinase more than inhibiting SIK3 and/or more than inhibiting SIK1 and/or SIK2.
64. The compound or pharmaceutical composition for use of any one of items 53 to 63, wherein the treatment involves inhibiting FLT3 kinase.
65. The compound or pharmaceutical composition for use of any one of items 53 to 64, wherein the treatment:
    involves inhibiting NEK11, WEE1 and/or WNK2 kinase;
    involves inhibiting Aurora-A and/or Aurora-B kinase; and/or
    involves inhibiting TBK1 kinase.

66. The compound or pharmaceutical composition for use of any one of items 53 to 65, wherein the treatment involves inhibiting a kinase mutation; in particular involves inhibiting BCR-ABL kinase and/or another mutant of ABL1 kinase, and/or involves inhibiting a mutant of KIT kinase.

67. The compound or pharmaceutical composition for use of any one of items 53 to 66, wherein the treatment comprises administering to an adult human subject in need thereof an amount of the compound of less than about 140 mg daily, optionally where the proliferative disorder is a proliferative disorder that is not chronic phase Ph+ CML.

68. The compound or pharmaceutical composition for use of item 67, wherein the treatment comprises administering to an adult human subject in need thereof an amount of the compound of less than about 100 mg daily, optionally where the proliferative disorder is chronic phase Ph+ CML.

69. The compound or pharmaceutical composition for use of any one of items 53 to 66, wherein the treatment comprises administering to a paediatric human subject in need thereof an amount of the compound of:
less than about 40 mg daily for paediatric patients with a body weight of 10 kg to less than 20 kg;
less than about 60 mg daily for paediatric patients with a body weight of 20 kg to less than 30 kg;
less than about 70 mg daily for paediatric patients with a body weight of 30 kg to less than 45 kg; or
less than about 100 mg daily for paediatric patients with a body weight of at least 45 kg.

70. The compound or pharmaceutical composition for use of any one of items 67 to 69, wherein the human subject is administered the amount of the compound less frequently than once daily.

71. The compound or pharmaceutical composition for use of any one of items 67 to 70, wherein the human subject is administered an amount of the compound and at a frequency to sensitise cells involved with a proliferative disorder to a cell-mediated immune-response, in particular to sensitise cells involved with a proliferative disorder to the killing (apoptotic/cytotoxic) effect of TNF.

72. The compound or pharmaceutical composition for use of any one of items 53 to 71, wherein the subject does not have an adverse reaction.

73. The compound or pharmaceutical composition for use of item 72, wherein the adverse reaction is myelosuppression.

74. The compound or pharmaceutical composition for use of item 72, wherein the adverse reaction is a non-haematological adverse reaction.

75. The compound or pharmaceutical composition for use of item 72, wherein the adverse reaction is a cardiological adverse reaction.

76. The compound or pharmaceutical composition for use of any one of items 53 to 75, wherein the subject does not concomitantly use a strong CYP3A4 inhibitor.

77. The compound or pharmaceutical composition for use of any one of items 53 to 76, wherein the proliferative disorder is a cancer or tumour.

78. The compound or pharmaceutical composition for use of item 77, wherein the cancer is a hematopoietic or lymphoid cancer.

79. The compound or pharmaceutical composition for use of any one of items 53 to 78, wherein the proliferative disorder is a Philadelphia chromosome-positive leukaemia.

80. The compound or pharmaceutical composition for use of any one of items 53 to 79, wherein the proliferative disorder is Philadelphia chromosome-positive chronic myeloid leukaemia (Ph+ CML) or Philadelphia chromosome-positive acute lymphoblastic leukaemia (Ph+ ALL).

81. The compound or pharmaceutical composition for use of any one of items 53 to 80, wherein the proliferative disorder is:
newly diagnosed (Ph+ CML) in the chronic phase;
chronic, accelerated or blast phase CML with resistance or intolerance to prior therapy including imatinib; or
Ph+ acute lymphoblastic leukaemia (ALL) and lymphoid blast CML with resistance or intolerance to prior therapy.

82. The compound or pharmaceutical composition for use of any one of items 53 to 80, wherein the subject is a paediatric human and the proliferative disorder is:
newly diagnosed Ph+ CML in chronic phase (Ph+ CML-CP) or Ph+ CML-CP resistant or intolerant to prior therapy including imatinib.

83. The compound or pharmaceutical composition for use of item 77, wherein the cancer is a solid tumour.

84. The compound or pharmaceutical composition for use of item 83, wherein the solid tumour is a cancer of a tissue selected from the list of tissues consisting of: pancreas, breast, lung, prostate, skin, ovary, oesophagus and colon/rectum.

85. The compound or pharmaceutical composition for use of any one of items 53 to 77, 83 or 84, wherein the proliferative disorder is pancreatic cancer.

86. The compound or pharmaceutical composition for use of item 85, wherein treatment further comprises administration of an EGFR inhibitor and/or gemcitabine.

87. The compound or pharmaceutical composition for use of any one of items 53 to 77, 83 or 84, wherein the proliferative disorder is prostate cancer.

88. The compound or pharmaceutical composition for use of item 87, wherein treatment further comprises administration of docetaxel.

89. The compound or pharmaceutical composition for use of any one of items 53 to 77, 83 or 84, wherein the proliferative disorder is lung cancer, in particular non-small cell lung cancer.

90. The compound or pharmaceutical composition for use of any one of items 53 to 89, wherein treatment further comprises administration of an immune checkpoint inhibitor.

91. The compound or pharmaceutical composition for use of item 90, wherein immune checkpoint inhibitor is nivolumab, relatlimab, ipilimumab or BMS-986205.

92. The compound or pharmaceutical composition for use of any one of items 53 to 91, wherein the proliferative disorder has progressed on standard therapy in the subject.

93. The compound or pharmaceutical composition for use of any one of items 53 to 91, wherein the subject is unable to receive standard therapy.

94. The compound or pharmaceutical composition for use of item 92 or 93, wherein the standard therapy is immunotherapy.

95. The compound or pharmaceutical composition for use of any one of items 53 to 91, wherein the proliferative disorder is CML or ALL with resistance, and/or the subject is intolerant to prior therapy, in particular resistance or intolerance to prior imatinib therapy.

96. The compound or pharmaceutical composition for use of any one of items 53 to 95, wherein the treatment involves inhibiting SIK3.

97. The compound or pharmaceutical composition for use of item 96, wherein the compound or pharmaceutical composition is administered in a therapeutically effective amount that is effective to reduce activity of SIK3; preferably of SIK3 in the cells involved with the proliferative disorder.

98. The compound or pharmaceutical composition for use of item 96 or 97, wherein the compound or pharmaceutical composition is administered in a therapeutically effective amount that is not effective to reduce the activity of ABL1 and/or SRC kinase; preferably ABL1 and/or SRC kinase in the cells involved with the proliferative disorder.

99. The compound or pharmaceutical composition for use of any one of items 96 to 98, wherein the treatment is mediated by inhibiting SIK3; and wherein the treatment is not mediated by inhibiting ABL1 and/or SRC kinase.

100. The compound or pharmaceutical composition for use of any one of items 96 to 99, wherein the treatment comprises that SIK3 in the cells involved with the proliferative disorder is inhibited; preferably wherein activity of the SIK3 is reduced; and wherein the treatment comprises that ABL1 and/or SRC in the cells involved with the proliferative disorder is not inhibited; preferably wherein activity of the ABL1 and/or SRC is not reduced.

101. The compound or pharmaceutical composition for use of any one of items 53 to 100, wherein the treatment involves sensitising cells involved with the proliferative disorder to a cell-mediated immune response.

102. The compound or pharmaceutical composition for use of any one of items 53 to 101, wherein the treatment comprises that the cell-mediated immune response induces killing of cells involved with the proliferative disorder.

103. The compound or pharmaceutical composition for use of any one of items 53 to 102, wherein the compound or pharmaceutical composition is administered to the subject to sensitise cells involved with the proliferative disorder to killing induced by TNF.

104. The compound or pharmaceutical composition for use of any one of items 101 to 103, wherein cells involved with the proliferative disorder are exposed to TNF and/or an agonist of TNFR1-signalling.

105. The compound or pharmaceutical composition for use of any one of items 101 to 104, wherein: (x) the subject is distinguished by having a plasma concentration of TNF greater than about 5 pg/mL; and/or (y) the proliferative disorder is a solid tumour that, in the subject, by having an intratumoural concentration of TNF greater than about 1 pg/mL.

106. The compound or pharmaceutical composition for use of any one of items 53 to 105, the treatment comprising exposing cells involved with the proliferative disorder in the subject to: (i) TNF and/or an agonist of TNFR1-signalling; and (ii) the compound or pharmaceutical composition.

107. The compound or pharmaceutical composition for use of item 106, wherein the amount of TNF exposed to cells involved with the proliferative disorder in the subject is increased.

108. The compound or pharmaceutical composition for use of item 106 or 107, wherein: (i) TNF or an agonist of TNFR1-signalling is administered to the subject; (ii) an agent that is capable of inducing or induces the exposure of the cells involved with the proliferative disorder to TNF or an agonist of TNFR1-signalling, is administered to the subject; or (iii) the exposure of the cells involved with the proliferative disorder to TNF is induced by a pharmaceutical, therapeutic or other procedure that increases the amount of TNF in the plasma of the subject and/or in the environment of such cells.

109. The compound or pharmaceutical composition for use of any one of items 106 to 108, wherein the treatment comprises that the compound or pharmaceutical composition is administered to the subject in a therapeutically effective amount effective to inhibit SIK3, in particular SIK3 in the cells involved with the proliferative disorder.

110. The compound or pharmaceutical composition for use of any one of items 106 to 109, wherein the treatment comprises that the compound or pharmaceutical composition is administered to the subject in a therapeutically effective amount not effective to inhibit ABL1 and/or SRC, in particular ABL1 and/or SRC in the cells involved with the proliferative disorder.

111. The compound or pharmaceutical composition for use of any one of items 106 to 110, wherein the treatment comprises that TNF or the agonist of TNFR1-signalling is administered to the subject.

112. The compound or pharmaceutical composition for use of any one of items 106 to 110, wherein the treatment comprises that an agent that is capable of inducing or induces the exposure of the cells involved with the proliferative disorder to TNF or an agonist of TNFR1-signalling, is administered to the subject.

113. The compound or pharmaceutical composition for use of any one of items 106 to 110, wherein the exposure of the cells involved with the proliferative disorder to TNF is induced by a pharmaceutical, therapeutic or other procedure that increases the amount of TNF in the plasma of the subject and/or in the environment of such cells.

114. The compound or pharmaceutical composition for use of item 113, wherein the pharmaceutical, therapeutic or other procedure comprises cancer immunotherapy and/or radiotherapy.

115. The compound or pharmaceutical composition for use of any one of items 106 to 114, wherein the subject is distinguished by having cells involved in the proliferative disorder characterised by expression and/or activity of SIK3, in particular such cells express mRNA and/or protein of SIK3, and/or are positive for such SIK3 expression and/or activity.

116. The compound or pharmaceutical composition for use of any one of items 106 to 115, wherein the proliferative disorder is a tumour, in particular a solid tumour.

117. The compound or pharmaceutical composition for use of item 116, wherein the subject is distinguished as having been previously treated with an immunotherapy and whose tumour has progressed, in particular whose tumour relapsed, recurred or did not respond.

118. The compound or pharmaceutical composition for use of item 116 or 117, wherein the subject is distinguished as having a tumour that progressed, in particular relapsed, recurred or did not respond to, prior radiotherapy.

119. A compound or a pharmaceutical composition for use in a treatment for the reduction in risk of developing a haematological proliferative disorder as a secondary disorder in a subject being treated with an anti-TNF agent, the treatment comprising administering a compound of any one of items 1 to 38, 39 and 40, or of any one of items 38a to 38c, or a pharmaceutical composition of any one of items 42 to 52.

120. The compound or pharmaceutical composition for use of item 119, wherein the subject suffers from, and/or the subject is being treated with the anti-TNF agent for, an autoimmune disorder; preferably an autoimmune disorder selected from the group consisting of: rheumatoid arthritis, psoriatic arthritis, ankylosing spondylitis, plaque psoriasis and Crohn's Disease, most preferably rheumatoid arthritis.

121. The compound or pharmaceutical composition for use of any one of items 53 to 120, wherein the compound is or the pharmaceutical composition comprises a SIK3 (or a SIK3-specific) inhibitor.

122. The compound or pharmaceutical composition for use of any one of items 53 to 121, wherein the compound is or the pharmaceutical composition comprises a SIK3 inhibitor that inhibits SIK3 less (or more) potently than it inhibits ABL1 and/or SRC kinase; and wherein the SIK3 inhibitor inhibits SIK3 less (or more) potently than it inhibits SIK2 and/or SIK2.

123. The compound or pharmaceutical composition for use of any one of items 53 to 122, wherein the subject is a human volunteer.

124. The compound or pharmaceutical composition for use of any one of items 53 to 122, wherein the subject is a laboratory animal, in particular an animal selected from the group consisting of: mouse, rat, rabbit, pig and monkey.

125. The compound or pharmaceutical composition for use of item 123 or 124, wherein a plurality of subjects are treated, in particular 5 or more subjects, such as between about 5 and 20, 10 and 50, 25 and 200, or 75 and 250 subjects, or more than about 250 subjects.

126. The compound or pharmaceutical composition for use of item 125, wherein the treatment comprises: (i) the administration to at least one of such subjects of one dosage of the compound and/or one formulation of the pharmaceutical composition; and (ii) the administration to at least one other of such subjects of a different dosage of the compound and/or a different formulation of the pharmaceutical composition.

127. The compound or pharmaceutical composition for use of item 125 or 126, wherein the treatment comprises: (i) the administration to at least one of such subjects of one dosage of the compound and/or one formulation of the pharmaceutical composition; and (ii) the administration to at least one other of such subjects of either: (a) a placebo; or (b) the dosage of the compound and/or the formulation of the pharmaceutical composition of the subject(s) of (i) as well as an additional pharmaceutical, therapeutic or other procedure.

128. The compound or pharmaceutical composition for use of any one of items 125 to 127, wherein the treatment is specifically designed for the investigation and/or determination of a therapeutically effective dosage of the compound and/or the identification of a therapeutically effective formulation of the pharmaceutical composition.

129. A method of diagnosing and treating a proliferative disorder characterised by the presence of or an amount of, and/or characterised by expression or activity of, an applicable biomarker in a subject, comprising the steps:
detecting the applicable biomarker in a biological sample from said subject, thereby diagnosing if the subject is suffering (or is likely to suffer) from such a disease, disorder or condition; and
administering an effective amount of a compound of items 1 to 38, 39 and 40, or of any one of items 38a to 38c, or a pharmaceutical composition of any one of items 42 to 52, to the so diagnosed subject (in particular, practicing a treatment method of the invention on the subject).

130. A use of an intermediate to prepare a compound of any one of items 1 to 38, 39 and 40, or of any one of items 38a to 38c wherein the intermediate comprises a substructure of $R^6$ or $R^{1a}$, or comprises the following substructure:

<chemical structure> wherein, $R^6$, $R^{1a}$, A and B are as defined in any one of items 1 to 38 or in any one of items 38a to 38c.

131. The use of an intermediate of item 130, wherein the intermediate is selected from the list consisting of:
4-chloro-2-methylpyridin-3-amine;
2,4-dimethylpyridin-3-amine;
3-methylpyridin-2-amine;
4-bromo-2-methylpyridin-3-amine;
3-chloro-5-methylpyridin-4-amine;
3,5-dimethylpyridin-4-amine;
2-methylpyridin-3-amine;
2-chloro-4-methylthiophen-3-amine;
1,3,5-trimethyl-1H-pyrazol-4-amine;
3,5-dimethylisoxazol-4-amine;
quinuclidine-3-amine; and
2-ethyl-4-methylpyridin-3-amine.

131a. The use of an intermediate of item 130, wherein the intermediate is selected from the list consisting of:
2-chloro-4-methylthiophen-3-amine.

131b. The use of an intermediate of item 130, wherein the intermediate is selected from the list consisting of:
4-chloro-2-methylthiophen-3-amine;
2,4-dimethylthiophen-3-amine;
2-methylthiophen-3-amine;
4-methylthiophen-3-amine;
2-chlorothiophen-3-amine;
2-bromothiophen-3-amine; and
2,4-dichlorothiophen-3-amine.

132. An intermediate selected from the group consisting of a compound having a structure of formula (I) as defined in any one of items 1 to 38, or in any one of items 38a to 38c, wherein $R^{1a}$ is a leaving group, such as a halogen, preferably Cl.

133. A method of preparing a compound of item 39, comprising the steps:
providing a compound of (any one of) items 1 to 38 or 40, or of any one of items 38a to 38c, in admixture with one or more impurities; and
removing at least a fraction of the impurities from the admixture.

134. The method of item 133, wherein the admixture is provided by synthesising an impure form of a compound of (any one of) items 1 to 38 or 40, or of any one of items 38a to 38c.
135. A method of manufacturing a pharmaceutical composition comprising the step of formulating a compound of any one of items 1 to 38, 39 and 40, or of any one of items 38a to 38c, together with a pharmaceutically acceptable excipient.
136. The method of item 135, wherein the pharmaceutical composition is manufactured in unit dose form.
137. The method of item 135 or 136, wherein the pharmaceutical composition is formed as a tablet, caplet or capsule, in particular as a film-coated tablet or as a film-coated caplet.
138. A method of preparing a pharmaceutical package, comprising the steps:
    inserting into packaging a pharmaceutical composition of any one of items 42 to 52 (preferably in finished pharmaceutical form), thereby forming a package containing the pharmaceutical composition; and optionally,
    inserting into the package a leaflet describing prescribing information for the pharmaceutical composition.
139. A pharmaceutical package containing a pharmaceutical composition of any one of items 42 to 52; preferably, wherein the pharmaceutical composition is in finished pharmaceutical form.
140. The pharmaceutical package of item 139, further containing a leaflet describing prescribing information for the pharmaceutical composition.
141. A method of delivering a pharmaceutical composition of any one or items 42 to 52, or a pharmaceutical package of item 139 or 140, from a first location to a second location, comprising the steps:
    receiving at a first location a request from a second location for the delivery of an amount of the pharmaceutical composition or the pharmaceutical package; and
    delivering at least a portion of (preferably, all of) the requested amount (of the pharmaceutical composition or the pharmaceutical package) from the first location to the second location in one or more deliveries,
wherein first location and the second location are separated by a distance of greater than about 10 m, and one or more of the deliveries is/are transported for at least part of the distance between the first location to the second location by wheeled transporters.

In view of the above, it will be appreciated that the present invention also relates to the following additional itemized embodiments:

A1. A compound selected from the group consisting of a kinase inhibitor of the formula:

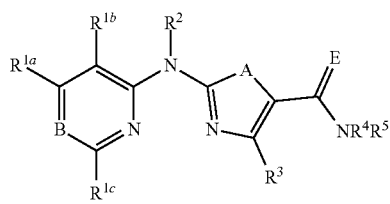

(I)

and solvates, salts, N-oxides, complexes, polymorphs, crystalline forms, racemic mixtures, diastereomers, enantiomers, tautomers, conformers, isotopically labeled forms, prodrugs, and combinations thereof;
wherein:
    $R^{1a}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;
    each of $R^{1b}$ and $R^{1c}$ is independently selected from the group consisting of H, C$_{1-6}$ alkyl, C$_{2-6}$ alkenyl, C$_{2-6}$ alkynyl, C$_{3-7}$ cycloalkyl, C$_{6-10}$ aryl, 3- to 7-membered heteroaryl, 3- to 7-membered heterocyclyl, —O(CH$_2$)$_{0-2}$(C$_{3-7}$ cycloalkyl), —O(CH$_2$)$_{0-2}$(C$_{6-10}$ aryl), —O(CH$_2$)$_{0-2}$(3- to 7-membered heteroaryl), —O(CH$_2$)$_{0-2}$(3- to 7-membered heterocyclyl), —NH(CH$_2$)$_{0-2}$(C$_{3-7}$ cycloalkyl), —NH(CH$_2$)$_{0-2}$(C$_{6-10}$ aryl), —NH(CH$_2$)$_{0-2}$(3- to 7-membered heteroaryl), —NH(CH$_2$)$_{0-2}$(3- to 7-membered heterocyclyl), halogen, —CF$_3$, —CN, azido, —NO$_2$, —OH, —O(C$_{1-6}$ alkyl), —OCF$_3$, —S(C$_{1-6}$ alkyl), —NH$_2$, —NH(C$_{1-6}$ alkyl), —N(C$_{1-6}$ alkyl)$_2$, —NHS(O)$_2$(C$_{1-6}$ alkyl), —S(O)$_2$NH$_{2-z}$(C$_{1-6}$ alkyl)$_z$, —C(=O)(C$_{1-6}$ alkyl), —C(=O)OH, —C(=O)O(C$_{1-6}$ alkyl), —C(=O)NH$_{2-z}$(C$_{1-6}$ alkyl)$_z$, —NHC(=O)(C$_{1-6}$ alkyl), —NHC(=NH)NH$_{z-2}$(C$_{1-6}$ alkyl)$_z$, and —N(C$_{1-6}$ alkyl)C(=NH)NH$_{2-z}$(C$_{1-6}$ alkyl)$_z$, wherein z is 0, 1, or 2 and each of the C$_{1-6}$ alkyl, C$_{2-6}$ alkenyl, C$_{2-6}$ alkynyl, C$_{3-7}$ cycloalkyl, C$_{6-10}$ aryl, 3- to 7-membered heteroaryl, and 3- to 7-membered heterocyclyl groups is optionally substituted with one, two, or three moieties independently selected from the group consisting of —OH, methyl, ethyl, —OCH$_3$, —SCH$_3$, and —NH$_{2-z}$(CH$_3$)$_z$; R$^2$ is H;
    $R^3$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;
    $R^4$ is H;
    $R^5$ is -L-R$^6$;
    L is selected from the group consisting of a bond, C$_{1-6}$ alkylene, C$_{2-6}$ alkenylene, C$_{2-6}$ alkynylene, and —(CH$_2$)$_m$—[Y—(CH$_2$)$_n$]$_o$—, wherein m is an integer between 1 and 6, n is an integer between 0 and 3, o is an integer between 1 and 3, wherein if n is 0 then o is 1; Y is independently selected from O, S, and —N(R$^{13}$)—; and each of the C$_{1-6}$ alkylene, C$_{2-6}$ alkenylene, C$_{2-6}$ alkynylene, —(CH$_2$)$_m$—, and —(CH$_2$)$_n$— groups is optionally substituted with one or two independently selected R$^{30}$;

R$^6$ is heteroaryl or heterocyclyl each of which is optionally substituted with one or more independently selected R$^7$;

R$^7$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, and/or any two R$^7$ which are bound to the same atom of R$^6$ being a heterocyclyl group may join together to form =O, wherein each of the alkyl, alkenyl, alkynyl, cycloalkyl, aryl, heterocyclyl, and heteroaryl groups is optionally substituted with one or more independently selected R$^{30}$;

A is selected from the group consisting of S, O, NR$^8$, and C(R$^9$)$_2$;

R$^8$ is selected from the group consisting of H, alkyl, alkenyl, alkynyl, cycloalkyl, aryl, heterocyclyl, and heteroaryl, wherein each of the alkyl, alkenyl, alkynyl, cycloalkyl, aryl, heterocyclyl, and heteroaryl groups is optionally substituted with one or more independently selected R$^{30}$;

R$^9$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

X is independently selected from the group consisting of O, S, and N(R$^{14}$);

E is O or S;

B is N or CR$^{1d}$;

R$^{1d}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

R$^{11}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected R$^{30}$;

each of R$^{12}$ and R$^{13}$ is independently selected from the group consisting of H, alkyl, alkenyl, alkynyl, cycloalkyl, aryl, heteroaryl, and heterocyclyl, or R$^{12}$ and R$^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more independently selected R$^{30}$;

R$^{14}$ is independently selected from the group consisting of H, alkyl, alkenyl, alkynyl, cycloalkyl, aryl, heteroaryl, heterocyclyl, and —OR$^{11}$, wherein each of the alkyl, alkenyl, alkynyl, cycloalkyl, aryl, heteroaryl, and heterocyclyl groups is optionally substituted with one or more independently selected R$^{30}$;

each of R$^{15}$ and R$^{16}$ is independently selected from the group consisting of H, alkyl, alkenyl, alkynyl, cycloalkyl, aryl, heteroaryl, heterocyclyl, and —NH$_y$R$^{20}_{2-y}$, or R$^{15}$ and R$^{16}$ may join together with the atom to which they are attached to form a ring which is optionally substituted with one or more independently selected R$^{30}$, wherein each of the alkyl, alkenyl, alkynyl, cycloalkyl, aryl, heteroaryl, and heterocyclyl groups is optionally substituted with one or more independently selected R$^{30}$;

y is an integer from 0 to 2;

R$^{20}$ is independently selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected R$^{30}$; and R$^{30}$ is a 1$^{st}$ level substituent and is, in each case, independently selected from the group consisting of alkyl, alkenyl, alkynyl, aryl, heteroaryl, cycloalkyl, heterocyclyl, halogen, —CN, azido, —NO$_2$, —OR$^{71}$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$R$^{71}$, —NR$^{71}$S(O)$_{1-2}$OR$^{71}$, —NR$^{71}$S(O)$_{1-2}$N(R$^{72}$)(R$^{73}$), —OP(O)(OR$^{71}$)$_2$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two R$^{30}$ which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups being a 1$^{st}$ level substituent is optionally substituted by one or more 2$^{nd}$ level substituents, wherein said 2$^{nd}$ level substituent is, in each case, independently selected from the group consisting of C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —S(O)$_{0-2}$R$^{81}$, —S(O)$_{1-2}$OR$^{81}$, —OS(O)$_{1-2}$R$^{81}$, —OS(O)$_{1-2}$OR$^{81}$, —S(O)$_{1-2}$N(R$^{82}$)(R$^{83}$), —OS(O)$_{1-2}$N(R$^{82}$)(R$^{83}$), —N(R$^{81}$)S(O)$_{1-2}$R$^{81}$, —NR$^{81}$S(O)$_{1-2}$OR$^{81}$, —NR$^{81}$S(O)$_{1-2}$N(R$^{82}$)(R$^{83}$), —OP(O)(OR$^{81}$)$_2$, —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two 2$^{nd}$ level substituents which are bound to the same carbon atom of a cycloalkyl or heterocyclyl group being a 1$^{st}$ level substituent may join together to form =X$^2$, wherein each of the C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl groups being a 2$^{nd}$ level substituent is optionally substituted with one or more 3$^{rd}$ level substituents, wherein said 3$^{rd}$ level substituent is, in each case, independently selected from the group consisting of C$_{1-3}$ alkyl, halogen, —CF$_3$, —CN, azido, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)

OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein each z is independently 0, 1, or 2 and each $C_{1-3}$ alkyl is independently methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N($C_{1-3}$ alkyl);

wherein each of $R^{71}$, $R^{72}$, and $R^{73}$ is independently selected from the group consisting of H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents independently selected from the group consisting of $C_{1-3}$ alkyl, halogen, —CF$_3$, —CN, azido, —NO$_2$, —OH, —O($C_{1-3}$ alkyl), —OCF$_3$, =O, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein each z is independently 0, 1, or 2 and each $C_{1-3}$ alkyl is independently methyl, ethyl, propyl or isopropyl;

each of $R^{81}$, $R^{82}$, and $R^{83}$ is independently selected from the group consisting of H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents independently selected from the group consisting of $C_{1-3}$ alkyl, halogen, —CF$_3$, —CN, azido, —NO$_2$, —OH, —O($C_{1-3}$ alkyl), —OCF$_3$, =O, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein each z is independently 0, 1, or 2 and each $C_{1-3}$ alkyl is independently methyl, ethyl, propyl or isopropyl; and each of $X^1$ and $X^2$ is independently selected from O, S, and N($R^{84}$), wherein $R^{84}$ is H or $C_{1-3}$ alkyl; with the proviso that (1) when $R^{1a}$ is 4-(2-hydroxyethyl)piperazin-1-yl or Cl; $R^{1b}$ is H; $R^{1c}$ is methyl; B is N; E is O; $R^3$ is H; A is S; and L is a bond; then $R^6$ is not 4-chloro-2-methylpyridin-3-yl;

(2) when $R^{1a}$ is methoxy; $R^{1b}$ is H; $R^{1c}$ is methoxy; B is N; E is O; $R^3$ is H; A is S; and L is a bond; then $R^6$ is not 2,2-difluoro-5H-1,3-dioxolo[4,5-f]benzimidazol-6-yl;

(3) when $R^3$ is H; A is S; L is a bond; $R^6$ is 1-methyl-4-piperidinyl; $R^{1b}$ is H; B is N; E is O; and (i) $R^{1a}$ is methyl; then $R^{1c}$ is not N-tert-butoxycarbonylpiperidin-4-yl; or (ii) $R^{1c}$ is methyl; then $R^{1a}$ is not N-tert-butoxycarbonylpiperidin-4-yl or N-tert-butoxycarbonylpiperidin-3-yl;

(4) when E is O; B is CR$^{1d}$ and $R^{1d}$ is either H, F, Cl or Br, then $R^{1a}$ is not H; and (5) when $R^{1a}$ is methyl; each of $R^{1b}$ and $R^{1c}$ is H; B is CH; E is O; A is S; and $R^3$ is methyl; then $R^5$ is not 1,3-benzodioxol-5-ylmethyl, 2-furanylmethyl, 1,3-benzodioxol-5-yl, 2-(2-thienyl)ethyl, 2-(4-morpholinyl)ethyl, 2-(2-pyridinyl)ethyl, 2-pyridinylmethyl, or tetrahydro-2-furanylmethyl.

A2. The compound of item A1, wherein $R^6$ is a mono- or bicyclic heteroaryl or a mono- or bicyclic heterocyclyl, each of which is optionally substituted with one, two, or three independently selected $R^7$.

A3. The compound of item A1 or A2, wherein $R^6$ is a 5- to 6-membered monocyclic heteroaryl optionally substituted with one, two, or three independently selected $R^7$.

A4. The compound of any one of items A1 to A3, wherein $R^7$ is independently selected from the group consisting of $C_{1-3}$ alkyl, halogen, —CN, —O($C_{1-3}$ alkyl), —NH($C_{1-3}$ alkyl), and —N($C_{1-3}$ alkyl)$_2$, and/or any two $R^7$ which are bound to the same atom of $R^6$ being a heterocyclyl group may join together to form =O, wherein each of the $C_{1-3}$ alkyl groups is optionally substituted with one or more independently selected $R^{30}$.

A5. The compound of any one of items A1 to A4, wherein $R^7$ is independently selected from the group consisting of halogen and $C_{1-2}$ alkyl, wherein the $C_{1-2}$ alkyl groups is optionally substituted with one, two, or three independently selected $R^{30}$.

A6. The compound of any one of items A1 to A5, wherein one $R^7$ group is bound to a ring atom of $R^6$ at position 2 relative to the ring atom by which $R^6$ is bound to the remainder of the compound.

A7. The compound of any one of items A1 to A6, wherein L is selected from the group consisting of a bond; $C_1$ alkylene, optionally substituted with one $R^{30}$; $C_2$ alkylene (in particular 1,2-ethylene or 1,1-ethylene), optionally substituted with one $R^{30}$; $C_3$ alkylene (in particular trimethylene), optionally substituted with one $R^{30}$; $C_4$ alkylene (in particular tetramethylene or 2,4-butandiyl), optionally substituted with one $R^{30}$; —(CH$_2$)$_m$O—; and —(CH$_2$)$_m$NH—, wherein m is 1, 2, or 3.

A8. The compound of any one of items A1 to A7, wherein L is a bond.

A9. The compound of any one of items A1 to A8, wherein $R^{1a}$ is selected from the group consisting of $C_{1-3}$ alkyl, —O($C_{1-3}$ alkyl), —S($C_{1-3}$ alkyl), —NH($C_{1-3}$ alkyl), piperazinyl, morpholinyl, piperidinyl, and pyrrolidinyl, wherein each of the piperazinyl, morpholinyl, piperidinyl, and pyrrolidinyl groups is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)($C_{1-3}$ alkyl), —(CH$_2$)$_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —OCH$_3$, —SCH₃, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2.

A10. The compound of any one of items A1 to A9, wherein R$^{1a}$ is selected from the group consisting of 4-(2-hydroxyethyl)piperazinyl, 4-methylpiperazinyl, 4-acetylpiperazinyl, and (2-hydroxyethyl)amino.

A11. The compound of any one of items A1 to A10, wherein R$^{1b}$ is H; and R$^{1c}$ is methyl, ethyl, propyl, isopropyl, or phenyl, preferably methyl.

A12. The compound of any one of items A1 to A11, wherein A is S, O, or N(CH$_3$)$_2$.

A13. The compound of any one of items A1 to A12, wherein A is S.

A14. The compound of any one of items A1 to A13, wherein B is N or CR$^{1d}$, wherein R$^{1d}$ is selected from the group consisting of C$_{1-3}$ alkyl, halogen, —O(C$_{1-3}$ alkyl), —S(C$_{1-3}$ alkyl), —NH(C$_{1-3}$ alkyl), and —N(C$_{1-3}$ alkyl)$_2$, wherein each of the C$_{1-3}$ alkyl groups is optionally substituted with one or two moieties independently selected from the group consisting of halogen, —OH, —OCH$_3$, —SCH, and —NH$_{2-z}$(CH$_3$)$_z$, wherein z is 0, 1, or 2.

A15. The compound of any one of items A1 to A13, wherein B is N.

A16. The compound of any one of items A1 to A15, wherein E is O.

A17. The compound of any one of items A1 to A16, wherein R$^3$ is selected from the group consisting of H, methyl, ethyl, propyl, isopropyl, phenyl, and halogen.

A18. The compound of any one of items A1 to A17, selected from the group consisting of:

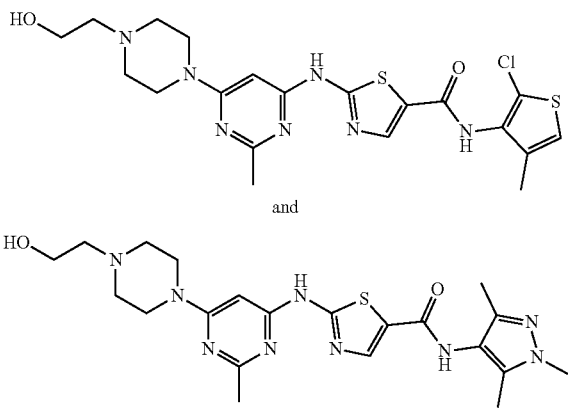

and solvates, salts, N-oxides, complexes, polymorphs, crystalline forms, tautomers, conformers, isotopically labeled forms, prodrugs, and combinations thereof.

A19. A pharmaceutical composition comprising the compound of any one of items A1 to A18, and optionally further comprising a pharmaceutically acceptable excipient.

A20. A compound or a pharmaceutical composition for use in a treatment of a proliferative disorder in a subject, the treatment comprising administering the compound or the pharmaceutical composition to the subject, wherein, the compound is a compound of any one of items A1 to A18, or the pharmaceutical composition is a pharmaceutical composition of item A19.

EXAMPLES

A selection of compounds within the scope of, or for use within the methods of, the present invention—and/or that represent examples of various exemplary or preferred R$^{1a}$ substituents, R$^{1b}$ substituents, R$^{1c}$ substituents, R$^2$ substituents, R$^3$ substituents, R$^4$ substituents, R$^5$ moieties, A moieties, B moieties and/or E moieties, each individually or in any combination are useful for synthesising further compounds of the invention—is listed in Table A and/or Table B. The compounds in Table A and/or Table B are synthesised and tested as described herein.

The examples show:

Example 1: Synthesis of the Kinase Inhibitors, Including Kinase Inhibitors of Formula (I)

General Methods and Materials

MPLC purification was performed using a Biotage Isolera Four system, using KP-Sil cartridges with technical grade organic solvents, i.e. dichloromethane and methanol, 3-4 N NH$_3$ in MeOH. A gradient of DCM to 3 N NH$_3$ (in MeOH) from 0% to 25% over 10 CV was used for the purification of the final compounds.

$^1$H NMR spectra were recorded on Bruker DPX 400 MHz spectrometers and are reported in ppm with the solvent resonance employed as the internal standard [CDCl$_3$ at 7.26 ppm, DMSO-d$_6$ at 2.50 ppm]. Peaks are reported as (s=singlet, d=doublet, t=triplet, q=quartet, m=multiplet or unresolved, bs=broad signal, coupling constant(s) in Hz, integration).

Reverse phase HPLC was performed on a Shimadzu HPLC system using following system [solvent A: acetonitrile, solvent B: 0.1% formic acid in water]. Formic acid was used as HPLC grade. All the separations were performed at ambient temperatures. For analytical RP-HPLC analysis [Interchim: Uptisphere Strategy 100 Å, 5 µm, 100×4.6 mm], the flow rate was 1.0 ml·min$^{-1}$; injection volume: 20 µL, detection wavelengths: 220 nm and 254 nm. The following gradient was used: 2.0 min 100% B, over 8 min to 10% B, 5 min 10% B.

LC-MS spectra were recorded on a Dionex Ultimate 3000 system using the following system [solvent A: acetonitrile, solvent B: 0.1% formic acid in water]. Formic acid was used as HPLC grade. All the separations were performed at ambient temperatures. For analytical RP-HPLC analysis [Interchim: Uptisphere Strategy C$_{18}$, 2.6 µm, 50×4.6 mm], the flow rate was 1.0 ml·min-1; detection wavelengths: 220 nm and 254 nm. The following gradient was used: 90% B, over 5 min to 5% B. The MS was recorded with the following settings: Dionex Surveyor MSQ plus, ESI+, Probe T (° C.) 350, Cone 30 (v), Needle (KV) 3.0.

Procedures:

I. Ethyl 2-((6-chloro-2-methylpyrimidin-4-yl)amino) thiazole-5-carboxylate

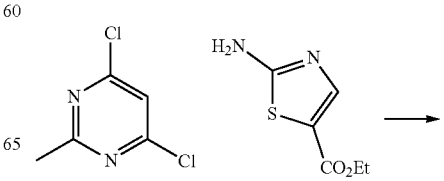

151
-continued

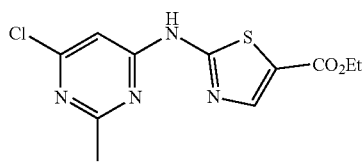

To a solution of 4,6-dichloro-2-methylpyrimidine (10 g, 61.4 mmol, 1.0 eq.) and ethyl 2-aminothiazole-5-carboxylate (10.6 g, 61.4 mmol, 1.0 eq.) in DMF (210 ml) at 0° C. under inert atmosphere was added sodium hydride (5.40 g, 135 mmol, 2.0 eq.) in portions and the reaction mixture was slowly warmed to room temperature and stirred for 3 d. Excess of the NaH was quenched by addition of saturated solution of ammonium chloride and the reaction mixture was poured on water (3000 ml) and stirred for 1 h at room temperature. Obtained precipitate was filtered off and air dried to get ethyl 2-((6-chloro-2-methylpyrimidin-4-yl) amino)thiazole-5-carboxylate (18 g, 60.0 mmol, 98% yield) as a beige solid.

$^1$H NMR (400 MHz, CDCl$_3$) δ 1.34-1.51 (t, 3H), 2.75 (s, 3H), 4.41 (q, J=7.1 Hz, 2H), 6.73 (s, 1H), 8.14 (s, 1H). LCMS: m/z=297.1 [M−H]$^−$.

II. 2-((6-Chloro-2-methylpyrimidin-4-yl)amino) thiazole-5-carboxylic acid

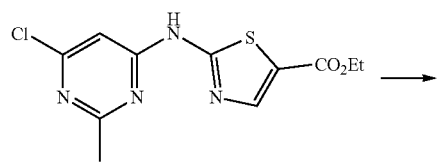

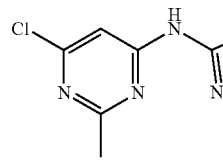

To a suspension of ethyl 2-((6-chloro-2-methylpyrimidin-4-yl)amino)thiazole-5-carboxylate (36.0 g, 121 mmol, 1.0 eq.) in methanol (350 ml) and water (150 ml) was added sodium hydroxide (38.6 g, 964 mmol, 8.0 eq.) at room temperature and the mixture was stirred at room temperature for 16 hrs. LCMS analysis showed complete conversion of starting material to product. The reaction mixture was concentrated to remove most of the solvent and then the aqueous layer was acidified using 6 M aqueous HCl. The obtained precipitate was filtered off and washed with water, dried under high vacuum for 3 d to afford 2-((6-chloro-2-methylpyrimidin-4-yl)amino)thiazole-5-carboxylic acid (27.0 g, 99.7 mmol, 83% yield) as a beige colored powder.

$^1$H NMR (400 MHz, DMSO-d$_6$) δ 2.57 (s, 3H), 6.93 (s, 1H), 8.04 (s, 1H), 12.46 (bs. 1H). LCMS: m/z=269.0 [M−H]$^−$.

General Procedure A1—GP A1—Amide Formation

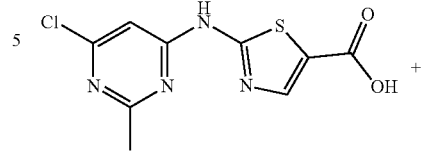

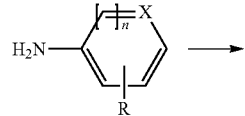

n = 0, 1
X = N, S, C

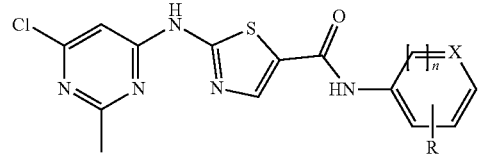

n = 0, 1
X = N, S, C

To a suspension of 2-((6-chloro-2-methylpyrimidin-4-yl) amino)thiazole-5-carboxylic acid (1.0 equiv.) and aniline (1.1 equiv.) in acetonitrile (0.2 M) was added N,N-diisopropylethylamine (3.5 equiv.) and tetramethylchloroformamidinium hexafluorophosphate (1.2 eq.) at room temperature under a nitrogen atmosphere. The reaction mixture was stirred at room temperature overnight. Acetonitrile was removed under vacuum and then reaction was poured into water (100 mL/mmol). The resulting precipitate was filtered off, washed with water [5×], air-dried and dried under high vacuum to afford the respective amide as a yellow powder, which was directly used in the next step without further purification. All substances were confirmed by $^1$H NMR analysis.

General Procedure B-GP B

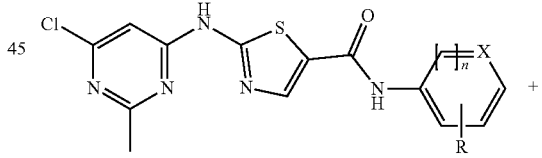

n = 0, 1
X = N, S, C

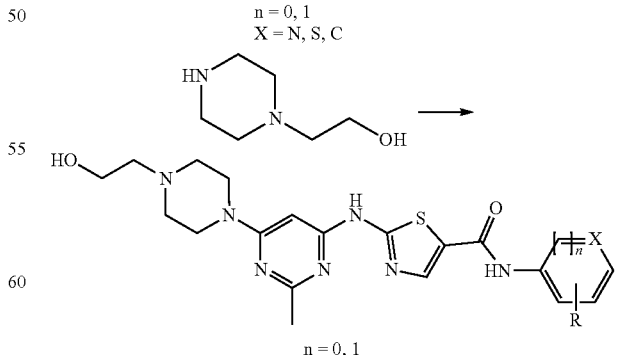

n = 0, 1
X = N, S, C

To a suspension of chloropyrimidine derivative (1.0 equiv.) in n-butanol (2 ml) was added 2-(piperazin-1-yl)

ethan-1-ol (5.0 equiv.) and N,N-diisopropylethylamine (0.4 equiv.) at room temperature under a nitrogen atmosphere. The tube was sealed and irradiated under microwave conditions (Biotage Initiator+) at 120° C. for 30 min. After cooling to room temperature, the reaction mixture was poured in water (200 ml/mmol) and stirred for minimum 30 min. The resulting precipitate was filtered off, washed with water [5×], air-dried to afford to afford the respective target. If no or <10% precipitate resulted, the aqueous layer was extracted with DCM/IPA (2:1, 3*). The combined organic layers were dried over Na₂SO₄, filtered and concentrated under reduced pressure. The crude product or a crude product with a purity of <95% was purified by flash chromatography (Biotage cartridge, DCM 100% 1 CV to 80% DCM/3 N NH₃ in MeOH over 10 CV, 80% DCM/3 N NH₃). For some substances with purities <95%, a trituration in Et₂O was done and all substances were dried under high vacuum (up to 65° C., if necessary) until purities >95% was obtained, unless otherwise stated. All substances were confirmed by ¹H NMR and LC-MS analysis.

Compound A8

N-(2-chloro-6-methylphenyl)-2-((6-(4-(2-hydroxyethyl)piperazin-1-yl)-2-methylpyrimidin-4-yl)amino)thiazole-5-carboxamide

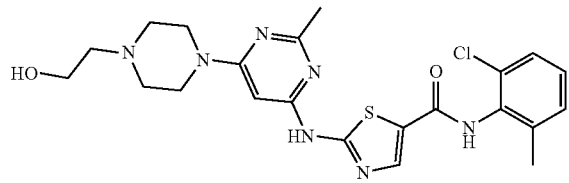 [SMILES: Cc1nc(Nc2ncc(C(=O)Nc3c(C)cccc3Cl)s2)cc(N2CCN(CCO)CC2)n1]

Step 1 was run according to GP A1 using 2-((6-chloro-2-methylpyrimidin-4-yl)amino)thiazole-5-carboxoxylic acid (750 mg, 2.77 mmol), 2-chloro-6-methylaniline (959 mg, 6.77 mmol), tetramethylchloroformamidinium hexafluorophosphate (959 mg, 3.42 mmol), N,N-diisopropylethylamine (1.25 g, 9.70 mmol) and acetonitrile (6.0 mL, 0.42 M). 2-((6-chloro-2-methylpyrimidin-4-yl)amino)-N-(2-chloro-6-methylphenyl)thiazole-5-carboxamide (480 mg, 1.22 mmol) was obtained after precipitation from H₂O as a yellow solid and used without further purification in the next step.

Step 2 was run according to GP B using 2-((6-chloro-2-methylpyrimidin-4-yl)amino)-N-(2-chloro-6-methylphenyl)thiazole-5-carboxamide (250 mg, 0.634 mmol), 2-(piperazin-1-yl)ethan-1-ol (413 mg, 3.17 mmol), N,N-diisopropylethylamine (33 mg, 0.25 mmol) and 1-butanol (2.0 mL, 0.3 M). A8 (FIG. 1A)

Compound B3

N-(4-chloro-2-methylpyridin-3-yl)-2-((6-(4-(2-hydroxyethyl)piperazin-1-yl)-2-methylpyrimidin-4-yl)amino)thiazole-5-carboxamide

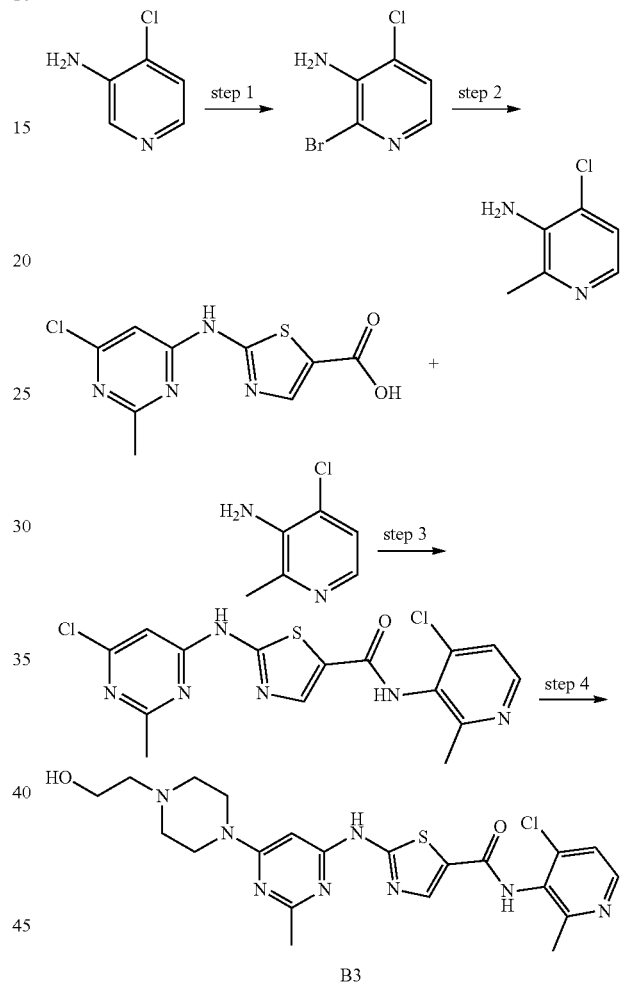

Step 1: 2-bromo-4-chloropyridin-3-amine (Compound IaB3)

To a solution of 4-chloropyridin-3-amine (7.00 g, 54.0 mmol, 1.0 eq.) in anhydrous TFA (200 mL, 0.27 M) was added NBS (10.7 g, 60.1 mmol, 1.1 eq.) under a nitrogen atmosphere at room temperature. and the solution was stirred for 18 h at room temperature. The solvent was removed under reduced pressure and the residue was dissolved in 2 N NaOH (200 mL). The aqueous layer was extracted with EtOAc (3*200 mL). The combined organic layers were dried over Na2SO4, filtered and concentrated under reduced pressure. The crude product was purified by flash chromatography (340 g biotage cartridge, cHex 100% 1 CV to 40% EtOAc over 10 CV, 2 CV 40% EtOAc) affording 2-bromo-4-chloropyridin-3-amine (3.07 g, 14.8 mmol, 27%) as a beige solid. IaB3

$R_f$=0.82 (cHex/EtOAc 1:1, UV 254 nm). $^1$H NMR (400 MHz, DMSO-$d_6$) δ 5.70 (s, 2H), 7.35 (d, J=5.0 Hz, 1H), 7.56 (d, J=5.0 Hz, 1H).

Step 2: 4-chloro-2-methylpyridin-3-amine (Compound IbB3)

In a 10-mL microwave vial was a mixture of 2-bromo-4-chloropyridin-3-amine (200 mg, 0.96 mmol, 1.0 eq.), trimethylboroxine (141 µL, 1.01 mmol, 1.05 eq.), $K_2CO_3$ (466 mg, 3.37 mmol, 3.5 eq.) and $PdCl_2(dppf)$-$CH_2Cl_2$ adduct (79 mg, 0.096 mmol, 0.1 eq.) in 1,4-dioxane:$H_2O$ (10:1, 3.3 mL, 0.28M) evacuated and back-filled with nitrogen three times and sealed with an aluminum/Teflon crimp top. The reaction mixture was then irradiated for 45 min at 120° C. After completion of the reaction, the vial was cooled to room temperature and opened. The reaction mixture was diluted with EtOAc, silica was added (2 g) and the reaction mixture concentrated under reduced pressure. The crude product was purified by flash chromatography (25 g biotage cartridge 100% cHex 1 CV to 100% EtOAc over 10 CV, 5 CV 100% EtOAc) affording 4-chloro-2-methylpyridin-3-amine (58 mg, 0.041 mmol, 42%) as violet oil. IbB3.

$R_f$=0.24 (UV 254 nm, cHex/EtOAc 1:1). $^1$H NMR (400 MHz, DMSO-$d_6$) δ 2.34 (s, 3H), 5.28 (s, 2H), 7.11 (d, J=5.2 Hz, 1H), 7.61 (d, J=5.2 Hz, 1H).

Steps 3 and 4: N-(4-chloro-2-methylpyridin-3-yl)-2-((6-(4-(2-hydroxyethyl)piperazin-1-yl)-2-methylpyrimidin-4-yl)amino)thiazole-5-carboxamide (Compound B3, FIG. 1B Step 3 was run according to GP A1 using 2-((6-chloro-2-methylpyrimidin-4-yl)amino)thiazole-5-carboxoxylic acid (530 mg, 1.96 mmol), 4-chloro-2-methylpyridin-3-amine (363 mg, 2.55 mmol), tetramethylchloroformamidinium hexafluorophosphate (659 mg, 2.35 mmol), N,N-diisopropylethylamine (886 mg, 6.85 mmol) and acetonitrile (5.8 mL, 0.3 M). N-(4-chloro-2-methylpyridin-3-yl)-2-((6-chloro-2-methylpyrimidin-4-yl)amino)thiazole-5-carboxamide (Compound IcB3) (326 mg, 0.825 mmol) was obtained after precipitation from $H_2O$ as a yellow solid and used without further purification in the next step. IcB3

Step 4 was run according to GP B using N-(4-chloro-2-methylpyridin-3-yl)-2-((6-chloro-2-methylpyrimidin-4-yl)amino)thiazole-5-carboxamide (320 mg, 0.810 mmol), 2-(piperazin-1-yl)ethan-1-ol (527 mg, 4.05 mmol), N,N-diisopropylethylamine (42 mg, 0.32 mmol) and 1-butanol (2.5 mL, 0.3 M). B3 (90 mg, 0.18 mmol, 10% yield over 2 steps) was obtained as a white solid after extraction with EtOAc, flash purification (100% DCM to 85% DCM/3 N $NH_3$ in MeOH over 10 CV) and trituration in $Et_2O$.

Compound C1

N-(2,4-dimethyl pyridin-3-yl)-2-((6-(4-(2-hydroxyethyl)piperazin-1-yl)-2-methylpyrimidin-4-yl)amino)thiazole-5-carboxamide

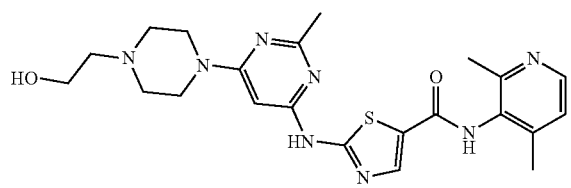 [SMILES: Cc1nc(Nc2ncc(C(=O)Nc3c(C)ccnc3C)s2)cc(N2CCN(CCO)CC2)n1]

Step 1 was run according to GP A1 using 2-((6-chloro-2-methylpyrimidin-4-yl)amino)thiazole-5-carboxoxylic acid (266 mg, 0.982 mmol), 2,4-dimethylpyridin-3-amine (120 mg, 0.982 mmol, 1.0 eq.), tetramethylchloroformamidinium hexafluorophosphate (331 mg, 1.18 mmol), N,N-diisopropylethylamine (444 mg, 3.44 mmol) and acetonitrile (5.0 mL, 0.2 M). 2-((6-chloro-2-methylpyrimidin-4-yl)amino)-N-(2,4-dimethylpyridin-3-yl)thiazole-5-carboxamide (123 mg, 0.328 mmol, 33%) was obtained after flash purification (100% DCM to 75% DCM/MeOH over 10 CV) as a yellow solid.

Step 2 was run according to GP B using 2-((6-chloro-2-methylpyrimidin-4-yl)amino)-N-(2,4-dimethylpyridin-3-yl)thiazole-5-carboxamide (118 mg, 0.315 mmol), 2-(piperazin-1-yl)ethan-1-ol (0.205 g, 1.57 mmol), N,N-diisopropylethylamine (16 mg, 0.13 mmol) and 1-butanol (2.5 mL, 0.1 M). $C_1$ (FIG. 1C, 133 mg, 0.284 mmol, 21% yield over 2 steps) was obtained as a beige solid after flash purification (100% DCM to 75% DCM/MeOH over 10 CV).

Purity (HPLC, 254 nm): 90% (couldn't be removed by trituration, $2^{nd}$ silica column or RP column).

Compound C2

N-((6-(4-(2-hydroxyethyl)piperazin-1-yl)-2-methylpyrimidin-4-yl)amino)-N-(3-methylpyridin-2-yl) thiazole-5-carboxamide

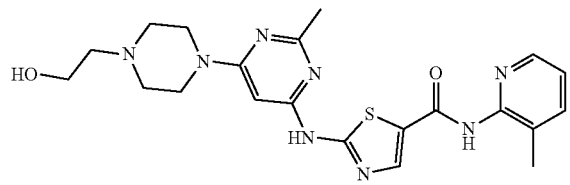 [SMILES: Cc1nc(Nc2ncc(C(=O)Nc3ncccc3C)s2)cc(N2CCN(CCO)CC2)n1]

Step 1 was run according to GP A1 using 2-((6-chloro-2-methylpyrimidin-4-yl)amino)thiazole-5-carboxoxylic acid (530 mg, 1.96 mmol), 3-methylpyridin-2-amine (275 mg, 2.55 mmol), tetramethylchloroformamidinium hexafluorophosphate (659 mg, 2.35 mmol), N,N-diisopropylethylamine (886 mg, 6.85 mmol) and acetonitrile (5.8 mL, 0.3 M). 2-((6-chloro-2-methylpyrimidin-4-yl)amino)-N-(3-methylpyridin-2-yl)thiazole-5-carboxamide (326 mg, 0.903 mmol) was obtained after extraction with EtOAc as a yellow solid and used without further purification in the next step.

Step 2 was run according to GP B using 2-((6-chloro-2-methylpyrimidin-4-yl)amino)-N-(3-methylpyridin-2-yl)thiazole-5-carboxamide (510 mg, 1.41 mmol), 2-(piperazin-1-yl)ethan-1-ol (920 mg, 7.07 mmol), N,N-diisopropylethylamine (73 mg, 0.57 mmol) and 1-butanol (4.3 mL, 0.3 M). $C_2$ (FIG. 1C, 105 mg, 0.231 mmol, 8% yield over 2 steps) was obtained as an off-white solid after flash purification (100% DCM to 85% DCM/3 N $NH_3$ in MeOH over 10 CV).

Compound C3

N-(4-bromo-2-methylpyridin-3-yl)-2-((6-(4-(2-hydroxyethyl)piperazin-1-yl)-2-methylpyrimidin-4-yl)amino)thiazole-5-carboxarmide

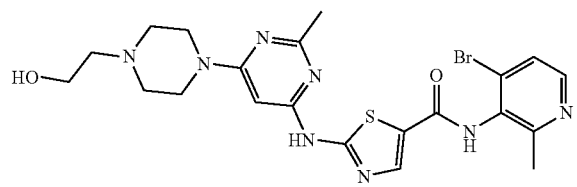 [SMILES: Cc1nc(Nc2ncc(C(=O)Nc3c(Br)ccnc3C)s2)cc(N2CCN(CCO)CC2)n1]

Step 1 was run according to GP A1 using 2-((6-chloro-2-methylpyrimidin-4-yl)amino)thiazole-5-carboxoxylic acid (145 mg, 0.535 mmol), 4-bromo-2-methylpyridin-3-amine (100 mg, 0.535 mmol), tetramethylchloroformamidinium hexafluorophosphate (180 mg, 0.642 mmol), N,N-diisopropylethylamine (242 mg, 1.87 mmol) and acetonitrile (2.7 mL, 0.2 M). N-(4-bromo-2-methylpyridin-3-yl)-2-((6-chloro-2-methylpyrimidin-4-yl)amino)thiazole-5-carboxamide (67 mg, 0.15 mmol) was obtained after extraction with EtOAc as a yellow solid and used without further purification in the next step.

Step 2 was run according to GP B using N-(4-bromo-2-methylpyridin-3-yl)-2-((6-chloro-2-methylpyrimidin-4-yl)amino)thiazole-5-carboxamide (65 mg, 0.15 mmol), 2-(piperazin-1-yl)ethan-1-ol (96 mg, 0.74 mmol), N,N-diisopropylethylamine (7.6 mg, 0.059 mmol) and 1-butanol (0.50 mL, 0.3 M). $C_3$ (FIG. 1C, 68 mg, 0.13 mmol, 24% yield over 2 steps) was obtained as a slight yellow solid after flash purification (100% DCM to 85% DCM/3 N $NH_3$ in MeOH over 10 CV) and trituration in $Et_2O$.

Compound C4

N-(3-chloro-5-methylpyridin-4-yl)-2-((6-(4-(2-hydroxyethyl)piperazin-1-yl)-2-methylpyrimidin-4-yl)amino)thiazole-5-carboxamide

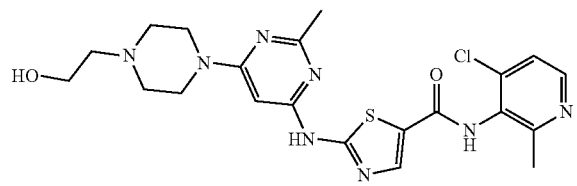 [SMILES: Cc1nc(Nc2ncc(C(=O)Nc3c(Cl)ccnc3C)s2)cc(N2CCN(CCO)CC2)n1]

Step 1 was run according to GP A1 using 2-((6-chloro-2-methylpyrimidin-4-yl)amino)thiazole-5-carboxoxylic acid (530 mg, 1.96 mmol), 3-chloro-5-methylpyridin-4-amine (363 mg, 2.55 mmol), tetramethylchloroformamidinium hexafluorophosphate (659 mg, 2.35 mmol), N,N-diisopropylethylamine (886 mg, 6.85 mmol) and acetonitrile (5.8 mL, 0.3 M). 2-((6-chloro-2-methylpyrimidin-4-yl)amino)-N-(3-chloro-5-methylpyridin-4-yl)thiazole-5-carboxamide (113 mg, purity ca. 60%) was obtained after extraction with EtOAc as a yellow solid and used without further purification in the next step.

Step 2 was run according to GP B using 2-((6-chloro-2-methylpyrimidin-4-yl)amino)-N-(3-chloro-5-methylpyridin-4-yl)thiazole-5-carboxamide (110 mg, 0.278 mmol), 2-(piperazin-1-yl)ethan-1-ol (181 mg, 1.39 mmol), N,N-diisopropylethylamine (14 mg, 0.11 mmol) and 1-butanol (0.84 mL, 0.3 M). $C_4$ (FIG. 1C, 28 mg, 0.058 mmol, 12% yield over 2 steps, 88% purity) was obtained as a yellow solid after flash purification (100% DCM to 80% DCM/MeOH over 10 CV) and trituration in $Et_2O$.

Compound C5

N-(3,5-dimethyl pyridin-4-yl)-2-((6-(4-(2-hydroxyethyl)piperazin-1-yl)-2-methylpyrimidin-4-yl)amino)thiazole-5-carboxamide

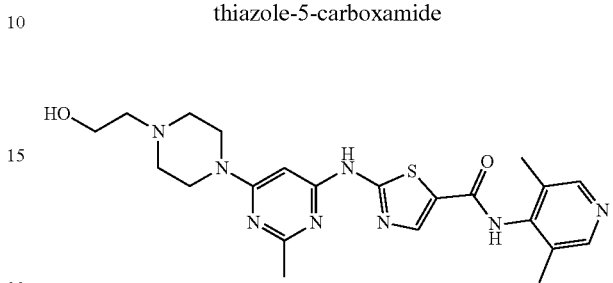

Step 1 was run according to GP A1 using 2-((6-chloro-2-methylpyrimidin-4-yl)amino)thiazole-5-carboxoxylic acid (500 mg, 1.85 mmol), 3,5-dimethylpyridin-4-amine (271 mg, 2.22 mmol), tetramethylchloroformamidinium hexafluorophosphate (622 mg, 2.22 mmol), N,N-diisopropylethylamine (836 mg, 6.46 mmol) and acetonitrile (10 mL, 0.2 M). 2-((6-chloro-2-methylpyrimidin-4-yl)amino)-N-(3,5-dimethylpyridin-4-yl)thiazole-5-carboxamide (273 mg) was obtained after precipitation from $H_2O$ as a green solid and used without further purification in the next step.

Step 2 was run according to GP B using 2-((6-chloro-2-methylpyrimidin-4-yl)amino)-N-(3,5-dimethylpyridin-4-yl)thiazole-5-carboxamide (270 mg, 0.720 mmol), 2-(piperazin-1-yl)ethan-1-ol (469 mg, 3.60 mmol), N,N-diisopropylethylamine (37 mg, 0.29 mmol) and 1-butanol (2.5 mL, 0.3 M). $C_5$ (FIG. 1C, 110 mg, 0.235 mmol, 12% yield over 2 steps) was obtained as a slight yellow solid after flash purification (100% DCM to 80% DCM/MeOH over 10 CV) and trituration in $Et_2O$.

Compound C6

2-((6-(4-(2-hydroxyethyl)piperazin-1-yl)-2-methylpyrimidin-4-yl)amino)-N-(2-methylpyridin-3-yl)thiazole-5-carboxamide

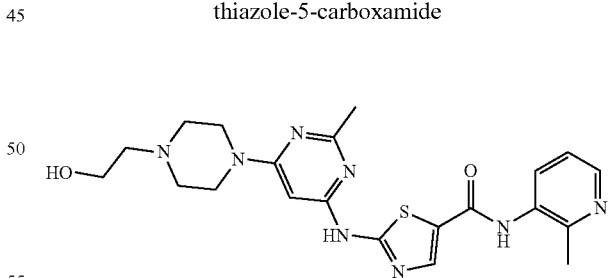

Step 1 was run according to GP A1 using 2-((6-chloro-2-methylpyrimidin-4-yl)amino)thiazole-5-carboxoxylic acid (530 mg, 1.96 mmol), 2-methylpyridin-3-amine (275 mg, 2.55 mmol), tetramethylchloroformamidinium hexafluorophosphate (659 mg, 2.35 mmol), N,N-diisopropylethylamine (886 mg, 6.85 mmol) and acetonitrile (5.8 mL, 0.3 M). 2-((6-chloro-2-methylpyrimidin-4-yl)amino)-N-(2-methylpyridin-3-yl)thiazole-5-carboxamide (442 mg, 1.22 mmol) was obtained after precipitation from $H_2O$ as a yellow solid and used without further purification in the next step.

Step 2 was run according to GP B using 2-((6-chloro-2-methylpyrimidin-4-yl)amino)-N-(2-methylpyridin-3-yl)thiazole-5-carboxamide (440 mg, 1.41 mmol), 2-(piperazin-1-yl)ethan-1-ol (920 mg, 7.07 mmol), N,N-diisopropylethylamine (73 mg, 0.57 mmol) and 1-butanol (4.3 mL, 0.3 M). $C_6$ (FIG. 1C, 355 mg, 0.781 mmol, 40% yield over 2 steps) was obtained as an off-white solid after precipitation from $H_2O$.

Compound C7

N-(2-chloro-4-methylthiophen-3-yl)-2-((6-(4-(2-hydroxyethyl)piperazin-1-yl)-2-methylpyrimidin-4-yl)amino)thiazole-5-carboxamide

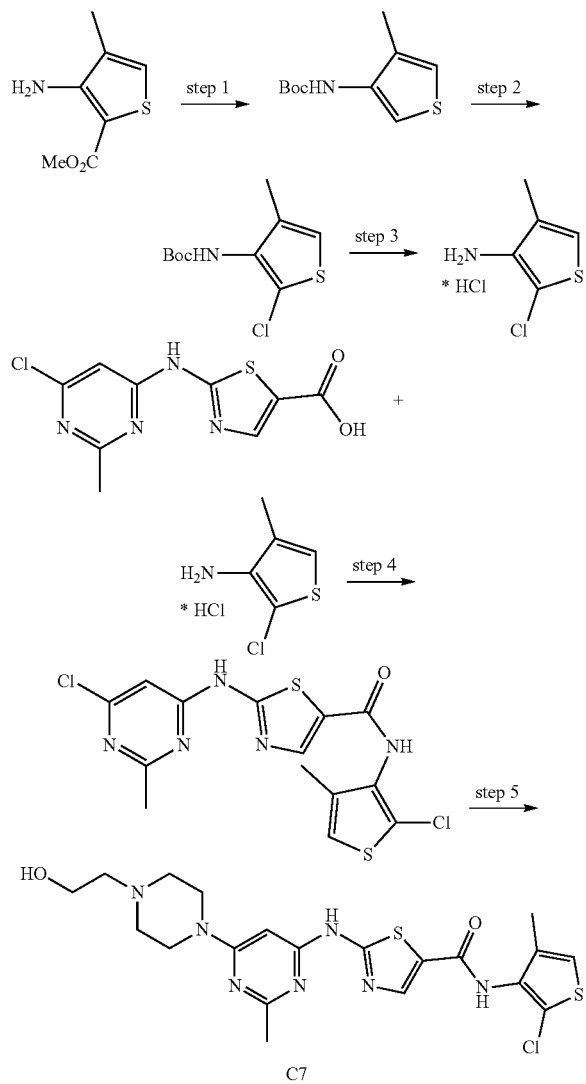

Step 1: tert-butyl (4-methylthiophen-3-yl)carbamate

To a solution of methyl 3-amino-4-methylthiophene-2-carboxylate (1.71 g, 10.0 mmol) in $H_2O$ (5.1 mL) was added KOH solution (45%, 1.90 mL, 14.0 mmol, 1.4 eq.) at room temperature. The reaction was stirred at 80° C. for 30 min and afterwards cooled to room temperature. This solution was slowly added to a 6 M HCl solution (5.50 mL, 33.0 mmol, 3.3 eq) at 50° C. After completion of the addition, the reaction was stirred at 60° C. for 15 min (gas evolution, clear solution was obtained). The solution was cooled to 5° C. (ice bath), hexanes (3.5 mL) was added, and the solution cooled to −10° C. (acetone, dry ice). A solution of KOH (45%, 3.70 mL, 27.0 mmol, 2.7 eq.) and di-tert-butyl dicarbonate (2.40 mL, 10.5 mmol, 1.05 eq.) were added at −10° C. The reaction solution was stirred overnight and slowly warmed to room temperature. The formed suspension was extracted with EtOAc (3*15 mL). The combined organic layers were washed with a saturated aqueous solution of $NaHCO_3$(1*25 mL), dried over $Na_2SO_4$, concentrated and filtered. tert-butyl (4-methylthiophen-3-yl)carbamate (2.32 g, quantitative yield) was obtained as an orange solid and used without further purification.

$R_f$=0.68 (cHex/EtOAc 9:1, UV 254 nm). $^1$H NMR ($CDCl_3$, 400 MHz): δ 7.40 (s, 1H), 6.86 (dq, J=3.3 Hz, J=1.1 Hz, 1H), 6.36 (s, 1H), 2.14 (d, J=1.1 Hz, 3H), 1.53 (s, 9H).

Step 2: tert-butyl (2-chloro-4-methylthiophen-3-yl)carbamate

To a solution of (4-methyl-thiophen-3-yl)-carbamic acid tert-butyl ester (1.07 g, 5.00 mmol, 1.0 eq.) in anhydrous EtOAc (8 mL) was added N-chlorosuccinimide (0.700 g, 5.25 mmol, 1.05 eq.) and a hydrochloric acid solution in EtOH (1.25 N, 200 uL, 0.05 eq) at room temperature under a nitrogen atmosphere. After 5 h, TLC indicated starting material still present (cHex/EtOAc 9:1: slightly more polar spot: 0.76 starting material, product: 0.68, longer reaction times didn't result in better conversions). The reaction was quenched by addition of a solution of 1.0 N sodium hydroxide (5.50 mL, 5.50 mmol, 1.1 eq) and sodium hydrogensulfite (40%, 0.05 eq). The lower aqueous layer was discarded. The organic phase was washed with water (10 mL). The organic layer was dried over $Na_2SO_4$, filtered and concentrated under reduced pressure. The crude product was purified by flash chromatography (100 g biotage cartridge, cHex 100% 1 CV, to 15% EtOAc over 10 CV, to 100% EtOAc over 5 CV) to obtain tert-butyl (2-chloro-4-methylthiophen-3-yl)carbamate (734 mg, 2.96 mmol, 59%) as an orange solid.

$R_f$=0.76 (cHex/EtOAc 9:1, UV 254 nm). $^1$H NMR ($CDCl_3$, 400 MHz): δ 6.71 (s, 1H), 5.91 (s, 1H), 2.13 (d, J=1.2 Hz, 3H), 1.49 (s, 9H).

Step 3: 2-chloro-4-methylthiophen-3-amine hydrochloride

To a solution of tert-butyl (2-chloro-4-methylthiophen-3-yl)carbamate (567 mg, 2.29 mmol, 1.0 eq.) in anhydrous dioxane (4.6 mL) was added a HCl solution (4.0 N in dioxane, 1.70 mL, 6.80 mmol, 3.0 eq.) at room temperature under a nitrogen atmosphere. The reaction mixture was stirred at room temperature for 16 h. TLC (cHex/EtOAc 9:1, UV 254 nm) showed still starting material present. A HCl solution (4.0 N in dioxane, 1.20 mL, 4.80 mmol, 2.1 eq.) and the suspension was stirred at room temperature for 5 h. The solvent was removed under reduced pressure and the crude product was triturated in $Et_2O$ (5 mL) with 5 min ultrasound sonication and 3 h stirring at room temperature. 2-chloro-4-methylthiophen-3-amine hydrochloride (360 mg, 1.89 mmol, 86%) was obtained as a grey solid after filtration and drying under high vacuum.

$R_f$=0.00 (cHex/EtOAc 9:1, UV 254 nm). $^1$H NMR (DMSO-d$_6$, 400 MHz): δ 7.06 (s, 1H), 5.54 (s, 3H), 2.14 (d, J=1.2 Hz, 3H).

Step 4 was run according to GP A1 using 2-((6-chloro-2-methylpyrimidin-4-yl)amino)thiazole-5-carboxoxylic acid (367 mg, 1.35 mmol), 2-chloro-4-methylthiophen-3-amine hydrochloride (200 mg, 1.16 mmol), tetramethylchloroformamidinium hexafluorophosphate (456 mg, 1.63 mmol), N,N-diisopropylethylamine (700 mg, 5.42 mmol, 4.0 eq.) and acetonitrile (6.9 mL, 0.3 M). 2-((6-chloro-2-methylpyrimidin-4-yl)amino)-N-(2-chloro-4-methylthiophen-3-yl)thiazole-5-carboxamide (462 mg, 1.15 mmol, purity ca. 70%) was obtained after extraction with EtOAc as a yellow solid and used without further purification in the next step.

Step 5 was run according to GP B using 2-((6-chloro-2-methylpyrimidin-4-yl)amino)-N-(2-chloro-4-methylthiophen-3-yl)thiazole-5-carboxamide (230 mg, 0.575 mmol), 2-(piperazin-1-yl)ethan-1-ol (374 mg, 2.87 mmol), N,N-diisopropylethylamine (30 mg, 0.23 mmol) and 1-butanol (2.0 mL, 0.3 M). C$_7$ (FIG. 1C, 92 mg, 0.19 mmol, 33% yield over 2 steps) was obtained as an off-white solid after flash purification (100% DCM to 25% DCM/MeOH over 10 CV) and trituration in Et$_2$O. $R_f$=0.15 (DCM/MeOH 9:1, UV 254 nm).

Compound C8

2-((6-(4-(2-hydroxyethyl)piperazin-1-yl)-2-methylpyrimidin-4-yl)amino)-N-(1,3,5-trimethyl-1H-pyrazol-4-yl)thiazole-5-carboxamide

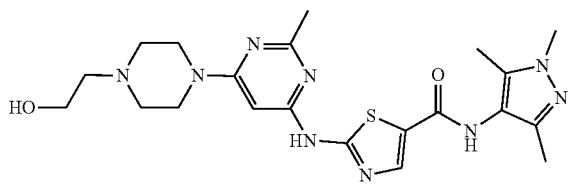 [SMILES: Cc1nc(Nc2ncc(C(=O)Nc3c(C)nn(C)c3C)s2)cc(N2CCN(CCO)CC2)n1]

Step 1 was run according to GP A1 using 2-((6-chloro-2-methylpyrimidin-4-yl)amino)thiazole-5-carboxoxylic acid (530 mg, 1.96 mmol), 1,3,5-trimethyl-1H-pyrazol-4-amine (319 mg, 2.55 mmol), tetramethylchloroformamidinium hexafluorophosphate (659 mg, 2.35 mmol), N,N-diisopropylethylamine (886 mg, 6.85 mmol) and acetonitrile (5.8 mL, 0.3 M). 2-((6-chloro-2-methylpyrimidin-4-yl)amino)-N-(1,3,5-trimethyl-1H-pyrazol-4-yl)thiazole-5-carboxamide (177 mg, 0.468 mmol) was obtained after precipitation from H$_2$O as a yellow solid and used without further purification in the next step.

Step 2 was run according to GP B using 2-((6-chloro-2-methylpyrimidin-4-yl)amino)-N-(1,3,5-trimethyl-1H-pyrazol-4-yl)thiazole-5-carboxamide (175 mg, 0.463 mmol), 2-(piperazin-1-yl)ethan-1-ol (301 mg, 2.32 mmol), N,N-diisopropylethylamine (24 mg, 0.19 mmol) and 1-butanol (1.4 mL, 0.3 M). C$_8$ (FIG. 1C, 142 mg, 0.301 mmol, 16% yield over 2 steps) was obtained as an off-white solid after flash purification (100% DCM to 85% DCM/3 N NH$_3$ in MeOH over 10 CV, 85% DCM/3 N NH$_3$ in MeOH 10 CV) and trituration in Et$_2$O.

Compound C9

N-(3,5-dimethyl-1,2-isoxazolyl)-3-((6-(4-(2-hydroxyethyl)piperazin-1-yl)-2-methylpyrimidin-4-yl)amino)thiazole-5-carboxamide

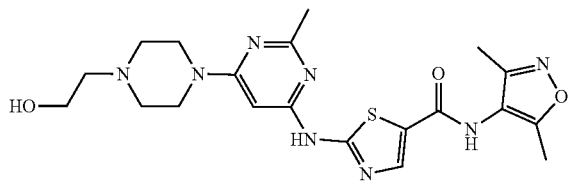 [SMILES: Cc1nc(Nc2ncc(C(=O)Nc3c(C)noc3C)s2)cc(N2CCN(CCO)CC2)n1]

Step 1 was run according to GP A1 using 2-((6-chloro-2-methylpyrimidin-4-yl)amino)thiazole-5-carboxoxylic acid (530 mg, 1.96 mmol), 3,5-dimethylisoxazol-4-amine (285 mg, 2.55 mmol), tetramethylchloroformamidinium hexafluorophosphate (659 mg, 2.35 mmol), N,N-diisopropylethylamine (886 mg, 6.85 mmol) and acetonitrile (5.8 mL, 0.3 M). 2-((6-chloro-2-methylpyrimidin-4-yl)amino)-N-(3,5-dimethylisoxazol-4-yl)thiazole-5-carboxamide (525 mg, 1.44 mmol) was obtained after precipitation from H$_2$O and washing with Et$_2$O as a yellow solid and used without further purification in the next step.

Step 2 was run according to GP B using 2-((6-chloro-2-methylpyrimidin-4-yl)amino)-N-(3,5-dimethylisoxazol-4-yl)thiazole-5-carboxamide (530 mg, 1.45 mmol), 2-(piperazin-1-yl)ethan-1-ol (946 mg, 7.26 mmol), N,N-diisopropylethylamine (75 mg, 0.58 mmol) and 1-butanol (4.4 mL, 0.3 M). C$_9$ (FIG. 1C, 280 mg, 0.611 mmol, 31% yield over 2 steps) was obtained as an off-white solid after flash purification (100% DCM to 75% DCM/MeOH over 10 CV, 75% DCM/MeOH 5 CV).

Compound C10

N-(4-chloro-2-methylpyridin-3-yl)-2-((2-methyl)-6-(4-methylpiperazin-1-yl)pyrimidin-4-yl)amino)thiazole-5-carboxamide

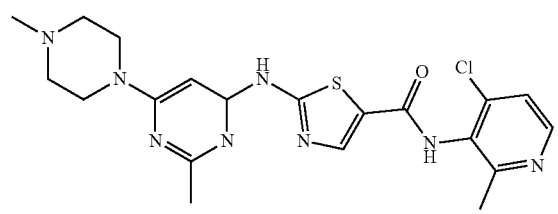 [SMILES: CC1=NC(N2CCN(C)CC2)=CC(Nc2ncc(C(=O)Nc3c(Cl)ccnc3C)s2)N1]

Step 1-3 was run according to the procedure for B3.

Step 4 was run according to GP B using N-(4-chloro-2-methylpyridin-3-yl)-2-((6-chloro-2-methylpyrimidin-4-yl)amino)thiazole-5-carboxamide (206 mg, 0.521 mmol), 1-methylpiperazine (261 mg, 2.61 mmol), N,N-diisopropylethylamine (27 mg, 0.21 mmol) and 1-butanol (1.5 mL, 0.3 M). C$_{10}$ (FIG. 1C, 50 mg, 0.11 mmol, 6% yield over 2 steps) was obtained as a white solid after extraction with EtOAc, flash purification (100% DCM to 80% DCM/3 N NH$_3$ in MeOH over 10 CV).

Compound C11

(4-chloro-2-methylpyridine-3-yl)-2-((6-((2-hydroxyethyl)amino)-2-methylpyrimidin-4-yl)amino)thiazole-5-carboxamide

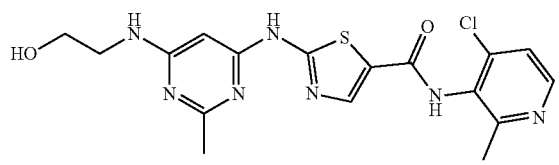 [SMILES: Cc1nc(NCCO)cc(Nc2ncc(C(=O)Nc3c(Cl)ccnc3C)s2)n1]

Step 1-3 was run according to the procedure for B3.

Figure 15:
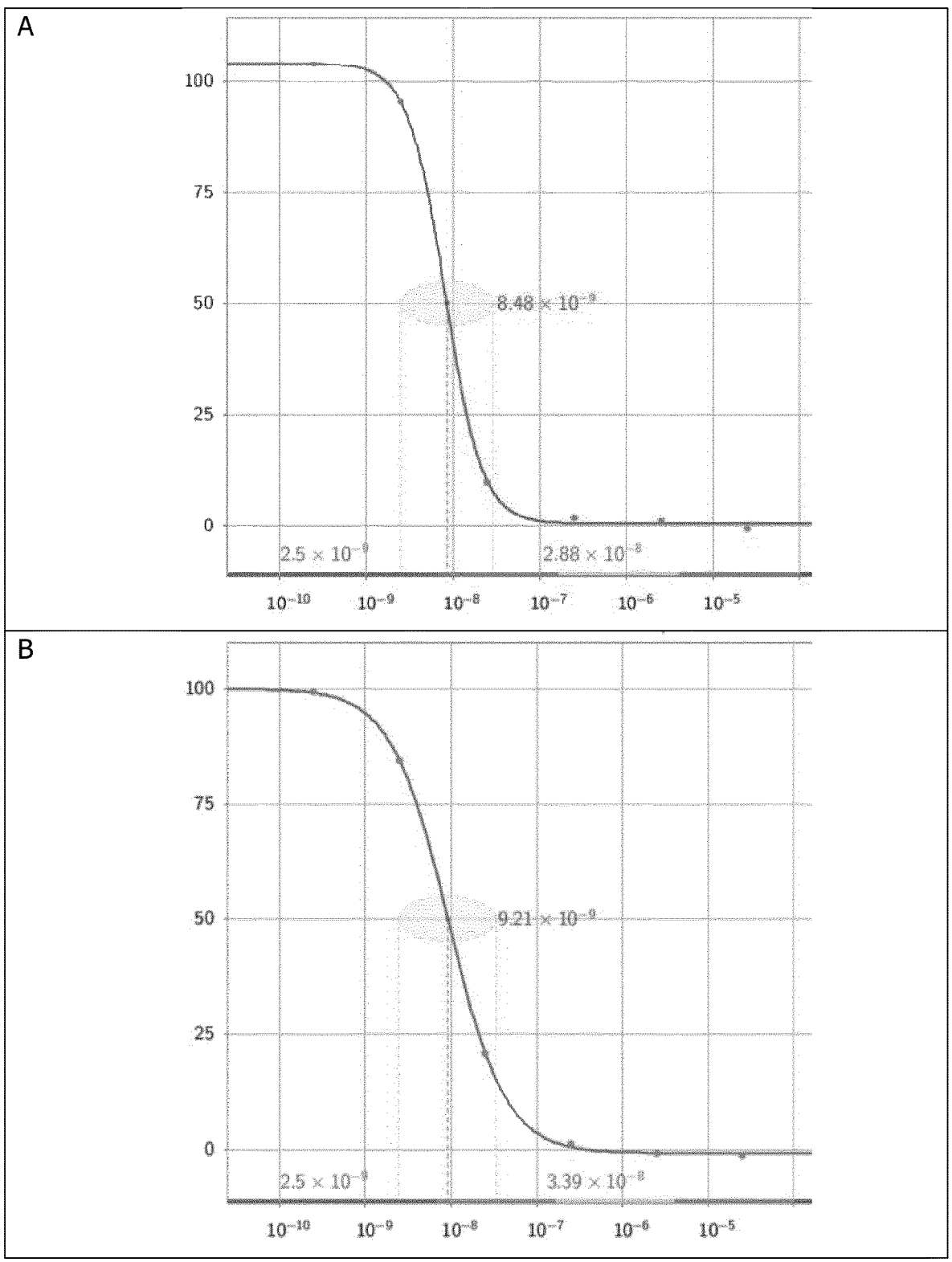
FIG. 15: depicts: growth inhibition by compound C7 of the WSU-NHL (A) and DOHH-2 (B) cell lines, showing GI50s of about 8 nM and 9 nM respectively. X-axes: compound concentration (M); Y-axes: Percentage Growth Inhibition (GI) at 96 h.

Step 4 was run according to GP B using N-(4-chloro-2-methylpyridin-3-yl)-2-((6-chloro-2-methylpyrimidin-4-yl)amino)thiazole-5-carboxamide (200 mg, 0.506 mmol), 2-aminoethan-1-ol (155 mg, 2.30 mmol), N,N-diisopropylethylamine (26 mg, 0.20 mmol) and 1-butanol (1.5 mL, 0.3 M). $C_{11}$ (FIG. 1C, 15 mg, 0.036 mmol, 1% yield over 2 steps) was obtained as a grey solid after extraction with EtOAc, flash purification (100% DCM to 80% DCM/3 N $NH_3$ in MeOH over 10 CV) and trituration in DCM/MeOH (96/4).

Compound C12

(R)-2-((6-(4-(2-hydroxyethyl)piperazin-1-yl)-2-methyl pyrimidin-4-yl)amino)-N-(quinuclidine-3-yl)thiazole-5-carboxamide

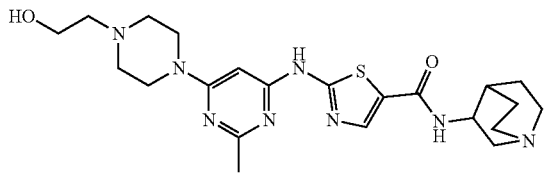 [SMILES: Cc1nc(Nc2ncc(C(=O)NC3CN4CCC3CC4)s2)cc(N2CCN(CCO)CC2)n1]

Step 1 was run according to GP A1 using 2-((6-chloro-2-methylpyrimidin-4-yl)amino)thiazole-5-carboxoxylic acid (500 mg, 1.85 mmol), (R)-quinuclidine-3-amine dihydrochloride (441 mg, 2.22 mmol), tetramethylchloroformamidinium hexafluorophosphate (622 mg, 2.22 mmol), N,N-diisopropylethylamine (1.31 g, 10.2 mmol, 5.5 eq.) and acetonitrile (10 mL, 0.2 M). 2-((6-chloro-2-methylpyrimidin-4-yl)amino)-N-(quinuclidine-3-yl)thiazole-5-carboxamide (250 mg, 0.491 mmol) was obtained after precipitation from $H_2O$ as a yellow solid and used without further purification in the next step.

Step 2 was run according to GP B using 2-((6-chloro-2-methylpyrimidin-4-yl)amino)-N-(quinuclidine-3-yl)thiazole-5-carboxamide (222 mg, 0.540 mmol), 2-(piperazin-1-yl)ethan-1-ol (553 mg, 4.25 mmol), N,N-diisopropylethylamine (44 mg, 0.34 mmol) and 1-butanol (2.5 mL, 0.3 M). $Cl_2$ (FIG. 1C, 30 mg, 0.063 mmol, 3% yield over 2 steps) was obtained as a white solid after preparative TLC (DCM/MeOH 4:1, $R_f$=0.00, UV 254 nm).

Compound C13

N-(2-ethyl-4-methylpyridin-3-yl)-2-((6-(4-(2-hydroxyethyl)piperazin-1-yl)-2-methylpyrimidin-4-yl)amino)thiazole-5-carboxamide Step 1 was run according to GP A1 using 2-((6-chloro-2-methylpyrimidin-4-yl)amino)thiazole-5-carboxoxylic acid (170 mg, 0.628 mmol), 2-ethyl-4-methylpyridin-3-amine (103 mg, 0.754 mmol), tetramethylchloroformamidinium hexafluorophosphate (211 mg, 0.754 mmol), N,N-diisopropylethylamine (284 mg, 2.20 mmol) and acetonitrile (5.0 mL, 0.1 M). 2-((6-chloro-2-methylpyrimidin-4-yl)amino)-N-(2-ethyl-4-methylpyridin-3-yl)thiazole-5-carboxamide (90 mg, 0.23 mmol) was obtained after extraction with EtOAc as a green solid and used without further purification in the next step.

Step 2 was run according to GP B using 2-((6-chloro-2-methylpyrimidin-4-yl)amino)-N-(2-ethyl-4-methylpyridin-3-yl)thiazole-5-carboxamide (87 mg, 0.22 mmol), 2-(piperazin-1-yl)ethan-1-ol (150 mg, 1.10 mmol), N,N-diisopropylethylamine (12 mg, 0.089 mmol) and 1-butanol (0.7 mL, 0.3 M). C13 (FIG. 1C, 48 mg, 0.099 mmol, 16% yield over 2 steps) was obtained as an off-white solid after flash purification (100% DCM to 75% DCM/MeOH over 10 CV).

The compounds C1 to C15, B3 and compound A8 (dasatinib) were characterised as set forth below in Table 1A.

TABLE 1A

Synthesis of kinase inhibitors.

| Compound Number | Mol. Wt. LCMS: m/z [M + H]⁺ | ¹H NMR |
|---|---|---|
| B3 | 489.1 | ¹H NMR (400 MHz, DMSO-$d_6$) δ 2.41 (s, 3H), 2.43-2.50 (m, 9H), 3.44-3.68 (m, 6H), 4.46 (s, 1H), 6.06 (s, 1H), 7.53 (d, J = 5.3 Hz, 1H), 8.25 (s, 1H), 8.37 (d, J = 5.3 Hz, 1H), 10.10 (s, 1H), 11.52 (s, 1H). |
| A8 (dasatinib) | 488.2 | ¹H NMR (400 MHz, DMSO-$d_6$) δ 2.23 (s, 3H), 2.38-2.50 (m, 9H), 3.38-3.62 (m, 6H), 4.45 (t, J = 5.3 Hz, 1H), 6.04 (s, 1H), 7.23-7.32 (m, 2H), 7.37-7.43 (m, 1H), 8.21 (s, 1H), 9.87 (s, 1H), 11.47 (s, 1H). |
| C1 | 469.2 | ¹H NMR (400 MHz, DMSO-$d_6$) δ 2.21 (s, 3H), 2.39 (s, 3H), 2.41 (s, 3H), 2.42-2.50 (m, 6H), 3.49-3.56 (m, 6H), 4.46 (t, J = 5.3 Hz, 1H), 6.06 (s, 1H), 7.18 (d, J = 4.8 Hz, 1H), 8.17-8.28 (m, 2H), 9.82 (s, 1H), 11.48 (s, 1H). |

TABLE 1A-continued

Synthesis of kinase inhibitors.

| Compound Number | Mol. Wt. LCMS: m/z [M + H]+ | 1H NMR |
|---|---|---|
| C2 | 455.1 | 1H NMR (400 MHz, DMSO-$d_6$) δ 2.21 (s, 3H), 2.38-2.51 (m, 9H), 3.49-3.57 (m, 6H), 4.48 (s, 1H), 6.08 (s, 1H), 7.26 (dd, J = 7.5, 4.8 Hz, 1H), 7.72 (dd, J = 7.7, 1.7 Hz, 1H), 8.26 (s, 1H), 8.31 (dd, J = 4.8, 1.8 Hz, 1H), 10.44 (s, 1H), 11.47 (s, 1H). |
| C3 | 533.1 ($^{81}$Br: 535.1) | 1H NMR (400 MHz, DMSO-$d_6$) δ 2.26-2.56 (m, 12H), 3.41-3.73 (m, 6H), 4.45 (s, 1H), 6.06 (s, 1H), 7.36 (s, 1H), 7.82 (s, 1H), 8.24 (s, 1H), 9.96 (s, 1H), 11.48 (s, 1H). |
| C4 | 489.1 | 1H NMR (400 MHz, DMSO-$d_6$) δ 2.25 (s, 3H), 2.40-2.50 (m, 9H), 3.43-3.67 (m, 6H), 4.47 (s, 1H), 6.08 (s, 1H), 8.28 (s, 1H), 8.48 (s, 1H), 8.57 (s, 1H), 10.19 (s, 1H), 11.56 (s, 1H). |
| C5 | 469.2 | 1H NMR (400 MHz, DMSO-$d_6$) δ 2.19 (s, 6H), 2.34-2.49 (m, 9H), 3.49-3.58 (m, 6H), 4.46 (s, 1H), 6.05 (s, 1H), 8.23 (s, 1H), 8.33 (s, 2H), 9.86 (s, 1H), 11.50 (s, 1H). |
| C6 | 455.1 | 1H NMR (400 MHz, DMSO-$d_6$) δ 2.37-2.50 (m, 12H), 3.48-3.61 (m, 6H), 4.46 (t, J = 5.6 Hz, 1H), 6.06 (s, 1H), 7.27 (dd, J = 7.9, 4.7 Hz, 1H), 7.74 (d, J = 7.9 Hz, 1H), 8.22 (s, 1H), 8.33 (d, J = 4.8 Hz, 1H), 9.87 (s, 1H), 11.49 (s, 1H). |
| C7 | 494.1 | 1H NMR (400 MHz, DMSO-$d_6$) δ 2.06 (s, 3H), 2.35-2.50 (m, 9H), 3.47-3.58 (m, 6H), 4.46 (s, 1H), 6.05 (s, 1H), 7.23-7.32 (m, 2H), 7.18 (m, 1H), 8.20 (s, 1H), 9.79 (s, 1H), 11.48 (s, 1H). |
| C8 | 472.2 | 1H NMR (400 MHz, DMSO-$d_6$) δ 2.00 (s, 3H), 2.09 (s, 3H), 2.35-2.51 (m, 9H), 3.40-3.60 (m, 6H), 3.66 (s, 3H), 4.45 (s, 1H), 6.04 (s, 1H), 8.15 (s, 1H), 9.36 (s, 1H), 11.39 (s, 1H). |
| C9 | 459.1 | 1H NMR (400 MHz, DMSO-$d_6$) δ 2.13 (s, 3H), 2.31 (s, 3H), 2.41 (s, 3H), 2.43-2.50 (m, 6H), 3.48-3.59 (m, 6H), 4.46 (t, J = 5.3 Hz, 1H), 6.05 (s, 1H), 8.18 (s, 1H), 9.66 (s, 1H), 11.48 (s, 1H). |
| C10 | 459.1 | 1H NMR (400 MHz, DMSO-$d_6$) δ 2.22 (s, 3H), 2.32-2.47 (m, 10H), 3.47-3.58 (m, 4H), 6.06 (s, 1H), 7.53 (d, J = 5.3 Hz, 1H), 8.24 (s, 1H), 8.37 (d, .7 = 5.3 Hz, 1H), 10.09 (s, 1H), 11.53 (s, 1H). |
| C11 | 420.0 | 1H NMR (400 MHz, CD$_3$OD) δ 2.48 (s, 3H), 2.54 (s, 3H), 3.44 (s, 2H), 3.72 (s, 2H), 5.95 (s, 1H), 7.49 (d, J = 5.0 Hz, 1H), 8.17 (s, 1H), 8.33 (d, J = 5.1 Hz, 1H). |
| C12 | 473.2 | 1H NMR (400 MHz, DMSO-$d_6$ + 1 drop D$_2$O) δ 1.45-1.55 (m, 1H), 1.68-1.73 (m, 1H), 1.83-2.01 (m, 2H), 2.38-2.48 (m, 7H), 2.55-2.58 (m, 2H), 2.77-3.15 (m, 7H), 3.33 (t, J = 11.7 Hz, 1H), 3.47-3.54 (m, 6H), 4.06 (t, J = 7.4 Hz, 1H), 6.02 (s, 1H), 8.10 (s, 1H). |
| C13 | 483.2 | 1H NMR (400 MHz, DMSO-$d_6$) δ 1.16 (t, J = 7.5 Hz, 3H), 2.21 (s, 3H), 2.38-2.50 (m, 9H), 2.73 (q, J = 7.5 Hz, 2H), 3.47-3.59 (m, 6H), 4.43 (s, 1H), 6.06 (s, 1H), 7.19 (d, J = 5.0 Hz, 1H), 8.23 (s, 1H), 8.31 (d, J = 4.9 Hz, 1H), 9.79 (s, 1H), 11.49 (s, 1H). |

Compounds D1 to D10

The compounds D1 to D10 (FIG. 1D) are made analogously to compound C$_7$ via Scheme 2, except that the applicable amine is used at step 4 (GP A1) and the applicable piperazinyl derivative is used at step 5 (GP B).

Compounds synthesised from Table B were characterised as set forth below in Table 1B.

TABLE 1B

Synthesis of further kinase inhibitors.

| Compound Number | Mol. Wt. LCMS: m/z [M + H]+ | 1H NMR* |
|---|---|---|
| D1 | 494.23 | 1H NMR (300 MHz, DMSO-$d_6$): δ 11.45 (s, 1H), 9.71 (s, 1H), 8.19 (s, 1H), 7.43 (s, 1H), 6.04 (s, 1H), 4.43 (t, J = 5.1 Hz, 1H), 3.54-3.50 (m, 6H), 2.45-2.42 (m, 6H), 2.40 (s, 3H), 2.29 (s, 3H) |
| D7 | 514.11 | 1H NMR [300 MHz, DMSO-$d_6$]: δ 11.51 (s, 1H), 9.98 (s, 1H), 8.20 (s, 1H), 7.66 (s, 1H), 6.04 (s, 1H), 4.45 (t, J = 5.1 Hz, 1H), 3.55-3.51 (m, 6H), 2.45-2.42 (m, 6H), 2.40 (s, 3H). |
| D8 | 492.17 | 1H NMR [300 MHz, DMSO-$d_6$]: δ 11.53 (s, 1H), 9.80 (s, 1H), 8.20 (s, 1H), 7.17 (s, 1H), 6.05 (s, 1H), 3.57-3.53 (m, 8H), 2.49 (s, 3H), 2.05 (s, 3H), 2.04 (s, 3H). |
| D9 | 464.19 | 1H NMR [300 MHz, DMSO-$d_6$]: δ 11.46 (s, 1H), 9.76 (s, 1H), 8.19 (s, 1H), 7.16 (s, 1H), 6.05 (s, 1H), 3.52-3.49 (m, 4H), 2.4 (s, 3H), 2.38-2.36 (m, 4H), 2.21 (s, 3H), 2.05 (s, 3H). |

*Determined at 300 MHz using a Bruker AV300 machine.

Additional Kinase Inhibitors of the Invention, Based on the Structure-Activity Relationship (SAR) of Dasatinib (A8):

Additional kinase inhibitors of the invention are synthesised to exemplify that a yet further diverse set of substitutions (in particular, at $R^{1a}$, $R^{1c}$, $R^7$ and B) of formula (I) provide compounds that are kinase inhibitors and/or possess cellular antiproliferative activity.

For example: (i) by reference to FIG. 8A (from Table 1 of Lombardo et al 2004, J Med Chem 47:6658), compounds of formula (I) are made with substituents at $R^{1a}$, $R^{1c}$ and B analogous to those independently selected from $R_2$, $R_1$ and X (respectively), as shown in FIG. 8A; and/or (ii) by reference to FIG. 8B (from Table 4 of Das et al 2006, J Med Chem 49:6819), compounds of formula (I) are made with substituents at $B/R^{1a}/R^{1c}$ and R7 analogous to those independently selected from $R_1$ and R (respectively), as shown in FIG. 8B.

Example 2: Inhibition of SIK; Abl and Src Kinases by the Kinase Inhibitors of Formula (I) and by Dasatinib The inventors demonstrate that, surprisingly, kinase inhibitors of formula (I) (eg C1 to C12 and B3, and compounds from Table B, D1 to D10) potently inhibit SIK, ABL1 and/or SRC kinases (Table 3A and Table 3A1), with many compounds inhibiting SRC with low single-digit nM IC50s, and inhibiting SIK (esp SIK3 and/or SIK2) and/or ABL1 with low double-digit nM IC50s. Compound C13 is similarly tested.

The IC50 for the inhibition of ABL1 by dasatinib, by C7 and by B3 is approximately 1.5 nM, 5.1 nM and 1.6 nM, and of SRC is 1.5 nM, 1.5 nM and 1.5 nM; each, respectively for dasatinib, C7 and by B3 (Table 3A). The compound C12 is also a strong inhibitor of SRC (<100 nM IC50), and is surprisingly selective to SRC over ABL1.

Briefly, a radiometric protein kinase assay (33PanQinase® Activity Assay) was used for measuring the kinase activity of the five protein kinases. All kinase assays were performed in 96-well FlashPlates™ from PerkinElmer (Boston, MA, USA) in a 50 uL reaction volume. The reaction cocktail was pipetted in four steps in the following order:

25 uL of assay buffer (standard buffer/[gamma-33P]-ATP)

10 uL of ATP solution (in water)

5 uL of test compound (in 10% DMSO)

20 uL enzyme/substrate mix

The assay for all protein kinases contained 70 mM HEPES-NaOH pH7.5, 3 mM $MgCl_2$, 3 mM $MnCl_2$, 3 μM Na-orthovanadate, 1.2 mM DTT, ATP (variable concentrations, corresponding to the apparent ATP-Km of the respective kinase, see Table 2A), [gamma-33P]-ATP (approx. $8 \times 10^5$ cpm per well), protein kinase (variable amount, see Table 2A), and substrate (variable amounts, see Table 2A).

The following amounts of enzyme and applicable substrate were used per well:

TABLE 2A

Assay parameters for the tested protein kinases.

| Kinase Name | Kinase Conc. (ng/50 μL) | Kinase Conc. (nM*) | ATP Conc. (μM) | Substrate | Substrate Conc. (μg/50 μL) |
|---|---|---|---|---|---|
| ABL1 wt | 5 | 1.3 | 0.3 | Poly(Ala, Glu, Lys, Tyr)6:2:5:1 | 0.125 |
| SRC (GST-HIS-tag) | 5 | 1.1 | 0.3 | Poly(Glu, Tyr)4:1 | 0.125 |
| SIK1 | 50 | 14.6 | 3.0 | RBER-CHKtide | 2 |
| SIK2 | 3 | 1 | 1.0 | RBER-CHKtide | 2 |
| SIK3 | 50 | 15.9 | 1.0 | RBER-CHKtide | 2 |

*Maximal molar enzyme assay concentrations, implying enzyme preparations exclusively containing 100% active enzyme The reaction cocktails were incubated at 30° C. for 60 minutes. The reaction was stopped with 50 uL of 2% (v/v) H3PO4, plates were aspirated and washed two times with 200 μL 0.9% (w/v) NaCl. Incorporation of 33Pi was determined with a microplate scintillation counter (Microbeta, Wallac). All assays were performed with a BeckmanCoulter/SAGIAN™ Core System.

Example 3: Improved Kinase Selectively of Kinase Inhibitors of Formula (I)

However, and yet further surprisingly, the inventors found that kinase inhibitors of formula (I) (eg C1 to C12 and B3, and compounds from Table B, D1 to D10) appeared to be selective (especially, SRC-selective) protein-tyrosine kinase inhibitors (favouring the inhibition of, eg ABL1, and particularly SRC kinase) than the kinase inhibitor dasatinib. Compound C13 is similarly tested.

In particular, although many of these kinase inhibitors inhibited each (or one or more) of the SIK family of kinases (SIK1, SIK2 and SIK3), some even at sub-micromolar concentrations, they were less potent inhibitors of these protein-serine/threonine kinases than dasatinib (Table 3A and Table 3A1).

In particular, and by way of example, compounds C3, C8 and C12 are significantly less active inhibitor of at least SIK1, SIK2, and SIK3 than dasatinib, yet remain strong inhibitors of both SRC and ABL1, especially SRC (IC50s: <2 nM, <25 nM, and <100 nM, respectively).

TABLE 3A

Biological activity of kinase inhibitors of formula (I)

| Kinase Name | Compound: IC50 (nM) | | | | | | | |
|---|---|---|---|---|---|---|---|---|
| | C1 | C2 | C3 | C4 | C5 | C6 | C7 | C8 |
| ABL1 | 13.0 | 14.4 | 39.7 | 17.7 | 28.2 | 14.7 | 5.02 | 296 |
| SRC | <1.50 | <1.50 | 1.59 | <1.50 | <1.50 | <1.50 | <1.50 | 22.8 |
| SIK1 | 132 | 177 | 571 | 32.7 | 30.6 | 336 | 13.4 | 2,800 |
| SIK2 | 641 | 427 | 1,540 | 130 | 119 | 385 | 17.7 | 4,440 |
| SIK3 | 867 | 1100 | 2,780 | 677 | 340 | 987 | 52.3 | 9,730 |

| Kinase Name | Compound: IC50 (nM) | | | | | |
|---|---|---|---|---|---|---|
| | C9 | C10 | C11 | C12 | B3 | A8 |
| ABL1 | 27.4 | 4.30 | 4.43 | 391 | ~1 to 2 | ~1 to 2 |
| SRC | 6.44 | <1.5 | <1.5 | 73.7 | ~1 to 2 | ~1 to 2 |
| SIK1 | 169 | 302 | 302 | 1,710 | ~30 | ~1 to 2 |
| SIK2 | 232 | 138 | 470 | 1,940 | ~60 | ~3 to 4 |
| SIK3 | 800 | 493 | 1,510 | 8,850 | ~250 | ~5 to 7 |

TABLE 3A1

Biological activity of further kinase inhibitors of formula (I).

| Compound | Kinase: IC50 (nM) | | |
|---|---|---|---|
| | SIK1 | SIK2 | SIK3 |
| D1 | NT | ~10 to 15 | ~40 to 45 |
| D7 | NT | ~2 to 5 | ~15 to 20 |
| D8 | ~20 to 25 | ~25 to 30 | ~150 |
| D9 | ~10 to 15 | ~10 to 15 | ~60 |

Figure 2:
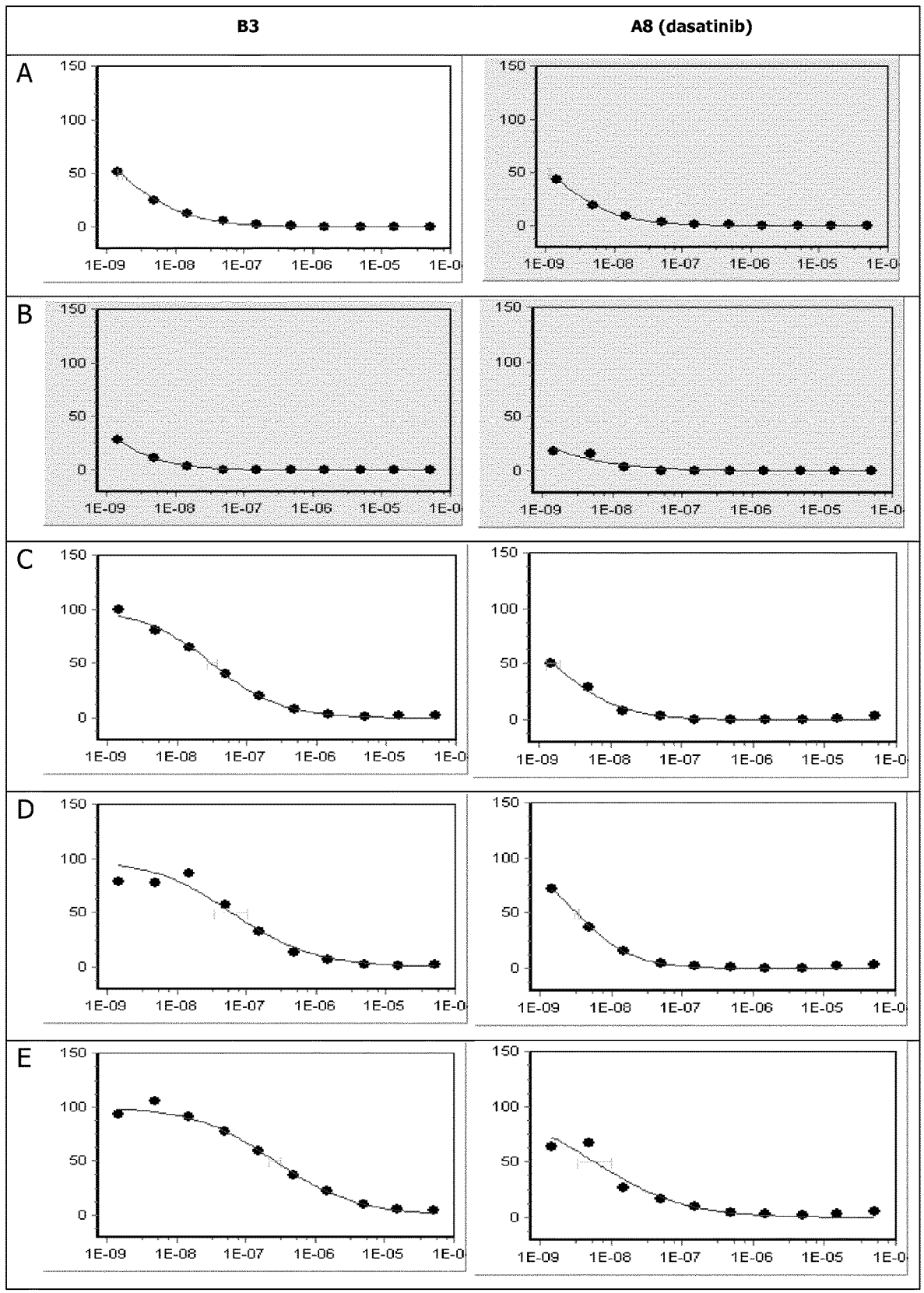
FIG. 2: depicts (in A to E) inhibitory activity of a kinase inhibitor of formula (I) (B3, left column) compared to dasatinib (A8, right column), against the kinases (A) ABL1; (B) SRC; (C) SIK1; (D) SIK2; and (E) SIK3; and depicts (in F to J) inhibitory activity of other kinase inhibitors of formula (I) (C3, left column; C12 right column), against the kinases (F) ABL1; (G) SRC; (H) SIK1; (I) SIK2; and (J) SIK3. X-axes compound concentration (M), and Y-axes kinase activity (%).
Figure 2:
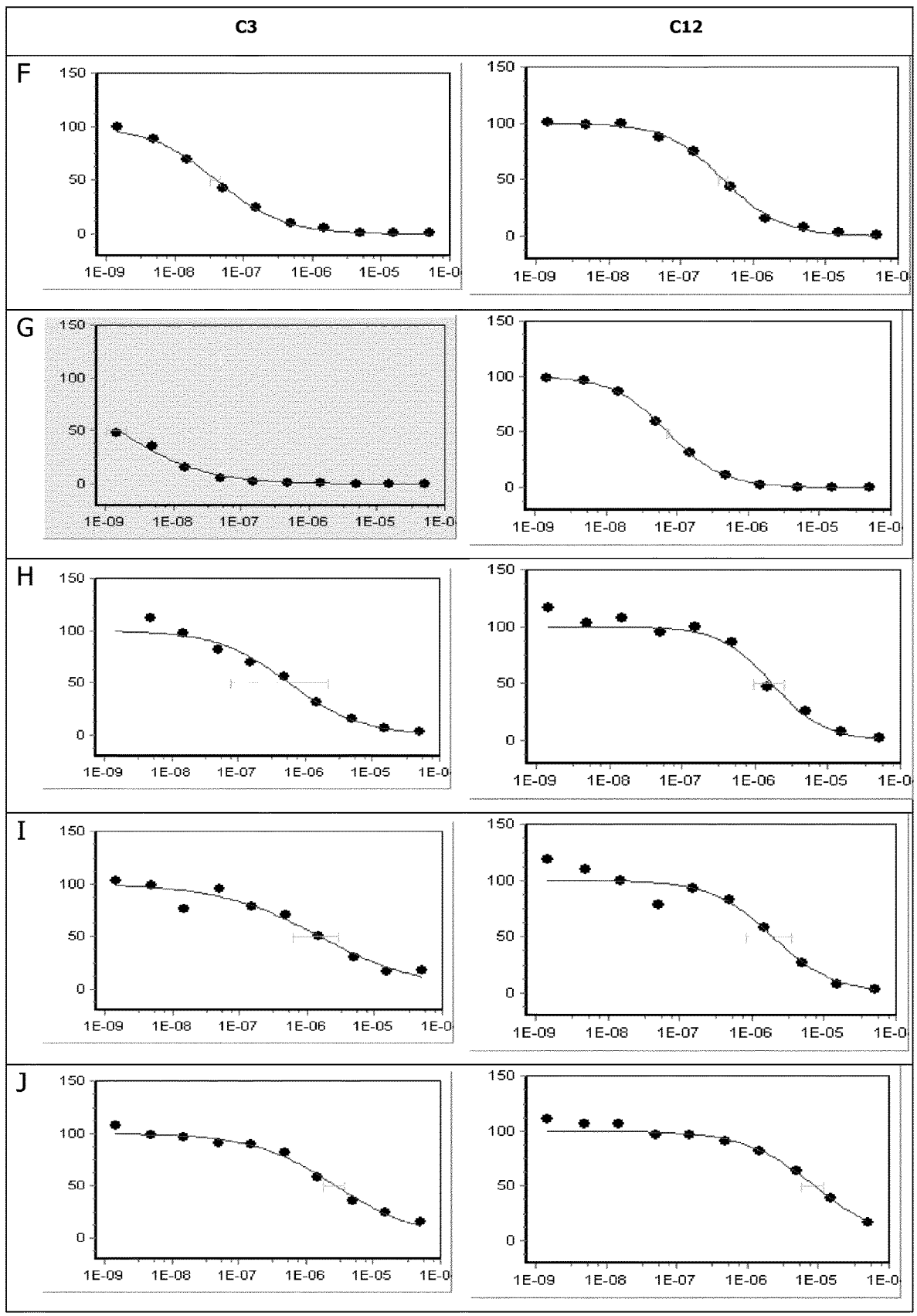

The IC50s of the compounds against the SIK family of protein-serine/threonine kinases (SIK1, SIK2 and SIK3) were determined as described in Example 2 (in particular, see Table 2A), with the inhibition curves for B3 and A8 shown in FIG. 2 (A to E) and for C3 and C12 in FIG. 2 (F to J). For example (FIG. 2F to J), compounds C3 and C12 retain potent inhibitory activity against SRC (IC50s: <2 nM and <100 nM, respectively), but compared to dasatinib (see FIG. 2A to E, right column) are significantly less active inhibitors against ABL1, and especially less active against SIK1, SIK2 and SIK3.

Figure 4:
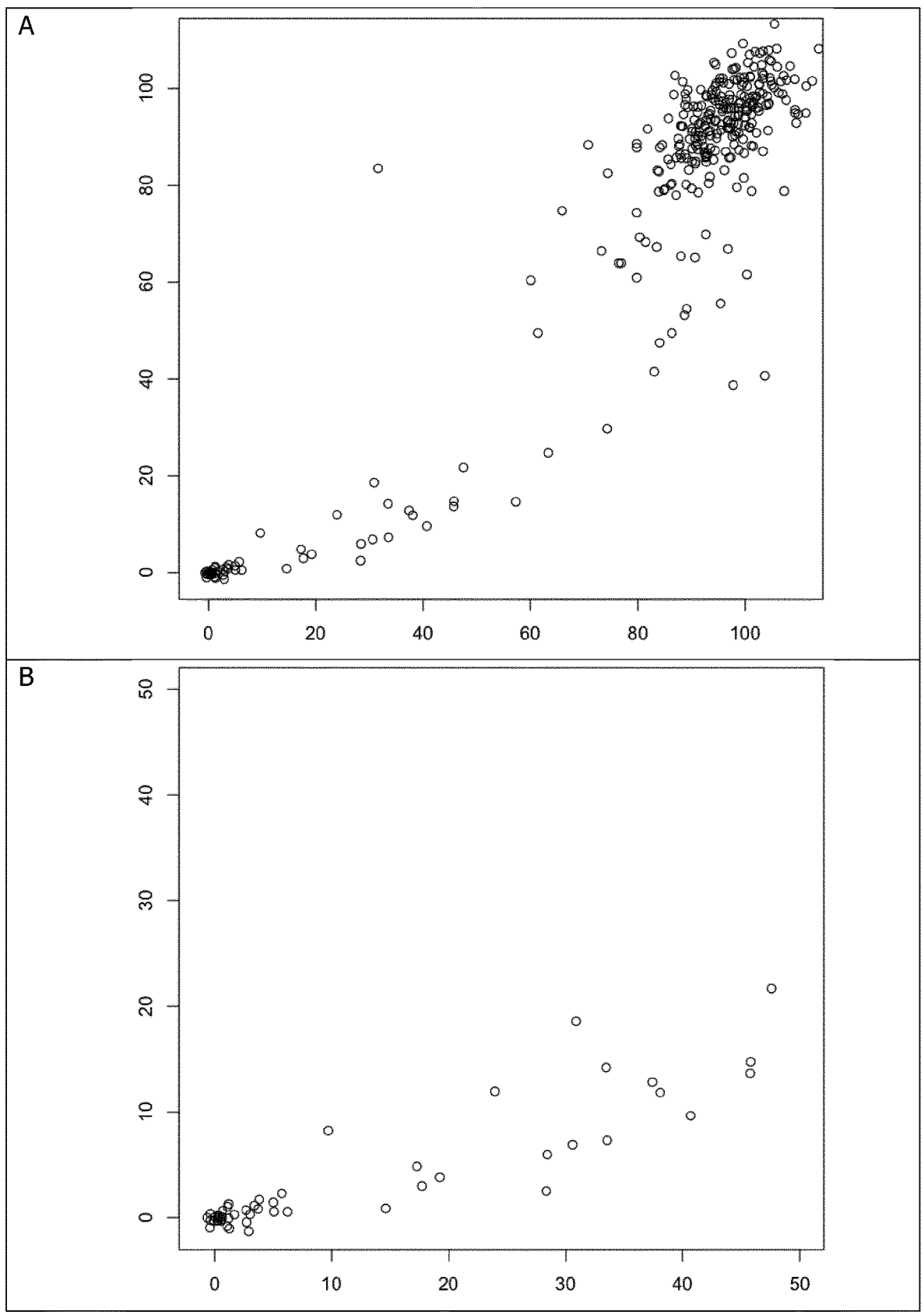
FIG. 4: depicts selectivity of kinase inhibition (by % residual activity at 1 uM compound) by a kinase inhibitor of formula (I), B3 (X-axis) compared to dasatinib (A8; Y-axis): (A) axes showing the full range of residual activity; and (B) axes showing the range of 0 to 50% residual activity.
Figure 5:
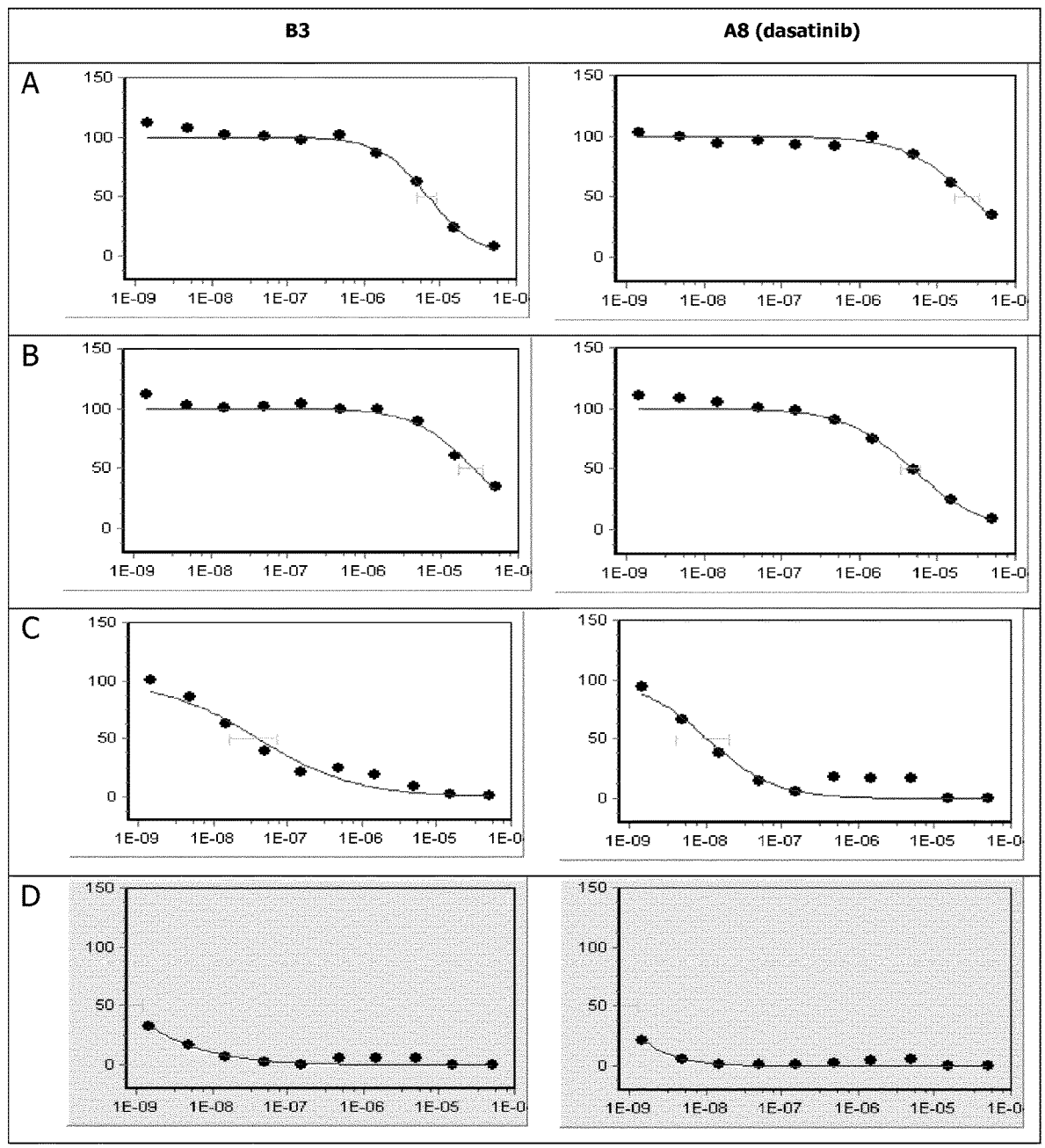
FIG. 5: depicts inhibitory activity of a kinase inhibitor of formula (I) (B3, left column) compared to dasatinib (A8, right column), against the kinases (A) FLT3; (B) SYK; (C) KIT; and (D) LCK. X-axes compound concentration (M), and Y-axes kinase activity (%).

Furthermore, conducting a single-point (1 uM) inhibition assay (in duplicate) over a diverse set of 320 wild-type protein (ProQinase "Kinase Profiler"; ProQinase, Freiburg, Germany) shows that compounds of formula (I) are more selective than dasatinib (FIGS. 3 and 4, Table 3AA). Other compounds of formula (I) are similarly tested (for example, one or more of compounds D1 to D10). Indeed, overall (and for one example compound of formula (I)) kinase inhibitor B3 is numerically more selective than dasatinib (A8), with B3 having a selectivity score of 0.163 compared to 0.188 for dasatinib. The selectivity score, according to Karaman et al (2008; Nat Biotech 26:127), is a compound concentration-dependent parameter describing the portion of kinases, which are inhibited to more than a predefined degree (eg, more than 50%), in relation to all tested kinases of the particular project.

TABLE 3AA

Selectivity score across 320 kinases for compounds of formula (I) and dasatinib (A8).

| Kinase Family* | Number | Compound Selectivity score at 1 uM | | | | | | |
|---|---|---|---|---|---|---|---|---|
| | | C2 | C4 | C7 | C8 | C9 | B3 | A8 |
| All tested | 320 | 0.144 | 0.169 | 0.234 | 0.940 | 0.172 | 0.163 | 0.188 |
| TK | 77 | 0.468 | 0.506 | 0.558 | 0.377 | 0.442 | 0.481 | 0.532 |
| TKL | 19 | 0.263 | 0.421 | 0.632 | 0.053 | 0.579 | 0.474 | 0.579 |
| CAMK | 45 | 0.067 | 0.067 | 0.067 | 0.067 | 0.000 | 0.067 | 0.089 |

*TK: Tyrosine Kinase; TKL: Tyrosine Kinase-like; CAMK: Calcium/Calmodulin-dependent protein kinases.

The selectivity score of the compounds at the tested concentration was calculated for a residual activity <50%; ie, an inhibition of >50%. The selectivity score for a particular compound at a particular concentration was calculated by using the following formula:

Selectivity Score=(count of data points<50%)/(total number of data points)

Indeed, virtually all tested compounds of formula (I) showed a significantly enhanced selectively score (ie, they inhibited a smaller number of kinases by more than 50%) than dasatinib. This selectivity was shown not just across all 320 kinases, but also by kinase family-specific selectively scores; and, for example, virtually all tested compounds of formula (I) were more selective even within the protein-tyrosine and protein-tyrosine-like families of kinases than dasatinib, and all (including $C_7$) were more selective to the CAMK family of kinases than dasatinib. Indeed, compound $C_9$ was shown to not inhibit any CAMK kinase (even SIK1, SIK2 or SIK3) by more than 50%.

By way of further example for one particular kinase inhibitor of formula (I), compound B3, in particular, with a few exceptions (eg, FLT3, showing only 32% residual activity after treatment with 1 μM of compound B3, yet over 80% of its activity remains on treatment with 1 uM dasatinib), unlike the kinases such as ABL1 and SRC that are equivalently inhibited by both compounds, this kinase inhibitor of formula (I) was a less potent inhibitor of most of these kinases tested (FIGS. 3 and 4). For example, WNK2 is not inhibited by B3 (100% residual activity at 1 μM B3), yet only 62% of WNK2 activity remains after treatment with 1 μM dasatinib; likewise, JAK1 is not inhibited by 1 μM B3, yet only 41% of activity remains after treatment with 1 μM dasatinib; almost 100% of RET activity remains after treatment with 1 μM B3, yet under 40% of its activity remains on treatment with 1 μM dasatinib. Also, treatment of the serine/threonine kinase MAP4K5 with 1 μM dasatinib shows a residual activity of only 3%, while treatment with 1 μM B3 shows 28% residual activity. Indeed, many kinases have less than 20% residual activity after inhibition with 1 μM dasatinib, yet retain almost 50% of their activity when inhibited with 1 μM B3. For example, B-RAF retains almost 50% activity when inhibited with 1 μM B3, yet retains only 15% when inhibited with 1 μM dasatinib.

Kinase inhibitors of formula (I) show differential inhibition of a number of other kinases and kinase-family members that are inhibited by dasatinib; for example, and in particular, inhibition of KIT and certain members of the EphA/B subfamilies by a kinase inhibitor of formula (I), compound B3, (Table 3B).

TABLE 3B

Certain kinases/kinase subfamilies showing differential inhibition between a compound of formula (I) and dasatinib (A8).

| Kinase Name | Kinase Family* | Compound Residual activity (%) at 1 μM | |
|---|---|---|---|
| | | B3 | A8 |
| NIK | STE | 100 | 82 |
| EPH-A1 | TK | 3 | 1 |
| EPH-A2 | TK | 0 | 0 |
| EPH-A3 | TK | 0 | 0 |
| EPH-A4 | TK | 10 | 8 |
| EPH-A5 | TK | 1 | 0 |
| EPH-A6 | TK | 86 | 50 |
| EPH-A7 | TK | 88 | 88 |
| EPH-A8 | TK | 3 | 0 |
| EPH-B1 | TK | 0 | 0 |
| EPH-B2 | TK | 15 | 1 |
| EPH-B3 | TK | 3 | 1 |
| EPH-B4 | TK | 1 | 0 |
| KIT | TK | 5 | 1 |
| PDGFR-alpha | TK | 18 | 3 |
| PDGFR-beta | TK | 6 | 2 |

*TK: Tyrosine Kinase; STE: Homologs of Yeast Sterile 7, Sterile 11, Sterile 20 Kinases Overall, 1 μM dasatinib inhibits 23 of these kinases to less than 1% or residual activity, while 1 μM B3 inhibits only 13 kinases to less than 1% residual activity. Similarly, given a threshold of <5% residual activity, dasatinib inhibits 38 kinases and 1 μM B3 inhibits only 30 kinases; and a threshold of <10% residual activity, dasatinib inhibits 43 kinases and 1 μM B3 inhibits only 34 kinases.

Table 3C shows those kinases retaining an activity of greater than 50% when treated with one compound and which show a residual activity of 50% or less when treated with the other compound. Compound A8 (dasatinib) inhibits 9 kinases by greater than 50%, where such kinases retain more than 50% of their activity when treated with compound B3, a kinase inhibitor of formula (I). In contrast, of all the kinases tested, the kinase inhibitor of formula (I) (B3) inhibited by greater than 50% only one kinase (FLT3) that was not also inhibited by dasatinib by greater than 50%.

TABLE 3C

Kinases showing differential inhibition (residual activity of 50%) between B3, a compound of formula (I), and dasatinib (A8).

| Kinase Name | Kinase Family* | Compound Residual activity (%) at 1 μM | |
|---|---|---|---|
| | | B3 | A8 |
| ACV-R2B | TKL | 57 | 15 |
| BMPR1A | TKL | 83 | 42 |
| EPHA6 | TK | 86 | 50 |
| ERBB2 | TK | 84 | 47 |
| FGF-R2 | TK | 74 | 30 |
| FLT3 | TK | 32 | 84 |
| JAK1 aa583-1154 wt | TK | 104 | 41 |
| MAP3K11 | STE | 61 | 50 |
| p38-beta | CMGC | 63 | 25 |
| RET | TK | 98 | 39 |

*TK: Tyrosine Kinase; STE: Homologs of Yeast Sterile 7, Sterile 11, Sterile 20 Kinases; TKL: Tyrosine Kinase-like; CMGC: containing CDK, MAPK, GSK3 and CLK families.

Indeed, in comparison to dasatinib (A8), kinase inhibitors of formula (I) (eg C2, C4, C7, C8, and C9, and B3) are confirmed to show differential biological inhibitory activity against one or more of the above kinases, when tested in a biochemical assay to determine IC50s (Table 3D), and the corresponding IC50 curves are shown in FIG. 5A to D (other compounds of formula (I) are similarly tested). Indeed, although both compounds B3 and A8 are (also) strong inhibitors of the kinases LCK and KIT, in contrast to dasatinib (A8) compound B3 inhibits FLT3 far more strongly than it does SYK (IC50s 6.9 μM and 26.0 μM, respectively, for B3; and 25.7 μM and 4.8 μM, respectively, for A8).

Accordingly, although B3 (a kinase inhibitor of formula (I)) is generally more selective than the kinase inhibitor A8 (dasatinib), B3 is shown to inhibit FLT3 more potently than compound A8 (and as reflected by the single outlying point in FIG. 4A, which represents FLT3).

TABLE 3D

Biological activity of the compound B3 compared to dasatinib (A8) tested against further kinases

| Kinase Name | Kinase Family* | Compound: IC50 (nM) | |
|---|---|---|---|
| | | B3 | A8 (dasatanib) |
| FLT3 | TK | 6,900 | 25,700 |
| SYK | TK | 26,000 | 4,820 |
| KIT | TK | 40.4 | 10.4 |
| LCK | TK | <1.5 | <1.5 |

The IC50 of each compound against these kinases was tested analogously to the IC50 assay described in Example 2 above, except that the following amounts of enzyme and applicable substrate were used per well (Table 3E):

TABLE 3E

Assay parameters for the additional tested protein kinases.

| Kinase Name | Kinase Conc. (ng/50 μl) | Kinase Conc. (nM*) | ATP Conc. (μM) | Substrate | Substrate Conc. (μg/50 μL) |
|---|---|---|---|---|---|
| FLT3 | 20 | 5.2 | 1 | Poly(Ala, Glu, Lys, Tyr)6:2:5:1 | 0.125 |

TABLE 3E-continued

Assay parameters for the additional tested protein kinases.

| Kinase Name | Kinase Conc. (ng/50 μl) | Kinase Conc. (nM*) | ATP Conc. (μM) | Substrate | Substrate Conc. (μg/50 μL) |
|---|---|---|---|---|---|
| SYK | 50 | 9.6 | 1 | Poly(Glu, Tyr)4:1 | 0.125 |
| KIT | 100 | 25.8 | 3 | Poly(Glu, Tyr)4:1 | 0.125 |
| LCK | 20 | 4.3 | 0.3 | Poly(Glu, Tyr)4:1 | 0.125 |

Figure 9:
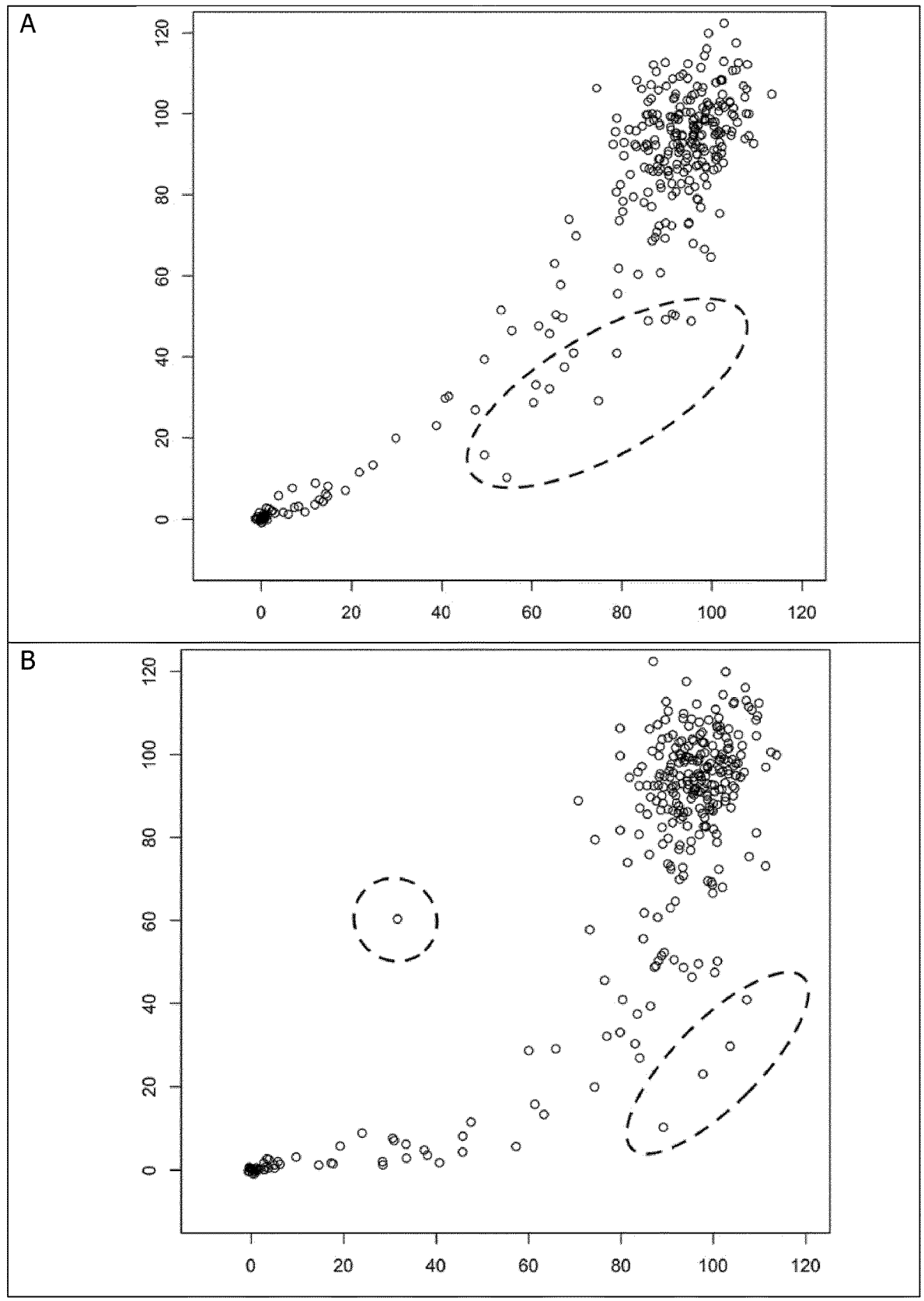
FIG. 9: depicts selectivity of kinase inhibition (by % residual activity at 1 uM compound) by a kinase inhibitor of formula (I), C7 (Y-axis) compared to: (A) dasatinib (A8; X-axis); and (B) another kinase inhibitor of formula (I), B3 (X-axis). The dashed areas highlight groups of kinases that are substantially differentially inhibited between the applicable compounds.

*Maximal molar enzyme assay concentrations, implying enzyme preparations exclusively containing 100% active enzyme Indeed, one preferred compound of the invention (C7) had a yet other profile of kinase inhibition (FIG. 3); exhibiting a profile being different to both of compound A8 and compound B3. FIG. 9 shows scatter plots of the % residual activity (mean, of duplicate 1 uM single-point inhibition assays) of a diverse set of 320 wild-type protein kinases (ProQuinase "Kinase Profiler", as described above), with the % residual activity of compound C7 shown on each Y axis, and the % residual activity of compound A8 and B3 shown on the X axis of FIGS. 9A and 9B, respectively.

Surprisingly, compound C7 was significantly more potent at inhibiting a number of kinases than both compounds A8 (dasatinib) and B3 (Tables 3F.1 and 3F.2, respectively), for example for those kinases included in the dashed-groups identified in FIGS. 9A and 9B. In addition, compound C7 was notably different to compound B3 by C7's relative inactivity in inhibiting FLT3 (60% residual activity for C7 compared to 32% residual activity for B3).

TABLE 3F.1

Certain kinases/kinase subfamilies showing differential inhibition between a compound C7 and dasatinib (A8).

| Kinase Name | Kinase Family | Compound Residual activity (%) at 1 μM | |
|---|---|---|---|
| | | C7 | A8 |
| Aurora A | Other | 37 | 67 |
| Aurora B | Other | 49 | 90 |
| MAP3K9 | STE | 43 | 64 |
| MAP3K10 | STE | 41 | 69 |
| MAP3K11 | STE | 16 | 49 |
| MST4 | STE | 41 | 79 |
| MYLK2 | CAMK | 51 | 91 |
| NEK11 | Other | 10 | 54 |
| RPS6KA6 | AGC | 49 | 95 |
| TBK1 | Other | 49 | 86 |
| TRKA | TK | 29 | 60 |
| TRKB | TK | 52 | 100 |
| TRKC | TK | 29 | 75 |
| VEGF-R1 | TK | 50 | 92 |
| WEE1 | Other | 33 | 61 |

TABLE 3F.2

Certain kinases/kinase subfamilies showing differential inhibition between a compound C7 and compound B3.

| Kinase Name | Kinase Family | Compound Residual activity (%) at 1 μM | |
|---|---|---|---|
| | | C7 | B3 |
| FLT3 | TK | 60 | 32 |
| JAK1 | TK | 30 | 104 |
| MST4 | STE | 41 | 107 |
| NEK11 | Other | 10 | 89 |
| RET | TK | 23 | 98 |

Indeed, of particular significance is the differential pattern of inhibition shown by compound C7 compared to both of compounds A8 and B3 for the following kinases (Table 3G). Compound C7 is demonstrated to be surprisingly more potent than the prior art compound A8 (dasatinib) to a number of key kinases listed in Table 3G, in particular such kinases that are TKLs (eg the ACV-family of kinases, RAF1 and BRAF and TBFB-R1), and to the CMGC kinases p38-alpha and -beta. Furthermore, compound C7 (a compound of formula (I) is significantly more potent as an inhibitor for such kinases than the compound B3 (also, a compound of formula (I)). Of particular note, is also that compound C7 is a very potent inhibitor of NEK11 (only 10% residual activity), while such kinase is only moderately inhibited by dasatinib (over 50% residual activity), and is hardly inhibited at all by compound B3 (almost 90% residual activity).

TABLE 3G

Differential pattern of inhibition shown by compound C7 compared to dasatinib (A8) and compound B3

| Kinase Name | Kinase Family | Compound Residual activity (%) at 1 μM | | |
|---|---|---|---|---|
| | | C7 | A8 | B3 |
| ACV-R1 | TKL | 12 | 22 | 48 |
| ACV-R1B | TKL | 1 to 2 | 10 | 41 |
| ACV-R2A | TKL | 2 to 3 | 7 to 8 | 34 |
| BRAF | TKL | 8 to 9 | 15 | 46 |
| JAK1 | TK | 30 | 41 | 107 |
| MAP3K11 | STE | 16 | 49 | 61 |
| NEK11 | Other | 10 | 54 | 89 |
| p38-alpha | CMGC | 3 to 4 | 12 | 38 |
| p38-beta | CMGC | 13 | 25 | 63 |
| RAF1 | TKL | 4 to 5 | 14 | 46 |
| RET | TK | 23 | 39 | 98 |
| TGFB-R1 | TKL | 1 to 2 | 5 to 6 | 28 |

IC50 testing reflects one or more of these (or other) differences, and confirms that, in comparison to PP18T compound A8 (dasatinb) [and/or to compound B3], compound C7 of formula (I) shows a differential profile of inhibitory activity against a number of the above kinases. For example, the IC50 of compound C7 to the kinase TGFB-R1 was determined to be about 490 nM for C7 and 880 nM for A8 (International Centre for Kinase Profiling, Dundee).

Example 4: Inhibition of Abl1 Kinase Mutants by the Kinase Inhibitors of Formula (I) and by Dasatinib The inventors demonstrated that kinase inhibitors of formula (I) (eg C3, C4 and C7, and B3) are also able to inhibit clinically relevant ABL1 mutants, eg, that are associated with CLL resistance to imatinib, a standard of care for CLL (Table 4A). For example, not only are the inhibitors of formula (I) more potent inhibitors of ABL1 wild-type (wt)

than imatinib (2.60 µM vs 1,060 nM), they are also potent inhibitors of all these relevant mutants of ABL (other than T315I), and showing IC50s comparable to A8. Other compounds of formula (I) are similarly tested.

TABLE 4A

Inhibition of Abl 1kinase mutants.

| ABL1 kinase wt/mutant | Kinase Region | Compound: IC50 (µM) | | | | | |
|---|---|---|---|---|---|---|---|
| | | C3 | C4 | C7 | B3 | imatinib | A8 (dasatinib) |
| wt | N/A | 18.3 | 9.20 | 2.13 | 2.60 | 1,060 | 1.70 |
| G250E | P-loop | 101 | 45.6 | 9.16 | 10.2 | 10,600 | 5.78 |
| Q252H | | 29.7 | 15.2 | 3.17 | 3.70 | 1,670 | 2.47 |
| Y253F | | 16.1 | 11.0 | 2.81 | 4.00 | 7,910 | 2.45 |
| E255K | | 111 | 51.6 | 12.5 | 15.3 | 14,500 | 8.88 |
| T315I | ATP | 43,800 | 23,400 | 1,990 | 33,100 | >100,000 | 5,230 |
| F317I | binding site | 823 | 189 | 9.83 | 12.8 | 3,440 | 4.21 |
| M351T | SH2 contact | 37.0 | 19.4 | 2.99 | 4.12 | 3,550 | 3.19 |
| H396P | A-loop | 32.5 | 13.2 | 2.87 | 3.70 | 1,410 | 2.48 |

Briefly, the ABL1 radiometric protein kinase assay as described in Example 1 was conducted, except that the [gamma-33P]-ATP activity was approx. $7 \times 10^5$ cpm per well, and the amount and substrate for each form of the ABL1 kinase was as shown in Table 4B.

TABLE 4B

Assay parameters for the ABL1 mutant protein kinases.

| Kinase Name | Kinase Conc. (ng/50 µL) | Kinase Conc. (nM*) | ATP Conc. (µM) | Substrate | Substrate Conc. (µg/50 µL) |
|---|---|---|---|---|---|
| ABL1 wt | 5 | 1.3 | 0.3 | Poly(Ala, Glu, Lys, Tyr)6:2:5:1 | 0.125 |
| ABL1 G250E | 10 | 2.6 | 0.3 | Poly(Ala, Glu, Lys, Tyr)6:2:5:1 | 0.25 |
| ABL1 Q252H | 10 | 2.6 | 0.3 | Poly(Ala, Glu, Lys, Tyr)6:2:5:1 | 0.125 |
| ABL1 Y253F | 5 | 1.3 | 0.3 | Poly(Ala, Glu, Lys, Tyr)6:2:5:1 | 0.25 |
| ABL1 E255K | 10 | 2.6 | 0.3 | Poly(Ala, Glu, Lys, Tyr)6:2:5:1 | 0.25 |
| ABL1 T315I | 10 | 2.6 | 0.1 | Poly(Ala, Glu, Lys, Tyr)6:2:5:1 | 0.125 |
| ABL1 F317I | 10 | 2.6 | 0.3 | Poly(Ala, Glu, Lys, Tyr)6:2:5:1 | 0.125 |
| ABL1 M351T | 10 | 2.6 | 0.3 | Poly(Ala, Glu, Lys, Tyr)6:2:5:1 | 0.125 |
| ABL1 H396P | 10 | 2.6 | 0.3 | Poly(Ala, Glu, Lys, Tyr)6:2:5:1 | 0.125 |

*Maximal molar enzyme assay concentrations, implying enzyme preparations exclusively containing 100% active enzyme

Example 5.1: Improved ADMET Properties of Kinase Inhibitors of Formula (I)

The inventors demonstrated that kinase inhibitors of formula (I) (eg C2, C4, C8, C9 and C12, and B3) surprisingly showed improved drug-like properties in a number of in-vitro ADMET (absorption, distribution, metabolism, excretion, toxicity) assays, including solubility, stability, plasma-protein binding, CYP450 inhibition and hERG inhibition assays (Tables 5A, 5B, 5C, and 5D). Other compounds of formula (I) are similarly tested For an orally administered drug, dasatinib is a poorly soluble compound, with a measured kinetic solubility of even less than 5 µM. However, kinase inhibitor B3 shows a significantly improved solubility of 82 µM.

In a separate experiment, compounds C2, C4, C7, C8, C9 and C12 of formula (I) were similarly tested, and all (except C7) showed a yet further enhanced kinetic solubility, of between 128 to even 195 µM (for compound C12).

Furthermore, and as described above, dasatinib has an extremely short half-life in humans (an overall mean terminal half-life of only 3-5 hours; section 12.3 "Pharmacokinetics" of the Full Prescribing Information for SPRYCEL). This is reflected in it showing a very short half-life when tested in human (h) and mouse (m) live microsomal (LM) stability assays. In contrast, the kinase inhibitor B3 shows a significantly improved stability in both the hLM and mLM assays, with significantly improved half-life, intrinsic clearance and % of compound remaining after 40 min incubation, with almost a 6-times longer half-life and 10 times more drug remaining at 40 min than dasatinib in the hLM assay.

In a separate experiment, compounds C2, C4, C7, C8, C9 and C12 were similarly tested, and all (except C7) showed improved stability in both human and mouse liver microsomes, with compounds C8, C9 and C12 having a half-life of over 100 min.

Both dasatinib and kinase inhibitors of formula (I) (eg, C2, C4, C8 and C9, and B3) were shown to bind moderately to both human and murine plasma-proteins with certain of the kinase inhibitors of formula (I) (eg, C2, C8 and C9, and B3) showed a marked increase (up to 2 to 5 times) in the amount of free-drug in human plasma (ie, unbound to plasma-proteins, and potentially available for pharmacological activity), than that of unbound dasatinib, and this effect was even more pronounced in murine plasma. Indeed, certain compounds of formula (I) showed very low plasma-protein binding: compound C12 remained over 90% unbound in both human and murine plasma.

Accordingly, kinase inhibitors of formula (I) show, in some cases (eg C2, C8, C9 and C12, and B33), highly improved drug-like properties over dasatinib for these in-vitro ADMET parameters (Table 5A). Other compounds of formula (I), eg one or more of compound D1 to D10, are similarly investigated,

TABLE 5A

Improved solubility and stability of kinase inhibitors, including those of formula (I).

| Assay | Parameter | Compound B3 | Compound A8 |
|---|---|---|---|
| Solubility | Kinetic solubility (µM) | 82 | <5 |
| Human liver microsomal stability | Half-life (min) | 58 | 10 |
|  | Intrinsic clearance (L/min/mg) | 24 | 141 |
|  | % Remaining at 40 min (%) | 60 | 6 |
| Mouse liver microsomal stability | Half-life (min) | 62 | 18 |
|  | Intrinsic clearance (L/min/mg) | 22 | 77 |
|  | % Remaining at 40 min (%) | 63 | 22 |
| Human plasma-protein binding | Percentage unbound (%) | 7 | 2 |
| Murine plasma protein binding | Percentage unbound (%) | 11 | 3 |

| Assay | Parameter | C2 | C4 | C7 | C8 | C9 | C12 |
|---|---|---|---|---|---|---|---|
| Solubility | Kinetic solubility (µM) | 160 | 128 | 13 | 189 | 174 | 195 |
| Human liver microsomal stability | Half-life (min) | >86 | 12 | 5 | >100 | >100 | >100 |
|  | Intrinsic clearance (L/min/mg) | <17 | 115 | 253 | <14 | <14 | <14 |
|  | % Remaining at 40 min (%) | 69 | 10 | 1 | 81 | 89 | 91 |
| Mouse liver microsomal stability | Half-life (min) | 40 | 37 | 12 | >100 | >100 | >100 |
|  | Intrinsic clearance (L/min/mg) | 35 | 38 | 111 | <14 | <14 | <14 |
|  | % Remaining at 40 min (%) | 48 | 45 | 10 | 86 | 83 | 105 |
| Human plasma-protein binding | Percentage unbound (%) | 9 | 2 | <1 | 5 | 6 | >90 |
| Murine plasma protein binding | Percentage unbound (%) | 30 | 14 | 5 | 62 | 44 | >90 |

Solubility and stability testing was conducted by Charles River Inc., at their UK Discovery site (Cambridge, UK), according to their applicable standard operating procedures (ADME-SOP-01 for solubility; AMDE-SOP-100 for microsome stability; AMDE-SOP-90 for plasma-protein binding).

Dasatinib is known to inhibit certain cytochrome P450 (CYP450) enzymes; including those that are involved in its metabolism. Indeed, although dasatinib is metabolised in humans primarily by the cytochrome P450 enzyme 3A4 (CYP3A4), it is also a time-dependent inhibitor of CYP3A4. Indeed, the dosage of dasatinib must be significantly reduced (eg from 100 mg daily to 20 mg daily) if the patient is concomitantly medicated with a strong CYP3A4 inhibitor (see above). However, kinase inhibitor B3 was shown not to significantly inhibit any of the CYP450 enzymes tested, importantly B3 was not an inhibitor of CYP3A4 or of CYP2C8 that is also known to be inhibited by dasatinib (Table 5B).

Other kinase inhibitors of formula (I) (eg, one or more of C1 to C13, and/or of D1 to D10) are tested in the same, similar or analogous assays for CYP450 inhibition.

TABLE 5B

Kinase inhibitor B3 does not inhibit the CYP450 enzymes 2C8 and 3A4.

| CYP450 Enzyme | Compound: IC50 (µM) B3 | A8 (dasatinib)* |
|---|---|---|
| 1A2 | >30 | >50 |
| 2A6 | NT | 35 |
| 2B6 | >30 | >50 |
| 2C8 | >30 | 12 |
| 2C9 | >30 | 50 |
| 2C19 | >30 | >50 |
| 2D6 | >30 | >50 |
| 3A4 (M) | >30 | 18 |
| 3A4 (T) | >30 | 17 |

*Values obtained from page 33, NDA 21-986 Pre-clinical Review for SPRYCEL (dasatinib)

CYP450 inhibition assays (not for A8) were conducted by Charles River Inc, at their UK Discovery site (Cambridge, UK), according to their applicable standard operating procedures (ADME-SOP-97). CYP450 inhibition values for dasatinib are taken from page 33 of the Pre-clinical Review of NDA 21-986 for SPRYCEL (dasatinib).

One "Warning and Precaution" of dasatinib (Full Prescribing Information for SPRYCEL) is that it has the potential to prolong cardiac ventricular repolarization (QT interval). Indeed, it is reported therein: that up to 1% of CML patients in clinical trials experienced a QT prolongation, and cardiac adverse reactions were reported in 5.8% of 258 patients taking dasatinib, including 1.6% of patients with cardiomyopathy, heart failure congestive, diastolic dysfunction, fatal myocardial infarction, and left ventricular dysfunction.

The potential cardiac risks of dasatinib was already recognised during the NDA process, with the Pharmacological/Toxicity Review and Evaluation of NDA 21-986 summarised on page 3 thereof: "Based on the in vitro hERG and rabbit Purkinje fibre assays, dasatinib has the potential to cause QT prolongation", and dasatinib was reported on page 31 therein as inhibiting hERG currents by about 6%, 36% and 77% at 3, 10 and 3 uM respectively, and a calculated IC50 of 14.3 uM.

In stark contrast, as shown in Table 5C, kinase inhibitor B3 essentially shows no hERG liability, generating an IC50 value of greater than or equal to the top concentration tested (30 uM), and at 30 uM inhibited hERG by only 7.7% (+/−1.0%) compared to the reported 76.8% (+/−4.5%) inhibition of hERG at 30 uM dasatinib.

Other kinase inhibitors of formula (I) (eg, one or more of C1 to C13, and/or of D1 to D10) are tested in the same, similar or analogous assays for hERG inhibition.

TABLE 5C

Kinase inhibitor B3 does not inhibit hERFG.

| hERG Assay parameter | Compound | |
|---|---|---|
| | B3 | A8 (dasatinib)* |
| IC50 (µM) | >30 | 14.3 |
| Top concentration tested (µM) | 30 | 30 |
| Inhibition at 30 µM (%) | 7.7 +/− 1.0% | 76.8 +/− 4.5% |

*Values obtained from page 31, NDA 21-986 Pharmacological/Toxicity Review and Evaluation for SPRYCEL hERG inhibition assays (not for A8) were conducted by Charles River Inc., at their UK Discovery site (Cambridge, UK). Briefly, the potential for test compound to inhibit the hERG potassium channel was determined using the Charles River ChanTest® hERG-HEK stably transfected cell line on the Sophion Qube automated electrophysiology platform. The assay was performed at room temperature and recordings of the hERG tail current from individual cells were made using single-hole QChips. The cells were held at a voltage of −80 mV and then stepped to +40 mV for 2 seconds before stepping to −40 mV for a further 2 seconds, this represents 1 experimental sweep. This voltage protocol was applied every 15 seconds for the duration of the experiment. Both the vehicle and 2 nd compound addition periods were applied for 20 sweeps. The 1st compound addition period was applied for 10 sweeps. The potency (IC50) of the test compound to inhibit the hERG channel was determined from a concentration-response curve generated from up to 8 test compound concentrations with up to 4 replicates per concentration. The compound concentration was added to the test well twice to assure complete exchange of the external buffer with the test compound. In total, compound was applied to the well for 450 seconds. Quality control filters used were: whole-cell membrane resistance ≥200 MOhm, and vehicle current amplitude ≥400 pA. The analysis methodology comprised: The peak tail currents evoked by the step to −40 mV were measured for the analysis of the percentage inhibition by test compounds. The peak tail currents were first normalised to the vehicle addition (0.3% DMSO) in the same well. The percent inhibition versus Log 10 compound concentration data was plotted and the IC50 determined using a sigmoidal dose response equation. The hERG inhibition values for dasatinib are taken from page 31 of Pharmacological/Toxicity Review and Evaluation of NDA 21-986 for SPRYCEL (dasatinib).

Assays to determine the MDR1-MDCK effective efflux ratio suggested that dasatinib is a substrate for the MDR1 pump and actively from cells that express this efflux pump (effective efflux ratio of 18.3). Although no definitive conclusion can be made on the relative efflux of B3, the compound of formula (I) (effective efflux ratio of >9.6) because of the limit of detection of the compound in the A>B direction in the MDCK-MDR1 cells, there is an indication that kinase inhibitor B3 shows significantly different parameters in this assay compared to dasatinib (Table 5D).

Other kinase inhibitors of formula (I) (eg, one or more of C1 to C13, and/or of D1 to D10) are tested in the same, similar or analogous assays for MDR1-MDCK effective efflux ratio.

TABLE 5D

Mean efflux ratios in MDCK wild type and MDCK-MDR1 cells.

| Assay | Parameter | Compound | |
|---|---|---|---|
| | | B3 | A8 (dasatinib) |
| MDCK-wild type cells | Mean Papp A > B ($10^{-6}$ cm/s) | 6.8 | 21 |
| | Mean Papp B > B ($10^{-6}$ cm/s) | 20 | 49 |
| | Mean recovery A > B (%) | 103 | 100 |
| | Mean recovery B > A (%) | 120 | 107 |
| | Mean Efflux Ratio (wt) | 2.9 | 2.4 |
| MDCK-MDR1 cells | Mean Papp A > B ($10^{-6}$ cm/s) | <0.8 | 2.4 |
| | Mean Papp B > B ($10^{-6}$ cm/s) | 20 | 105 |
| | Mean recovery A > B (%) | 93 | 94 |
| | Mean recovery B > A (%) | 103 | 117 |
| | Mean Efflux Ratio (MDR1) | >27 | 43.4 |
| Effective efflux ratio (MDR1/wt) | | >9.6 | 18.3 |

The MDR1-MDCK effective efflux assay was conducted by Charles River Inc, at their UK Discovery site (Cambridge, UK), according to their applicable standard operating procedures (ADME-SOP-56).

Example 5.2: Pharmacokinetic and Tolerability Studies of Kinase Inhibitors Disclosed Herein The inventors were surprised to observe that although compound C7 (a compound of formula I) exhibited less favourable in-vitro ADMET properties compared to dasatinib or compound B3 (also a compound of formula I), when tested in-vivo, compound C7 showed substantially improved pharmacokinetic properties compared to compound B3 (and also a suitable pharmacokinetic profile with reference to dasatinib). For example, Table 5A (Example 5.1) shows that compound C7 had decreased metabolic stability when tested in-vitro with human or mouse liver microsomes, and higher binding to human and mouse plasma proteins, in each case compared to dasatinib (and also to compound B3). Yet, when tested in-vivo, compound C7 exhibited drug metabolism and pharmacokinetic (DMPK) properties that were significantly improved over the structurally related compound B3 (Table 5.2A).

The inventors were also surprised to observe that the suitable pharmacokinetic properties of compound C7 were yet distinct compared to dasatinib (A8), and this provides new opportunities to dose this active compound C7 compared to those opportunities using dasatinib. For example, after oral administration compound C7 showed similar half-life and bioavailability as dasatinib, yet displayed a higher clearance and about ⅓ of the AUC of dasatinib (Table 5.2A).

It is well known that dosage regimens, especially in combination (order and timing thereof) with other therapeutics, form the basis of many important and successful anti-cancer therapies. Accordingly, to have a compound such as C7—having similar kinase activity to dasatinib, yet a different pharmacokinetic profile—enables the design, research and (clinical) testing of new and (potentially) therapeutically effective treatment regimens for the treatment of cancer.

In particular, it has recently been shown that dasatinib can act as a pharmacological on/off switch for CAR T cells (Mestermann et al 2019, Sci Transl Med 11: eaau5907).

CAR T cells are administered as a single-shot "living drug" treatment. They are able to persist in patients for several years and to undergo sequential expansion, contraction, and re-expansion in vivo upon (re-)exposure to antigen, and as a consequence, CAR T cell therapy has been associated with substantial acute and chronic side effects that have restricted clinical utilisation to medically fit patients at highly specialised cancer center. The most common acute toxicity associated with CAR T cell therapy is cytokine release syndrome (CRS), which is triggered by release of inflammatory cytokines from CAR T cells and, subsequently, from innate immune cells that produce the key CRS cytokine interleukin 6 (IL-6). Mestermann showed that treatment with dasatinib halted cytolytic activity, cytokine production, and proliferation of CAR T cells in vitro and in vivo. The dose of dasatinib could be titrated to achieve partial or complete inhibition of CAR T cell function. Upon discontinuation of dasatinib, the inhibitory effect was rapidly and completely reversed, and CAR T cells resumed their antitumor function. As a kinase inhibitor with an analogous inhibitory profile yet different pharmacodynamic attributes to dasatinib, compound C7 could be exploited to steer the activity of CAR T cells in "function-on-off-on" sequences in real time, and at a different resolution of timing than that for dasatinib. By further (pre- and clinical) testing, it would be determined which dosage of compound C7 would be efficacious for such CAR T cell "function switching" effect; and this dosage could be very different (eg lower) than the dosage required for C7 for tumour growth inhibition in a monotherapy setting (and associated modification of the immune response) such as that shown by Example 8.

dose of 30 mg/kg po (per os) administered mice can be determined for certain time points after administrations (Table 5.2B).

TABLE 5.2B

Screening PK-properties of certain kinase inhibitors of formula (I) compared to dasatinib and B3.

| Compound | Free concentration (nM) at timepoint after 30 mg/kg po | | | | |
|---|---|---|---|---|---|
| | 2 hours | 6 hours | 7 hours | 12 hours | 24 hours |
| C7 | 32 | NT | 3 | NT | 0.10 |
| A8 (dasatinib) | 30 | NT | 60 | NT | 0.14 |
| B3 | 13 | NT | 3 | NT | ND |
| D1 | 80 | 4 | NT | 2.14 | NT |
| D7 | 43 | 5 | NT | 1.10 | NT |
| D9 | 44 | 8 | NT | 2.71 | NT |

ND = not determinable

Maximal tolerable dose (MTD) of compound C7 was investigated by once (QD) or twice daily (BID) administration of different concentrations (33 and 100 mg/kg) of C7 by gavage in female C57Bl/6 mice for 7 consecutive days. Compound C7 was diluted in 4% (v/v) DMSO, 72% (v/v) propylene glycol+24% (v/v) dd-water. Compound C7 was tolerable up to 100 mg/kg BID in female C57BL/6 animals for seven days. Compound C7 was safe and did not show any signs of intolerance (posture, vocalization, ease of handling, lacrimation, chromodacryorrhea, salivation, intact fur/coat, rearing, arousal, piloerection, normal motor movements, tail pinch, diarrhoea). A minor reduction in body

TABLE 5.2A

DMPK properties of compound C7 compared to dasatinib and B3.

| DMPK Parameter | Compound | | | | | |
|---|---|---|---|---|---|---|
| | C7 | | A8 (dasatinib) | | B3 | |
| Dose: | 1 mg/kg iv | 30 mg/kg po | 1 mg/kg iv | 30 mg/kg po | 1 mg/kg iv | 30 mg/kg po |
| $C_{max}$ (nM): | 603 | 702 | 1,285 | 1,127 | 1,234 | 202 |
| $T_{max}$ (h): | 0.08 | 2.0 | 0.08 | 2.0 | 0.083 | 0.5 |
| $t_{1/2}$ (h): | 1.2 | 3.3 | 1.9 | 3.0 | 0.2 | 2.4 |
| $AUC_{last}$ (nM*h): | 340 | 2,328 | 1,020 | 6,465 | 437 | 589 |
| $AUC_{inf}$ (nM*h): | 360 | 2,337 | 1,065 | 6,487 | 450 | 687 |
| % $AUC_{extrap}$: | 5.81 | 0.45 | 4 | 0.3 | 3 | 14 |
| $MRT_{last}$ (h): | 0.7 | | 1.3 | | 0.25 | |
| $MRT_{inf}$ (h): | 1.0 | | 1.6 | | 0.29 | |
| Vss (L/kg): | 5.4 | | 3.1 | | 1.31 | |
| CL (mL/min/kg): | 94 | | 32 | | 75 | |
| F (%): | | 23 | | 21 | | 4 |

Pharmacokinetic characteristics of C7, B3 and A8 were investigated after single administration of each compound per gavage in male CD1 mice (Charles River hc, UK Discovery site). The compounds were diluted in a propylene glycol:water 1:1 mixture (v:v). Plasma level (sampling 0.25 h; 0.5 h; 1 h; 1.5 h; 2 h; 4 h; 7 h; 24 h after drug administration) of C7, A8 and B3 were analysed by LC-MS/MS and pharmacokinetic parameters were determined using non-compartmental analysis and nominal dose levels of 30 mg/kg. Three animals were analysed per time point and each mouse was used for three plasma samplings in total.

Figure 10:
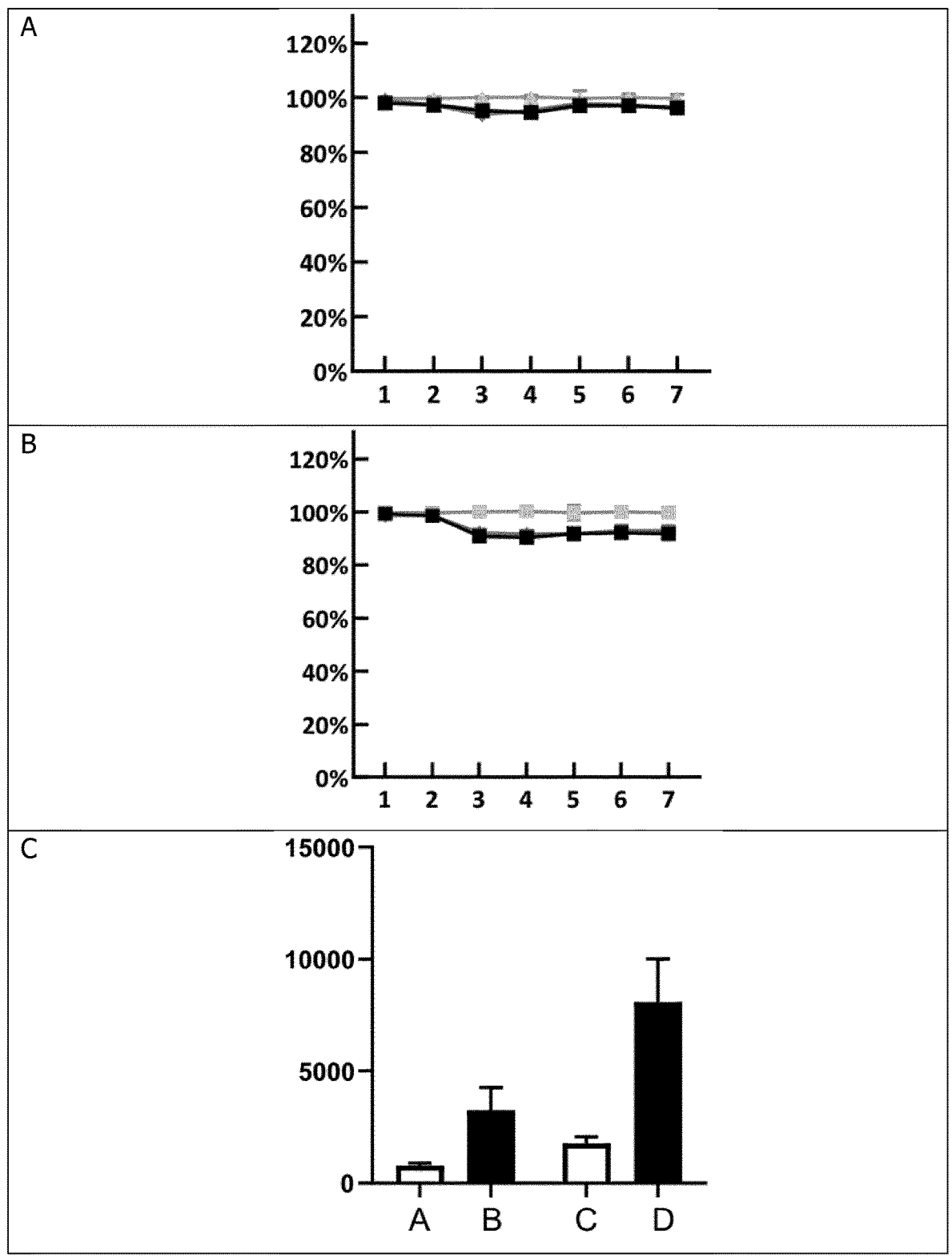
FIG. 10: depicts body weight of female C57 Bl/6 mice after once daily (QD=A) and twice daily (BID=B) administration of different concentrations 33 mg/kg (black squares) and 100 mg/kg (grey diamonds) of C7 by gavage, compared to control animals (grey squares). X-axes: days after administration; Y-axes Bodyweight change (%). (C) Plasma-level of C7 measured by LC-MS/MS. A=33 mg/kg QD; B=100 mg/kg QD; C=33 mg/kg BID; D=100 mg/kg BID. Y-axis: Plasma concentration of C7 (nM).

DMPK properties of other kinase inhibitors of the invention (eg, those from Table B, D1 to D10) are similarly tested, and can be compared to those of C7, A8 (dasatinib) and B3. For example, the free concentration of compound after a weight was observed in all dosing groups compared to non-treated control animals, which was caused by the plasma sampling on day 2 (FIGS. 10A and B). Plasma-level of C7 were measured by LC-MS/MS and showed a dose-dependent increase in plasma concentration (FIG. 10C).

Example 6: In-Vitro Cell-Based Anti-Cancer and Anti-Leukaemia Efficacy of Kinase Inhibitors Kinase inhibitors of formula (I) (eg, one or more of C1 to C13, or B3, and/or of D1 to D10) are tested for anti-cancer activity in one or more cell-based assays, and their activity in such assay(s) is compared to dasatinib (A8) to determine its differentiation and/or superiority.

In one method, the direct cytotoxic effects of one or more of such compounds is tested on solid tumour cell lines in vitro using with the CellTiter-Glo® (CTG) Luminescent Cell Viability Assay (Promega, Cat. G7570). Tumour cells such as MDA-MB-231 (breast cancer), M579 primary melanoma cultures (as described in Khandelwal et al, 2015, EMBO Mol Med 7:540), PANC-1 (pancreatic cancer), SW480 (colorectal cancer), DMS273 (lung cancer) or murine tumour cell lines such as B16.ova, MC38, 4T1, and 1956 etc. are incubated (37° C./5% C02) in wells of a microtitre plate with dasatinib (A8) or a kinase inhibitor of formula (I) (eg, C2, C8, C9 or C12, or B3, and/or one or more of D1 to D10) in a concentration series (eg, at 0, 1, 10, 100, 1,000, and 10,000 nM) for 48 hours. The protein-tyrosine kinase inhibitor (TKI)-susceptible K562 cell line is used as a control with 100 nM dasatinib. Viable cells are determined by adding 100 uL of CTG reagent to the wells and incubating at room temperature for 10 min before luminescence readout using a Tecan Spark 10M luminometer.

Indeed compound C7 was tested for its anticancer activity across a cell-panel representing a large number of haematological cancers and cell-lines (Oncolead, Karlsfeld Germany), and was found to inhibit the growth of numerous of such cell lines; showing a, sub-nanomolar GI50 activity on about 5 such cell lines and a GI50 activity of less than 10 nM on about an further 10 such cell lines. For example, after 96 hours compound C7 showed a GI50 of about 8 nM on the growth of the WSU-NKL B cell lymphoma cell line (FIG. 15A), and a GI50 of about 9 nM on the growth of the DIHH-2 B cell lymphoma cell line (FIG. 15B). Other kinase inhibitors of formula (I) (eg, one or more of C1 to C13, or B3, and/or of D1 to D10) are similarly investigated.

In an additional or alternative method, the anti-leukaemia activity of one or more of such compounds is tested, in particular in one or more cell-line(s) driven by BCR-ABL or mutants thereof (such as described by Gibbons et al 2014, PNAS 111:3550). Gene constructs for wild-type (wt) and T315I mutant Bcr-Abl (C-terminally tagged with eGFP) are constructed as previously described (Donato et al 2004, Cancer Res 64:672). The wt or T351I single mutant pMX/eGFP-Bcr-Abl template is used to generate templates for further or double mutants of BCR-ABL that are also associated with resistance to drug therapy with various TKIs of leukaemia (for example, T315I/V299L, T315I/F317L, T315I/F359V, or other mutations listed in Table 6A) by site-directed mutagenesis (Stratagene). Following mutagenesis, the 4-kb XhoI/SgrAI sequence carrying the mutant (or double mutant) is sequenced and subcloned into the pMX/eGFP-BcrAbl template (at XhoI/SgrAI sites) to ensure that no other mutations are introduced during mutagenesis.

TABLE 6A

* BCR-ABL mutations associated with resistance to TKIs and therapeutic options. Complied from studies reporting IC50 values derived using cell-line models.

| BCR-ABL mutation | Drug resistance | Therapeutic options |
|---|---|---|
| Wild type | — | imatinib |
| M244V | | dasatinib |
| Q252H | | nilotinib |
| M315T | | bosutinib |
| F311L | | |
| L387M | | |
| H396P | | |
| G250E | imatinib | dasatinib |
| F311I | | nilotinib |
| H396R | | bosutinib |
| V299L | dasatinib | nilotinib |
| T315A | bosutinib | imatinib |
| F317L/V/I/C | | |
| Y253H/F | imatinib | dasatinib |
| E255K/V | nilotinib | |
| E355G | | |
| V279I | | |
| F359V/C/I | | |
| T315I | imatinib dasatinib nilotinib bosutinib | ponatinib |
| T315M | All TKIs | — |

* Taken from Pophali & Patnik 2016, Canc J 22: 40

Parental Ba/F3 cells (murine IL-3 dependent murine pro B cell line) are maintained in RPMI medium with 10% FBS and 1 ng/mL mouse IL-3. Parental Ba/F3 cells at $2.5 \times 10^6$ are electroporated with 2.5 µg plasmid using the Amaxa Nucleofector system. After electroporation, Ba/F3 cells are rested overnight, and puromycin then added to the medium at a final concentration of 1 µg/mL. Transfected Ba/F3 cells are cultured in the RPMI medium/IL-3/puromycin media for more than a week. To ensure equivalent expression of BCR-ABL1 between wild-type and mutant cells, Ba/F3 cells are sorted by flow cytometry for eGFP positivity. Sorted eGFP-positive Ba/F3 cells are further selected in medium without IL-3. Cell growth rates are confirmed to be equivalent in all BCR-ABL1-transformed cells. Cells maintained in the absence of IL-3 for more than 1 week are used to examine inhibitor activity. For this, cells are incubated for 72 h with the applicable TKIs to determine their effect on growth and survival of BaF3 cells as previously described (Wu et al 2010, Leukemia 24:869); for example by using a concentration series of a kinase inhibitor of formula (I) or dasatinib as described above.

Analogously, the effect of kinase inhibitors of formula (I) (eg, one or more of C1 to C13, or B3, and/or D1 to D10) or dasatinib in leukaemia cell models carrying KIT mutations can be tested. For example, vectors carrying KIT wt or mutations (eg, those associated with drug resistance) can be transfected into transfect FDC-P1 murine bone-marrow cells and the effect of the compounds investigated on proliferation and clonogenic activity of FDC-P1/KIT (wt or mutant) cells, such as based on that described by Liu et al (2010, Cancer Cell 17:333).

Example 7 [Prophetic]: In-Vivo Anti-Leukemic Efficacy of Kinase Inhibitors of Formula (I) and of Dasatinib The in-vivo pharmacological activity of dasatinib, and the experiments used to show it are described in the EMEA's Committee for Medicinal Products for Human Use (CMHP) Scientific Discussion on dasatinib in 2006. In particular, as follows:

The tumour inhibiting activity of dasatinib was evaluated in human CML xenograft models grown subcutaneously (SC) in SCID mice. Cures were defined as the absence of detectable tumour at a time greater than ten times the tumour volume doubling time after the cessation of treatment.

Dasatinib was curative in mice bearing K562 human CML tumours over a range of dose levels (8-50 mg/kg) when administered PO once a day for 10 days using a "5-days-on and 2-days off" treatment regimen. Treatment was initiated when the tumours reached a size of 200 to 500 mg. High doses of imatinib failed to produce a comparative response. The minimum effective dose for dasatinib was determined as 2.5 mg/kg. In addition, dasatinib was highly efficient in this model when administered IV. Dasatinib was curative in mice bearing large KU812 tumours (up to >1 g tumour) when treated with 50 mg/kg/day for 5 days.

The SRC phosphorylation was investigated in peripheral mononuclear cell (PBMCs) collected from human prostate cancer cell (PC-3) bearing mice administered 1, 5, 15 or 50 mg/kg dasatinib. Dasatinib treatment resulted in a dose-dependent inhibition of SRC phosphorylation with an almost complete inhibition within 5 hours following administration of 15 and 50 mg/kg. Administration of 5 mg/kg resulted in 44% inhibition of SRC phosphorylation whereas 1 mg/kg was almost inactive. Based on AUC 0-24 h values, the animal:human plasma exposure ratios were 0.8 and 1.9 for the 5 mg/kg and 15 mg/kg dose groups, respectively. Based on pharmacokinetic data it was estimated that the dasatinib plasma concentration required to inhibit 50% of phospho-SRC was 91 nM in PBMCs.

Dasatinib treatment (10 mg/kg/day) increased survival in mice inoculated intracranially with K562 CML cells and the survival efficacy was superior to what was observed with imatinib (300 mg/kg/day). In a similar study, increased survival was observed following treatment with 10 and 30 mg/kg/day dasatinib whereas 200 mg/kg/day imatinib failed to inhibit intracranial tumour growth. Thus dasatinib appears to have a therapeutic advantage over imatinib in the treatment of intracranial CML.

Dasatinib was active against a human CML model in mice whether treatment was administered daily for ten consecutive days or if a short treatment break (5-days-on and 2-days off) was introduced into the dosing regimen. Moreover, a twice-daily dosing regimen produced efficacy that was superior to the once daily dosing regimen. Consequently, in mice bearing K562 human CML tumours, a superior anti-tumour activity (cure) was observed in the twice-daily 1.25 mg/kg dose group when compared to the dose group administered 2.5 mg/kg dasatinib on a once-daily schedule (growth inhibition).

One or more kinase inhibitor of formula (I) (eg, C1 to C13, or B3, and/or D1 to D10) is tested in one or more of such investigations (for example, at doses of 1, 1.25, 2.5, 5, 10, 25, 30 or 50 mg/Kg/day) to determine its differentiation and/or superiority in comparison to dasatinib (A8); in particular, one or more of C2, C8, C9 or C12, or B3 are so tested.

In addition or alternatively, one or more of such compounds are compared in the animal model described by Puttini et al (2006, Cancer Res 66: 11314), briefly as follows:

Five- to 7-week-old female CD1 nu/nu mice are purchased from Charles River Breeding Laboratories and kept under standard laboratory conditions. Human KU812Bcr-Abl+ cells are suspended at 50 million cells in 0.5 mL PBS and this cell suspension injected s.c. in the left flank of each animal. In another group of mice, murine Ba/F3 pro-B cells expressing Bcr-Abl WT or imatinib-resistant point mutants (Y253F, E255K, D276G, and T315I) are suspended at 10 million cells in 0.4 mL PBS and injected s.c. to syngeneic nude mice. Tumour weight and body weight are monitored twice or thrice weekly. Tumour weight is calculated by the formula tumour weight (mg)=(d2 D/2), where d and D are the shortest and longest diameters of the tumour, respectively, measured in millimetres. Tumour weight is calculated considering tumour-bearing animals only. Dasatinib (A8), or a kinase inhibitor of formula (I) (eg, C2, C8, C9 or C12, or B3), is given by oral gavage from day after cell infusion (for example, at doses of 1.25, 2.5, 5, 10, 30 or 50 mg/Kg/day), at 8 days after cell injection when tumours entered growth phase or at 15 days to mice bearing measurable tumours. Placebo-treated animals received the same regimen with vehicle alone.

As a further additional or alternative method, one or more of such compounds are compared in the animal model described by Fauvel et al (2013, Am J Can Sci 2:28), briefly as follows:

A xenograft mouse model of imatinib-resistant leukemia is prepared by subcutaneously injecting Ba/F3 BCR-ABLT315I ($1 \times 10^8$ cell/mL sterile PBS) into the right flank of athymic nude male mice (HSD, 6-7 weeks old). When the tumour volume reaches approximately 50 mm3, mice are assigned randomly to vehicle alone or treatment (dasatinib or compound B3) groups (five mice per group). Mice are treated with either vehicle (eg., DMSO or propylene glycol:water 1:1) or compounds (eg, 5, 10 or 40 mg/kg q.d.; per os for 11 consecutive days) in vehicle. Tumour volumes in $mm^3$ are determined three times a week with a digital calliper and calculated using the following formula: Tumour Volume ($mm^3$)=length (mm)×width (mm)×width (mm)×½. Body weight is measured three times a week, and mice observed daily for monitoring signs of stress to detect possible toxicities. One-way ANOVA is used for statistical comparisons using Prism 5.0b (GraphPad Software) by one-way ANOVA with Bonferroni post hoc.

Example 8: In-Vivo Anti-Cancer (Solid Tumour) Efficacy of Kinase Inhibitors of Formula (I) and of Dasatinib The anti-cancer activity of kinase inhibitors of formula (I) (eg, C1 to C13, or B3) and of dasatinib (A8) against solid tumours are investigated in an in vivo syngeneic mouse model, whereby murine colorectal carcinoma cells MC38 are implanted subcutaneously in the flanks of C57Bl/6N mice and treated with the test compound (eg, C2, C8, C9 or C12, or B3 or A8, at doses of between eg 2.5 mg/mL/day up to 50, 60 or 100 mg/Kg/day*). In detail, female C57Bl/6N mice (4-6 weeks old), are implanted with of $1 \times 10^6$ MC38 colorectal carcinoma cells (100 μl in PBS). Mice are randomised into treatment groups after reaching 150 $mm^3$ tumour volume, and treatment groups may, for example, comprise those as set forth in Table 8A, with treatment starting within 24 h of randomisation.

TABLE 8A

Example treatment groups.

| Group | Treatment | Total daily dose [mg/kg/d] | Dosing days | Route** | Vehicle | Number of mice |
|---|---|---|---|---|---|---|
| 1 | Vehicle | — | daily | po | — | 15 |
| 2 | B3 | 60 mg/Kg*# | daily# | po | Vehicle** | 15 |
| 2 | B3 | 30 mg/Kg* | daily | po | Vehicle** | 15 |
| 3 | A8 (dasatinib) | 30 mg/Kg* | daily | po | Vehicle** | 15 |

*Based on last body weight measurement;
**po = per os, oral administration via gavage
For at least 3 weeks, up to about 5-8 weeks. Lower dosage (eg, 10, 15 or 20 mg/Kg) for C2, C8, C9 and C12 can be adapted according to their ADMET/PK properties.
**Propylene glycol:water 1:1

Mice are measured for body weight and tumour volume (mm$^3$) by calliper measurement twice weekly for up to 8 weeks until termination criteria (tumour volume>2000 mm$^3$) is reached.

Additionally, 5 mice per group are sacrificed after day 9 of first treatment to analyse tumour and blood samples for various immune-response markers, for example those set forth in Table 8B below, (as well as using Aqua Zombie (BioLegend) to determine live/dead cells).

Briefly, peripheral blood samples are collected (however, the day before sacrifice) from these mice into heparin-precoated tubes by making an incision in the tail of the mice. After treating the blood samples with ammonium-chloride-potassium (ACK) lysing buffer (Life Technologies, Cat. A10492-01), the cells are stained with fluorochrome-conjugated mAbs to one or more of the example immune-phenotyping markers (eg, Table 8B).

For immune-phenotyping of the tumours, tumours are surgically removed on the day of sacrifice with a scalpel and then divided in half. One part of the tumour is fixed in 4% paraformaldehyde (PFA) for immunohistochemistry for one or more of the example immune-phenotype markers. For IHC, PFA-fixed tumor tissues are embedded into paraffin blocks and cut at 4 mm thickness. After fixing on glass slides and antigen-retrieval step, the sections are stained with anti-CD8 antibody and counterstained with Mayer-Hematoxylin. The counting of the tumour infiltrating CD8 T cells is done at 50× magnification starting from capsule area and counting 3 fields toward to the core of the tissue. The same process was repeated 3 times. All counts were summed, and the median calculated (as described in Hekim et al 2017, Can Imm Res 5:157).

The other half of the tumour is transferred into 1.5-mL tubes containing RPMI 1640 medium and then homogenized manually using micro tube pellet pestle. After centrifugation at 300×g, the supernatant was discarded, and cells were resuspended in RPMI medium equal to the tumour weight. Tumour homogenate is diluted 1:1 in PBS and stained with fluorochrome-labelled antibodies for one or more of the example immune-phenotype markers. For all Foxp3-specific staining (peripheral or intra-tumoural), cells are first labelled with the anti-CD4 antibody before incubation with the anti-Foxp3 antibody using an Intracellular Fixation and Permeabilization Kit as recommended by the manufacturer (eBioscience)

TABLE 8B

Example immune-phenotype markers.

| Marker | Antibody clone | Supplier |
|---|---|---|
| Populations: T-cells, CD4+ T cells, CD8+ T-cells, Tregs: | | |
| CD45 | 30-F11 | Biolegend |
| CD3e | 145-2C11 | BD Biosciences |
| CD4 | RM4-5 | BD Biosciences |
| CD8 | 53-6.7 | BD Biosciences |
| CD25 | PC61 | BD Biosciences |
| FOXP3 | FJK-16s | Thermo Fisher (eBioscience) |
| IFN-g | XMG1.2 | Biolegend |
| Granzyme B | NGZB | Thermo Fisher (eBioscience) |
| CD107a | 1D4B | Biolegend |
| CD69 | H1.2F3 | BD Biosciences |
| Populations: M1 macrophages, M2 macrophages, monocytic MDSC's, granulocytic MDSC's, NK cells: | | |
| CD45 | 30-F11 | Biolegend |
| CD3e | 500A2 | BD Biosciences |
| CD11b | M1/70 | BD Biosciences |
| F4/80 | BM8 | ThermoFisher |
| CD206 | MR6F3 | ThermoFisher |
| LY6G | M1/70 | BD Biosciences |
| LY6C | AL-21 | BD Biosciences |
| CD49b | DX5 | BD Biosciences |
| CD335 | 29A1.4 | BD Biosciences |

The inventors demonstrated both the anti-cancer activity of kinase inhibitor C7, compared to dasatinib (A8), against solid tumours in an in vivo syngeneic mouse model, as well as the immune-oncology effect of this compound of formula (I). Dosage and administration regimens for the compounds of formula (I) (eg, C7) are adapted according to their respective SIK3 kinase inhibition and DMPK properties (see previous examples), such that their plasma free-drug concentration in relation to their SIK3 IC50 value was comparable to that for dasatinib. Compound A8 (dasatinib) was treated as previously described (Hekim et al 2017). One or more other kinase inhibitor of formula (I) (eg, C1 to C13, or B3, and/or D1 to D10) are analogously investigated.

Figure 11:
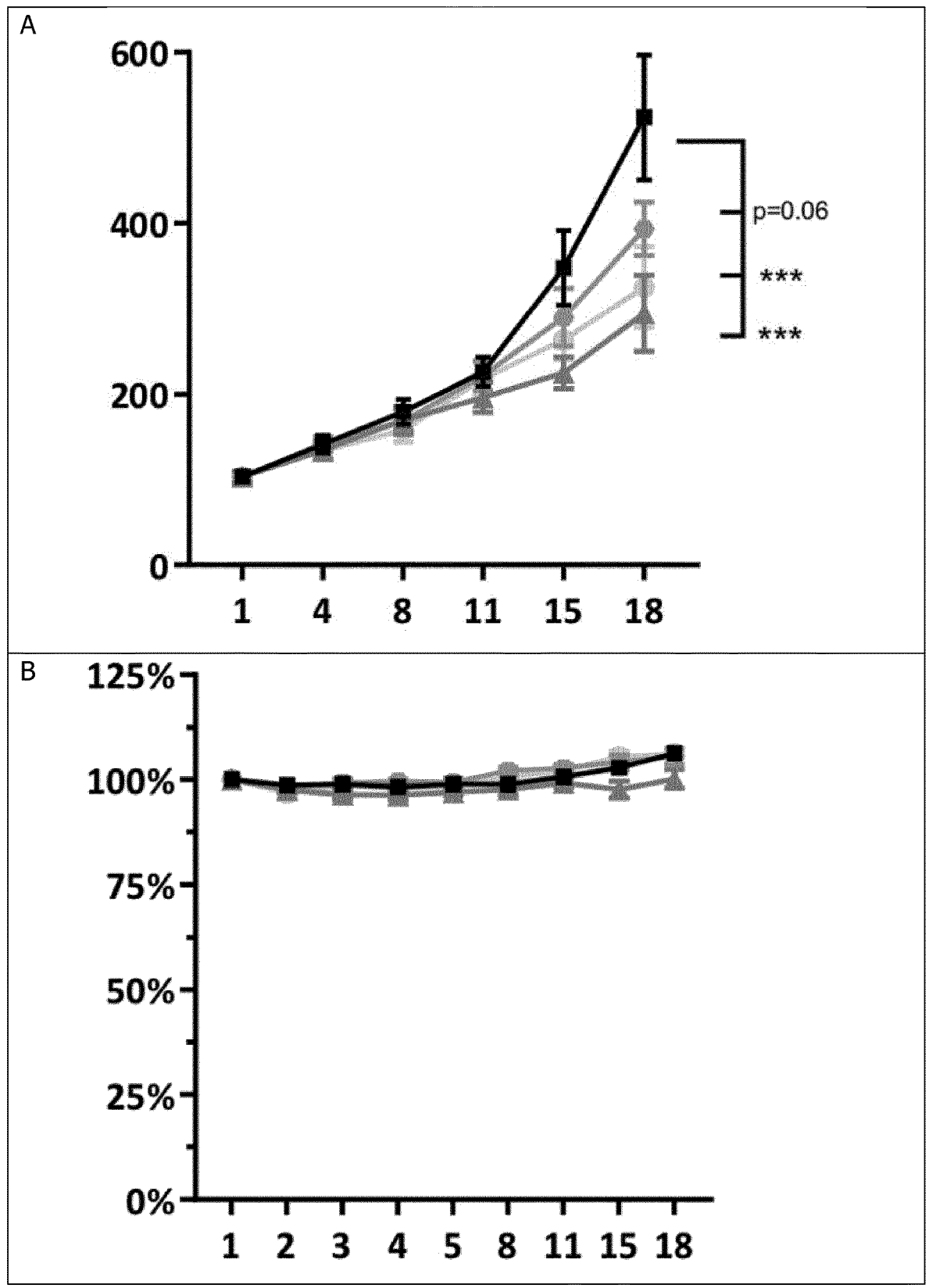
FIG. 11: depicts (A) tumour growth kinetics in a mice implanted with MC38 cells upon treatment with vehicle (black squares), C7100 mg/kg QD (grey hexagons), C7100 mg/kg BID (grey triangles) and A8 (dasatinib) 30 mg/kg QD A8 (grey circles); Y-axis=Mean tumour volume (mm3). Error bars SEM. X-axes: Days. Statistical significance was calculated with two-way ANOVA analysis including Tukey's multiple comparison analysis. ***p<0.001; (B) Body weight kinetics of the mice in (A). Y-axis: Mean body weight change (%).

Twice daily treatment with C7 (100 mg/kg) demonstrated significant tumour growth retardation (44% TGI) whereas once daily C7 treatment showed 29% tumour growth inhibition compared to vehicle control (FIG. 11A). In comparison, daily treatment with A8 (30 mg/kg) demonstrated a tumour growth inhibition of 38%. Animals were weighed at least twice per week until completion of the study. No treatment related side effects and clinical signs, such as loss of body weight were observed (FIG. 11B).

Figure 12:
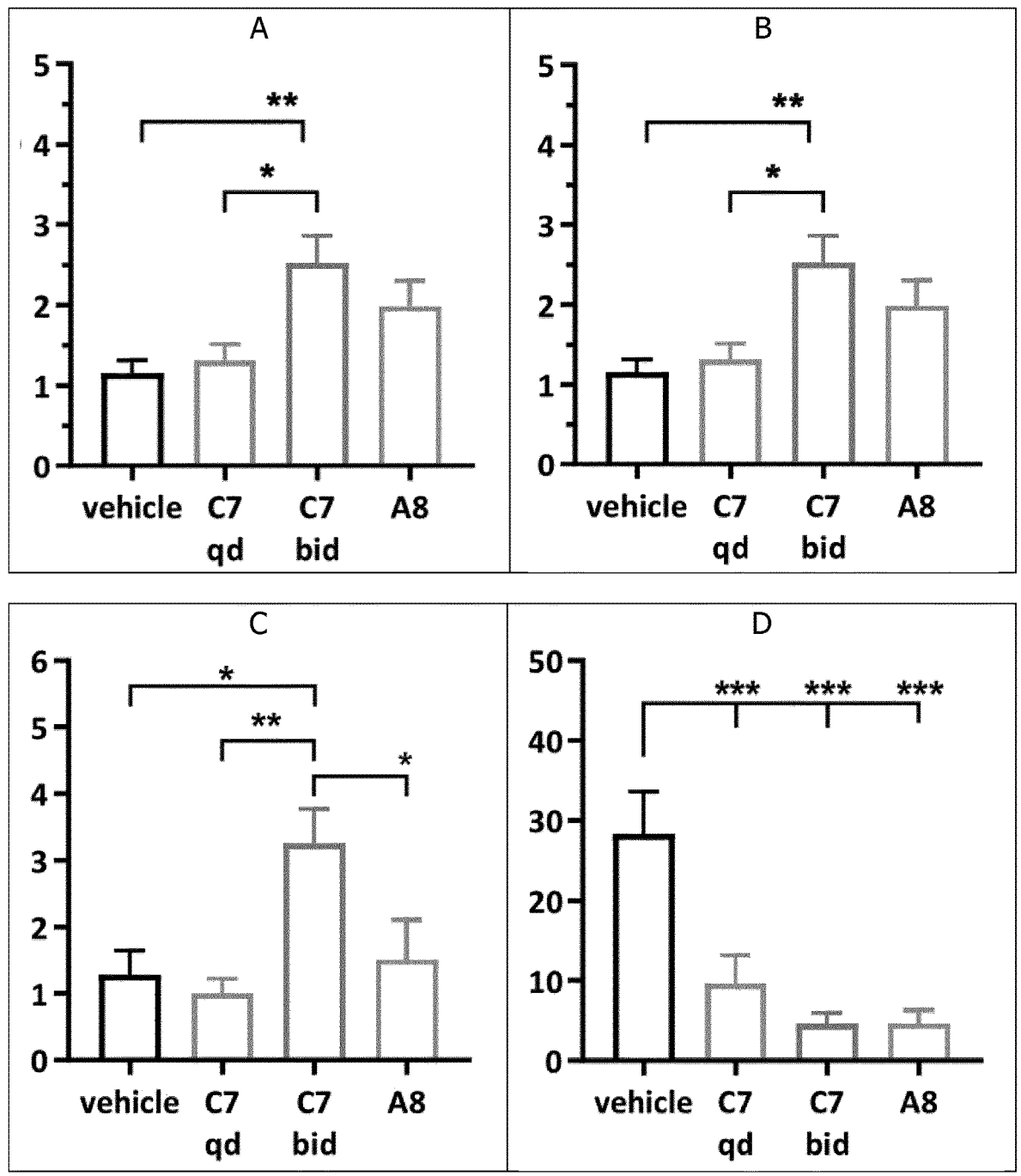
FIG. 12: depicts an immuno-oncology effect of C7, a compound of formula (I), upon immune cells present in the tumour microenvironment. Intra-tumoural immune infiltrate was calculated as the percentage of intra-tumoural CD45+ cells. Statistical significance was calculated with one-way ANOVA analysis including Tukey's multiple comparison analysis. (A) Y-axis: Ratio of CTL to Treg cells. (B) Activated CTLs (CD25+CD69+); Y-axis: % of CD45+ cells. (C) Activated CTLs (granzyme B+); Y-axis: % of CD45+ cells. (D) Immunosuppressive M2-like tumour-associated macrophages (TAMs) (CD206+MHC-II+); Y-axis: % of CD45+ cells; *p<0.05; p<0.01; *p<0.00.

In addition, compound C7 was demonstrated to have a significant effect on the immune cells present in the tumour microenvironment (FIG. 12). Twice daily treatment with C7 induced a prominent anti-tumour immune-phenotype; with significantly increased ratio (FIG. 12A) of cytotoxic T lymphocytes (CD3+CD8+) to regulatory T cells (CD3+CD4+CD25+FoxP3+), as well as increased activation of cytotoxic T lymphocytes indicated by CD25+CD69+(FIG. 12B) and granzyme B (FIG. 12C) expression. In addition, immunosuppressive M2 macrophages (CD206+MHC-II+) were significantly reduced by once and twice daily treatment with C7 as well as A8 (FIG. 12D).

The in vivo syngeneic mouse model was conducted as follows: female C57Bl/6N mice (4-6 weeks old), were implanted with of 5×10e5 MC38 colorectal carcinoma cells (100 ul in PBS). Mice were distributed into treatment groups (Table 8C) to reach an average tumour volume of 100 mm$^3$, and per-oral treatment by gavage was started within 24 h of randomisation.

TABLE 8C

Treatment groups.

| Group | Treatment | Dose* | Dosing | Route | Number doses | Animals |
|---|---|---|---|---|---|---|
| 1 | PBS | 10 ml/kg | QD x 18 | **p.o | 18 | 10 |
| 2 | vehicle# | 10 ml/kg | QD x 18 | p.o | 18 | 10 |
| 3 | Dasatinib | 30 mg/kg | QD x 18 | p.o | 18 | 10 |
| 4 | C7 | 100 mg/kg | QD x 18 | p.o | 18 | 10 |
| 5 | C7 | 100 mg/kg | BID x 18 | p.o | 36 | 10 |

*Based on last bodyweight measurement;
**p.o. = per os, oral administration via gavage;
4%(v/v) DMSO, 72%(v/v) propylene glycol and 24%(v/v) dd-water On Day 18, two hours after the last dose, at least 100 uL of whole blood, as well as tumour tissue, of six animals in each group were analysed by flow cytometry for CD4+ and CD8+ T cells, Tregs, granulocytic and monocytic MDSCs, M1 and M2 macrophages and NK cells. Immediately following blood collection, tumours were excised and processed for analysis by flow cytometry. Tumour and blood samples were analysed for various immune-response markers (Table 8D), as well as using a Zombie dye (BioLegend) to determine live/dead cells. Intracellular cytokines within the lymphoid panel were detected after ex vivo stimulation of T cells with PMA/ionomycin/Brefeldin A.

TABLE 8D

Immune-phenotype markers.

| T cell panel | | Myeloid cell panel | |
|---|---|---|---|
| Target | Clone | Target | Clone |
| CD45 | 30-F11 | CD45 | 30-F11 |
| CD3e | 145-2C11 | CD3e | 145-2C11 |
| CD4 | RM4-5 | CD11b | M1/70 |
| CD8 | 53-6.7 | F4/80 | BM8 |
| CD25 | PC61 | Ly6C | AL-21 |
| FoxP3 | FJK-16s | Ly6G | 1A8 |
| IFNy | XMG1.2 | CD206 | C068C2 |
| GrzB | NGZB | MHC-II | 10-3.6 |
| CD69 | H1.2F3 | CD49b | DX5 |
| CD107a | 1D4B | CD335 | 29A1.4 |
| Live/dead | (Zombie Dye) | Live/dead | (Zombie Dye) |

Sample preparation for flow cytometry was conducted as follows: whole blood samples were processed by adding a ten-fold volume of ammonium-chloridepotassium (ACK) buffer at ambient temperature, mixed gently and incubated for 3-5 minutes at room temperature. Immediately after incubation, a ten-fold volume of cold PBS was added to stop the lysis reaction, and cells were pelleted at 400 g for five minutes and washed again in PBS. Mouse tumour samples were dissociated according to the manufacturer's instructions using the gentleMACS™ protocol "Tumor Dissociation Kit". Briefly, tumours were excised, cut into small pieces (2-4 mm), placed into an enzymatic buffer and processed on a gentleMACS Dissociator, incubated for 20 minutes at 37° C. with continuous rotation. Samples were filtered through a 70 um cell strainer and rinsed twice in PBS/2.5% FBS buffer to remove enzymatic buffer. All single cell suspensions were prepared at ~1×10e7 cells/mL in PBS and kept on ice. Ex vivo stimulation of samples was performed for T-cell marker-panel populations with PMA/ionomycin/Brefeldin A. 100 uL of single cell suspensions were added into 96-well plates, stained, and analysed with an LSRFortessa™ (BD) and analysed with FlowJo software (Tree Star, Inc.; version 10.0.7r2).

Example 9: Sensitisation of Tumour Cells to In-Vitro TNF Attack by the Kinase Inhibitor of Formula (I) and of Dasatinib The inventors investigated the effect of the kinase inhibitors of formula (I) (eg C2, C8, C9 or C12, or C4, or C7 or B3; or in particular, C7; and/or one or more of D1 to D10), and dasatinib (A8) in comparison, on the killing (apoptotic/cytoxic) effect of TNF to tumour cells in vitro, and determined the sensitisation—by the kinase inhibitor of formula (I)—of a modified PANC1 or M579-A2 cell-line to TNF attack. Other compounds of formula (I), such as C5, are similarly tested.

Treatment with the kinase inhibitor (eg, C7 or B3) (tested at one or more concentrations of, for example, between about 1 nM to 10,000 nM, such as about 10 nM, 25 nM, 50 nM, 100 nM, 150 nM, 500 nM, 1,000 nM, 2,500 nM and/or 5,000 nM in DMSO) is used to investigate sensitisation of PANC-1-luc or M579-A2-luc tumour cells to the cytotoxic effects of recombinant human TNF (rHuTNF; R&D Systems), and also the speed of onset of this effect. PANC1-luc is an HLA-A2.1+ luciferase-expressing pancreatic adenocarcinoma (PDAC) tumour cell line, and M579-A2-luc is an HLA-A2.1+ luciferase-expressing melanoma tumour cell line.

Figure 6:
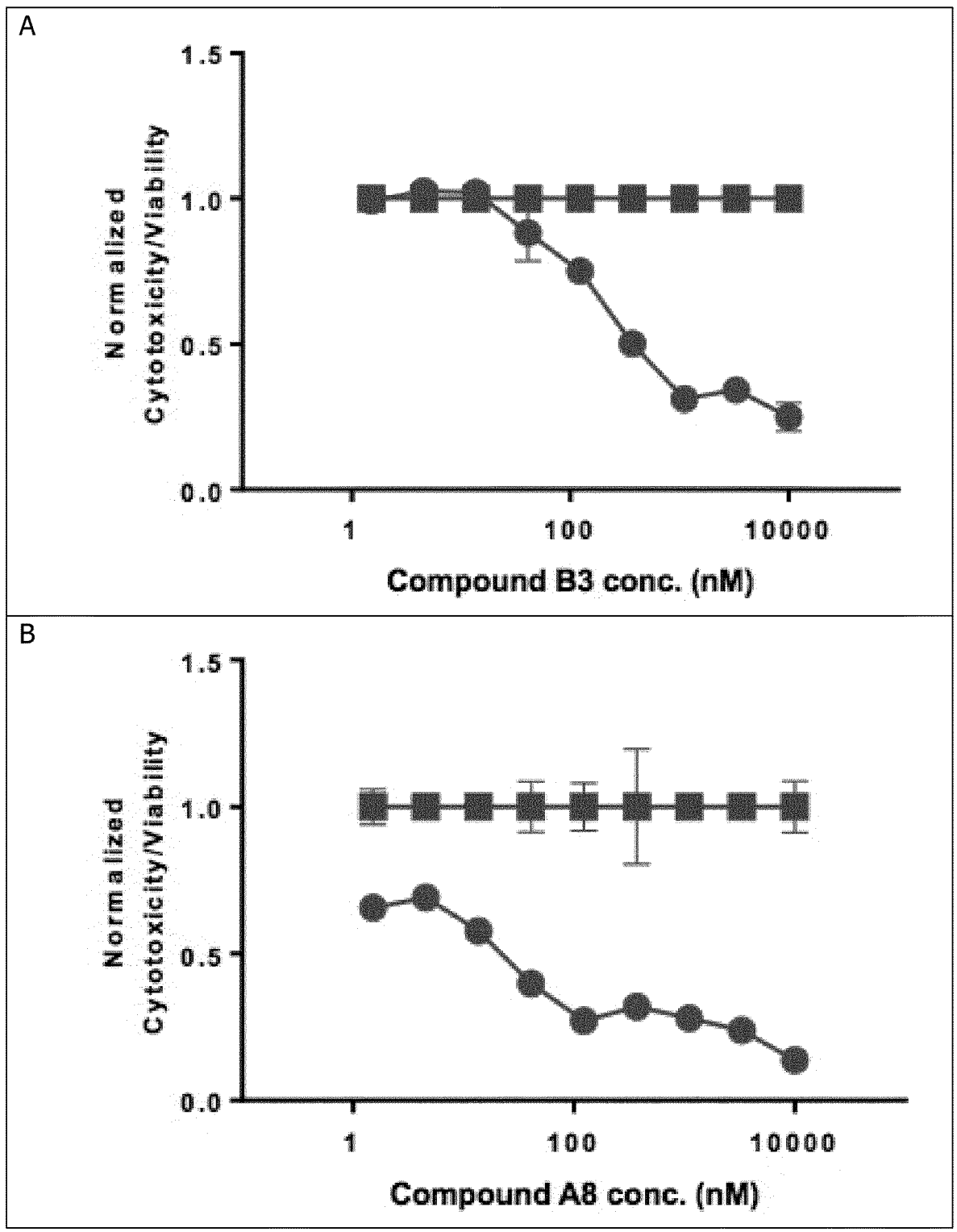
FIG. 6: depicts sensitisation of tumour-cells to in-vitro TNF-attack by (A) the kinase inhibitor B3; and (B) A8 (dasatinib). Circles: compound (concentration as shown) plus rHuTNF (10 ng/mL); squares: compound alone (concentration as shown) without rHuTNF.

The dose-response effect of rHuTNF treatment on the viability of the indicated PANC-1-luc cells is shown as a graph (FIG. 6) of the relative (cytotoxicity/viability) of tumour cells after treatment with rHuTNF at the respective concentration with the respective test compound (eg, B3 or A8) or control (eg, DMSO), and Y-axis is the normalised RLU (as a measure of cytotoxicity) of +TNF (cytotoxicity)/relative to without TNF (viability) measured using a luciferase-based killing assay: cells, test compound and then rHuTNF (10 ng/mL) are incubated for 24 h at 37° C., 5% C02, supernatant removed after culture and the remaining PANC-1-Luc cells lysed with luciferase cell lysis reagent (0.3% Triton-X in water) for 10 min. After lysis, luciferase assay buffer is added and immediately the luciferase intensity was measured by using the TECAN-Spark microplate reader.

To determine speed of onset of cell death, tumour cells are pre-labelled with nuclear incorporation of YOYO-1 dye and treated with inhibitors and TNF as indicated above. Tumour death kinetics is evaluated using real-time live cell microscopy with IncuCyte Zoom (Essen BioScience) by a graph showing the area of YOYO-1+ cells/well (μm$^2$/well) (ie, apoptotic cell area) of images after 6 h stimulation, with cumulative data of (eg 5-10) different pictures from the same experiment. Indeed, compound C7 is shown to sensitise PANC-1 cells to the effect of rHuTNF in such real-time live cell assay (FIG. 13A), and also in the luciferase-based tumour cell viability readout described above (data not shown).

The PANC1-luc cell line is constructed as follows: PANC-1 cells acquired from the American Type Cell Culture (ATCC). Tumour cells are transfected with a pEGFP-Luc plasmid, using TransIT-LT1 (Mirus) as transfection reagent. Transfected cells are selected with 1 mg/mL of G418/Geneticin, and 14 days after selection EGFP+ cells are sorted using, eg a BD FACSARIA II cell sorter.

Figure 7:
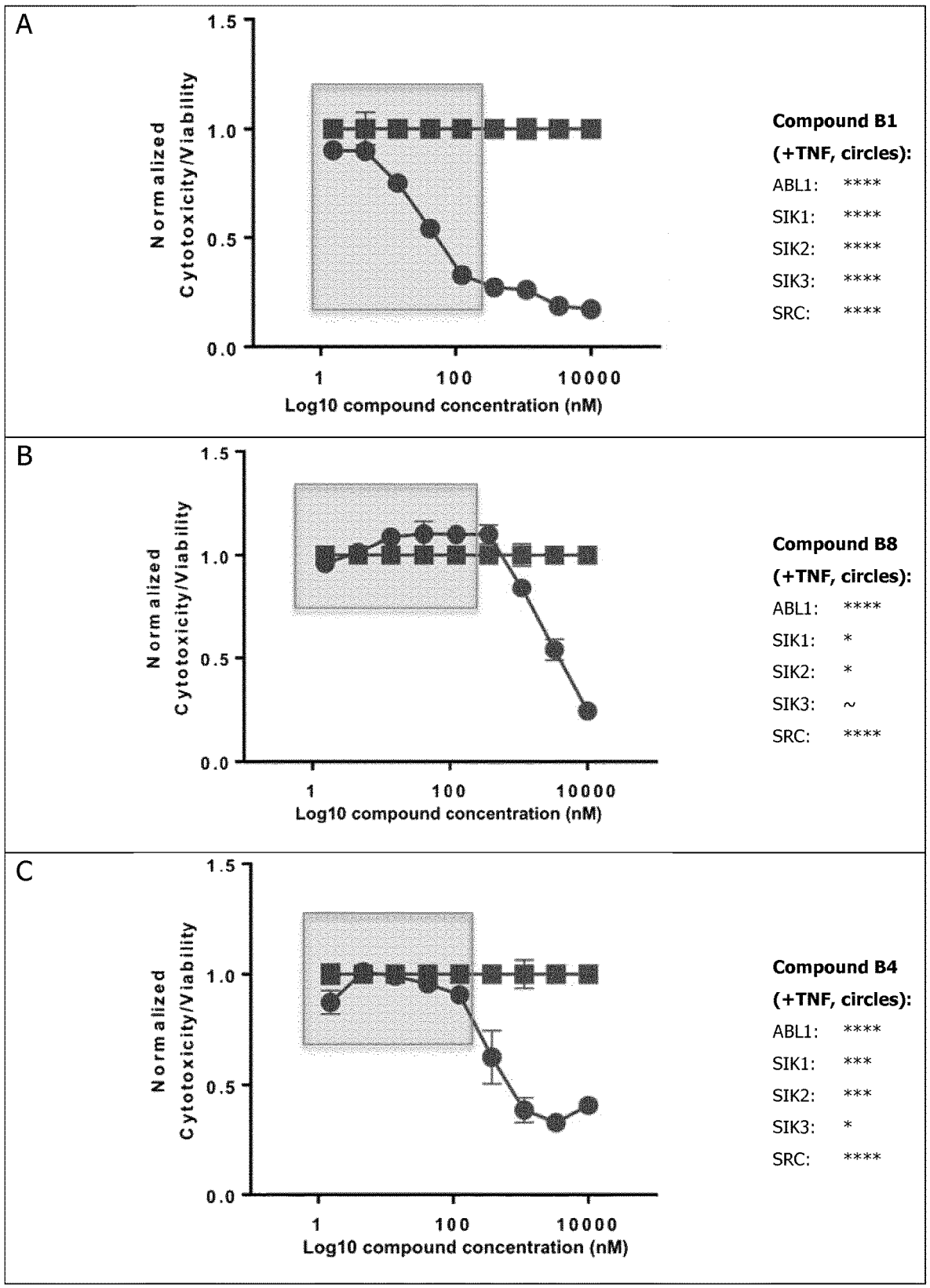
FIG. 7: depicts relative tumour cell survival (Normalised RLU by cytotoxicity/viability) of certain kinase inhibitors described in PCT/EP2018/060172 in the assay using M579-A2-luc described in Example 9 at various concentrations either alone (squares) or in combination with 10 ng/mL of TNF (circles). Also shown are indicative inhibitory activities of the compound for SIK-family members and for the related kinases ABL1 and SRC, shown with the indicators used for Table 3. (A) The pan-SIK and ABL1 & SRC inhibitor, compound B1; (B) The ABL1 & SRC inhibitor, compound B8. (C) The SIK1, SIK2 and ABL1 & SRC inhibitor, compound B4.

The tumour immuno-oncology effect is demonstrated to be mediated by SIK family members, and by SIK3 in particular. Using the luciferase-based tumor cell viability readout described above, tumour cells show increased cytotoxicity in the presence of TNF (10 ng/mL) and a pan-SIK and ABL1 & SRC inhibitor (compound B1) at a concentration of between about 10 and 100 nM (circles), compared to in the presence of inhibitor alone (squares) (FIG. 7A). In contrast however, compound B8 which is a potent ABL1 & SRC inhibitor but with low inhibitory activity against SIK family members (in particular SIK3), in combination with TNF (circles) fails to exhibit cytotoxicity of M579 A2 cells at such concentration range, compared to inhibitor alone (squares) (FIG. 7B). Indeed, in combination with TNF compound B4 (circles) also fails to exhibit cytotoxicity of M579 A2 cells at such concentration range, compared to inhibitor alone (squares) (FIG. 7C), despite compound B4 being not only a potent inhibitor of ABL1 & SRC but also a strong inhibitor or SIK1 and SIK2, but only a weak inhibitor of SIK3.

Taken together, these data implicate SIK family members, and in particular SIK3, as being the mediator of the anti-tumour immuno-oncology effect and not the other kinase ABL1 or SRC.

Compounds B1, B4 and B8 are as described, including their synthesis, in PCT/EP2018/060172, and are shown in Table 9A.

TABLE 9A

Compounds B1, B4 and B8

| Compound Number | Structure | Name |
|---|---|---|
| B1 | 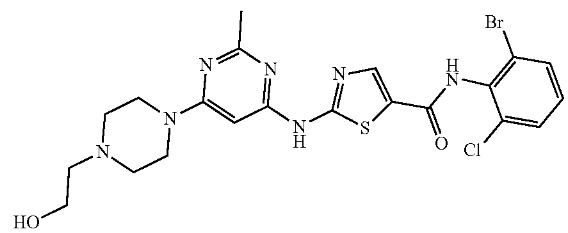 [SMILES: Cc1nc(Nc2ncc(C(=O)Nc3c(Cl)cccc3Br)s2)cc(N2CCN(CCO)CC2)n1] | N-(2-bromo-6-chlorophenyl)-2-((6-(4-(2-hydroxyethyl)piperazin-1-yl)-2-methylpyrimidin-4-yl)amino)thiazole-5-carboxamide |
| B4 | 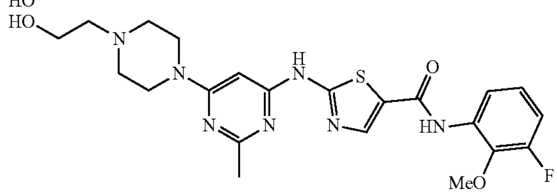 | N-(3-fluoro-2-methoxyphenyl)-2-((6-(4-(2-hydroxyethyl)piperazin-1-yl)-2-methylpyrimidin-4-yl)amino)thiazole-5-carboxamide |
| B8 | 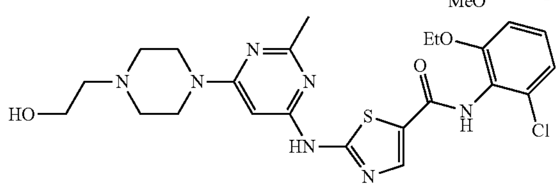 | N-(2-chloro-6-ethoxyphenyl)-2-((6-(4-(2-hydroxyethyl)piperazin-1-yl)-2-methylpyrimidin-4-yl)amino)thiazole-5-carboxamide |

Figure 13:
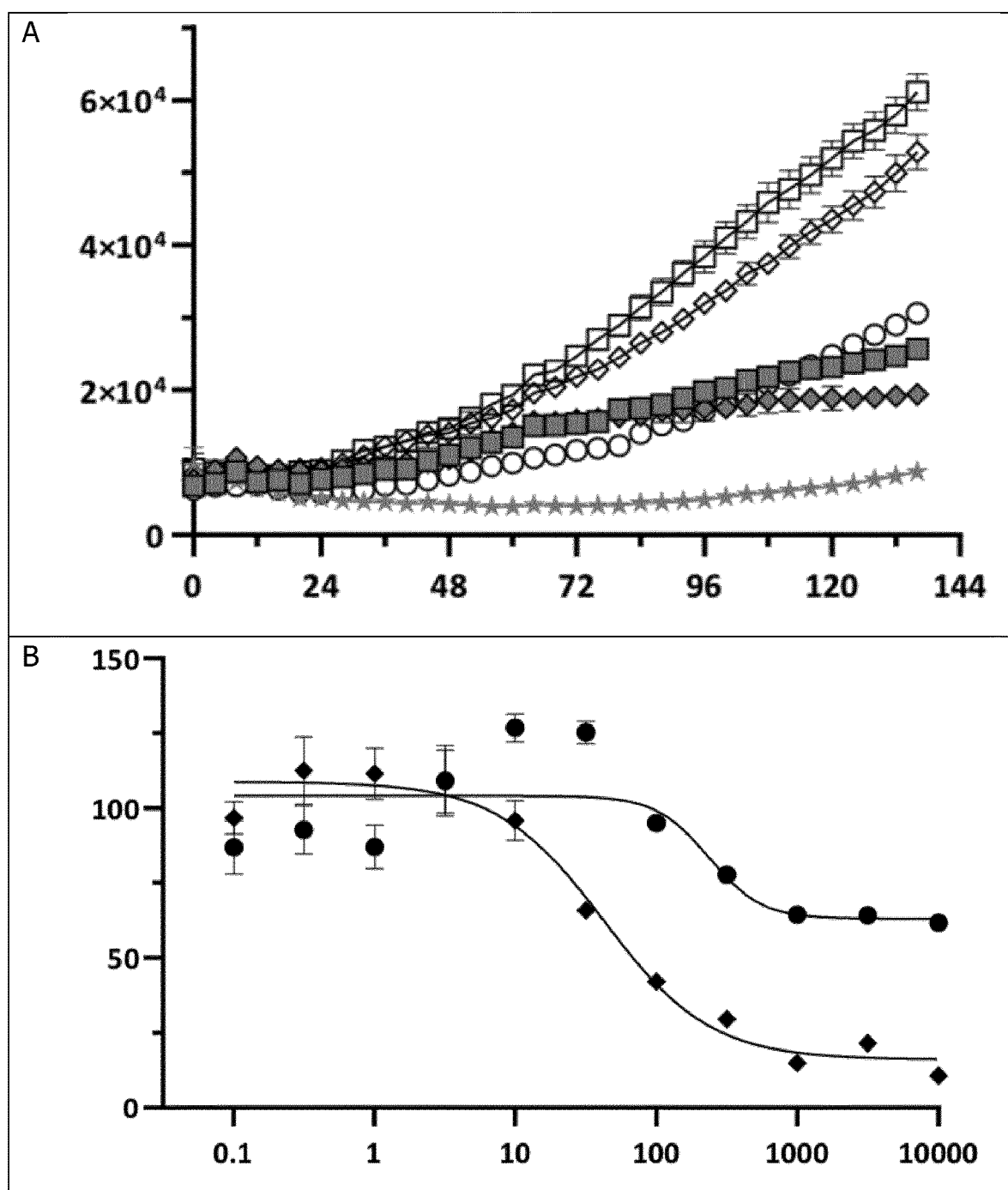
FIG. 13: depicts cell killing by TNF, sensitised by compound C7. (A) TNF-induced apoptosis of PANC-1 cells. PANC-1 cells were treated with C7 at 370 nM ("diamonds"), 3333 nM ("squares") and DMSO only ("stars") before addition of 100 ng/ml rHuTNF for 120 h (+rHuTNF=open shapes; −rHuTNF=solid shapes; open circles 10 ng/mL rHuTNF control). Cell death was evaluated using real-time live cell microscopy, measuring the nuclear incorporation of YOYO-1 dye (area of YOYO-1+ cells/well). Y-axis=Tumor cell death (um2/well). X-axes=Time (h); (B) Effect of C7 on TNF-induced (100 ng/ml rMuTNF) apoptosis of murine MC38 (+rMuTNF="diamonds"; −rMuTNF="circles"). Cell viability was measured after 72 h using a CellTiter-Glo assay. Luciferase values were normalized to cells treated with rMuTNF without inhibitor (DMSO only). Y-axis=Viability (%). X-axis=compound concentration (nM).

Other kinase inhibitors of formula (I) (e.g., one or more of C1 to C13, such as C7, and/or one or more compounds from Table B, D1 to D10) are used to investigate sensitisation of tumour cells to the cytotoxic effects of recombinant human TNF, including in a TNF-sensitised (100 ng/mL) cell viability assay using the MC38 murine tumour cell line (Table 9B). Indeed, MC38 tumour cells are sensitised to the cytotoxic effect of TNF by compound C7 (FIG. 13B).

TABLE 9B

Sensitisation to TNF-mediated killing of MC38 cells by compounds of formula (I)

| Compound | MC38 IC50 (nM at 100 ng/mL TNF) |
|---|---|
| A8 (dasatinib) | ++ |
| C7 | ++ |
| D1 | + |
| D7 | + |
| D8 | / |
| D9 | ++ |

++ = <100 nM;
+ = <200 nM;
/ = >200 nM

The assay demonstrating that compounds of formula (I) sensitise MC38 cells to TNF-mediated killing is conducted as follows. Cell viability of MC38 tumour cells was measured using the CellTiter-Glo (CTG) luminescent cell viability assay (Promega, Madison, USA) according to the manufacturer's protocol. In short, $1\times10^3$ MC38 cells were seeded in a 384-well plate for 24 h and subsequently treated with different concentrations of compounds of formula (I)/C7 and 100 ng/ml rMuTNF for 72 h at 37° C. and 5% C02. After incubation, CTG reagent was added to the wells and cells were lysed for 10 min. Read-out was performed using the Tecan reader with 0.1 sec counting time.

Figure 14:
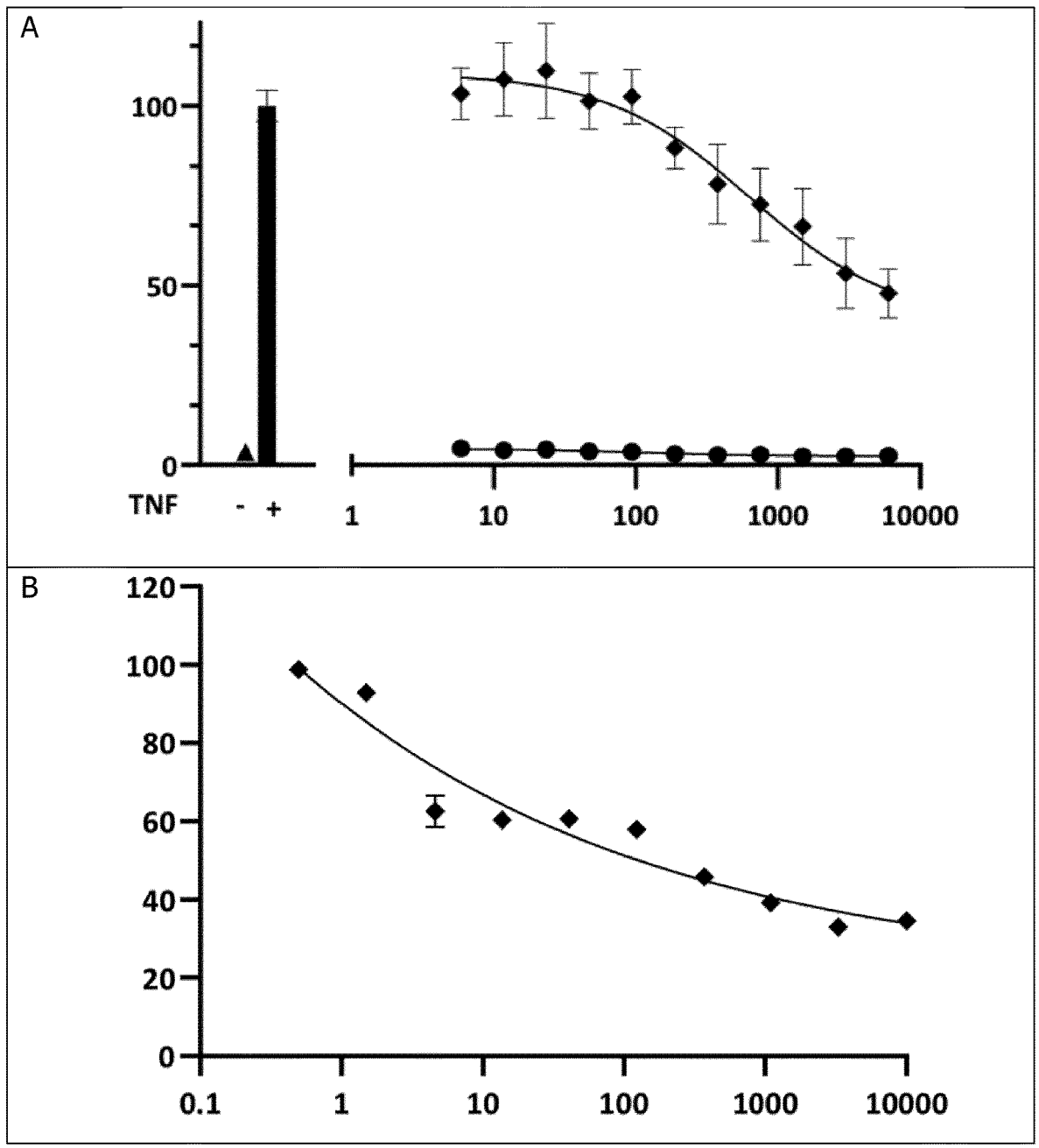
FIG. 14: depicts: (A) Effect of compound C7 on NFKB activity. Reporter PANC-1 cells expressing luciferase under the control of a NFKB promotor were treated with different concentrations of C7 before addition of 10 ng/ml rHuTNF for 8 h (+rHuTNF="diamonds"; −rHuTNF="circles"). Luciferase activity was normalized to PANC-1 cells treated with rHuTNF without inhibitor (DMSO only). Y-axis=NFKB activity (%). X-axis=compound concentration (nM); (B) Effect of compound C7 on HDAC4 phosphorylation. PANC-1 cells were treated with C7 at various concentrations (in the presence of 10 ng/mL rHuTNF) for 3 h. Whole cell lysates were analyzed in a Meso Scale Discovery (MSD) assay with anti-HDAC4 capture and anti-pHDAC4 detection antibodies. HDAC4 phosphorylation was normalized to untreated PANC-1 cells (DMSO only). Y-axis=HDAC4 phosphorylation (%). X-axis=Compound concentration (nM).

Compound C7 is also shown to inhibit TNF-induced activity of NFkB in a dose-dependent manner (FIG. 14A), and also to inhibit the phosphorylation of HDAC4, the key mediator of NFkB activity (FIG. 14B). Other compounds disclosed herein, such as dasatinib (A8), and/or those selected from compounds C2 to C12 and/or D1 to D10 are investigated for analogous activities (Table 9C).

TABLE 9C

Inhibition of NFKB activity and HDAC4 phosphorylation by compounds of formula (I)

| Compound | Inhibition of NFKB activity | Inhibition of HDAC4 phosphorylation |
|---|---|---|
| A8 (dasatinib) | + | ++ |
| C7 | + | + |
| D9 | + | + |

+ = Significant inhibition;
++ = Strong and significant inhibition

TNF-induced NFKB activity in PANC-1 cells was measured using NFKB-dependent luciferase activity. PANC-1 clones were generated to express luciferase under the control of a NFKB promotor. NFKB reporter PANC-1 cells (1,250 per well) were seeded in 384-well plates for 24 h. Afterwards, cells were treated with different concentrations compounds of formula (I)/C7 for one hour at 37° C. and 5% $CO_2$ before addition of 10 ng/ml rHuTNF. After 7 h incubation, cells were lysed, and luciferase activity was measured as before.

HDAC4 phosphorylation levels in PANC-1 cells were measured using a Meso Scale Discovery (MSD) assay. PANC-1 cells ($6\times10^4$) were seeded in a 96-well plate overnight and subsequently treated with different concentrations of compounds of formula (I)/C7 (in the presence of l0 ng/mL rHuTNF) for 3 h at 37° C. and 5% C02. Whole cell lysates were generated using RIPA lysis buffer (Thermo Scientific) and incubated on GAM plates coated with anti-total HDAC4 antibody (Abcam ab12171) overnight at 4° C. Afterwards, phosphorylated HDAC4 was detected using the pHDAC4 antibody (CST #3443). ECL signal was measured using an MSD reader.

Example 10 [Prophetic]: In-Vivo Immune-Oncology Activity of Kinase Inhibitors of Formula (I)

To investigate the synergistic effect of TNF-inducing therapy (eg, an anti-PD1 antibody, such as murine anti-PD1 clone: RMP1-14, BioLegend) with a kinase inhibitor of formula (I) (eg, C2, C7, C8, C9 or C12, or B3; and/or one or more of compounds D1 to D10), and dasatinib (A8) in comparison (at doses of between eg 2.5 mg/Km/day up to 50, 60 or 100 mg/Kg/day*), a further in vivo syngeneic mouse model as described in Example 9 is conducted, but with treatment groups addressing applicable combinations (and controls), for example treatment groups which may, for example, comprise those as set forth in Table 10A, below.

TABLE 10A

Example treatment groups.

| Group | Treatment | Total daily dose rmg/kg/dl | Dosing days | Route** | Vehicle | Number of mice |
|---|---|---|---|---|---|---|
| 5 | Vehicle** + ratIgG2a (control) | 10 mg/Kg* | 2x weekly | ip | + PBS | 15 |
| 6 | Vehicle** + anti-PD-1 | 10 mg/Kg* | daily + 2x weekly | po + ip | + PBS | 15 |
| 7a | B3 + anti-PD-1 | 60 mg/Kg*# + 10 mg/Kg* | daily# + 2x weekly | po + ip | Vehicle** + PBS | 15 |
| 7b | B3 + anti-PD-1 | 30 mg/Kg* + 10 mg/Kg* | daily# + 2x weekly | po + ip | Vehicle** + PBS | 15 |
| 8 | A8 (dasatinib) + anti-PD-1 | 30 mg/Kg* + 10 mg/Kg* | daily# + 2x weekly | po + ip | Vehicle** + PBS | 15 |

*Based on last bodyweight measurement;
**po = per os, oral administration via gavage, ip = intra-peritoneal
Compound dosed for at least 3 weeks, up to between 5 and 8 weeks. Anti-PD-1 and vehicle treatment for duration. Lower dosage (eg, 10, 15 or 20 mg/Kg) or higher dosage (eg, 50, 75 or 100 mg/Kg) for C2, C7, C8, C9 and C12 can be adapted according to their ADMET/PK properties.
**Propylene glycol:water 1:1

As described in Example 8: (i) mice are measured for body weight and tumour volume ($mm^3$) by calliper measurement twice weekly for up to 8 weeks until termination criteria (tumour volume>2000 $mm^3$) is reached; and (ii) 5 mice per group are sacrificed after day 9 of first treatment to analyse tumour and blood samples for various immune response markers (eg, as described in Example 8).

Example 11 [Prophetic]: Formulation for and Preparation of Unit Dose Form of Kinase Inhibitors of Formula (I) for Oral Administration A caplet unit dose form of a pharmaceutical composition of the invention is made, briefly as follows.

First, a tableting blend comprising the kinase inhibitor of formula (I) (eg, C7, C8 or B3) is prepared by dry granulation of an amount of C7 or C8 (or B3) together with one or more excipients. Example excipients in the tableting blend can include a binder, such as lactose (monohydrate), microcrystalline cellulose and/or hydroxypropyl cellulose, and optionally with a disintegrant such as starch. The blend may also include a lubricant such as magnesium stearate. Alternatively, the tableting blend is prepared by wet granulation followed by drying.

Second, using a rotary tablet press, the blend is filled into a suitably shaped die from above, and compressed to a porosity of between about 5% and 20% by lowering an upper punch into the die. Compression can take pace in in one or two stages (main compression, and optionally pre-compression or tamping), with compression occurring rapidly for scaled manufacturing (eg within 500 ms per caplet). The upper punch is pulled up and out of the die (decompression), and the caplet is ejected from the die.

Third, the caplet is coated using an automatic coater. The coating can comprise hypromellose, titanium dioxide, polyethylene glycol and purified water.

The tableting blend comprises an amount of the kinase inhibitor (C7, C8 or B3, as used) such that each caplet is made to include a therapeutically effective amount of C7 or C8 (or B3), and caplets of different dosages may be made to aid the administration of the correct overall dose of C7 or C8 (or B3). For example, each caplet may include about 20 mg, 50 mg or 70 mg of C7 or C8 (or B3, as applicable), or may include less than these amounts such as about 5 mg, 10 mg or 40 mg of C7 or C8 (or B3, as applicable).

The invention claimed is:

1. A pharmaceutical composition comprising a compound selected from the group consisting of a kinase inhibitor of the formula:

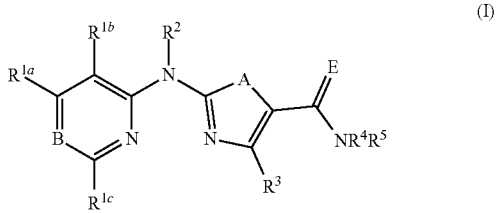

(I)

and solvates, salts, polymorphs, crystalline forms, racemic mixtures, diastereomers, enantiomers, and isotopically labeled forms thereof, and further comprising a pharmaceutically acceptable excipient, wherein:

$R^{1a}$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

each of $R^{1b}$ and $R^{1c}$ is independently selected from the group consisting of H, $C_{1-6}$ alkyl, $C_{2-6}$ alkenyl, $C_{2-6}$ alkynyl, $C_{3-7}$ cycloalkyl, $C_{6-10}$ aryl, 3- to 7-membered heteroaryl, 3- to 7-membered heterocyclyl, —O(CH$_2$)$_{0-2}$(C$_{3-7}$ cycloalkyl), —O(CH$_2$)$_{0-2}$(C$_{6-10}$ aryl), —O(CH$_2$)$_{0-2}$(3- to 7-membered heteroaryl), —O(CH$_2$)$_{0-2}$(3- to 7-membered heterocyclyl), —NH(CH$_2$)$_{0-2}$(C$_{3-7}$ cycloalkyl), —NH(CH$_2$)$_{0-2}$(C$_{6-10}$ aryl), —NH(CH$_2$)$_{0-2}$(3- to 7-membered heteroaryl), —NH(CH$_2$)$_{0-2}$(3- to 7-membered heterocyclyl), halogen, —CF$_3$, —CN, azido, —NO$_2$, —OH, —O(C$_{1-6}$ alkyl), —OCF$_3$, —S(C$_{1-6}$ alkyl), —NH$_2$, —NH(C$_{1-6}$ alkyl), —N(C$_{1-6}$ alkyl)$_2$, —NHS(O)$_2$(C$_{1-6}$ alkyl), —S(O)$_2$NH$_{2-z}$(C$_{1-6}$ alkyl)$_z$, —C(=O)(C$_{1-6}$ alkyl), —C(=O)OH, —C(=O)O(C$_{1-6}$ alkyl), —C(=O)NH$_{2-z}$(C$_{1-6}$ alkyl)$_z$, —NHC(=O)(C$_{1-6}$ alkyl), —NHC(=NH)NH$_{2-z}$(C$_{1-6}$ alkyl)$_z$, and —N(C$_{1-6}$ alkyl)C(=NH)NH$_{2-z}$(C$_{1-6}$ alkyl)$_z$, wherein z is 0, 1, or 2 and each of the $C_{1-6}$ alkyl, $C_{2-6}$ alkenyl, $C_{2-6}$ alkynyl, $C_{3-7}$ cycloalkyl, $C_{6-10}$ aryl, 3- to 7-membered heteroaryl, and 3- to 7-membered heterocyclyl groups is optionally substituted with one, two, or three moieties independently selected from the group consisting of —OH, methyl, ethyl, —OCH$_3$, —SCH$_3$, and —NH$_{2-z}$(CH$_3$)$_z$;

$R^2$ is H;

$R^3$ is selected from the group consisting of H, alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{12}$N(R$^{12}$)(R$^{13}$), —P(O)(OR$^{11}$)$_2$, —OP(O)(OR$^{11}$)$_2$, —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

$R^4$ is H;

$R^5$ is -L-R$^6$;

L is a bond;

$R^6$ is thienyl substituted with one, two, or three independently selected R$^7$;

$R^7$ is independently selected from the group consisting of halogen and $C_{1-2}$ alkyl, wherein the $C_{1-2}$ alkyl is optionally substituted with one, two, or three independently selected R$^{30}$;

A is selected from the group consisting of S, O, NR$^8$, and C(R$^9$)$_2$;

$R^8$ is selected from the group consisting of H, alkyl, alkenyl, alkynyl, cycloalkyl, aryl, heterocyclyl, and heteroaryl, wherein each of the alkyl, alkenyl, alkynyl, cycloalkyl, aryl, heterocyclyl, and heteroaryl groups is optionally substituted with one or more independently selected R$^{30}$;

$R^9$ is independently selected from the group consisting of alkyl, alkenyl, alkynyl, cycloalkyl, aryl, heterocyclyl, heteroaryl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{1}$S(O)$_{1-2}$R$^{11}$, —NR$^{1}$S(O)$_{12}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, cycloalkyl, aryl, heterocyclyl, and heteroaryl groups is optionally substituted with one or more independently selected R$^{30}$;

X is independently selected from the group consisting of O, S, and N(R$^{14}$);

E is O or S;

B is N or $CR^{1d}$;

$R^{1d}$ is selected from the group consisting of H, alkyl, alkenyl, alkynyl, cycloalkyl, aryl, heterocyclyl, heteroaryl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^1S(O)_{1-2}OR^{11}$, —$NR^1S(O)_{12}N(R^{12})(R^{13})$, —$P(O)(OR^{11})_2$, —$OP(O)(OR^{11})_2$, —C(=X)$R^{11}$, —C(=X)$XR^{11}$, —XC(=X)$R^{11}$, and —XC(=X)$XR^{11}$, wherein each of the alkyl, alkenyl, alkynyl, cycloalkyl, aryl, heterocyclyl, and heteroaryl groups is optionally substituted with one or more independently selected $R^{30}$;

$R^{11}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

each of $R^{12}$ and $R^{13}$ is independently selected from the group consisting of H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=$CR^{15}R^{16}$, wherein each of the alkyl, alkenyl, alkynyl, cycloalkyl, aryl, heteroaryl, and heterocyclyl groups is optionally substituted with one or more independently selected $R^{30}$;

$R^{14}$ is independently selected from the group consisting of H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more independently selected $R^{30}$;

each of $R^{15}$ and $R^{16}$ is independently selected from the group consisting of H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more independently selected $R^{30}$, wherein each of the alkyl, alkenyl, alkynyl, cycloalkyl, aryl, heteroaryl, and heterocyclyl groups is optionally substituted with one or more independently selected $R^{30}$;

y is an integer from 0 to 2;

$R^{20}$ is independently selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-20}R^{71}$, —$NR^{71}S(O)_{1-2}N(R^{72})(R^{73})$, —$OP(O)(OR^{71})_2$, —C(=$X^1$)$R^{71}$, —C(=$X^1$)$X^1R^{71}$, —$X^1$C(=$X^1$)$R^{71}$, and —$X^1$C(=$X^1$)$X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$OP(O)(OR^{81})_2$, —C(=$X^2$)$R^{81}$, —C(=$X^2$)$X^2R^{81}$, —$X^2$C(=$X^2$)$R^{81}$, and —$X^2$C(=$X^2$)$X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups being a $2^{nd}$ level substituent is optionally substituted with one or more $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$$NH_{2-z}$($C_{1-3}$ alkyl)$_z$, —C(=O)OH, —C(=O)O($C_{1-3}$ alkyl), —C(=O)$NH_{2-z}$($C_{1-3}$ alkyl)$_z$, —NHC(=O)($C_{1-3}$ alkyl), —NHC(=NH)$NH_{2-z}$ ($C_{1-3}$ alkyl)$_z$, and —N($C_{1-3}$ alkyl)C(=NH)$NH_{2-z}$ ($C_{1-3}$ alkyl)$_z$, wherein each z is independently 0, 1, or 2 and each $C_{1-3}$ alkyl is independently methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =N($C_{1-3}$ alkyl);

wherein each of $R^{71}$, $R^{72}$, and $R^{73}$ is independently selected from the group consisting of H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents independently selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$$NH_{2-z}$($C_{1-3}$ alkyl)$_z$, —C(=O)($C_{1-3}$ alkyl), —C(=O)OH, —C(=O)O($C_{1-3}$ alkyl), —C(=O)$NH_{2-z}$($C_{1-3}$ alkyl)$_z$, —NHC(=O)($C_{1-3}$ alkyl), —NHC(=NH)$NH_{2-z}$($C_{1-3}$ alkyl)$_z$, and —N($C_{1-3}$ alkyl)C(=NH)$NH_{2-z}$($C_{1-3}$ alkyl)$_z$, wherein each z is independently 0, 1, or 2 and each $C_{1-3}$ alkyl is independently methyl, ethyl, propyl or isopropyl;

each of $R^{81}$, $R^{82}$, and $R^{83}$ is independently selected from the group consisting of H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents independently selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein each z is independently 0, 1, or 2 and each $C_{1-3}$ alkyl is independently methyl, ethyl, propyl or isopropyl; and each of $X^1$ and $X^2$ is independently selected from O, S, and N($R^{84}$), wherein $R^{84}$ is H or $C_{1-3}$ alkyl;

with the proviso that when E is O; B is $CR^{1d}$ and $R^{1d}$ is either H, F, $C_1$ or Br, then $R^{1a}$ is not H.

2. The pharmaceutical composition of claim 1 formulated for oral administration and/or in unit dose form.

3. A method for the treatment of a proliferative disorder in a subject, comprising administering to the subject the pharmaceutical composition of claim 1, wherein the proliferative disorder is a cancer or tumor.

4. The method of claim 3, wherein the proliferative disorder that is a cancer or tumor is associated with a kinase selected from the group consisting of ABL1, mutants of ABL1, SRC, SIK1, SIK2, and SIK3.

5. The method of claim 3, wherein the cancer is a solid tumor.

6. The method of claim 3, wherein treatment further comprises administration of an immune checkpoint inhibitor.

7. The method of claim 3, the treatment comprising exposing cells involved with the proliferative disorder in the subject to: (i) TNF, a TNF variant, and/or an agonist of TNFR12 or TNFR1-signalling; and (ii) the compound or pharmaceutical composition and/or wherein the amount of TNF exposed to cells involved with the proliferative disorder in the subject is increased.

8. The pharmaceutical composition of claim 1, wherein $R^7$ is independently selected from the group consisting of Cl, Br, and methyl.

9. The pharmaceutical composition of claim 1, wherein $R^6$ is selected from the group consisting of

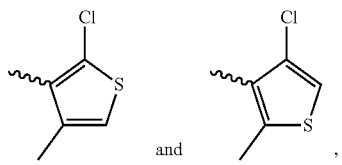

wherein ⌇ represents the bond by which $R^6$ is bound to the remainder of the compound.

10. The pharmaceutical composition of claim 1, wherein $R^{1a}$ is selected from the group consisting of alkyl, —O(alkyl), —S(alkyl), —NH(alkyl), —N(alkyl)$_2$, and heterocyclyl, wherein each of the alkyl and heterocyclyl groups is optionally substituted with one or more independently selected $R^{30}$.

11. The pharmaceutical composition of claim 1, wherein $R^{1a}$ is selected from the group consisting of $C_{1-3}$ alkyl, —O($C_{1-3}$ alkyl), —S($C_{1-3}$ alkyl), —NH($C_{1-3}$ alkyl), piperazinyl, morpholinyl, piperidinyl, and pyrrolidinyl, wherein each of the piperazinyl, morpholinyl, piperidinyl, and pyrrolidinyl groups is optionally substituted with one or two moieties independently selected from the group consisting of methyl, ethyl, —OH, —$OCH_3$, —$SCH_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)($C_{1-3}$ alkyl), —(CH$_2$)$_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —$OCH_3$, —$SCH_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2.

12. The pharmaceutical composition of claim 1, wherein $R^{1a}$ is selected from the group consisting of 4-(2-hydroxyethyl)piperazinyl, 4-methylpiperazinyl, 4-acetylpiperazinyl, and (2-hydroxyethyl)amino.

13. The pharmaceutical composition of claim 5, wherein at least one of $R^{1b}$ and $R^{1c}$ is selected from the group consisting of H, methyl, ethyl, —OH, —$OCH_3$, —$SCH_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, and phenyl, wherein z is 0, 1, or 2.

14. The pharmaceutical composition of claim 1, wherein $R^{1b}$ is H; and $R^{1c}$ is methyl, ethyl, propyl, isopropyl, or phenyl.

15. The pharmaceutical composition of claim 1, wherein A is S, O, or N(CH$_3$)$_2$.

16. The pharmaceutical composition of claim 1, wherein B is N or $CR^{1d}$, wherein $R^{1d}$ is selected from the group consisting of $C_{1-3}$ alkyl, halogen, —O($C_{1-3}$ alkyl), —S($C_{1-3}$ alkyl), —NH($C_{1-3}$ alkyl), and —N($C_{1-3}$ alkyl)$_2$, wherein each of the $C_{1-3}$ alkyl groups is optionally substituted with one or two moieties independently selected from the group consisting of halogen, —OH, —$OCH_3$, —SCH, and —NH$_{2-z}$(CH$_3$)$_z$, wherein z is 0, 1, or 2.

17. The pharmaceutical composition of claim 1, wherein E is O.

18. The pharmaceutical composition of claim 1, wherein $R^3$ is selected from the group consisting of H, methyl, ethyl, propyl, isopropyl, phenyl, and halogen.

19. The pharmaceutical composition of claim 1, wherein:
(A) $R^{1a}$ is selected from the group consisting of alkyl, —O(alkyl), —S(alkyl), —NH(alkyl), —N(alkyl)$_2$, and heterocyclyl, wherein each of the alkyl and heterocyclyl groups is optionally substituted with one or more independently selected $R^{30}$;
(B) each of $R^{1b}$ and $R^{1c}$ is independently selected from the group consisting of H, methyl, ethyl, —OH, —$OCH_3$, —$SCH_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, phenyl, pyridinyl, pyrazolyl, phenoxy, pyridinyloxy, imidazolylamino, and tetrahydrofuranylmethoxy, wherein z is 0, 1, or 2; and each of the phenyl, pyridinyl, pyrazolyl, phenoxy, pyridinyloxy, imidazolylamino, and tetrahydrofuranylmethoxy groups is optionally substituted with one, two or three moieties independently selected from methyl, ethyl, —OH, —$OCH_3$, —$SCH_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, and —NH$_{2-z}$(CH$_3$)$_z$, wherein z is 0, 1, or 2;
(C) $R^3$ is selected from the group consisting of H, $C_{1-6}$ alkyl, $C_{2-6}$ alkenyl, $C_{2-6}$ alkynyl, $C_{3-6}$ cycloalkyl, phenyl, halogen, —CN, azido, —NO$_2$, —O(C$_{1-6}$ alkyl), —OCF$_3$, —S(C$_{1-6}$ alkyl), —NH$_2$, —NH(C$_{1-6}$ alkyl), —N(C$_{1-6}$ alkyl)$_2$, —NHS(O)$_2$(C$_{1-6}$ alkyl), —S(O)$_2$NH$_{2-z}$(C$_{1-6}$ alkyl)$_z$, —C(=O)(C$_{1-6}$ alkyl), —C(=O)OH, —C(=O)O(C$_{1-6}$ alkyl), —C(=O)NH$_{2-z}$(C$_{1-6}$ alkyl)$_z$, —NHC(=O)(C$_{1-6}$ alkyl), NHC(=NH)NH$_{2-z}$(C$_{1-6}$ alkyl)$_z$, and —N(C$_{1-6}$ alkyl)C(=NH)NH$_{2-z}$(C$_{1-6}$ alkyl)$_z$, wherein z is 0, 1, or 2 and wherein each of the C$_{1-6}$ alkyl, C$_{2-6}$ alkenyl, C$_{2-6}$ alkynyl, C$_{3-6}$ cycloalkyl, and phenyl groups is optionally substituted with one or more independently selected R$^{30}$;

(D) R$^6$ is thienyl substituted with one, two, or three independently selected R$^7$;

(E) A is selected from the group consisting of S, O, NH, N(C$_{1-6}$ alkyl), and C(C$_{1-6}$ alkyl)$_2$;

(F) B is N or CR$^{1d}$, wherein R$^{1d}$ is selected from the group consisting of C$_{1-3}$ alkyl, halogen, —O(C$_{1-3}$ alkyl), —S(C$_{1-3}$ alkyl), —NH(C$_{1-3}$ alkyl), and —N(C$_{1-3}$ alkyl)$_2$, wherein each of the C$_{1-3}$ alkyl groups is optionally substituted with one or two moieties independently selected from the group consisting of halogen, —OH, —OCH$_3$, —SCH, and —NH$_{2-z}$(CH$_3$)$_z$, wherein z is 0, 1, or 2; and (G) E is O or S.

20. The pharmaceutical composition of claim 1, wherein:
(A') R$^{1a}$ is selected from the group consisting of C$_{1-3}$ alkyl, —O(C$_{1-3}$ alkyl), —S(C$_{1-3}$ alkyl), —NH(C$_{1-3}$ alkyl), —N(C$_{1-3}$ alkyl)$_2$, and 3- to 7-membered heterocyclyl, wherein the 3- to 7-membered heterocyclyl group is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, 4-methylpiperazinyl, —C(=O)(C$_{1-3}$ alkyl), —(CH$_2$)$_{1-3}$COOH, and —NH$_{2-z}$(CH$_3$)$_z$, wherein z is 0, 1, or 2; and each of the C$_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl)piperazinyl, 2-(N,N-dimethylamino)ethoxy, and —NH$_{2-z}$(CH$_3$)$_z$, wherein z is 0, 1, or 2;

(B') at least one of R$^{1b}$ and R$^{1c}$ is selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, and phenyl, wherein z is 0, 1, or 2, and the other of R$^{1b}$ and R$^{1c}$ is selected from the group consisting of H, methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, —NH$_{2-z}$(CH$_3$)$_z$, phenyl, pyridinyl, pyrazolyl, phenoxy, pyridinyloxy, imidazolylamino, and tetrahydrofuranylmethoxy, wherein z is 0, 1, or 2; and each of the phenyl, pyridinyl, pyrazolyl, phenoxy, pyridinyloxy, imidazolylamino, and tetrahydrofuranylmethoxy groups is optionally substituted with one, two or three moieties independently selected from methyl, ethyl, —OH, —OCH$_3$, —SCH$_3$, cyclopropyl, 2-hydroxyethyl, 2-(N,N-dimethylamino)ethyl, 2-(N,N-dimethylamino)ethoxy, 2-aminoethyl, 2-(N-methylamino)ethyl, 2-(methoxy)ethyl, and —NH$_{2-z}$(CH$_3$)$_z$, wherein z is 0, 1, or 2;

(C') R$^3$ is selected from the group consisting of H, C$_{1-4}$ alkyl, C$_{3-6}$ cycloalkyl, phenyl, halogen, —CN, —O(C$_{1-4}$ alkyl), —OCF$_3$, —S(C$_{1-4}$ alkyl), —NH$_2$, —NH(C$_{1-4}$ alkyl), —N(C$_{1-4}$ alkyl)$_2$, —C(=O)(C$_{1-4}$ alkyl), —C(=O)OH, —C(=O)O(C$_{1-4}$ alkyl), —C(=O)NH$_{2-z}$(C$_{1-4}$ alkyl)$_z$, —NHC(=O)(C$_{1-4}$ alkyl), —NHC(=NH)NH$_{2-z}$(C$_{1-4}$ alkyl)$_z$, and —N(C$_{1-4}$ alkyl)C(=NH)NH$_{2-z}$(C$_{1-4}$ alkyl)$_z$, wherein the phenyl group is optionally substituted with one or two groups independently selected from the group consisting of halogen, methyl, isopropyl, —CN, —CF$_3$, —OCF$_3$, —OH, —NH$_2$, —NH(C$_{1-3}$ alkyl), —N(C$_{1-3}$ alkyl)$_2$, —NHC(=O)(C$_{1-3}$ alkyl), —C(=O)NH$_{2-z}$(C$_{1-3}$ alkyl)$_z$, —(CH$_2$)$_{1-3}$NH$_2$, —(CH$_2$)$_{1-3}$NH(C$_{1-3}$ alkyl), —(CH$_2$)$_{1-3}$N(C$_{1-3}$ alkyl)$_2$, —(CH$_2$)$_{1-30}$H, and —(CH$_2$)$_{1-30}$(C$_{1-3}$ alkyl); and wherein z is 0, 1, or 2;

(D') R$^6$ is thienyl substituted with one, two, or three independently selected R$^7$;

(E') A is S, O, or N(CH$_3$)$_2$;

(F') B is N or CR$^{1d}$, wherein R$^{1d}$ is selected from the group consisting of C$_{1-3}$ alkyl, halogen, —O(C$_{1-3}$ alkyl), —S(C$_{1-3}$ alkyl), —NH(C$_{1-3}$ alkyl), and —N(C$_{1-3}$ alkyl)$_2$; and (G') E is O or S.

21. The pharmaceutical composition of claim 19, wherein R$^7$ is independently selected from the group consisting of Cl, Br, and methyl.

22. The pharmaceutical composition of claim 19, wherein R$^{1a}$ is selected from the group consisting of —NH(C$_{1-3}$ alkyl), piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the C$_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2.

23. The pharmaceutical composition of claim 19, wherein R$^{1b}$ is H; and R$^{1c}$ is methyl, ethyl, propyl, isopropyl, or phenyl.

24. The pharmaceutical composition of claim 19, wherein A is S, B is N and/or E is O.

25. The pharmaceutical composition of claim 19, wherein R$^3$ is selected from the group consisting of H, methyl, ethyl, propyl, isopropyl, phenyl, and halogen.

26. The pharmaceutical composition of claim 1, wherein the compound is in greater than about 95% pure form.

27. The method of claim 4, wherein the proliferative disorder is associated with SIK3 kinase.

28. The method of claim 3, wherein the subject is distinguished as having been previously treated with an immunotherapy and whose tumor has progressed, or whose tumor has relapsed or recurred after, or did not respond to, the immunotherapy.

29. The method of claim 3, wherein the subject is distinguished as having a tumor that progressed, relapsed or recurred after, or did not respond to, prior radiotherapy.

30. The method of claim 3, wherein treatment involves inhibiting SIK3.

31. The method of claim 3, wherein the subject is a mammalian subject.

32. The method of claim 3, wherein, wherein the subject is a human subject.

33. The method of claim 7, wherein the exposure of the cells involved with the proliferative disorder to TNF is induced by a pharmaceutical, therapeutic or other procedure that increases the amount of TNF in the plasma of the subject and/or in the environment of such cells.

34. The method of claim 33, wherein the pharmaceutical, therapeutic or other procedure comprises cancer immunotherapy and/or radiotherapy.

35. The pharmaceutical composition of claim 1, wherein $R^{1a}$ is selected from the group consisting of $C_{1-3}$ alkyl, —O($C_{1-3}$ alkyl), —S($C_{1-3}$ alkyl), —NH($C_{1-3}$ alkyl), —N($C_{1-3}$ alkyl)$_2$, and 3- to 7-membered heterocyclyl, wherein the 3- to 7-membered heterocyclyl group is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino) ethoxy, 2-aminoethyl, 2-(N-methylamino)ethyl, 2-(methoxy)ethyl, 4-methylpiperazinyl, —C(=O)($C_{1-3}$ alkyl), —(CH$_2$)$_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl) piperazinyl, 2-(N,N-dimethylamino) ethoxy, and —NH$_{2-z}$(CH$_3$)$_z$, wherein z is 0, 1, or 2.

36. The pharmaceutical composition of claim 1, wherein $R^{1a}$ is selected from the group consisting of —NH($C_{1-3}$ alkyl), piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the $C_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2.

37. The pharmaceutical composition of claim 1, wherein $R^{1a}$ is selected from the group consisting of 4-(2-hydroxyethyl) piperazinyl, 4-methylpiperazinyl, 4-acetylpiperazinyl, (2-hydroxyethyl)amino, 4-aminopiperidinyl, 4-(4-methylpiperazinyl) piperidinyl, 4-carboxymethylpiperazinyl, and 3-hydroxypyrrolidinyl.

38. The pharmaceutical composition of claim 1, wherein $R^{1b}$ is H; and $R^{1c}$ is methyl.

39. The pharmaceutical composition of claim 1, wherein A is S.

40. The pharmaceutical composition of claim 1, wherein B is N.

41. The pharmaceutical composition of claim 1, wherein $R^3$ is H.

42. The pharmaceutical composition of claim 19, wherein E is O.

43. The pharmaceutical composition of claim 20, wherein E is O.

44. The pharmaceutical composition of claim 19, wherein $R^{1b}$ is H; and $R^{1c}$ is methyl.

45. The pharmaceutical composition of claim 19, wherein A is S, B is N and E is O.

46. The pharmaceutical composition of claim 19, wherein $R^3$ is H.

47. The pharmaceutical composition of claim 19, wherein $R^{1a}$ is selected from the group consisting of $C_{1-3}$ alkyl, —O($C_{1-3}$ alkyl), —S($C_{1-3}$ alkyl), —NH($C_{1-3}$ alkyl), —N($C_{1-3}$ alkyl)$_2$, and 3- to 7-membered heterocyclyl, wherein the 3- to 7-membered heterocyclyl group is optionally substituted with one or two moieties independently selected from the group consisting of methyl, ethyl, —OH, —OCH$_3$, —SCH$_3$, cyclopropyl, 2-hydroxyethyl, 2-(N,N-dimethylamino)ethyl, 2-(N,N-dimethylamino) ethoxy, 2-aminoethyl, 2-(N-methylamino)ethyl, 2-(methoxy)ethyl, 4-methylpiperazinyl, —C(=O)($C_{1-3}$ alkyl), —(CH$_2$)$_{1-3}$COOH, and —NH$_{2-z}$(CH$_3$)$_z$, wherein z is 0, 1, or 2; and each of the $C_{1-3}$ alkyl groups is optionally substituted with one or two moieties independently selected from the group consisting of —OH, —OCH$_3$, —SCH$_3$, cyclopropyl, piperazinyl, 4-methyl-piperazinyl, 4-(2-hydroxyethyl) piperazinyl, 2-(N,N-dimethylamino) ethoxy, and —NH$_{2-z}$(CH$_3$)$_z$, wherein z is 0, 1, or 2.

48. The pharmaceutical composition of claim 19, wherein $R^{1a}$ is selected from the group consisting of —NH($C_{1-3}$ alkyl), piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the $C_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2.

49. The pharmaceutical composition of claim 19, wherein $R^{1a}$ is selected from the group consisting of 4-(2-hydroxyethyl) piperazinyl, 4-methylpiperazinyl, 4-acetylpiperazinyl, (2-hydroxyethyl)amino, 4-aminopiperidinyl, 4-(4-methylpiperazinyl) piperidinyl, 4-carboxymethylpiperazinyl, and 3-hydroxypyrrolidinyl.

50. The pharmaceutical composition of claim 19, wherein $R^{1a}$ is selected from the group consisting of 4-(2-hydroxyethyl) piperazinyl, 4-methylpiperazinyl, 4-acetylpiperazinyl, and (2-hydroxyethyl)amino.

51. The pharmaceutical composition of claim 1, wherein the compound is selected from the group consisting of the kinase inhibitor of formula (I), and solvates and pharmaceutically acceptable salts thereof, wherein:
(A") $R^{1a}$ is selected from the group consisting of —NH ($C_{1-3}$ alkyl), piperazinyl, piperidinyl, and pyrrolidinyl, wherein the piperazinyl group is optionally substituted with one or two moieties independently selected from the group consisting of 2-hydroxyethyl, methyl, —CH$_2$COOH, and —C(=O)CH$_3$; the piperidinyl group is optionally substituted with one or two moieties independently selected from the group consisting of —NH$_2$ and 4-methylpiperazinyl; the pyrrolidinyl is optionally substituted with one or two —OH; and each of the $C_{1-3}$ alkyl groups is optionally substituted with one or two moieties independently selected from the group consisting of —OH, —OCH$_3$, and —NH$_{2-z}$(CH$_3$)$_z$, wherein z is 0, 1, or 2;
(B") $R^{1b}$ is H; and $R^{1c}$ is methyl;
(C") $R^3$ is H;
(D") $R^6$ is thienyl substituted with one, two, or three independently selected $R^7$;
(E") A is S;
(F") B is N; and
(G") E is O.

52. The pharmaceutical composition of claim 51, wherein $R^{1a}$ is selected from the group consisting of 4-(2-hydroxyethyl) piperazinyl, 4-methylpiperazinyl, 4-acetylpiperazinyl, (2-hydroxyethyl)amino, 4-aminopiperidinyl, 4-(4-methylpiperazinyl) piperidinyl, 4-carboxymethylpiperazinyl, and 3-hydroxypyrrolidinyl.

53. A method for the treatment of a proliferative disorder in a human subject, comprising administering to the human subject the pharmaceutical composition of claim 51, wherein the proliferative disorder is a cancer or tumor.

* * * * *